US009539254B2

(12) United States Patent
Gu et al.

(10) Patent No.: US 9,539,254 B2
(45) Date of Patent: Jan. 10, 2017

(54) MUTANT ROS EXPRESSION IN HUMAN CANCER

(71) Applicant: Cell Signaling Technology, Inc., Danvers, MA (US)

(72) Inventors: Ting-Lei Gu, Woburn, MA (US); Meghan Ann Tucker, Salem, MA (US); Herbert Haack, South Hamilton, MA (US); Katherine Eleanor Crosby, Middelton, MA (US); Victoria McGuinness Rimkunas, Somerville, MA (US)

(73) Assignee: CELL SIGNALING TECHNOLOGY, INC., Danvers, MA (US)

( * ) Notice: Subject to any disclaimer, the term of this patent is extended or adjusted under 35 U.S.C. 154(b) by 9 days.

(21) Appl. No.: 14/483,681

(22) Filed: Sep. 11, 2014

(65) Prior Publication Data

US 2015/0119403 A1 Apr. 30, 2015

Related U.S. Application Data

(63) Continuation of application No. 13/146,705, filed as application No. PCT/US2010/024109 on Feb. 12, 2010, now Pat. No. 9,364,477.

(60) Provisional application No. 61/207,484, filed on Feb. 12, 2009.

(51) Int. Cl.

*A61K 31/4545* (2006.01)
*A61K 31/506* (2006.01)
*C12Q 1/68* (2006.01)
*G01N 33/574* (2006.01)

(52) U.S. Cl.

CPC ......... *A61K 31/506* (2013.01); *A61K 31/4545* (2013.01); *C12Q 1/6827* (2013.01); *C12Q 1/6858* (2013.01); *C12Q 1/6869* (2013.01); *C12Q 1/6886* (2013.01); *G01N 33/57438* (2013.01); *G01N 33/57484* (2013.01); *G01N 2333/9121* (2013.01); *G01N 2800/52* (2013.01)

(58) Field of Classification Search

None

See application file for complete search history.

(56) References Cited

U.S. PATENT DOCUMENTS

2005/0181375 A1 8/2005 Aziz et al.
2012/0208824 A1 8/2012 Rimkunas et al.
2016/0206608 A1* 7/2016 Christensen ....... A61K 31/4545

FOREIGN PATENT DOCUMENTS

WO 2007/084631 A2 7/2007
WO 2008/066498 A1 6/2008
WO WO 2013/017989 A1 2/2013

OTHER PUBLICATIONS

McDermott et al. (Cancer Res. May 1, 2008 68 (9): 3389-3395).*
Zou et al. (Cancer Res. 2007 67 (9): 4408-4417).*
Rikova et al. (Cell Dec. 14, 2007 131:1190-1203).*
Kwak E.L. et al., "Anaplastic Lymphoma Kinase Inhibition in Non-Small-Cell Lung Cancer", The New England Journal of Medicine 363(18)1693-1703 (Oct. 28, 2010).
Shaw A.T. et al., "Crizotinib in ROS1-Rearranged Non-Small-Cell Lung Cancer", The New England Journal of Medicine 371(21):1963-1971 (Nov. 20, 2014).
Rikova, K. et al., "Global Survey of Phosphotyrosine Signaling Identifies Oncogenic Kinases in Lung Cancer" Cell (Dec. 14, 2007) pp. 1190-1203, vol. 131, No. 6.
Gu, T.-L. et al., "Survey of Tyrosine Kinase Signaling Reveals ROS Kinase Fusions in Human Cholangiocarcinoma" Plos One (Jan. 6, 2011) pp. 1-9, vol. 6, No. 1.
Zhao, J.-F. et al., "Expression of the ROS1 Oncogene for Tyrosine Receptor Kinase in Adult Human Meningiomas" Cancer Genetics and Cytogenetics (Sep. 1, 1995) pp. 148-154, vol. 83, No. 2.
Acuaviva, J. et al., "The Multifaceted Roles of the Receptor Tyrosine Kinase ROS in Development and Cancer" BBA—Reviews on Cancer (Jan. 1, 2009) pp. 37-52, vol. 1795, No. 1.
Ruhe, J. E. et al., "Genetic Alterations in the Tyrosine Kinase Transcriptome of Human Cancer Cell Lines" Cancer Research (Dec. 1, 2007) pp. 11368-11376, vol. 67, No. 23.
Birchmeier, C. et al., "Characterization of ROS1 cDNA from a Human Glioblastoma Cell Line" Proc. Natl. Acad. Sci. USA (Jun. 1990) pp. 4799-4803, vol. 87.
Charest, A. et al., "ROS Fusion Tyrosine Kinase Activates a SH2 Domain-Containing Phosphatase-2/Phosphatidylinositol 3-Kinase/Mammalian Target of Rapamycin Signaling Axis to Form Glioblastoma in mice" Cancer Research (Aug. 1, 2006) pp. 7473-7481, vol. 66, No. 15.
Charest, A. et al., "Oncogenic Targeting of an Activated Tyrosine Kinase to the Golgi Apparatus in a Glioblastoma" PNAS (Feb. 4, 2003) pp. 916-921, vol. 100, No. 3.

(Continued)

*Primary Examiner* — Peter J Reddig

(74) *Attorney, Agent, or Firm* — Scully, Scott, Murphy & Presser, P.C.

(57) ABSTRACT

The invention provides the identification of the presence of mutant ROS protein in human cancer. In some embodiments, the mutant ROS are FIG-ROS fusion proteins comprising part of the FIG protein fused to the kinase domain of the ROS kinase. In some embodiments, the mutant ROS is the overexpression of wild-type ROS in cancerous tissues (or tissues suspected of being cancerous) where, in normal tissue of that same tissue type, ROS is not expressed or is expressed at lower levels. The mutant ROS proteins of the invention are anticipated to drive the proliferation and survival of a subgroup of human cancers, particularly in cancers of the liver (including bile duct), pancreas, kidney, and testes. The invention therefore provides, in part, isolated polynucleotides and vectors encoding the disclosed mutant ROS polypeptides (e.g., a FIG-ROS(S) fusion polypeptide), probes for detecting it, isolated mutant polypeptides, recombinant polypeptides, and reagents for detecting the fusion and truncated polypeptides. The identification of the mutant ROS polypeptides enables new methods for determining the presence of these mutant ROS polypeptides in a biological sample, methods for screening for compounds that inhibit the proteins, and methods for inhibiting the progression of a cancer characterized by the mutant polynucleotides or polypeptides, which are also provided by the invention.

8 Claims, 21 Drawing Sheets

(56) References Cited

OTHER PUBLICATIONS

Blechacz, B. et al., "Cholangiocarcinoma: Advances in Pathogenesis, Diagnosis, and Treatment" Hepatology (2008) pp. 308-321, vol. 48, No. 1.

Birchmeier, C. et al., "Expression and Rearrangement of the ROS1 gene in Human Glioblastoma Cells" Proc. Natl. Acad. Sci. USA (Dec. 1987) pp. 9270-9274, vol. 84.

Kurzrock, R. et al., "The Molecular Genetics of Philadelphia Chromosome-Positive Leukemias" The New England Journal of Medicine (1988) pp. 990-998, vol. 319, No. 15.

Falini, B. et al., "Proteins Encoded by Genes Involved in Chromosomal Alterations in Lymphoma and Leukemia: Clinical Value of Their Detection by Immunocytochemistry" Blood (Jan. 2002) pp. 409-426, vol. 99, No. 2.

Charest, A. et al., "Fusion of FIG to the Receptor Tyrosine Kinase ROS in a Glioblastoma with an Interstitial del(6) (q21Q21)" Genes Chromosomes and Cancer (May 2003) pp. 58-71, vol. 37, No. 1.

International Search Report dated Sep. 14, 2010 issued in corresponding International Publication No. WO 2010/093928 A3.

Galkin, A.V. et al., "Identification of NVP-TAE684, a potent, selective, and efficacious inhibitor of NPM-ALK" PNAS (Jan. 2, 2007) pp. 270-275, vol. 104, No. 1.

European Search Report dated May 11, 2015 issued in European Application No. EP 14 18 4691.5.

European Communication dated Jul. 13, 2016 received from European Patent Application No. 14 184 691.5.

Christensen J.G. et al., "Cytoreductive Antitumor Activity of PF-2341066, a Novel Inhibitor of Anaplastic Lymphoma Kinase and c-Met, in Experimental Models of Anaplastic Large-Cell Lymphoma", Mol Cancer Ther 6 (12):3314-3322 (Dec. 2007).

Kodama T. et al., "Alectinib Shows Potent Antitumor Activity Against Both ALK- and RET-Rearranged Non-Small Cell Lung Cancers", Cancer Research 75:773 (Aug. 1, 2015), Abstract 773.

* cited by examiner

Figure 1: Genomic information of FIG-ROS

Figure 2: FIG-ROS in liver cancer

•FIG-ROS (L): exon 7 of FIG fused to exon 34 of ROS
•FIG-ROS (S): exon 3 of FIG fused to exon 35 of ROS Expression of FIG-ROS in liver cancer

2/23=8.7%

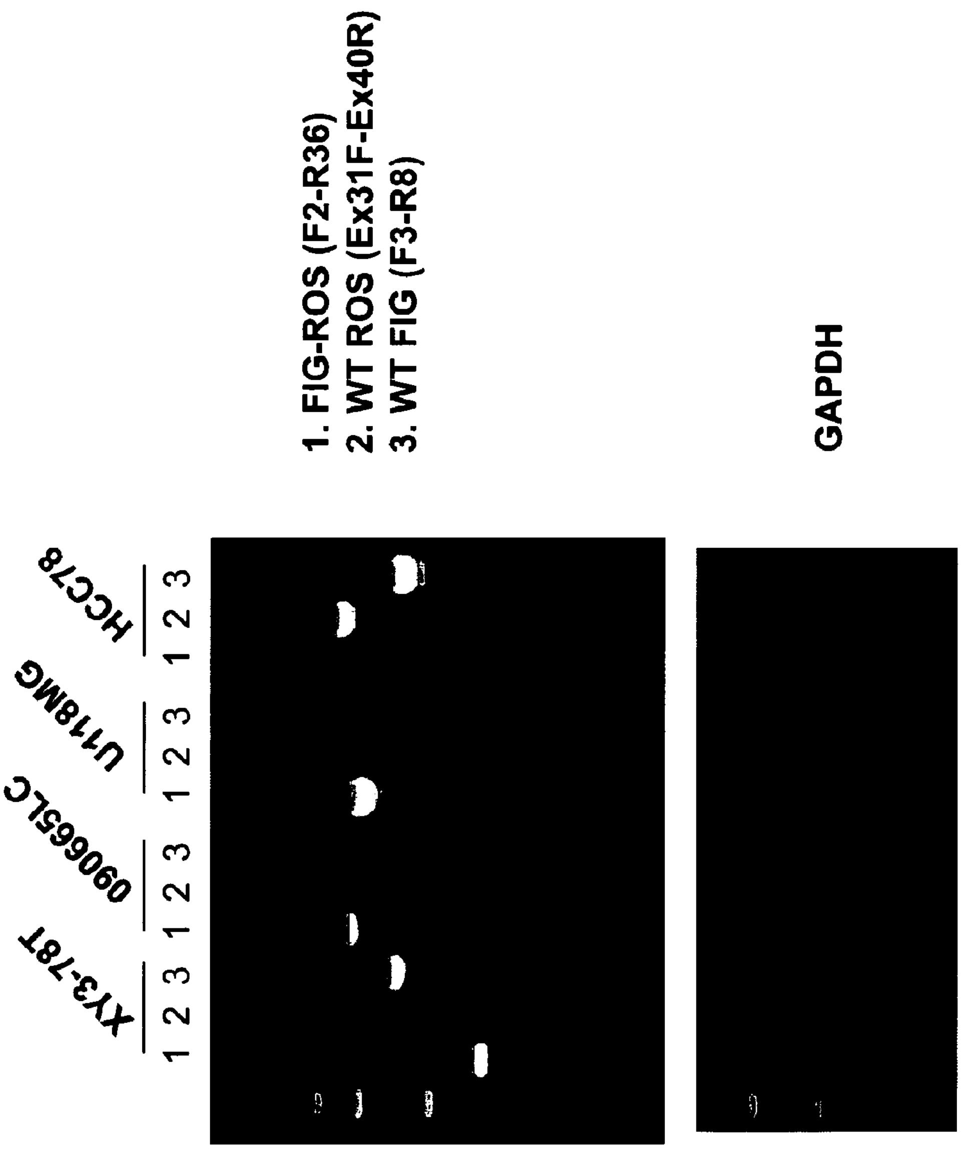
Figure 4: Expression of FIG-ROS in MS positive samples

Figure 5: Genomic PCR of FIG-ROS
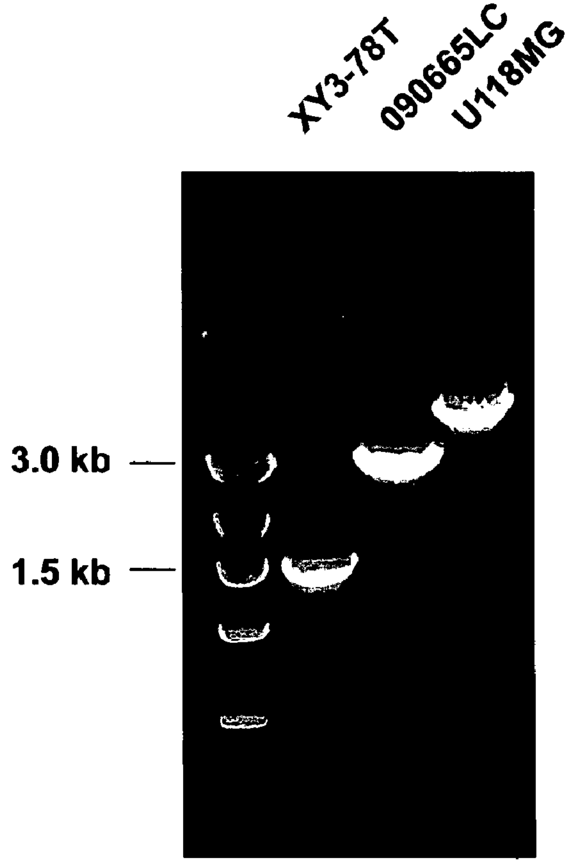

Figure 6: Stable expression of FIG-ROS fusions
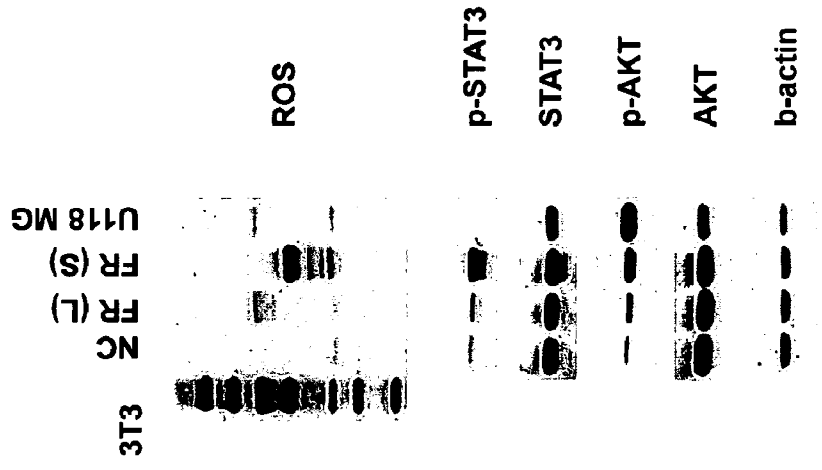

Figure 7: Soft Agar Assay (3T3 cells)
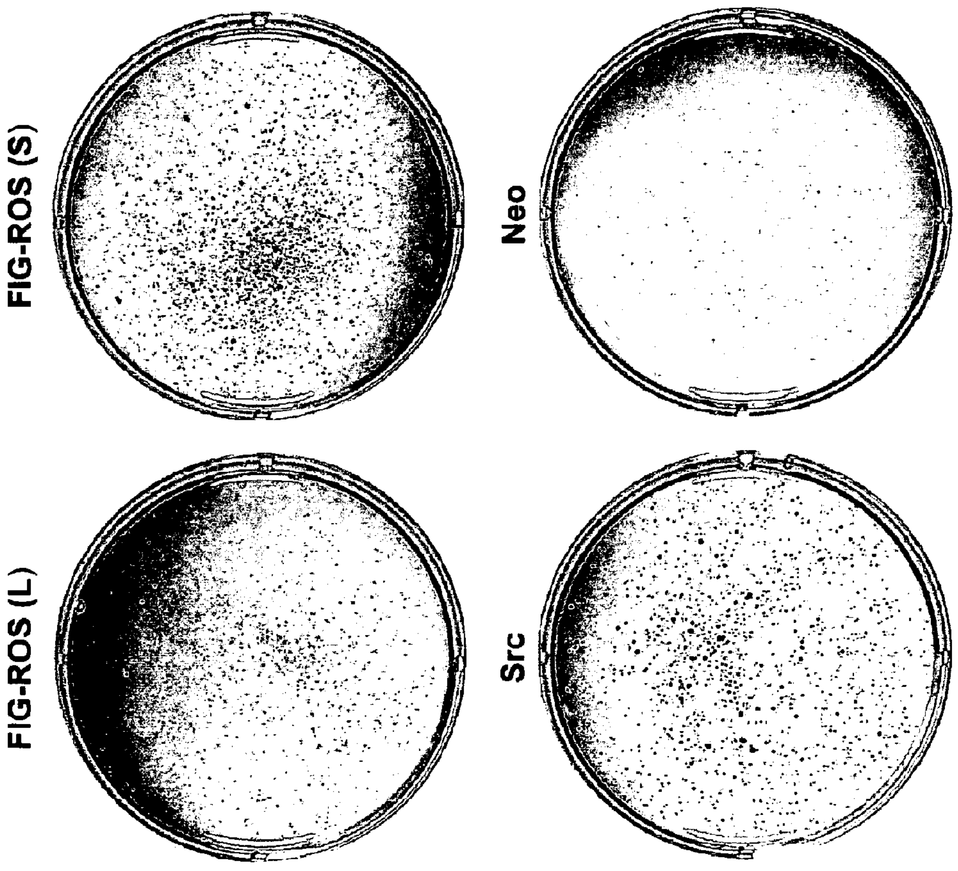

Figure 8: Transforming activity of FIG-ROS
| | Neo | FIG-ROS (L) | FIG-ROS (S) |
|---|---|---|---|
| Nude mice (Day 16) | 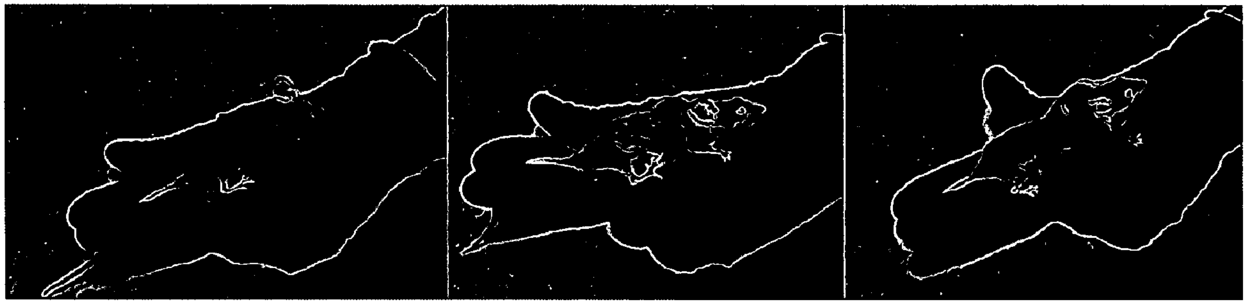 | | |
| Tumor/Injection | 0/8 | 8/8 | 8/8 |

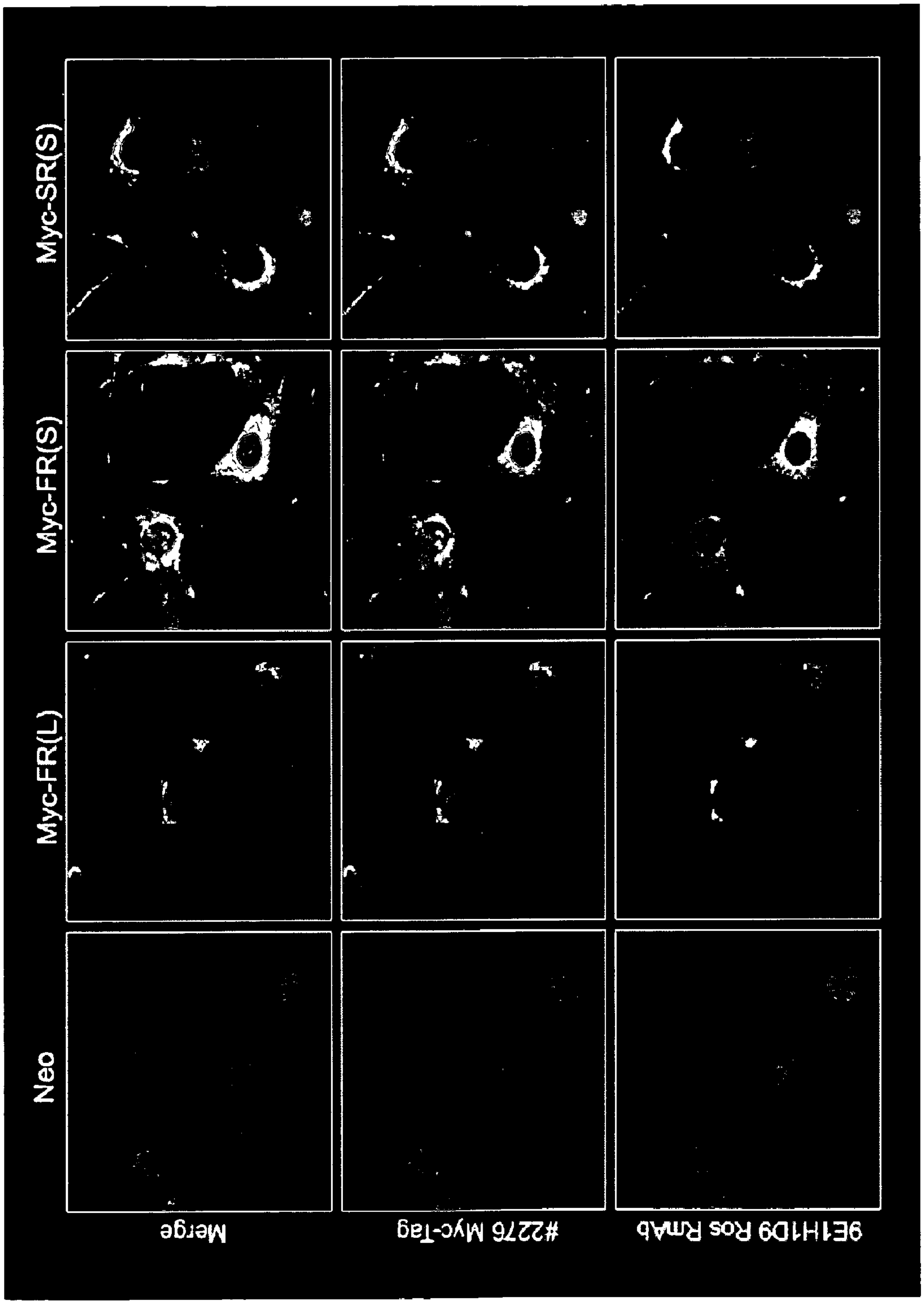
Figure 9A: Subcellular localization of FIG-ROS fusions

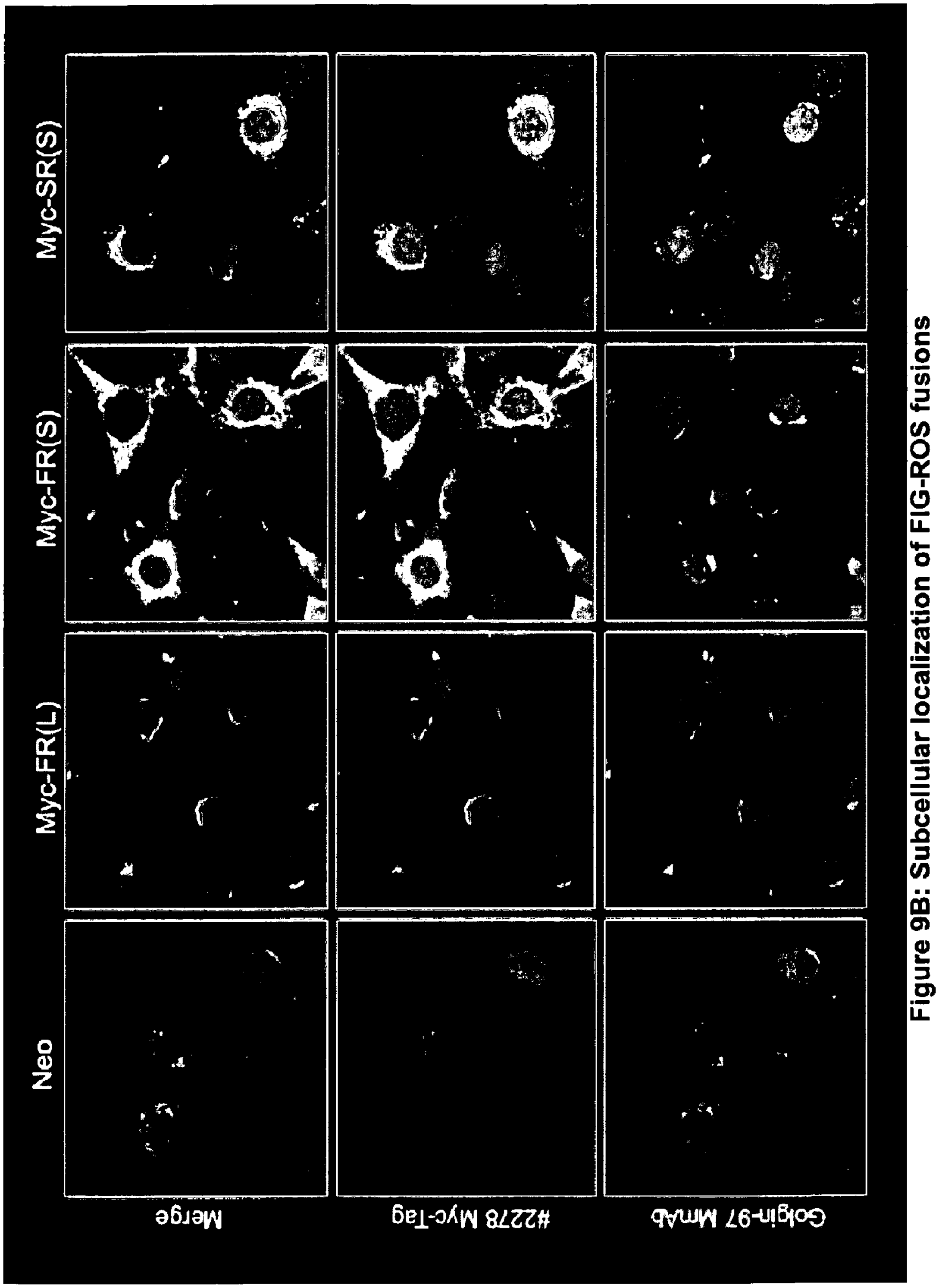
Figure 9B: Subcellular localization of FIG-ROS fusions

Figure 10: Stable expression of FIG-ROS fusions
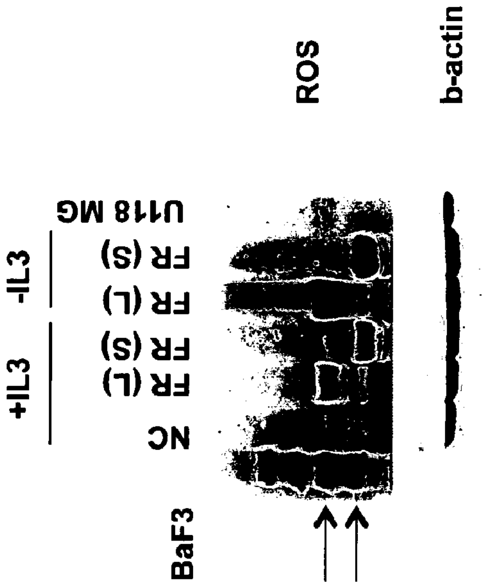

Figure 11: IL3 independent growth (BaF3 cells)
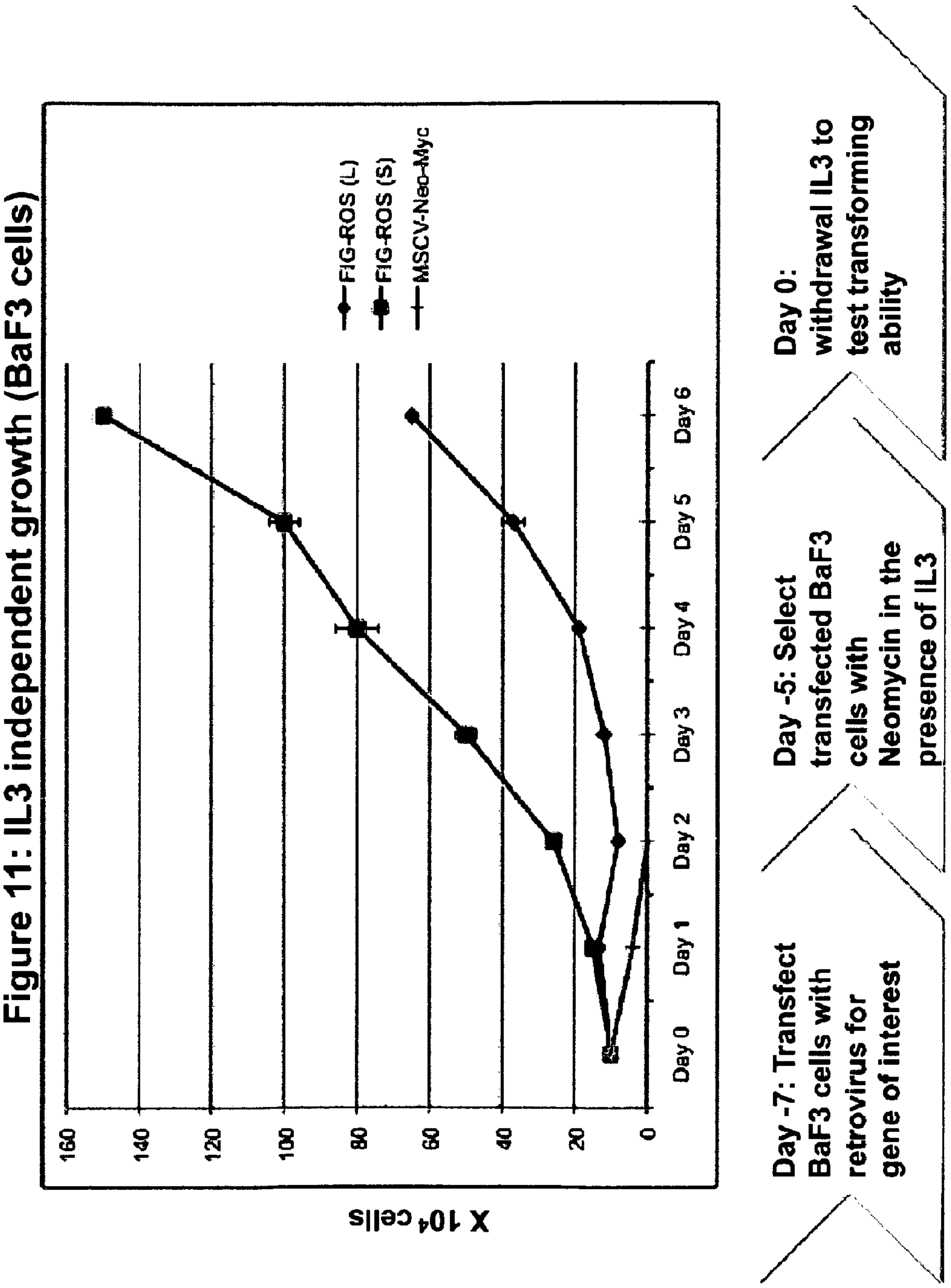

Figure 12: In vitro kinase assay
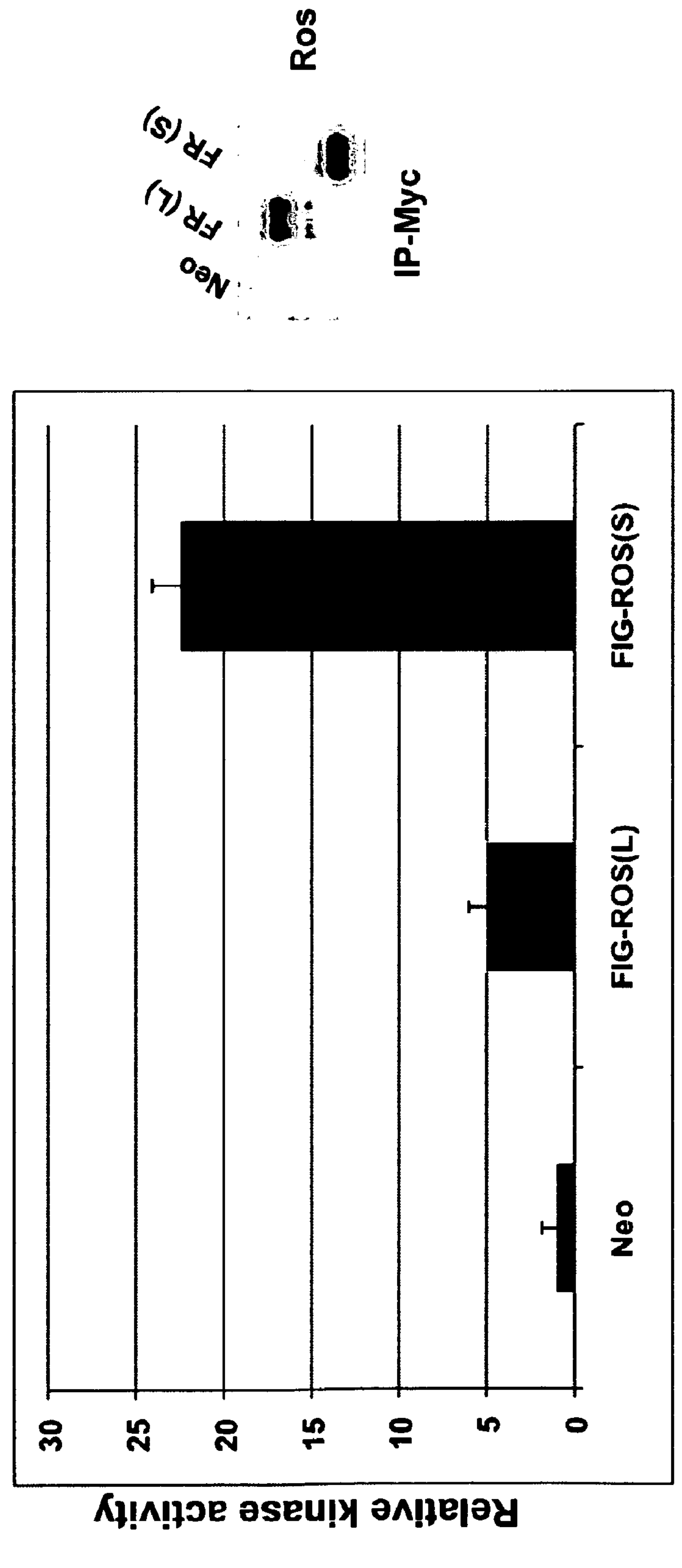

FIG-ROS is sensitive to TAE-684

* 72 h MTT assay

| TAE-684 | IC50 | IC50 |
|---|---|---|
| FIG-ROS (L) | 1.78 nM | 2.84 nM |
| FIG-ROS (S) | 10.16 nM | 15.01 nM |
| FLT3/ITD | 419.35 nM | 316.44 nM |
| Neo-Myc | NA | 1641.84 nM |
| Karpas-299 | 4.85 nM | 4.36 nM |

Figure 14: TAE-684 induces apoptosis in FIG-ROS expression BaF3 cells

Figure 15: Phosphorylation of FIG-ROS is inhibited by TAE-684

MUTANT ROS EXPRESSION IN HUMAN CANCER

RELATED APPLICATIONS

This application is a continuation of U.S. patent application Ser. No. 13/146,705, filed Jul. 28, 2011, issued as U.S. Pat. No. 9,364,477 which is a national stage entry of International Application No. PCT/US2010/024109 filed Feb. 12, 2010, which itself claims priority to U.S. Provisional Application Ser. No. 61/207,484 filed Feb. 12, 2009, the entire contents of which are incorporated by reference herein.

INCORPORATION BY REFERENCE OF SEQUENCE LISTING

The Sequence Listing in an ASCII text file, named as 28126_SEQ.txt of 147 KB, created on Jul. 12, 2013 in U.S. patent application Ser. No. 13/146,705, and submitted to the United States Patent and Trademark Office via EFS-Web, is incorporated herein by reference.

FIELD OF THE INVENTION

The invention relates generally to ROS kinase proteins and genes involved in cancer, and to the detection, diagnosis and treatment of cancer.

BACKGROUND OF THE INVENTION

Many cancers are characterized by disruptions in cellular signaling pathways that lead to aberrant control of cellular processes, or to uncontrolled growth and proliferation of cells. These disruptions are often caused by changes in the activity of particular signaling proteins, such as kinases.

It is known that gene translocations resulting in kinase fusion proteins with aberrant signaling activity can directly lead to certain cancers. For example, it has been directly demonstrated that the BCR-ABL oncoprotein, a tyrosine kinase fusion protein, is the causative agent and drives human chronic myelogenous leukemia (CML). The BCR-ABL oncoprotein, which is found in at least 90-95% of CML cases, is generated by the translocation of gene sequences from the c-ABL protein tyrosine kinase on chromosome 9 into BCR sequences on chromosome 22, producing the so-called Philadelphia chromosome. See, e.g. Kurzock et al., *N. Engl. J. Med.* 319: 990-998 (1988). The translocation is also observed in acute lymphocytic leukemia and AML cases.

Gene translocations leading to mutant or fusion proteins implicated in a variety of other cancers have been described. For example, Falini et al., *Blood* 99(2): 409-426 (2002), review translocations known to occur in hematological cancers.

Identifying translocations and mutations in human cancers is highly desirable because it can lead to the development of new therapeutics that target such fusion or mutant proteins, and to new diagnostics for identifying patients that have such gene translocations. For example, BCR-ABL has become a target for the development of therapeutics to treat leukemia. Most recently, Gleevec® (Imatinib mesylate, STI-571), a small molecule inhibitor of the ABL kinase, has been approved for the treatment of CML. This drug is the first of a new class of anti-proliferative agents designed to interfere with the signaling pathways that drive the growth of tumor cells. The development of this drug represents a significant advance over the conventional therapies for CML and ALL, chemotherapy and radiation, which are plagued by well known side-effects and are often of limited effect since they fail to specifically target the underlying causes of the malignancies. Likewise, reagents and methods for specifically detecting BCR-ABL fusion protein in patients, in order to identify patients most likely to respond to targeted inhibitors like Gleevec®, have been described.

Accordingly, there remains a need for the identification of gene translocations or mutations resulting in fusion or mutant proteins implicated in the progression of human cancers, and the development of new reagents and methods for the study and detection of such fusion proteins. Identification of such fusion proteins will, among other things, desirably enable new methods for selecting patients for targeted therapies, as well as for the screening of new drugs that inhibit such mutant/fusion proteins.

SUMMARY OF THE INVENTION

The invention provides a gene translocation involving the ROS kinase gene in human cancer, such as liver, kidney, pancreatic, and testicular cancers (including cancers in the ducts of these tissues, such as bile duct liver cancer), which results in fusion proteins combining part of the FIG protein (a Golgi apparatus protein) with the kinase domain of the ROS kinase. The FIG-ROS fusion proteins (namely, FIG-ROS(S), FIG-ROS(L), and FIG-ROS(XL)) retain ROS tyrosine kinase activity. The invention also provides methods of detection and treatment of human cancers such as liver, kidney, pancreatic, and testicular cancers (including cancers in the ducts of these tissues, such as bile duct liver cancer), which arise not only from gene translocations involving the ROS kinase, but also from aberrant expression of the ROS kinase in these tissues. The invention also provides a truncated ROS kinase whereby the kinase domain (with or without the transmembrane domain) of the ROS kinase is active but separated from the rest of the full-length ROS kinase (e.g., separate from the extracellular domain of the ROS protein). The expression of a mutant ROS kinase with active kinase activity may drive the proliferation and survival of liver, pancreatic, kidney, and testicular cancers in a subset of such cancers in which a truncated ROS kinase with active kinase activity is expressed.

Accordingly, in a first aspect, the invention provides a purified FIG-ROS fusion polypeptide. In some embodiments, the FIG-ROS fusion polypeptide comprises the amino acid sequence set forth in SEQ ID NO: 4. In some embodiments, the FIG-ROS fusion polypeptide comprises the amino acid sequence set forth in SEQ ID NO: 2. In some embodiments, the FIG-ROS fusion polypeptide comprises the amino acid sequence set forth in SEQ ID NO: 17. In some embodiments, the FIG-ROS fusion polypeptide is encoded by the nucleic acid sequence set forth in SEQ ID NO: 3. In some embodiments, the FIG-ROS fusion polypeptide is encoded by the nucleic acid sequence set forth in SEQ ID NO: 1. In some embodiments, the FIG-ROS fusion polypeptide is encoded by the nucleic acid sequence set forth in SEQ ID NO: 16.

In a further aspect, the invention provides a purified FIG-ROS fusion polynucleotide. In some embodiments, the FIG-ROS fusion polynucleotide comprises the nucleotide sequence set forth in SEQ ID NO: 3. In some embodiments, the FIG-ROS fusion polynucleotide comprises the nucleotide sequence set forth in SEQ ID NO: 1. In some embodiments, the FIG-ROS fusion polynucleotide comprises the nucleotide sequence set forth in SEQ ID NO: 16.

In another aspect, the invention provides a binding agent that specifically binds to a FIG-ROS fusion polypeptide. In some embodiments, the binding agent specifically binds to a fusion junction between a FIG portion and a ROS portion in said FIG-ROS fusion polypeptide. In some embodiments, the fusion junction comprises an amino acid sequence selected from the group consisting of AGSTLP (SEQ ID NO: 59), LQVWHR (SEQ ID NO: 60), and LQAGVP (SEQ ID NO: 61). In some embodiments, the FIG-ROS fusion polypeptide is a FIG-ROS(S) fusion polypeptide, is a FIG-ROS (XL) fusion polypeptide, or is a FIG-ROS (L) fusion polypeptide. In some embodiments, the binding agent is an antibody and an AQUA peptide. In some embodiments, the AQUA peptide comprises an amino acid sequence selected from the group consisting of AGSTLP (SEQ ID NO: 59), LQVWHR (SEQ ID NO: 60), and LQAGVP (SEQ ID NO: 61).

In yet another aspect, the invention provides a nucleotide probe for detecting a FIG-ROS fusion polynucleotide, wherein said probe hybridizes to said FIG-ROS fusion polynucleotide under stringent conditions. In some embodiments, the FIG-ROS fusion polynucleotide comprises the nucleotide sequence set forth in SEQ ID NO: 3. In some embodiments, the FIG-ROS fusion polynucleotide encodes a polypeptide comprising the amino acid sequence set forth in SEQ ID NO: 4. In some embodiments, the FIG-ROS fusion polynucleotide comprises the nucleotide sequence set forth in SEQ ID NO: 1. In some embodiments, the FIG-ROS fusion polynucleotide encodes a polypeptide comprising the amino acid sequence set forth in SEQ ID NO: 2 In some embodiments, the FIG-ROS fusion polynucleotide comprises the nucleotide sequence set forth in SEQ ID NO: 16. In some embodiments, the FIG-ROS fusion polynucleotide encodes a polypeptide comprising the amino acid sequence set forth in SEQ ID NO: 17.

In another aspect, the invention provides a method for detecting a FIG-ROS gene translocation, the method comprising contacting a biological sample with a binding agent that specifically binds to a FIG-ROS fusion polypeptide (e.g., a FIG-ROS(S), FIG-ROS(XL), or a FIG-ROS(L) fusion polypeptide), where specific binding of the binding agent to the biological sample indicates the presence of a FIG-ROS gene translocation (e.g., that encodes a FIG-ROS(S), FIG-ROS(XL), or FIG-ROS(L) fusion polypeptide) in said biological sample.

In a further aspect, the invention provides a method for detecting a FIG-ROS gene translocation by contacting a biological sample with a nucleotide probe that hybridizes to a FIG-ROS fusion polynucleotide under stringent conditions, wherein hybridization of said nucleotide probe to said biological sample indicates a FIG-ROS gene translocation (e.g., that encodes a FIG-ROS(S), FIG-ROS(XL) or FIG-ROS(L) fusion polypeptide) in said biological sample.

In yet another aspect, the invention provides a method for diagnosing a patient as having a cancer or a suspected cancer characterized by a ROS kinase. In some embodiments, the cancer or suspected cancer is not non-small cell lung carcinoma or glioblastoma. The method includes contacting a biological sample of said cancer or suspected cancer (where the biological sample comprising at least one polypeptide) with a binding agent that specifically binds to a mutant ROS polypeptide, wherein specific binding of said binding agent to at least one polypeptide in said biological sample identifies said patient as having a cancer or a suspected cancer characterized by a ROS kinase.

In another aspect, the invention provides a method for identifying a cancer (or a suspected cancer) that is likely to respond to a ROS inhibitor. In some embodiments, the cancer or suspected cancer is not non-small cell lung carcinoma or glioblastoma. The method includes contacting a biological sample of said cancer (or suspected cancer) comprising at least one polypeptide, with a binding agent that specifically binds to a mutant ROS polypeptide, wherein specific binding of said binding agent to at least one polypeptide in said biological sample identifies said cancer or suspected cancer as a cancer or suspected cancer that is likely to respond to a ROS inhibitor.

In various embodiments, the mutant ROS polypeptide is aberrantly expressed wild-type ROS polypeptide. For example, aberrant expression can be where wild-type ROS kinase is overexpressed in a cancer or a suspected cancer as compared to the level of expression of wild-type ROS kinase in normal tissue of the same tissue type as the cancer or suspected cancer. ROS protein expression levels can be determined by standard means (e.g., Western blotting analysis, mass spectrometry, IHC staining).

In various embodiments, the mutant ROS polypeptide is a truncated ROS polypeptide or a ROS fusion polypeptide. Non-limiting examples of ROS fusion polypeptides include a FIG-ROS(S) fusion polypeptide, a FIG-ROS(L) fusion polypeptide, a FIG-ROS(XL) fusion polypeptide, a SLC34A2-ROS(S) fusion polypeptide, a SLC34A2-ROS(L) fusion polypeptide, a SLC34A2-ROS(VS) fusion polypeptide, and a CD74-ROS fusion polypeptide. Non-limiting examples of a truncated ROS polypeptide include the kinase domain of ROS lacking the extracellular and transmembrane domains of wild-type ROS and the transmembrane and kinase domains of ROS lacking the extracellular domain of wild-type ROS.

In some embodiments, the binding agent is an antibody or an AQUA peptide. In some embodiments, the cancer is from a patient (e.g., a human patient).

In a further aspect, the invention provides a method for diagnosing a patient as having a cancer or a suspected cancer characterized by a ROS kinase. In some embodiments, the cancer or suspected cancer is not non-small cell lung carcinoma or glioblastoma. The method includes contacting a biological sample of said cancer or a suspected cancer (where the biological sample comprising at least one nucleic acid molecule) with a probe that hybridizes under stringent conditions to a nucleic acid molecule selected from the group consisting of a FIG-ROS fusion polynucleotide, a SLC34A2-ROS fusion polypeptide, a CD74-ROS fusion polypeptide, and a truncated ROS polynucleotide, and wherein hybridization of said probe to at least one nucleic acid molecule in said biological sample identifies said patient as having a cancer or a suspected cancer characterized by a ROS kinase.

In yet another aspect, the invention provides another method for identifying a cancer (or suspected cancer) that is likely to respond to a ROS inhibitor. The method includes contacting a biological sample of said cancer comprising at least one nucleic acid molecule with a nucleotide probe that hybridizes under stringent conditions to a either a FIG-ROS fusion polynucleotide (e.g., a FIG-ROS(S) or FIG-ROS(L) fusion polynucleotide) or a mutant ROS polynucleotide, and wherein hybridization of said nucleotide probe to at least one nucleic acid molecule in said biological sample identifies said cancer as a cancer that is likely to respond to a ROS inhibitor.

In some embodiments, the FIG-ROS fusion polynucleotide encodes a FIG-ROS(S) fusion polypeptide, a FIG-ROS (L) fusion polypeptide, or a FIG-ROS(XL) fusion polypeptide. In some embodiments, the SCL34A2-ROS fusion polynucleotide encodes a SCL34A2-ROS(S) fusion polypeptide, a SCL34A2-ROS(L) fusion polypeptide, or a SCL34A2-ROS(VS) fusion polypeptide. In some embodiments, the cancer is from a patient (e.g., a cancer patient). In some embodiments, the patient is human.

In various embodiments of all aspects of the invention, the cancer may be a liver cancer, a pancreatic cancer, a kidney cancer, or a testicular cancer. In various embodiments, the cancer may be a duct cancer (e.g., a liver bile duct cancer or a pancreatic duct cancer). In further embodiments, the cancer is not a non-small cell lung cancer (NSCLC). In further embodiments, the cancer is not a glioblastoma). In further embodiments, the ROS inhibitor also inhibits the activity of an ALK kinase an LTK kinase, an insulin receptor, or an IGF1 receptor. In further embodiments, the ROS inhibitor is PF-02341066 or NVP-TAE684).

In further embodiments, the ROS inhibitor is a binding agent that specifically binds to a FIG-ROS fusion polypeptide, a binding agent that specifically binds to a truncated ROS polypeptide, an siRNA targeting a FIG-ROS fusion polynucleotide, or an siRNA targeting a truncated ROS polynucleotide.

BRIEF DESCRIPTION OF THE DRAWINGS

FIG. 4 is a depiction of an agarose gel showing the expression of wild-type FIG, wild-type ROS, and the FIG-ROS fusion transcript by RT-PCR in the liver cancer samples from two patients, namely XY3-78T and 090665LC. The U118MG human glioblastoma cell line, which has a FIG-ROS(L) translocation, is also shown. HCC78 a human non-small cell lung cancer cell line, which contains SLC34A2-ROS translocation, was served as a negative control.

FIG. 5 is a depiction of an agarose gel showing the PCR products generated by amplifying genomic DNA from liver cancer samples from patients XY3-78T and 090665LC, and from cell line U118MG.

FIG. 6 is a depiction of a Western blotting analysis showing the expression of FIG-ROS(S) from XY3-78T, FIG-ROS(L) from 090665LC, and FIG-ROS(L) from U118MG cells.

FIG. 7 is a photograph of four tissue culture plates containing 3t3 cells cultured in soft agar, where the 3T3 cells are stably transfected with FIG-ROS(L) (upper left), FIG-ROS(S) (upper right), src kinase (lower left) and empty vector (lower right).

FIG. 8 is a photograph showing nude mice injected with 3T3 cells stably transfected with empty vector (left), FIG-ROS(L) (middle), or FIG-ROS(S).

FIGS. 9A and 9B are photographs of cells showing the subcellular localization of FIG-ROS(L) and FIG-ROS(S) in 3T3 cells.

FIG. 10 is a depiction of a Western blotting analysis showing the stable expression of FIG-ROS(S), FIG-ROS (L), and FIG-ROS(L) from U118MG in BaF3 cells grown with or without IL-3.

FIG. 11 is a line graph showing the ability of BAF3 cells transduced with retrovirus encoding FIG-ROS (S) (squares) or FIG-ROS(L) (diamonds) to grow without the presence of IL-3. BAF3 cells transduced with empty retrovirus is also shown (line).

FIG. 12 is a bar graph showing the results of an in vitro kinase assay (top) made by quantitating the bands on the gel (below) from BaF3 cells transduced with retrovirus encoding FIG-ROS(S), FIG-ROS(L) or empty virus ("neo").

FIGS. 19A and 9B are images of representative, non-limiting IHC slides stained with the ROS-specific antibody following the addition of peptide ROS-1 (FIG. 19A) and peptide ROS-9 (FIG. 19B).

DETAILED DESCRIPTION OF THE PREFERRED EMBODIMENTS

Figure 1:
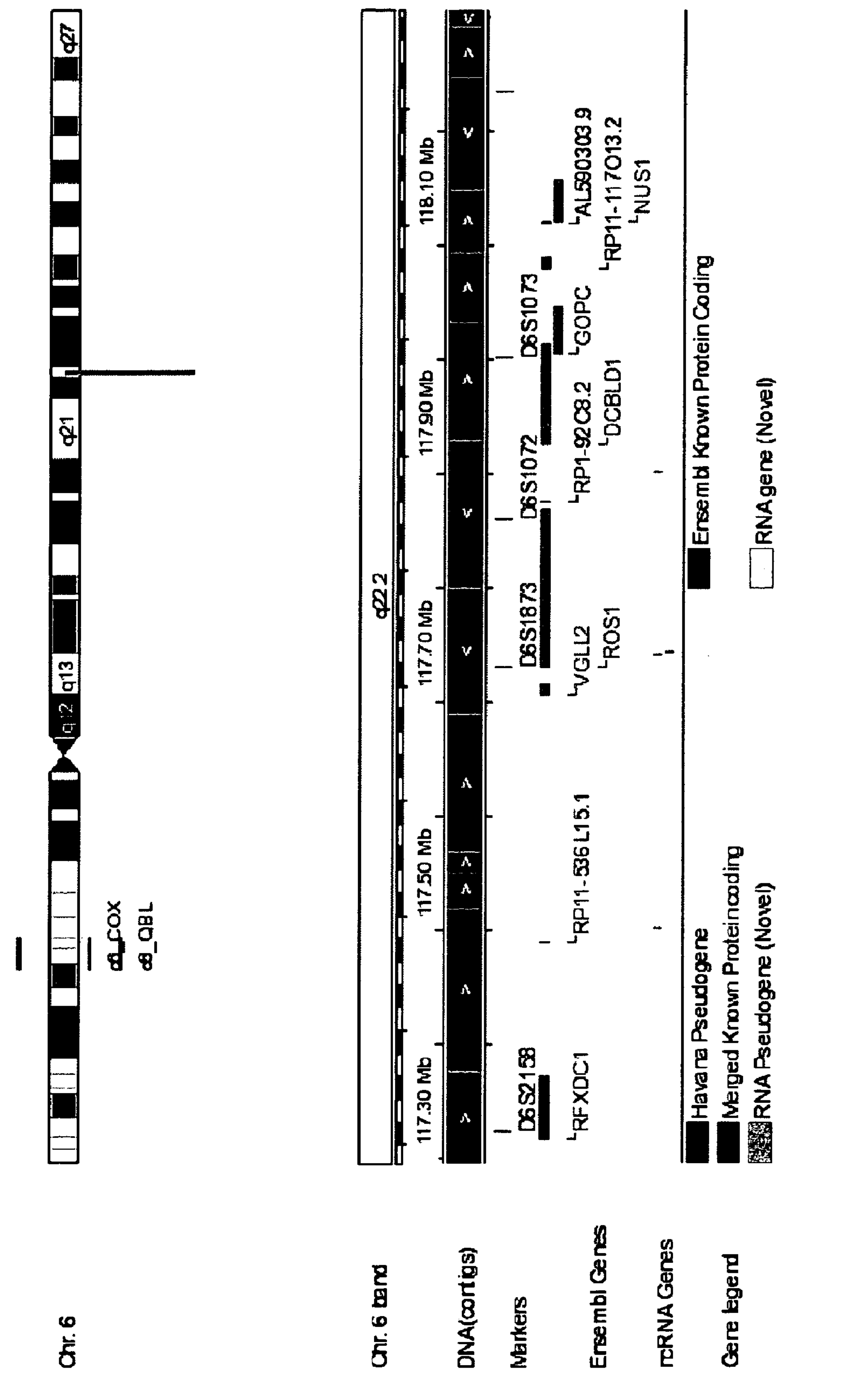
FIG. 1 shows the location of the FIG gene and ROS gene on chromosome 6. Both FIG and ROS genes are localized on chromosome 6q22.2 with about 0.2 Mega base pairs apart. The FIG gene is also known as the GOPC gene.

The invention provides a mutant ROS kinase which is expressed in a subset of human liver, kidney, pancreatic, and testicular cancers (e.g., bile duct liver cancer). The mutant ROS kinase may drive the proliferation and survival of liver, pancreatic, kidney, and testicular cancers in a subset of such cancers in which the mutant ROS kinase is expressed.

The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

The further aspects, advantages, and embodiments of the invention are described in more detail below. The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 11th Ed., McGraw Hill Companies Inc., New York (2006).

The invention relates to the discovery of mutant ROS (i.e., aberrantly expressed full length ROS, truncated (i.e., less than full length) ROS, or ROS fusion proteins (e.g., the FIG-ROS fusions, the SLC34A2-ROS fusions, or the CD74-ROS fusion)) in liver cancer (including bile duct cancer), pancreatic cancer, kidney cancer, and testicular cancer. The invention further relates to the discovery of new ROS gene translocations, resulting in fusions between the FIG gene and the ROS gene.

Full length (wild-type) ROS kinase is a 2347 amino acid long receptor tyrosine kinase. In humans, ROS kinase RNA has been detected in placenta, lung and skeletal muscle, with possible low levels of expression in testes (see J. Acquaviva, et al., Biochim. Biophys. Acta 1795(1):37-52, 2009. However, full-length ROS kinase does not appear to be expressed in normal liver, kidney, and pancreas tissue in humans (see J. Acquaviva, et al., supra). While Abcam Inc. (Cambridge, Mass.) sells a ROS-specific antibody (clone ab5512) that allegedly stains (i.e., specifically binds to) human hepatocarcinoma tissue by IHC, this ab5512 was found to stain paraffin-embedded HCC78 cells (lung carcinoma which express ROS) and HCC827 cells (lung adenocarcinoma which do not express ROS) with equal intensity (cells obtained from the ATCC, data not shown). Additionally, although ROS kinase may be present in human testicular tissue, its expression appears to be limited to the epididymis (see Acquaviva, et al., supra).

Accordingly, in a first aspect, the invention provides a purified FIG-ROS fusion polypeptide. By "FIG-ROS fusion polypeptide" is meant the FIG-ROS fusion polypeptide (e.g., FIG-ROS(L), FIG-ROS(XL), or FIG-ROS (S)) described herein, obtained from any species, particularly mammalian, including bovine, ovine, porcine, murine, equine, and human, from any source whether natural, synthetic, semi-synthetic, or recombinant.

By "purified" (or "isolated"") refers to a nucleic acid sequence (e.g., a polynucleotide) or an amino acid sequence (e.g., a polypeptide) that is removed or separated from other components present in its natural environment. For example, an isolated FIG-ROS fusion polypeptide is one that is separated from other components of a eukaryotic cell (e.g., the endoplasmic reticulum or cytoplasmic proteins and RNA). An isolated FIG-ROS polynucleotide is one that is separated from other nuclear components (e.g., histones) and/or from upstream or downstream nucleic acid sequences (e.g., an isolated FIG-ROS polynucleotide is separated from the endogenous FIG gene promoter). An isolated nucleic acid sequence of amino acid sequence of the invention is at least 60% free, or at least 75% free, or at least 90% free, or at least 95% free from other components present in natural environment of the indicated nucleic acid sequence or acid sequence.

A FIG-ROS fusion polypeptide of the invention is a non-limiting example of mutant ROS polypeptide.

As used herein, the term "mutant ROS" polypeptide or polynucleotide means either the aberrant expression of the wild-type ROS kinase polypeptide or polynucleotide in a tissue in which ROS kinase is not normally expressed (or expressed at a different level) or the kinase domain of a ROS or a polynucleotide encoding the kinase domain of a ROS kinase without the extracellular domain or without the transmembrane domains of wild-type (i.e., full length) ROS, where the kinase domain (with or without the transmembrane domain) is either alone (also referred to as truncated ROS) or is fused to all or a portion of a second protein (e.g., a FIG protein).

Wild-type ROS kinase is a 2347 amino acid long receptor tyrosine kinase, where approximately the first 36 amino acids (i.e., the N-terminal 36 amino acids) are the signal peptide. The sequence of human ROS kinase can be found at GenBank Accession No. M34353, and the protein sequence (including the signal peptide) is provided herein as SEQ ID NO: 9.

Non-limiting examples of the mutant ROS polypeptide of the invention include polypeptides comprising the amino acid sequences set forth in SEQ ID NO: 12 or SEQ ID NO: 13. Likewise, in certain embodiments, non-limiting examples of mutant ROS polynucleotides of the invention include polynucleotides encoding polypeptides comprising the amino acid sequences set forth in SEQ ID NO: 12 or SEQ ID NO: 13. In some embodiments, the mutant ROS polynucleotide comprises a portion of the nucleotide sequence set forth in SEQ ID NO: 5, SEQ ID NO: 6, SEQ ID NO:7, or SEQ ID NO: 8. In certain embodiments, the mutant ROS polypeptide of the invention does not include the sequences of SEQ ID NO: 10 or SEQ ID NO: 11. Likewise, in certain embodiments, non-limiting examples of mutant ROS polynucleotides of the invention do not include polynucleotides encoding polypeptides comprising the amino acid sequences set forth in SEQ ID NO: 10 or SEQ ID NO: 11.

Thus, a mutant ROS comprises the kinase domain, with or without the transmembrane domain, of ROS (or nucleotide sequences encoding the same) such that the kinase domain of the ROS kinase (with or without the transmembrane domain) is separated from the other domains (e.g., the extracellular domain) of wild-type (i.e., full-length) ROS kinase. The full length amino acid sequence of ROS kinase is provided in SEQ ID NO: 9. The kinase domain of the ROS kinase is provided in SEQ ID NOs: 12 and 13; however the term “mutant ROS” includes also those amino acid residues which flank the kinase domain provided that the flanking amino acid residues are not within the transmembrane domain or extracellular domain of the full-length ROS protein. In some embodiments, the mutant ROS excludes the sequence set forth in SEQ ID NO: 11. In some embodiments, the mutant ROS excludes the sequence set forth in SEQ ID NO: 10. Thus, the mutant ROS described herein includes the amino acid sequence set forth in SEQ ID NO: 3 and a nucleotide sequence encoding the same. The term “mutant ROS polypeptide” also includes a chimeric protein that includes all or part of a second protein fused by a peptide bond to the kinase domain of a ROS polypeptide. As discussed above, one non-limiting example of a mutant ROS polypeptide that is a chimeric protein is the FIG-ROS(S) fusion polypeptide described herein. Likewise, the term “mutant ROS polynucleotide also includes a polynucleotide encoding a chimeric protein that includes all or part of a second protein fused by a peptide bond to the kinase domain of a ROS polypeptide.

Thus, as used herein, the term mutant ROS includes, without limitation, the FIG-ROS (L) fusion polypeptide (see nucleic acid sequence in SEQ ID NO: 1 and amino acid sequence in SEQ ID NO: 2), the FIG-ROS (S) fusion polypeptide (see nucleic acid sequence in SEQ ID NO: 3 and amino acid sequence in SEQ ID NO: 4), the FIG-ROS(XL) fusion polypeptide (see nucleic acid sequence in SEQ ID NO: 16 and amino acid sequence in SEQ ID NO: 17), the SLC34A2-ROS (L) fusion polypeptide (see nucleic acid sequence in SEQ ID NO: 18 and amino acid sequence in SEQ ID NO: 19), the SLC34A2-ROS (S) fusion protein (see nucleic acid sequence in SEQ ID NO: 20 and amino acid sequence in SEQ ID NO: 21), the SLC34A2-ROS (VS) fusion protein (see nucleic acid sequence in SEQ ID NO: 22 and amino acid sequence in SEQ ID NO: 23), and the CD74-ROS fusion protein (see nucleic acid sequence in SEQ ID NO: 24 and amino acid sequence in SEQ ID NO: 25). Note that additional ROS fusion polypeptides are disclosed in PCT Publication No. WO2007084631; Rikova, K et al., Cell 131:1190-1203, 2007, and PCT Publication No. WO/2009/051846, the entire contents of which are hereby incorporated by reference.

As used herein, by “polynucleotide” (or “nucleotide sequence” or “nucleic acid molecule”) refers to an oligonucleotide, nucleotide, or polynucleotide, and fragments or portions thereof, and to DNA or RNA of genomic or synthetic origin, which may be single- or double-stranded, and represent the sense or anti-sense strand.

As used herein, by “polypeptide” (or “amino acid sequence” or protein) refers to an oligopeptide, peptide, polypeptide, or protein sequence, and fragments or portions thereof, and to naturally occurring or synthetic molecules. “Amino acid sequence” and like terms, such as “polypeptide” or “protein”, are not meant to limit the indicated amino acid sequence to the complete, native amino acid sequence associated with the recited protein molecule.

In accordance with the invention, human FIG-ROS gene translocation have been identified using global phosphopeptide profiling in liver cancer samples taken from human patients (see Examples below). These gene translocations which occurs on human chromosome (6q22) result in expression of two variant fusion proteins, namely the FIG-ROS(S) fusion polypeptide and the FIG-ROS(L) fusion polypeptide) that combine the N-terminus of FIG with the kinase domain of ROS.

As used herein, by “cancer” or “cancerous” is meant a cell that shows abnormal growth as compared to a normal (i.e., non-cancerous) cell of the same cell type. For example, a cancerous cell may be metastatic or non-metastatic. A cancerous cell may also show lack of contact inhibition where a normal cell of that same cell type shows contact inhibition. As used herein, by “suspected cancer” or “tissue suspected of being cancerous” is meant a cell or tissue that has some aberrant characteristics (e.g., hyperplastic or lack of contact inhibition) as compared to normal cells or tissues of that same cell or tissue type as the suspected cancer, but where the cell or tissue is not yet confirmed by a physician or pathologist as being cancerous.

Figure 2:
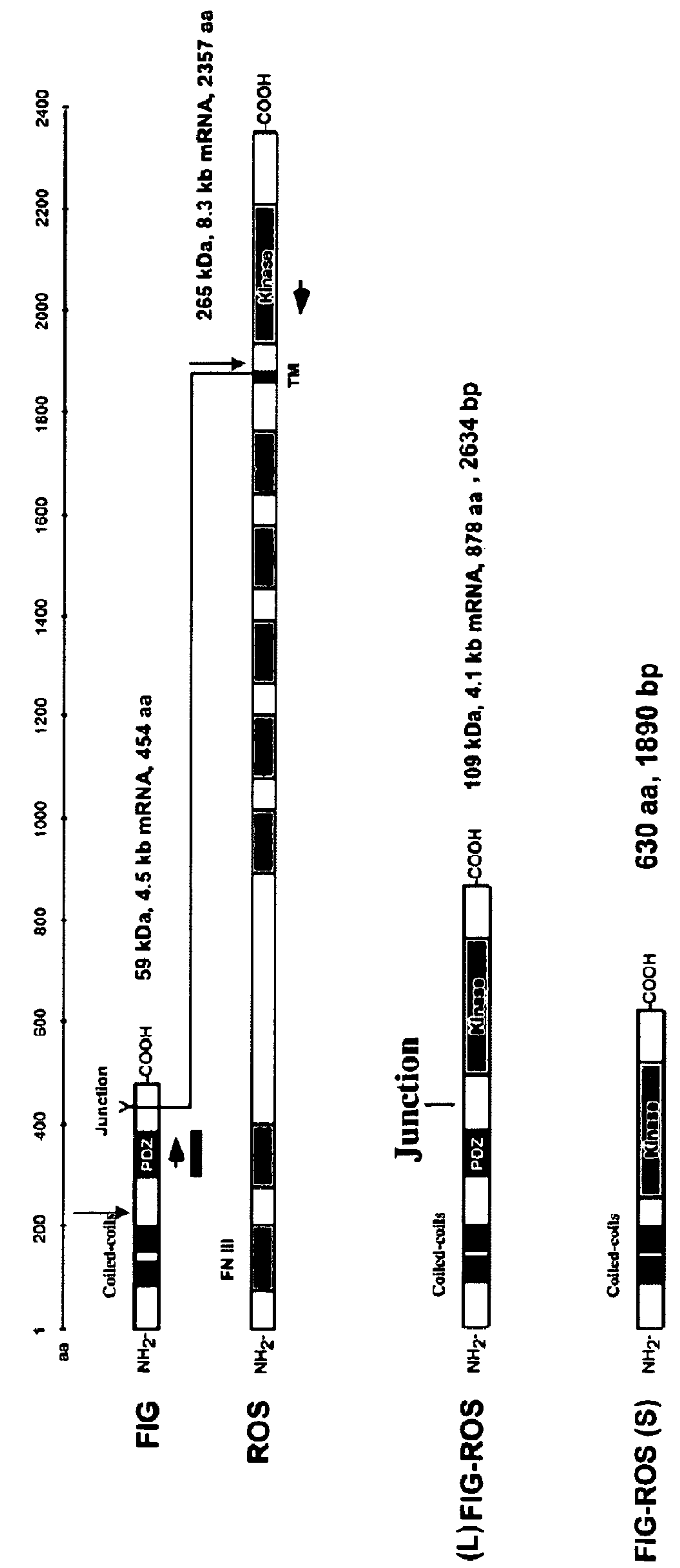
FIG. 2 shows the breakpoint in the FIG and the ROS proteins, forming two FIG-ROS fusion proteins. The FIG-ROS (L) fusion protein results from a break in the Fig gene (indicated by the arrow between the PDZ domain and the C-terminus) and a break in the Ros gene (indicated by the vertical line above the TM domain), while the FIG-ROS (S) fusion protein results from a break in the Fig gene (indicated by the arrow to the right of the coiled-coils domain) and a break in the Ros gene at the arrow to the right of the TM domain.

As shown in FIGS. 1 and 2, the FIG-ROS(L) translocation combines the nucleic acid sequence encoding the N-terminus of FIG (amino acids 1-412) with the nucleic acid sequences encoding the kinase domain of ROS (amino acids 413-878 which correspond to amino acids 1882-2347 from ROS) (see SEQ ID NO: 2), to produce a fusion, namely FIG-ROS(L) fusion polypeptide. The resulting FIG-ROS(L) fusion protein, which comprises 878 amino acids, was found to retain the kinase activity of ROS. In some embodiments, the FIG-ROS fusion polypeptide is a FIG-ROS(L) fusion polypeptide. In some embodiments, the FIG-ROS (L) fusion polypeptide comprises the amino acid sequence set forth in SEQ ID NO: 2. In some embodiments, the FIG-ROS (L) fusion polypeptide is encoded by the nucleic acid sequence set forth in SEQ ID NO: 1.

Also shown in FIGS. 1 and 2, the FIG-ROS(S) translocation combines the nucleic acid sequence encoding the N-terminus of FIG (amino acids 1-209) with the nucleic acid sequence encoding the kinase domain of ROS (amino acids 210-630 which correspond to amino acids 1927-2347 from ROS) (see also SEQ ID NO:4), to produce a fusion, namely the FIG-ROS(S) fusion polypeptide. The resulting FIG-ROS (S) fusion protein, which comprises 630 amino acids, was found to retain the kinase activity of ROS. Thus, in some embodiments, the FIG-ROS fusion polypeptide of the invention is a FIG-ROS(S) fusion polypeptide. In some embodiments, the FIG-ROS(S) fusion polypeptide comprises the amino acid sequence set forth in SEQ ID NO: 4. In some embodiments, the FIG-ROS(S) fusion polypeptide is encoded by the nucleic acid sequence set forth in SEQ ID NO: 3.

The invention further provides a third FIG-ROS fusion, namely FIG-ROS(XL), which translocation combines the nucleic acid sequence encoding the N-terminus of FIG (amino acids 1-411 or 1-412) with the nucleic acid sequences encoding the transmembrane and kinase domains of ROS kinase to result in a fusion protein of 1009 amino acids in length.

It should be noted that in all of the ROS fusion proteins described herein (e.g., the FIG-ROS fusion proteins, the SLC34A2-ROS fusion proteins, and the CD74-ROS fusion protein), the amino acid at the fusion junction (regardless of the numbering) may appear in either wild-type protein member of the fusion (e.g., the amino acid at the fusion junction in a FIG-ROS fusion polypeptide may appear in either wild-type FIG protein or wild-type ROS protein), or the amino acid, being created by a codon with nucleotides from fused exons of both protein members, may be unique to the fusion polypeptide and not appear in either wild-type protein member of the fusion.

The invention provides that mutant ROS may be present liver cancer (including bile duct cancer), kidney cancer, testicular cancer, and pancreatic cancer. Based on these discoveries, patients suffering from these cancers whose cancers express mutant ROS (e.g., over-express wild-type ROS or express a truncated ROS or a ROS fusion polypeptide such as one of the FIG-ROS fusion polypeptides disclosed herein) may respond favorably to administration of a ROS inhibitor (e.g., the growth of their cancer may slow or stop as compared to untreated patients suffering from the same cancer).

Thus, the invention provides isolated FIG-ROS fusion polypeptides and fragments thereof. In one embodiment, the invention provides an isolated polypeptide comprising an amino acid sequence at least 95% identical or at least 99% identical to a sequence selected from the group consisting of: (a) an amino acid sequence comprising the amino acid sequence of SEQ ID NO: 2; (b) an amino acid sequence comprising the amino acid sequence of SEQ ID NO: 17; (c) an amino acid sequence comprising all or a portion of the FIG polypeptide with the kinase domain of ROS (e.g., SEQ ID NO: 12 or 13)); and (d) an amino acid sequence comprising at least six contiguous amino acids encompassing the fusion junction of a FIG-ROS fusion polypeptide (e.g., AGSTLP (SEQ ID NO: 59) of FIG-ROS (S), LQVWHR (SEQ ID NO: 60) of FIG-ROS(L), or LQAGVP (SEQ ID NO: 61) of FIG-ROS(XL)).

In one embodiment, the invention provides an isolated FIG-ROS (S) fusion polypeptide having the amino acid sequence set forth in SEQ ID NO: 4. In one embodiment, the invention provides an isolated FIG-ROS (XL) fusion polypeptide having the amino acid sequence set forth in SEQ ID NO: 17. In another embodiment, recombinant mutant polypeptides of the invention are provided, which may be produced using a recombinant vector or recombinant host cell as described above.

It will be recognized in the art that some amino acid sequences of a FIG-ROS fusion polypeptide can be varied without significant effect of the structure or function of the mutant protein. If such differences in sequence are contemplated, it should be remembered that there will be critical areas on the protein which determine activity (e.g. the kinase domain of ROS). In general, it is possible to replace residues that form the tertiary structure, provided that residues performing a similar function are used. In other instances, the type of residue may be completely unimportant if the alteration occurs at a non-critical region of the protein.

Thus, the invention further includes a FIG-ROS variant of a FIG-ROS fusion polypeptide that shows substantial ROS kinase activity or that includes regions of FIG and ROS proteins. In some embodiments, a FIG-ROS variant of the invention contains conservative substitutions as compared to FIG-ROS(L), FIG-ROS (XL), or FIG-ROS(S). Some non-limiting conservative substitutions include the exchange, one for another, among the aliphatic amino acids Ala, Val, Leu and Ile; exchange of the hydroxyl residues Ser and Thr; exchange of the acidic residues Asp and Glu; exchange of the amide residues Asn and Gln; exchange of the basic residues Lys and Arg; and exchange of the aromatic residues Phe and Tyr. Further examples of conservative amino acid substitutions known to those skilled in the art are: Aromatic: phenylalanine tryptophan tyrosine (e.g., a tryptophan residue is replaced with a phenylalanine); Hydrophobic: leucine isoleucine valine; Polar: glutamine asparagines; Basic: arginine lysine histidine; Acidic: aspartic acid glutamic acid; Small: alanine serine threonine methionine glycine. As indicated in detail above, further guidance concerning which amino acid changes are likely to be phenotypically silent (i.e., are not likely to have a significant deleterious effect on a function) can be found in Bowie et al., Science 247, supra.

In some embodiments, a variant may have “nonconservative” changes, e.g., replacement of a glycine with a tryptophan. Similar variants may also include amino acid deletions or insertions, or both. Guidance in determining which amino acid residues may be substituted, inserted, or deleted without abolishing biological or immunological activity may be found using computer programs well known in the art, for example, DNASTAR software.

The FIG-ROS fusion polypeptides, fragments thereof, and variants thereof of the present invention may be provided in an isolated or purified form. A recombinantly produced version of a FIG-ROS fusion polypeptide of the invention can be substantially purified by the one-step method described in Smith and Johnson, *Gene* 67: 31-40 (1988).

The polypeptides of the present invention include the FIG-ROS fusion polypeptides having the sequences set forth in SEQ ID NOs: 2 and 4, and 17 (whether or not including a leader sequence), an amino acid sequence encoding a polypeptide comprising at least six contiguous amino acids encompassing the fusion junction of a FIG-ROS fusion polypeptide of the invention, as well as polypeptides that have at least 90% similarity, more preferably at least 95% similarity, and still more preferably at least 96%, 97%, 98% or 99% similarity to those described above.

By “% similarity” for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2: 482-489 (1981)) to find the best segment of similarity between two sequences.

By a polypeptide having an amino acid sequence at least, for example, 95% “identical” to a reference amino acid sequence of a mutant ROS polypeptide of the invention is intended that the amino acid sequence of the polypeptide is identical to the reference sequence except that the polypeptide sequence may include up to five amino acid alterations per each 100 amino acids of the reference amino acid sequence of the FIG-ROS fusion polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

A FIG-ROS fusion polypeptide of the present invention could be used as a molecular weight marker on SDS-PAGE gels or on molecular sieve gel filtration columns, for example, using methods well known to those of skill in the art.

As further described in detail below, the polypeptides of the present invention can also be used to generate fusion polypeptide specific reagents, such as polyclonal and monoclonal antibodies, which are useful in assays for detecting mutant ROS polypeptide expression as described below or as agonists and antagonists capable of enhancing or inhibiting mutant ROS protein function/activity. Further, such polypeptides can be used in the yeast two-hybrid system to "capture" FIG-ROS fusion polypeptide binding proteins, which are also candidate agonist and antagonist according to the present invention. The yeast two hybrid system is described in Fields and Song, *Nature* 340: 245-246 (1989).

In another aspect, the invention provides a peptide or polypeptide comprising an epitope-bearing portion of a polypeptide of the invention, such as an epitope comprising the fusion junction of a FIG-ROS fusion polypeptide variant An "epitope" refers to either an immunogenic epitope (i.e., capable of eliciting an immune response) or an antigenic epitope (i.e., the region of a protein molecule to which an antibody can specifically bind. The number of immunogenic epitopes of a protein generally is less than the number of antigenic epitopes. See, for instance, Geysen et al., *Proc. Natl. Acad. Sci. USA* 81:3998-4002 (1983). The production of FIG-ROS fusion polypeptide-specific antibodies of the invention is described in further detail below.

The antibodies that specifically bind to an epitope-bearing peptides or polypeptides are useful to detect a mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37: 767-778 (1984) at 777. The anti-peptide antibodies of the invention also are useful for purification of the mimicked protein, for instance, by adsorption chromatography using methods well known in the art. Immunological assay formats are described in further detail below.

Recombinant mutant ROS kinase polypeptides are also within the scope of the present invention, and may be producing using fusion polynucleotides of the invention, as described above. For example, the invention provides a method for producing a recombinant FIG-ROS fusion polypeptide by culturing a recombinant host cell (as described above) under conditions suitable for the expression of the fusion polypeptide and recovering the polypeptide. Culture conditions suitable for the growth of host cells and the expression of recombinant polypeptides from such cells are well known to those of skill in the art.

In a further aspect, the invention provides a purified FIG-ROS fusion polynucleotide. By "FIG-ROS fusion polynucleotide" or "FIG-ROS polynucleotide" is meant a FIG-ROS translocation gene (i.e., a gene that has undergone translocation) or polynucleotide encoding a FIG-ROS fusion polypeptide (e.g., the FIG-ROS(L), FIG-ROS (XL), or FIG-ROS (S)) fusion polypeptides described herein), obtained from any species, particularly mammalian, including bovine, ovine, porcine, murine, equine, and human, from any source whether natural, synthetic, semi-synthetic, or recombinant.

In some embodiments, the FIG-ROS fusion polynucleotide comprises the nucleotide sequence set forth in SEQ ID NO:1. In some embodiments, the FIG-ROS fusion polynucleotide encodes a polypeptide having the amino acid sequence set forth in SEQ ID NO: 2. In some embodiments, the FIG-ROS fusion polynucleotide comprises the nucleotide sequence set forth in SEQ ID NO:3. In some embodiments, the FIG-ROS fusion polynucleotide encodes a polypeptide having the amino acid sequence set forth in SEQ ID NO: 4. In some embodiments, the FIG-ROS fusion polynucleotide comprises the nucleotide sequence set forth in SEQ ID NO:16. In some embodiments, the FIG-ROS fusion polynucleotide encodes a polypeptide having the amino acid sequence set forth in SEQ ID NO: 17.

In some embodiments, the FIG-ROS fusion polynucleotide comprises a portion of the nucleotide sequence set forth in SEQ ID NO: 5, SEQ ID NO: 6, SEQ ID NO:7, SEQ ID NO: 8, SEQ ID NO: 14, SEQ ID NO: 15, or SEQ ID NO: 26. As used herein, a "portion" or "fragment" means a sequence fragment less than the whole sequence (e.g., a 50 nucleotide sequence is a portion of a 100 nucleotide long sequence). In other words, the FIG-ROS fusion polynucleotide may comprise portions of intron sequences that do not encode any amino acids in the resulting FIG-ROS fusion polypeptide.

Thus, the present invention provides, in part, isolated polynucleotides that encode a FIG-ROS fusion polypeptide of the invention, nucleotide probes that hybridize to such polynucleotides, and methods, vectors, and host cells for utilizing such polynucleotides to produce recombinant fusion polypeptides. Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were determined using an automated peptide sequencer. As is known in the art for any DNA sequence determined by this automated approach, any nucleotide sequence determined herein may contain some errors. Nucleotide sequences determined by automation are typically at least about 90% identical, and more typically at least about 95% to about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion. Unless otherwise indicated, each nucleotide sequence set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO: 3 or set forth using deoxyribonucleotide abbreviations is intended to indicate an RNA molecule having a sequence in which each deoxyribonucleotide A, G or C of SEQ ID NO: 3 has been replaced by the corresponding ribonucleotide A, G or C, and each deoxyribonucleotide T has been replaced by a ribonucleotide U.

In one embodiment, the invention provides an isolated polynucleotide comprising a nucleotide sequence at least about 95% identical to a sequence selected from the group consisting of: (a) a nucleotide sequence encoding a FIG-ROS fusion polypeptide comprising the amino acid sequence of SEQ ID NO: 4 (FIG-ROS(S)); (b) a nucleotide sequence encoding a FIG-ROS fusion polypeptide comprising the amino acid sequence of SEQ ID NO: 17 (FIG-ROS (XL)); (c) a nucleotide sequence comprising at least six contiguous nucleotides encompassing the fusion junction of a FIG-ROS(S) fusion polynucleotide (e.g., AAGTAC), a nucleotide sequence comprising at least six contiguous nucleotides encompassing the fusion junction of a FIG-ROS (XL) fusion polynucleotide (e.g., AAGctg); (d) a nucleotide sequence encoding at least six contiguous amino acid residues encompassing the fusion junction of a FIG-ROS(S) fusion polypeptide (e.g., AGSTLP (SEQ ID NO: 59)), (e) a nucleotide sequence encoding at least six contiguous amino acid residues encompassing the fusion junction of a FIG-ROS(XL) fusion polypeptide (e.g., LQAGVP (SEQ ID NO: 61)) and (f) a nucleotide sequence complementary to any of the nucleotide sequences of (a), (b), (c), (d), or (e).

Using the information provided herein, such as the nucleotide sequences set forth in SEQ ID NOs: 1, 3, and 16, a nucleic acid molecule of the present invention encoding a FIG-ROS fusion polypeptide of the invention may be obtained using standard cloning and screening procedures, such as those for cloning cDNAs using mRNA as starting material. The fusion gene can also be identified in cDNA libraries in other human cancers in which the FIG-ROS translocation occurs, or in which a deletion or alternative translocation results in expression of a truncated ROS kinase lacking the extracellular domain and may additionally lack the transmembrane domain of the wild type ROS kinase.

The determined nucleotide sequence of the FIG-ROS translocation genes encode the FIG-ROS(S) fusion polypeptide, the FIG-ROS(L) fusion polypeptide, and the FIG-ROS (XL) fusion polypeptide. The FIG-ROS fusion polynucleotides comprise the portion of the nucleotide sequence of wild type FIG that encodes the N-terminus of that protein with the portion of the nucleotide sequence of wild type ROS that encodes the kinase domain of that protein As indicated, the present invention provides, in part, the mature form of the FIG-ROS fusion proteins. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides, in part, nucleotide sequences encoding a mature FIG-ROS(S) fusion polypeptide having the nucleotide sequence set forth in SEQ ID NO: 3 with additional nucleic acid residues located 5' to the 5'-terminal residues of SEQ ID NO. 3 and includes the amino acid sequence of a FIG-ROS(S) fusion polypeptide having the amino acid sequence set forth in SEQ ID NO: 4 with additional amino acid residues located N-terminally to the N-terminal residue of SEQ ID NO. 4. The invention also provides, in part, nucleotide sequences encoding a mature FIG-ROS(XL) fusion polypeptide having the nucleotide sequence set forth in SEQ ID NO: 16 with additional nucleic acid residues located 5' to the 5'-terminal residues of SEQ ID NO. 16 and includes the amino acid sequence of a FIG-ROS(XL) fusion polypeptide having the amino acid sequence set forth in SEQ ID NO: 17 with additional amino acid residues located N-terminally to the N-terminal residue of SEQ ID NO. 17.

As indicated, polynucleotides of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

Isolated polynucleotides of the invention are nucleic acid molecules, DNA or RNA, which have been removed from their native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated polynucleotides of the invention include the nucleic acid molecules having the sequences set forth in (SEQ ID NOs: 1, 3, and 16, nucleic acid molecules comprising the coding sequence for the FIG-ROS(S), FIG-ROS (L), and FIG-ROS(XL) fusion proteins that comprise a sequence different from those described above but which, due to the degeneracy of the genetic code, still a mutant ROS polypeptide of the invention. The genetic code is well known in the art, thus, it would be routine for one skilled in the art to generate such degenerate variants.

In another embodiment, the invention provides an isolated polynucleotide encoding the FIG-ROS fusion polypeptide comprising the FIG-ROS translocation nucleotide sequence contained in the above-described cDNA clones. In some embodiments, such nucleic acid molecule will encode the mature FIG-ROS (S) fusion polypeptide, the mature FIG-ROS(L) fusion polypeptide, or the mature FIG-ROS(XL) fusion polypeptide. In another embodiment, the invention provides an isolated nucleotide sequence encoding a FIG-ROS fusion polypeptide comprising the N-terminal amino acid sequence of FIG and the kinase domain of ROS. In one embodiment, the polypeptide comprising the kinase domain of ROS comprises the amino acid sequence set forth in SEQ ID NO: 12 or SEQ ID NO: 13. In another embodiment, the N-terminal amino acid sequence of FIG and kinase domain of ROS are encoded by the nucleotide sequences set forth in SEQ ID NO: 1, SEQ ID NO: 3, or SEQ ID NO: 16.

The invention further provides isolated polynucleotides comprising nucleotide sequences having a sequence complementary to one of the mutant ROS polypeptides of the invention. Such isolated molecules, particularly DNA molecules, are useful as probes for gene mapping, by in situ hybridization with chromosomes, and for detecting expression of the FIG-ROS fusion protein or truncated ROS kinase polypeptide in human tissue, for instance, by Northern blot analysis.

The present invention is further directed to fragments of the isolated nucleic acid molecules described herein. By a fragment of an isolated FIG-ROS polynucleotide or truncated ROS polynucleotide of the invention is intended fragments at least about 15 nucleotides, or at least about 20 nucleotides, still more preferably at least about 30 nucleotides, or at least about 40 nucleotides in length, which are useful as diagnostic probes and primers as discussed herein. Of course, larger fragments of about 50-1500 nucleotides in length are also useful according to the present invention, as are fragments corresponding to most, if not all, of the FIG-ROS nucleotide sequence of the cDNAs having sequences set forth in SEQ ID NOs: 1, 3, or 16. By "a fragment at least 20 nucleotides in length", for example, is meant fragments that include 20 or more contiguous bases from the respective nucleotide sequences from which the fragments are derived.

Generation of such DNA fragments is routine to the skilled artisan, and may be accomplished, by way of example, by restriction endonuclease cleavage or shearing by sonication of DNA obtainable from the cDNA clone described herein or synthesized according to the sequence disclosed herein. Alternatively, such fragments can be directly generated synthetically.

In another aspect, the invention provides an isolated polynucleotide (e.g., a nucleotide probe) that hybridizes under stringent conditions to a mutant ROS kinase polynucleotide of the invention, such as a FIG-ROS fusion polynucleotide). The term "stringent conditions" with respect to nucleotide sequence or nucleotide probe hybridization conditions is the "stringency" that occurs within a range from about $T_m$ minus 5° C. (i.e., 5° C. below the melting temperature ($T_m$) of the probe or sequence) to about 20° C. to 25° C. below $T_m$. Typical stringent conditions are: overnight incubation at 42° C. in a solution comprising: 50% formamide, 5×.SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1×SSC at about 65° C. As will be understood by those of skill in the art, the stringency of hybridization may be altered in order to identify or detect identical or related polynucleotide sequences.

By a polynucleotide or nucleotide probe that hybridizes to a reference polynucleotide (e.g., a FIG-ROS(S) fusion polynucleotide) is intended that the polynucleotide or nucleotide probe (e.g., DNA, RNA, or a DNA-RNA hybrid) hybridizes along the entire length of the reference polynucleotide or hybridizes to a portion of the reference polynucleotide that is at least about 15 nucleotides (nt), or to at least about 20 nt, or to at least about 30 nt, or to about 30-70 nt of the reference polynucleotide. These nucleotide probes of the invention are useful as diagnostic probes and primers (e.g. for PCR) as discussed herein.

Of course, polynucleotides hybridizing to a larger portion of the reference polynucleotide (e.g. the FIG-ROS(S) fusion polynucleotide having the sequence set forth in SEQ ID NO: 3, for instance, a portion 50-750 nt in length, or even to the entire length of the reference polynucleotide, are useful as probes according to the present invention, as are polynucleotides corresponding to most, if not all, of the nucleotide sequence of the cDNAs described herein or the nucleotide sequences set forth in SEQ ID NOs: 1 or 3.

As used herein, by "a portion of a polynucleotide of 'at least 15 nucleotides' in length", for example, is intended 15 or more contiguous nucleotides from the nucleotide sequence of the reference polynucleotide. As indicated, such portions are useful as nucleotide probes for use diagnostically according to conventional DNA hybridization techniques or for use as primers for amplification of a target sequence by the polymerase chain reaction (PCR), as described, for instance, in Molecular Cloning, A Laboratory Manual, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference. Of course, a polynucleotide which hybridizes only to a poly A sequence (such as the 3' terminal poly(A) tract of the FIG-ROS sequences (e.g., SEQ ID NOs: 1 or 3) or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention, which encode a mutant ROS kinase polypeptide of the invention, may include but are not limited to those encoding the amino acid sequence of the mature polypeptide, by itself; the coding sequence for the mature polypeptide and additional sequences, such as those encoding the leader or secretory sequence, such as a pre-, or pro- or pre-pro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide that facilitates purification of the fused polypeptide. In certain embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86: 821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the FIG-ROS fusion polypeptide itself fused to Fc at the N- or C-terminus.

The present invention further relates to variants of the nucleic acid molecules of the present invention, which encode portions, analogs or derivatives of a FIG-ROS fusion polypeptide or truncated ROS kinase polypeptide disclosed herein. Variants may occur naturally, such as a natural allelic variant. By an "allelic variant" is intended one of several alternate forms of a gene occupying a given locus on a chromosome of an organism. See, e.g. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Some alterations included in the invention are silent substitutions, additions and deletions, which do not alter the properties and activities (e.g. kinase activity) of the FIG-ROS fusion polypeptides disclosed herein.

Further embodiments of the invention include isolated polynucleotides comprising a nucleotide sequence at least 90% identical. In some embodiments of the invention the nucleotide is at least 95%, 96%, 97%, 98% or 99% identical, to a mutant ROS polynucleotide of the invention (for example, a nucleotide sequence encoding the FIG-ROS(S) fusion polypeptide having the complete amino acid sequence set forth in SEQ ID NOs: 4, or a nucleotide sequence encoding the N-terminal of FIG and the kinase domain of ROS; or a nucleotide complementary to such exemplary sequences.

By a polynucleotide having a nucleotide sequence at least, for example, 95% "identical" to a reference nucleotide sequence encoding a mutant ROS polypeptide is intended that the nucleotide sequence of the polynucleotide is identical to the reference sequence except that the polynucleotide sequence may include up to five point mutations per each 100 nucleotides of the reference nucleotide sequence encoding the mutant ROS polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5" terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequences set forth in SEQ ID NOs: 1 and 3 or to the nucleotide sequence of the cDNA clones described herein can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference FIG-ROS fusion polynucleotide sequence according to the present invention, the parameters are set, of course, such that the percentage of identity is calculated over the full length of the reference nucleotide sequence and that gaps in homology of up to 5% of the total number of nucleotides in the reference sequence are allowed.

The present invention includes in its scope nucleic acid molecules at least 90%, 95%, 96%, 97%, 98% or 99% identical to the nucleic acid sequences set forth in SEQ ID NOs: 1 or 3, or nucleotides encoding the amino acid sequences set forth in SEQ ID NOs 2, 4, D, or E, irrespective of whether they encode a polypeptide having ROS kinase activity. This is because even where a particular nucleic acid molecule does not encode a fusion polypeptide having ROS kinase activity, one of skill in the art would still know how to use the nucleic acid molecule, for instance, as a hybridization probe or a polymerase chain reaction (PCR) primer. Uses of the nucleic acid molecules of the present invention that do not encode a polypeptide having kinase include, inter alia, (1) isolating the FIG-ROS translocation gene or allelic variants thereof in a cDNA library; (2) in situ hybridization (e.g., "FISH") to metaphase chromosomal spreads to provide precise chromosomal location of the FIG-ROS translocation gene, as described in Verma et al., Human Chromosomes: A Manual of Basic Techniques, Pergamon Press, New York (1988); and Northern Blot analysis for detecting FIG-ROS fusion protein mRNA expression in specific tissues.

Within the invention are also nucleic acid molecules having sequences at least 95% identical to a nucleic acid sequence that encodes a FIG-ROS fusion polypeptide (e.g., FIG-ROS(S)) or truncated ROS lacking an extracellular domain of wild-type ROS kinase or lacking both the extracellular domain and transmembrane domain of wild-type ROS kinase. In some embodiments, the encoded Fig-ROS fusion polypeptide and/or truncated ROS has kinase activity. Such activity may be similar, but not necessarily identical, to the activity of the FIG-ROS fusion protein disclosed herein (either the full-length protein, the mature protein, or a protein fragment that retains kinase activity), as measured in a particular biological assay. For example, the kinase activity of ROS can be examined by determining its ability to phosphorylate one or more tyrosine containing peptide substrates, for example, "Src-related peptide" (RRLIEDAEYAARG), which is a substrate for many receptor and nonreceptor tyrosine kinases.

Due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the cDNAs described herein, to the nucleic acid sequences set forth in SEQ ID NOs 1, 3, or 16 or to nucleic acid sequences encoding the amino acid sequences set forth in SEQ ID NOs: 2, 4, or 17 will encode a fusion polypeptide having ROS kinase activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide that retains ROS kinase activity. This is because the skilled artisan is fully aware of amino acid substitutions that are either less likely or not likely to significantly effect protein function (e.g., replacing one aliphatic amino acid with a second aliphatic amino acid). For example, guidance concerning how to make phenotypically silent amino acid substitutions is provided in Bowie et al., "Deciphering the Message in Protein Sequences: Tolerance to Amino Acid Substitutions," *Science* 247: 1306-1310 (1990), which describes two main approaches for studying the tolerance of an amino acid sequence to change. Skilled artisans familiar with such techniques also appreciate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., supra., and the references cited therein.

Methods for DNA sequencing that are well known and generally available in the art may be used to practice any polynucleotide embodiments of the invention. The methods may employ such enzymes as the Klenow fragment of DNA polymerase I, SEQUENASE® (US Biochemical Corp, Cleveland, Ohio), Taq polymerase (Invitrogen), thermostable T7 polymerase (Amersham, Chicago, Ill.), or combinations of recombinant polymerases and proofreading exonucleases such as the ELONGASE Amplification System marketed by Gibco BRL (Gaithersburg, Md.). The process may be automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Applied Biosystems).

Polynucleotide sequences encoding a mutant ROS polypeptide of the invention may be extended utilizing a partial nucleotide sequence and employing various methods known in the art to detect upstream sequences such as promoters and regulatory elements. For example, one method that may be employed, "restriction-site" PCR, uses universal primers to retrieve unknown sequence adjacent to a known locus (Sarkar, G., *PCR Methods Applic.* 2: 318-322 (1993)). In particular, genomic DNA is first amplified in the presence of primer to linker sequence and a primer specific to the known region. Exemplary primers are those described in Example 4 herein. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia et al., *Nucleic Acids Res.* 16: 8186 (1988)). The primers may be designed using OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom et al., *PCR Methods Applic.* 1: 111-119 (1991)). In this method, multiple restriction enzyme digestions and ligations may also be used to place an engineered double-stranded sequence into an unknown portion of the DNA molecule before performing PCR. Another method which may be used to retrieve unknown sequences is that described in Parker et al., *Nucleic Acids Res.* 19: 3055-3060 (1991)). Additionally, one may use PCR, nested primers, and PROMOTERFINDER® libraries to walk in genomic DNA (Clontech, Palo Alto, Calif.). This process avoids the need to screen libraries and is useful in finding intron/exon junctions.

When screening for full-length cDNAs, libraries that have been size-selected to include larger cDNAs may be used or random-primed libraries, which contain more sequences that contain the 5' regions of genes. A randomly primed library is useful for situations in which an oligo d(T) library does not yield a full-length cDNA. Genomic libraries may be useful for extension of sequence into the 5' and 3' non-transcribed regulatory regions.

Capillary electrophoresis systems, which are commercially available, may be used to analyze the size or confirm the nucleotide sequence of sequencing or PCR products. In particular, capillary sequencing may employ flowable polymers for electrophoretic separation, four different fluorescent dyes (one for each nucleotide) that are laser activated, and detection of the emitted wavelengths by a charge coupled device camera. Output/light intensity may be converted to electrical signal using appropriate software (e.g., GENOTYPER™ and SEQUENCE NAVIGATOR™, Applied Biosystems) and the entire process from loading of samples to computer analysis and electronic data display may be computer controlled. Capillary electrophoresis is useful for the sequencing of small pieces of DNA that might be present in limited amounts in a particular sample.

The present invention also provides recombinant vectors that comprise an isolated polynucleotide of the present invention, host cells which are genetically engineered with the recombinant vectors, and the production of recombinant FIG-ROS polypeptides or fragments thereof by recombinant techniques.

Recombinant constructs may be introduced into host cells using well-known techniques such infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells. The invention may be practiced with vectors comprising cis-acting control regions to the polynucleotide of interest. Appropriate trans-acting factors may be supplied by the host, supplied by a complementing vector or supplied by the vector itself upon introduction into the host. In certain embodiments in this regard, the vectors provide for specific expression, which may be inducible and/or cell type-specific (e.g., those inducible by environmental factors that are easy to manipulate, such as temperature and nutrient additives).

The DNA insert comprising a FIG-ROS polynucleotide or truncated ROS polynucleotide of the invention should be operatively linked to an appropriate promoter, such as the phage lambda PL promoter, the *E. coli* lac, trp and tac promoters, the SV40 early and late promoters and promoters of retroviral LTRs, to name a few. Other suitable promoters are known to the skilled artisan. The expression constructs will further contain sites for transcription initiation, termination and, in the transcribed region, a ribosome binding site for translation. The coding portion of the mature transcripts expressed by the constructs may include a translation initiating at the beginning and a termination codon (UAA, UGA or UAG) appropriately positioned at the end of the polypeptide to be translated.

As indicated, the expression vectors may include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Non-limiting vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Non-limiting eukaryotic vectors include pWL-NEO, pSV2CAT, pOG44, pXT1 and pSG available from Stratagene; and pSVK3, pBPV, pMSG and pSVL available from Pharmacia. Other suitable vectors will be readily apparent to the skilled artisan.

Non-limiting bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast, *Saccharomyces cerevisiae*, a number of vectors containing constitutive or inducible promoters such as alpha factor, alcohol oxidase, and PGH may be used. For reviews, see Ausubel et al. (1989) Current Protocols in Molecular Biology, John Wiley & Sons, New York, N.Y., and Grant et al., *Methods Enzymol.* 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

Transcription of DNA encoding a FIG-ROS fusion polypeptide of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at basepairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein (e.g., a GST-fusion), and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

In one non-limiting example, a FIG-ROS fusion polypeptide of the invention may comprise a heterologous region from an immunoglobulin that is useful to solubilize proteins. For example, EP-A-0 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5—has been fused with Fc portions for the purpose of high-throughput screening assays to identify antagonists of hIL-5. See Bennett et al., *Journal of Molecular Recognition* 8: 52-58 (1995) and Johanson et al., *The Journal of Biological Chemistry* 270 (16): 9459-9471 (1995).

FIG-ROS polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In some embodiments, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Accordingly, in one embodiment, the invention provides a method for producing a recombinant FIG-ROS fusion polypeptide by culturing a recombinant host cell (as described above) under conditions suitable for the expression of the fusion polypeptide and recovering the polypeptide. Culture conditions suitable for the growth of host cells and the expression of recombinant polypeptides from such cells are well known to those of skill in the art. See, e.g., Current Protocols in Molecular Biology, Ausubel F M et al., eds., Volume 2, Chapter 16, Wiley Interscience.

In a further aspect, the invention provides a binding agent that specifically binds to a FIG-ROS fusion polypeptide. In some embodiments, the binding agent specifically binds to a fusion junction between a FIG portion and a ROS portion in said FIG-ROS fusion polypeptide. In some embodiments, the FIG-ROS fusion polypeptide is a FIG-ROS(S) fusion polypeptide, a FIG-ROS(L) fusion polypeptide, or a FIG-ROS (XL) fusion polypeptide.

In some embodiments, the binding agent of the invention is attached to a detectable label. By "detectable label" with respect to a polypeptide, polynucleotide, or binding agent disclosed herein means a chemical, biological, or other modification of or to the polypeptide, polynucleotide, or binding agent, including but not limited to fluorescence, mass, residue, dye, radioisotope, label, or tag modifications, etc., by which the presence of the molecule of interest may be detected. The detectable label may be attached to the polypeptide, polynucleotide, or binding agent by a covalent or non-covalent chemical bond.

The invention provides binding agents, such as antibodies or AQUA peptides, or binding fractions thereof, that specifically bind to the FIG-ROS fusion polypeptides (e.g., FIG-ROS(S), FIG-ROS(L), or FIG-ROS(XL) of the invention). By "specifically binding" or "specifically binds" means that a binding agent of the invention (e.g., an antibody or AQUA peptide) interacts with its target molecule (e.g., a FIG-ROS fusion polypeptide), where the interaction is interaction is dependent upon the presence of a particular structure (i.e., the antigenic determinant or epitope) on the protein; in other words, the reagent is recognizing and binding to a specific protein structure rather than to all proteins in general. By "binding fragment thereof" means a fragment or portion of a binding reagent that specifically binds the target molecule (e.g., an Fab fragment of an antibody). A binding agent that specifically binds to the target molecule may be referred to as a target specific binding agent. For example, an antibody that specifically binds to a FIG-ROS(L) polypeptide may be referred to as a FIG-ROS(L) specific antibody. In some embodiments, a binding agent of the invention has a binding affinity ($K_D$) for its target molecule (e.g., a FIG-ROS fusion polypeptide) of $1\times10^{-6}$M or less. In some embodiments, a binding agent of the invention binds to its target molecule with a $K_D$ of $1\times10^{-7}$ M or less, or a $K_D$ of $1\times10^{-8}$ M or less, or a $K_D$ of $1\times10^{-9}$ M or less, or a $K_D$ of $1\times10^{-10}$ M or less, of a $K_D$ of $1\times10^{-11}$ M or less, of a $K_D$ of $1\times10^{-12}$ M or less. In certain embodiments, the $K_D$ of a binding agent of the invention for its target molecule is 1 pM to 500 pM, or between 500 pM to 1 μM, or between 1 μM to 100 nM, or between 100 mM to 10 nM. Non-limiting examples of a target molecule to which a binding agent of the invention specifically binds to include the FIG-ROS(L) fusion polypeptide, the FIG-ROS(S) fusion polypeptide, and fragments thereof, particularly those fragments that include the junction between the FIG portion and the ROS portion of a FIG-ROS fusion polypeptide of the invention.

The binding agent of the invention, including those useful in the practice of the disclosed methods, include, among others, FIG-ROS fusion polypeptide specific antibodies and AQUA peptides (heavy-isotope labeled peptides) corresponding to, and suitable for detection and quantification of, FIG-ROS fusion polypeptide expression in a biological sample. Thus, a "FIG-ROS fusion polypeptide-specific binding agent" is any reagent, biological or chemical, capable of specifically binding to, detecting and/or quantifying the presence/level of expressed FIG-ROS fusion polypeptide in a biological sample. The term includes, but is not limited to, the antibodies and AQUA peptide reagents discussed below, and equivalent binding agent are within the scope of the present invention.

In some embodiments, the binding agent that specifically binds to a FIG-ROS fusion polypeptide is an antibody (i.e., a FIG-ROS fusion polypeptide-specific antibody). In some embodiments, a FIG-ROS fusion polypeptide-specific antibody of the invention is an isolated antibody or antibodies that specifically bind(s) a FIG-ROS fusion polypeptide of the invention (e.g., FIG-ROS(L), FIG-ROS (XL) or FIG-ROS(S)) but does not substantially bind either wild-type FIG or wild-type ROS. Also useful in practicing the methods of the invention are other reagents such as epitope-specific antibodies that specifically bind to an epitope in the extracelluar or kinase domains of wild-type ROS protein sequence (which domains are not present in the truncated ROS kinase disclosed herein), and are therefore capable of detecting the presence (or absence) of wild type ROS in a sample.

Human FIG-ROS fusion polypeptide-specific antibodies may also bind to highly homologous and equivalent epitopic peptide sequences in other mammalian species, for example murine or rabbit, and vice versa. Antibodies useful in practicing the methods of the invention include (a) monoclonal antibodies, (b) purified polyclonal antibodies that specifically bind to the target polypeptide (e.g., the fusion junction of FIG-ROS fusion polypeptide, (c) antibodies as described in (a)-(b) above that bind equivalent and highly homologous epitopes or phosphorylation sites in other non-human species (e.g., mouse, rat), and (d) fragments of (a)-(c) above that bind to the antigen (or more preferably the epitope) bound by the exemplary antibodies disclosed herein.

The term "antibody" or "antibodies" refers to all types of immunoglobulins, including IgG, IgM, IgA, IgD, and IgE, including binding fragments thereof (i.e., fragments of an antibody that are capable of specifically binding to the antibody's target molecule, such as $F_{ab}$, and $F(ab')_2$ fragments), as well as recombinant, humanized, polyclonal, and monoclonal antibodies and/or binding fragments thereof. Antibodies of the invention can be derived from any species of animal, such as from a mammal. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Antibodies of the invention may be also be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed specific antibodies made according to the method disclosed in U.S. Pat. No. 4,676, 980 (Segel et al.).

Natural antibodies are the antibodies produced by a host animal, however the invention contemplates also genetically altered antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics. The term "humanized antibody", as used herein, refers to antibody molecules in which amino acids have been replaced in the non-antigen binding regions in order to more closely resemble a human antibody, while still retaining the original binding ability. Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule. In view of the assays and epitopes disclosed herein, those skilled in the art can generate or select antibodies or mixtures of antibodies that are applicable for an intended purpose and desired need.

Recombinant antibodies are also included in the present invention. These recombinant antibodies have the same amino acid sequence as the natural antibodies or have altered amino acid sequences of the natural antibodies. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety). Antibodies can be engineered in numerous ways. They can be made as single-chain antibodies (including small modular immunopharmaceuticals or SMIPs™), Fab and $F(ab')_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203. The genetically altered antibodies of the invention may be functionally equivalent to the above-mentioned natural antibodies. In certain embodiments, modified antibodies of the invention provide improved stability or/and therapeutic efficacy. Non-limiting examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of the invention can be modified post-translationally (e.g., acetylation, and/or phosphorylation) or can be modified synthetically (e.g., the attachment of a labeling group). Antibodies with engineered or variant constant or Fc regions can be useful in modulating effector functions, such as, for example, antigen-dependent cytotoxicity (ADCC) and complement-dependent cytotoxicity (CDC). Such antibodies with engineered or variant constant or Fc regions may be useful in instances where a parent singling protein (Table 1) is expressed in normal tissue; variant antibodies without effector function in these instances may elicit the desired therapeutic response while not damaging normal tissue. Accordingly, certain aspects and methods of the present disclosure relate to antibodies with altered effector functions that comprise one or more amino acid substitutions, insertions, and/or deletions. The term "biologically active" refers to a protein having structural, regulatory, or biochemical functions of a naturally occurring molecule. Likewise, "immunologically active" refers to the capability of the natural, recombinant, or synthetic FIG-ROS fusion polypeptide or truncated ROS polypeptide, or any oligopeptide thereof, to induce a specific immune response in appropriate animals or cells and to bind with specific antibodies.

Also within the invention are antibody molecules with fewer than 4 chains, including single chain antibodies, Camelid antibodies and the like and components of an antibody, including a heavy chain or a light chain. In some embodiments an immunoglobulin chain may comprise in order from 5' to 3', a variable region and a constant region. The variable region may comprise three complementarity determining regions (CDRs), with interspersed framework (FR) regions for a structure FR1, CDR1, FR2, CDR2, FR3, CDR3 and FR4. Also within the invention are heavy or light chain variable regions, framework regions and CDRs. An antibody of the invention may comprise a heavy chain constant region that comprises some or all of a CH1 region, hinge, CH2 and CH3 region.

One non-limiting epitopic site of a FIG-ROS fusion polypeptide specific antibody of the invention is a peptide fragment consisting essentially of about 11 to 17 amino acids of a human FIG-ROS fusion polypeptide sequence, which fragment encompasses the fusion junction between the FIG portion of the molecule and the ROS portion of the molecule. It will be appreciated that antibodies that specifically binding shorter or longer peptides/epitopes encompassing the fusion junction of a FIG-ROS fusion polypeptide are within the scope of the present invention.

The invention is not limited to use of antibodies, but includes equivalent molecules, such as protein binding domains or nucleic acid aptamers, which bind, in a fusion-protein or truncated-protein specific manner, to essentially the same epitope to which a FIG-ROS fusion polypeptide-specific antibody or ROS truncation point epitope-specific antibody useful in the methods of the invention binds. See, e.g., Neuberger et al., *Nature* 312: 604 (1984). Such equivalent non-antibody reagents may be suitably employed in the methods of the invention further described below.

Polyclonal antibodies useful in practicing the methods of the invention may be produced according to standard techniques by immunizing a suitable animal (e.g., rabbit, goat, etc.) with an antigen encompassing a desired fusion-protein specific epitope (e.g. the fusion junction between FIG and ROS in the FIG-ROS fusion polypeptide), collecting immune serum from the animal, and separating the polyclonal antibodies from the immune serum, and purifying polyclonal antibodies having the desired specificity, in accordance with known procedures. The antigen may be a synthetic peptide antigen comprising the desired epitopic sequence, selected and constructed in accordance with well-known techniques. See, e.g., Antibodies: A Laboratory Manual, Chapter 5, p. 75-76, Harlow & Lane Eds., Cold Spring Harbor Laboratory (1988); Czernik, *Methods In Enzymology,* 201: 264-283 (1991); Merrifield, *J. Am. Chem. Soc.* 85: 21-49 (1962)). Polyclonal antibodies produced as described herein may be screened and isolated as further described below.

Monoclonal antibodies may also be beneficially employed in the methods of the invention, and may be produced in hybridoma cell lines according to the well-known technique of Kohler and Milstein. *Nature* 265: 495-97 (1975); Kohler and Milstein, *Eur. J. Immunol.* 6: 511 (1976); see also, Current Protocols in Molecular Biology, Ausubel et al. Eds. (1989). Monoclonal antibodies so produced are highly specific, and improve the selectivity and specificity of assay methods provided by the invention. For example, a solution containing the appropriate antigen (e.g. a synthetic peptide comprising the fusion junction of FIG-ROS fusion polypeptide) may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are desired for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immunol. Methods,* 74: 307 (1984)). The antigen combining site of the monoclonal antibody can be cloned by PCR and single-chain antibodies produced as phage-displayed recombinant antibodies or soluble antibodies in *E. coli* (see, e.g., Antibody Engineering Protocols, 1995, Humana Press, Sudhir Paul editor.)

Further still, U.S. Pat. No. 5,194,392, Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, this method involves detecting or determining a sequence of monomers which is a topographical equivalent of a ligand which is complementary to the ligand binding site of a particular receptor of interest. Similarly, U.S. Pat. No. 5,480,971, Houghten et al. (1996) discloses linear $C_1$-C-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Antibodies useful in the methods of the invention, whether polyclonal or monoclonal, may be screened for epitope and fusion protein specificity according to standard techniques. See, e.g., Czernik et al., *Methods in Enzymology,* 201: 264-283 (1991). For example, the antibodies may be screened against a peptide library by ELISA to ensure specificity for both the desired antigen and, if desired, for reactivity only with a FIG-ROS fusion polypeptide of the invention and not with wild type FIG or wild type ROS. The antibodies may also be tested by Western blotting against cell preparations containing target protein to confirm reactivity with the only the desired target and to ensure no appreciable binding to other fusion proteins involving ROS. The production, screening, and use of fusion protein-specific antibodies is known to those of skill in the art, and has been described. See, e.g., U.S. Patent Publication No. 20050214301.

FIG-ROS fusion polypeptide-specific antibodies useful in the methods of the invention may exhibit some limited cross-reactivity with similar fusion epitopes in other fusion proteins or with the epitopes in wild type FIG and wild type ROS that form the fusion junction. This is not unexpected as most antibodies exhibit some degree of cross-reactivity, and anti-peptide antibodies will often cross-react with epitopes having high homology or identity to the immunizing peptide. See, e.g., Czernik, supra. Cross-reactivity with other fusion proteins is readily characterized by Western blotting alongside markers of known molecular weight. Amino acid sequences of cross-reacting proteins may be examined to identify sites highly homologous or identical to the FIG-ROS fusion polypeptide sequence to which the antibody binds. Undesirable cross-reactivity can be removed by negative selection using antibody purification on peptide columns (e.g. selecting out antibodies that bind either wild type FIG and/or wild type ROS).

FIG-ROS fusion polypeptide-specific antibodies of the invention that are useful in practicing the methods disclosed herein are ideally specific for human fusion polypeptide, but are not limited only to binding the human species, per se. The invention includes the production and use of antibodies that also bind conserved and highly homologous or identical epitopes in other mammalian species (e.g., mouse, rat, monkey). Highly homologous or identical sequences in other species can readily be identified by standard sequence comparisons, such as using BLAST, with the human FIG-ROS fusion polypeptide sequences disclosed herein (SEQ ID NOs: 1).

Antibodies employed in the methods of the invention may be further characterized by, and validated for, use in a particular assay format, for example FC, IHC, and/or ICC. The use of FIG-ROS fusion polypeptide-specific antibodies in such methods is further described herein. The antibodies described herein, used alone or in the below-described assays, may also be advantageously conjugated to fluorescent dyes (e.g. Alexa488, phycoerythrin), or labels such as quantum dots, for use in multi-parametric analyses along with other signal transduction (phospho-AKT, phospho-Erk 1/2) and/or cell marker (cytokeratin) antibodies, as further described below.

In practicing the methods of the invention, the expression and/or activity of wild type FIG and/or wild type ROS in a given biological sample may also be advantageously examined using antibodies (either phospho-specific or total) for these wild type proteins. For example, CSF receptor phosphorylation-site specific antibodies are commercially available (see Cell Signaling Technology, Inc., Danvers, Mass., 2005/06 Catalogue, #'s 3151, 3155, and 3154; and Upstate Biotechnology, 2006 Catalogue, #06-457). Such antibodies may also be produced according to standard methods, as described above. The amino acid sequences of both human FIG and ROS are published, as are the sequences of these proteins from other species.

Detection of wild type FIG and wild type ROS expression and/or activation, along with FIG-ROS fusion polypeptide expression, in a biological sample (e.g. a tumor sample) can provide information on whether the fusion protein alone is driving the tumor, or whether wild type ROS is also activated and driving the tumor. Such information is clinically useful in assessing whether targeting the fusion protein or the wild type protein(s), or both, or is likely to be most beneficial in inhibiting progression of the tumor, and in selecting an appropriate therapeutic or combination thereof. Antibodies specific for the wild type ROS kinase extracellular domain, which is not present in the truncated ROS kinase disclosed herein, may be particularly useful for determining the presence/absence of the mutant ROS kinase.

It will be understood that more than one antibody may be used in the practice of the above-described methods. For example, one or more FIG-ROS fusion polypeptide-specific antibodies together with one or more antibodies specific for another kinase, receptor, or kinase substrate that is suspected of being, or potentially is, activated in a cancer in which FIG-ROS fusion polypeptide is expressed may be simultaneously employed to detect the activity of such other signaling molecules in a biological sample comprising cells from such cancer.

Those of skill in the art will appreciate that FIG-ROS fusion polypeptides of the present invention and the epitope-bearing fragments thereof described above can be combined with parts of other molecules to create chimeric polypeptides. For example, an epitope-bearing fragment of a FIG-ROS fusion polypeptide may be combined with the constant domain of immunoglobulins (IgG) to facilitate purification of the chimeric polypeptide and increase the in vivo half-life of the chimeric polypeptide (see, e.g., examples of CD4-Ig chimeric proteins in EPA 394,827; Traunecker et al., *Nature* 331: 84-86 (1988)). Fusion proteins that have a disulfide-linked dimeric structure (e.g., from an IgG portion may also be more efficient in binding and neutralizing other molecules than the monomeric FIG-ROS fusion polypeptide alone (see Fountoulakis et al., *J Biochem* 270: 3958-3964(1995)).

In some embodiments, a binding agent that specifically binds to a FIG-ROS fusion polypeptide is a heavy-isotope labeled peptide (i.e., an AQUA peptide). Such an AQUA peptide may be suitable for the absolute quantification of an expressed FIG-ROS fusion polypeptide in a biological sample. As used herein, the term "heavy-isotope labeled peptide" is used interchangeably with "AQUA peptide". The production and use of AQUA peptides for the absolute quantification or detection of proteins (AQUA) in complex mixtures has been described. See WO/03016861, "Absolute Quantification of Proteins and Modified Forms Thereof by Multistage Mass Spectrometry," Gygi et al. and also Gerber et al., *Proc. Natl. Acad. Sci. U.S.A.* 100: 6940-5 (2003) (the teachings of which are hereby incorporated herein by reference, in their entirety). The term "specifically detects" with respect to such an AQUA peptide means the peptide will only detect and quantify polypeptides and proteins that contain the AQUA peptide sequence and will not substantially detect polypeptides and proteins that do not contain the AQUA peptide sequence.

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al., supra.) AQUA peptides are spiked in to the complex peptide mixture obtained by digestion of the whole cell lysate with a proteolytic enzyme and subjected to immunoaffinity purification as described above. The retention time and fragmentation pattern of the native peptide formed by digestion (e.g., trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures.

Since an absolute amount of the AQUA peptide is added (e.g., 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known sequence previously identified by the IAP-LC-MS/MS method within in a target protein. If the site is modified, one AQUA peptide incorporating the modified form of the particular residue within the site may be developed, and a second AQUA peptide incorporating the unmodified form of the residue developed. In this way, the two standards may be used to detect and quantify both the modified an unmodified forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g., PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, in some embodiments, the peptide is not longer than about 20 amino acids. In some embodiments, the peptide is between about 7 to 15 amino acids in length. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e., the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^{2}H$, $^{13}C$, $^{15}N$, $^{17}O$, $^{18}O$, or $^{34}S$, are some non-limiting labels. Pairs of peptide internal standards that incorporate a different isotope label may also be prepared. Non-limiting amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g., an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a one non-limiting method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

AQUA internal peptide standards (heavy-isotope labeled peptides) may desirably be produced, as described above, to detect any quantify any unique site (e.g., the fusion junction within a FIG-ROS fusion polypeptide) within a mutant ROS polypeptide of the invention. For example, an AQUA phosphopeptide may be prepared that corresponds to the fusion junction sequence of FIG-ROS fusion polypeptide Peptide standards for may be produced for the FIG-ROS fusion junction and such standards employed in the AQUA methodology to detect and quantify the fusion junction (i.e. the presence of FIG-ROS fusion polypeptide) in a biological sample.

For example, an exemplary AQUA peptide of the invention comprises the amino acid sequence AGSTLP (SEQ ID NO: 59), which corresponds to the three amino acids immediately flanking each side of the fusion junction in the second (short) variant of FIG-ROS fusion polypeptide (i.e., FIG-ROS(S) fusion polypeptide). It will be appreciated that larger AQUA peptides comprising the fusion junction sequence (and additional residues downstream or upstream of it) may also be constructed. Similarly, a smaller AQUA peptide comprising less than all of the residues of such sequence (but still comprising the point of fusion junction itself) may alternatively be constructed. Such larger or shorter AQUA peptides are within the scope of the present invention, and the selection and production of AQUA peptides may be carried out as described above (see Gygi et al., Gerber et al., supra.).

In another aspect, the invention provides a method for detecting a FIG-ROS gene translocation, the method comprising contacting a biological sample with a binding agent that specifically binds to a FIG-ROS fusion polypeptide (e.g., a FIG-ROS(S), FIG-ROS(XL) or a FIG-ROS(L) fusion polypeptide), where specific binding of the binding agent to the biological sample indicates the presence of a FIG-ROS gene translocation (e.g., that encodes a FIG-ROS (S), FIG-ROS(XL) or FIG-ROS(L) fusion polypeptide) in said biological sample.

In a further aspect, the invention provides a method for detecting a FIG-ROS gene translocation by contacting a biological sample with a nucleotide probe that hybridizes to a FIG-ROS fusion polynucleotide under stringent conditions, wherein hybridization of said nucleotide probe to said biological sample indicates a FIG-ROS gene translocation (e.g., that encodes a FIG-ROS(S), FIG-ROS(XL), or FIG-ROS(L) fusion polypeptide) in said biological sample.

In another aspect, the invention provides a method for identifying a cancer that is likely to respond to a ROS inhibitor. The method includes contacting a biological sample of said cancer comprising at least one polypeptide with a binding agent that specifically binds to either a FIG-ROS fusion polypeptide (e.g., a FIG-ROS(S), FIG-ROS(XL), or FIG-ROS(L) fusion polypeptide) or a mutant ROS polypeptide, wherein specific binding of said binding agent to at least one polypeptide in said biological sample identifies said cancer as a cancer that is likely to respond to a ROS inhibitor. In some embodiments, the binding agent is an antibody or an AQUA peptide. In some embodiments, the cancer is from a patient (e.g., a cancer patient). In further embodiments, the cancer may be a liver cancer, a pancreatic cancer, a kidney cancer, a testicular cancer, or may be a duct cancer (e.g., a bile duct cancer or a pancreatic duct cancer).

As used herein, by “likely to respond” is meant that a cancer is more likely to show growth retardation or abrogation in response to (e.g., upon contact with or treatment by) a ROS inhibitor. In some embodiments, a cancer that is likely to respond to a ROS inhibitor is one that dies (e.g., the cancer cells apoptose) in response to the ROS inhibitor.

As described herein, certain normal cells (e.g., liver cells) do not express any ROS kinase (or show any ROS kinase activity) while cancerous cells of that cell type do. This may be, for example, because the cancerous cell expresses a truncated ROS polypeptide or a ROS fusion protein (e.g., a FIG-ROS fusion polypeptide). The cancerous cell may also simply overexpress wild-type, full-length ROS kinase (where “overexpress” simply means that the cancerous cell expresses more ROS kinase than a non-cancerous cell of that same cell type). As mentioned above, such overexpression of ROS is included in the term “mutant ROS”. For example, as described below, normal liver cells do not express ROS kinase (and do not show any ROS kinase activity) while cancerous liver cells do. Thus, in some embodiments of the invention, the identification of the presence of the ROS kinase (or the identification of the presence of ROS kinase activity) in a cell type that does not normally express ROS (or show any ROS kinase activity) may be an indicator that the cell thus identified is a cancer that is likely to respond to a ROS inhibitor. This identification of the presence of ROS kinase (or ROS kinase acitivity) may be followed by further analysis of the ROS kinase within that cell (e.g., binding of a protein in the cell with a binding agent that specifically binds to a mutant ROS polypeptide or hybridization of a nucleic acid molecule from the cell with a probe that hybridizes to a mutant ROS polynucleotide).

In yet another aspect, the invention provides another method for identifying a cancer that is likely to respond to a ROS inhibitor. The method includes contacting a biological sample of said cancer comprising at least one nucleic acid molecule with a nucleotide probe that hybridizes under stringent conditions to a either a FIG-ROS fusion polynucleotide (e.g., a FIG-ROS(S), FIG-ROS(XL), or FIG-ROS(L) fusion polynucleotide) or a mutant ROS polynucleotide, and wherein hybridization of said nucleotide probe to at least one nucleic acid molecule in said biological sample identifies said cancer as a cancer that is likely to respond to a ROS inhibitor. In some embodiments, the FIG-ROS fusion polynucleotide encodes a FIG-ROS(S) fusion polypeptide. In some embodiments, the FIG-ROS fusion polynucleotide encodes a FIG-ROS(L) fusion polypeptide. In some embodiments, the FIG-ROS fusion polynucleotide encodes a FIG-ROS(XL) fusion polypeptide. In some embodiments, the cancer is from a patient (e.g., a cancer patient). In further embodiments, the cancer may be a liver cancer, a pancreatic cancer, a kidney cancer, a testicular cancer, or may be a duct cancer (e.g., a bile duct cancer or a pancreatic duct cancer).

The methods of the invention may be carried out in a variety of different assay formats known to those of skill in the art. Some non-limiting examples of methods include immunoassays and peptide and nucleotide assays.

Immunoassays.

Immunoassays useful in the practice of the methods of the invention may be homogenous immunoassays or heterogeneous immunoassays. In a homogeneous assay the immunological reaction usually involves a mutant ROS polypeptide-specific reagent (e.g. a FIG-ROS fusion polypeptide-specific antibody), a labeled analyte, and the biological sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radio-isotopes, fluorescent dyes, enzymes, bacteriophages, coenzymes, and so forth. Semi-conductor nanocrystal labels, or “quantum dots”, may also be advantageously employed, and their preparation and use has been well described. See generally, K. Barovsky, *Nanotech. Law & Bus.* 1(2): Article 14 (2004) and patents cited therein.

In a heterogeneous assay approach, the reagents are usually the biological sample, a mutant ROS kinase polypeptide-specific reagent (e.g., an antibody), and suitable means for producing a detectable signal. Biological samples as further described below may be used. The antibody is generally immobilized on a support, such as a bead, plate or slide, and contacted with the sample suspected of containing the antigen in a liquid phase. The support is then separated from the liquid phase and either the support phase or the liquid phase is examined for a detectable signal employing means for producing such signal. The signal is related to the presence of the analyte in the biological sample. Means for producing a detectable signal include the use of radioactive labels, fluorescent labels, enzyme labels, quantum dots, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well known to those of skill in the art. See id. FIG-ROS fusion polypeptide-specific monoclonal antibodies may be used in a "two-site" or "sandwich" assay, with a single hybridoma cell line serving as a source for both the labeled monoclonal antibody and the bound monoclonal antibody. Such assays are described in U.S. Pat. No. 4,376,110. The concentration of detectable reagent should be sufficient such that the binding of FIG-ROS fusion polypeptide is detectable compared to background.

Antibodies useful in the practice of the methods disclosed herein may be conjugated to a solid support suitable for a diagnostic assay (e.g., beads, plates, slides or wells formed from materials such as latex or polystyrene) in accordance with known techniques, such as precipitation. Antibodies or other FIG-ROS fusion polypeptide-binding reagents may likewise be conjugated to detectable groups such as radiolabels (e.g., $^{35}S$, $^{125}I$, $^{131}I$) enzyme labels (e.g., horseradish peroxidase, alkaline phosphatase), and fluorescent labels (e.g., fluorescein) in accordance with known techniques.

Cell-based assays, such flow cytometry (FC), immunohistochemistry (IHC), or immunofluorescence (IF) are particularly desirable in practicing the methods of the invention, since such assay formats are clinically-suitable, allow the detection of mutant ROS polypeptide expression in vivo, and avoid the risk of artifact changes in activity resulting from manipulating cells obtained from, e.g. a tumor sample in order to obtain extracts. Accordingly, in some embodiments, the methods of the invention are implemented in a flow-cytometry (FC), immuno-histochemistry (IHC), or immunofluorescence (IF) assay format.

Flow cytometry (FC) may be employed to determine the expression of mutant ROS polypeptide in a mammalian tumor before, during, and after treatment with a drug targeted at inhibiting ROS kinase activity. For example, tumor cells from a fine needle aspirate may be analyzed by flow cytometry for FIG-ROS fusion polypeptide expression and/or activation, as well as for markers identifying cancer cell types, etc., if so desired. Flow cytometry may be carried out according to standard methods. See, e.g. Chow et al., *Cytometry* (*Communications in Clinical Cytometry*) 46: 72-78 (2001). Briefly and by way of example, the following protocol for cytometric analysis may be employed: fixation of the cells with 2% paraformaldehyde for 10 minutes at 37° C. followed by permeabilization in 90% methanol f0 minutes on ice. Cells may then be stained with the primary FIG-ROS fusion polypeptide-specific antibody, washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed FIG-ROS fusion polypeptide in the tumor. Similar analysis after treatment of the tumor with a ROS-inhibiting therapeutic would reveal the responsiveness of a FIG-ROS fusion polypeptide-expressing tumor to the targeted inhibitor of ROS kinase.

Immunohistochemical (IHC) staining may be also employed to determine the expression and/or activation status of mutant ROS kinase polypeptide in a mammalian cancer (e.g., a liver or pancreatic cancer) before, during, and after treatment with a drug targeted at inhibiting ROS kinase activity. IHC may be carried out according to well-known techniques. See, e.g., Antibodies: A Laboratory Manual, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary anti-FIG-ROS fusion polypeptide antibody and secondary antibody; and finally detecting using ABC avidin/biotin method according to manufacturer's instructions.

Immunofluorescence (IF) assays may be also employed to determine the expression and/or activation status of FIG-ROS fusion polypeptide in a mammalian cancer before, during, and after treatment with a drug targeted at inhibiting ROS kinase activity. IF may be carried out according to well-known techniques. See, e.g., J. M. polak and S. Van Noorden (1997) Introduction to Immunocytochemistry, 2nd Ed.; Royal Microscopy Society Microscopy Handbook 37, BioScientific/Springer-Verlag. Briefly, and by way of example, patient samples may be fixed in paraformaldehyde followed by methanol, blocked with a blocking solution such as horse serum, incubated with the primary antibody against FIG-ROS fusion polypeptide followed by a secondary antibody labeled with a fluorescent dye such as Alexa 488 and analyzed with an epifluorescent microscope.

A variety of other protocols, including enzyme-linked immunosorbent assay (ELISA), radio-immunoassay (RIA), and fluorescent-activated cell sorting (FACS), for measuring mutant ROS kinase polypeptides are known in the art and provide a basis for diagnosing altered or abnormal levels of FIG-ROS fusion polypeptide expression. Normal or standard values for FIG-ROS fusion polypeptide expression are established by combining body fluids or cell extracts taken from normal mammalian subjects, preferably human, with antibody to FIG-ROS fusion polypeptide under conditions suitable for complex formation. The amount of standard complex formation may be quantified by various methods, but preferably by photometric means. Quantities of FIG-ROS fusion polypeptide expressed in subject, control, and disease samples from biopsied tissues are compared with the standard values. Deviation between standard and subject values establishes the parameters for diagnosing disease.

Peptide & Nucleotide Assays.

Similarly, AQUA peptides for the detection/quantification of expressed mutant ROS polypeptide in a biological sample comprising cells from a tumor may be prepared and used in standard AQUA assays, as described in detail above. Accordingly, in some embodiments of the methods of the invention, the FIG-ROS fusion polypeptide-specific reagent comprises a heavy isotope labeled phosphopeptide (AQUA peptide) corresponding to a peptide sequence comprising the fusion junction of FIG-ROS fusion polypeptide, as described above.

FIG-ROS fusion polypeptide-specific reagents useful in practicing the methods of the invention may also be mRNA, oligonucleotide or DNA probes that can directly hybridize to, and detect, fusion or truncated polypeptide expression transcripts in a biological sample. Such probes are discussed in detail herein. Briefly, and by way of example, formalin-fixed, paraffin-embedded patient samples may be probed with a fluorescein-labeled RNA probe followed by washes with formamide, SSC and PBS and analysis with a fluorescent microscope.

Polynucleotides encoding mutant ROS kinase polypeptide may also be used for diagnostic purposes. The polynucleotides that may be used include oligonucleotide sequences, antisense RNA and DNA molecules, and PNAs. The polynucleotides may be used to detect and quantitate gene expression in biopsied tissues in which expression of FIG-ROS fusion polypeptide or truncated ROS polypeptide may be correlated with disease. The diagnostic assay may be used to distinguish between absence, presence, and excess expression of FIG-ROS fusion polypeptide, and to monitor regulation of FIG-ROS fusion polypeptide levels during therapeutic intervention.

In one embodiment, hybridization with PCR probes which are capable of detecting polynucleotide sequences, including genomic sequences, encoding FIG-ROS fusion polypeptide or truncated ROS kinase polypeptide or closely related molecules, may be used to identify nucleic acid sequences that encode mutant ROS polypeptide. The construction and use of such probes is described herein. The specificity of the probe, whether it is made from a highly specific region, e.g., 10 unique nucleotides in the fusion junction, or a less specific region, e.g., the 3' coding region, and the stringency of the hybridization or amplification (maximal, high, intermediate, or low) will determine whether the probe identifies only naturally occurring sequences encoding mutant ROS kinase polypeptide, alleles, or related sequences.

Probes may also be used for the detection of related sequences, and should preferably contain at least 50% of the nucleotides from any of the mutant ROS polypeptide encoding sequences. The hybridization probes of the subject invention may be DNA or RNA and derived from the nucleotide sequences of SEQ ID NOs: 2 or SEQ ID NO: 16, most preferably encompassing the fusion junction, or from genomic sequence including promoter, enhancer elements, and introns of the naturally occurring FIG and ROS polypeptides, as further described above.

A FIG-ROS fusion polynucleotide or truncated ROS polynucleotide of the invention may be used in Southern or northern analysis, dot blot, or other membrane-based technologies; in PCR technologies; or in dip stick, pin, ELISA or chip assays utilizing fluids or tissues from patient biopsies to detect altered mutant ROS kinase polypeptide expression. Such qualitative or quantitative methods are well known in the art. In a particular aspect, the nucleotide sequences encoding mutant ROS polypeptide may be useful in assays that detect activation or induction of various cancers, including cancers of the liver, pancreas, kidneys, and testes (as well as cancers that arise in the ducts, such as the bile duct, of these tissues). Mutant ROS polynucleotides may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding FIG-ROS fusion polypeptide or truncated ROS kinase polypeptide in the sample indicates the presence of the associated disease. Such assays may also be used to evaluate the efficacy of a particular therapeutic treatment regimen in animal studies, in clinical trials, or in monitoring the treatment of an individual patient.

Another aspect of the invention provides a method for diagnosing a patient as having a cancer or a suspected cancer driven by a ROS kinase. The method includes contacting a biological sample of said cancer or a suspected cancer (where the biological sample comprising at least one nucleic acid molecule) with a probe that hybridizes under stringent conditions to a nucleic acid molecule selected from the group consisting of a FIG-ROS fusion polynucleotide, a SLC34A2-ROS fusion polypeptide, a CD74-ROS fusion polypeptide, and a truncated ROS polynucleotide, and wherein hybridization of said probe to at least one nucleic acid molecule in said biological sample identifies said patient as having a cancer or a suspected cancer driven by a ROS kinase.

Yet another aspect of the invention provides a method for diagnosing a patient as having a cancer or a suspected cancer driven by a ROS kinase. The method includes contacting a biological sample of said cancer or suspected cancer (where said biological sample comprises at least one polypeptide) with a binding agent that specifically binds to a mutant ROS polypeptide, wherein specific binding of said binding agent to at least one polypeptide in said biological sample identifies said patient as having a cancer or a suspected cancer driven by a ROS kinase.

In order to provide a basis for the diagnosis of disease (e.g., a cancer) characterized by expression of mutant ROS polypeptide (e.g., a FIG-ROS(S) fusion polypeptide), a normal or standard profile for expression is established. This may be accomplished by combining body fluids or cell extracts taken from normal subjects, either animal or human, with a sequence, or a fragment thereof, which encodes FIG-ROS fusion polypeptide or truncated ROS kinase polypeptide, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

Additional diagnostic uses for FIG-ROS fusion polynucleotides and truncated ROS polynucleotides (i.e., either lacking the sequences encoding the extracellular domain of wild-type ROS or lacking the sequences encoding both the extracellular and transmembrane domains of wild-type ROS) of the invention may involve the use of polymerase chain reaction (PCR), another assay format that is standard to those of skill in the art. See, e.g., Molecular Cloning, A Laboratory Manual, 2nd. edition, Sambrook, J., Fritsch, E. F. and Maniatis, T., eds., Cold Spring Harbor Laboratory Press, Cold Spring Harbor, N.Y. (1989). PCR oligomers may be chemically synthesized, generated enzymatically, or produced from a recombinant source. Oligomers will preferably consist of two nucleotide sequences, one with sense orientation (5' to 3') and another with antisense (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of FIG-ROS fusion polypeptide or truncated ROS kinase polypeptide include radiolabeling or biotinylating nucleotides, coamplification of a control nucleic acid, and standard curves onto which the experimental results are interpolated (Melby et al., *J. Immunol. Methods,* 159: 235-244 (1993); Duplaa et al. *Anal. Biochem.* 229-236 (1993)). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the mutant ROS polynucelotides of the invention may be used to generate hybridization probes which are useful for mapping the naturally occurring genomic sequence. The sequences may be mapped to a particular chromosome or to a specific region of the chromosome using well known techniques. Such techniques include fluorescence in-situ hybridization (FISH), FACS, or artificial chromosome constructions, such as yeast artificial chromosomes, bacterial artificial chromosomes, bacterial P1 constructions or single chromosome cDNA libraries, as reviewed in Price, C. M., *Blood Rev.* 7: 127-134 (1993), and Trask, B. J., *Trends Genet.* 7: 149-154 (1991).

In one embodiment, fluorescence in-situ hybridization (FISH) is employed (as described in Verma et al. Human Chromosomes: A Manual of Basic Techniques, Pergamon Press, New York, N.Y. (1988)) and may be correlated with other physical chromosome mapping techniques and genetic map data. The FISH technique is well known (see, e.g., U.S. Pat. Nos. 5,756,696; 5,447,841; 5,776,688; and 5,663,319). Examples of genetic map data can be found in the 1994 Genome Issue of *Science* (265: 1981f). Correlation between the location of the gene encoding FIG-ROS fusion polypeptide or truncated ROS polypeptide on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti et al., *Nature* 336: 577-580 (1988)), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

It shall be understood that all of the methods (e.g., PCR and FISH) that detect mutant ROS polynucleotides (e.g., aberrantly expressed wild-type ROS, FIG-ROS fusion polynucleotides, SLC34A2-ROS fusion polynucleotides, and the CD74-ROS fusionpolynucleotide of the invention) may be combined with other methods that detect either mutant ROS polynucleotides or mutant ROS polypeptides. For example, detection of a FIG-ROS polynucleotide in the genetic material of a biological sample (e.g., FIG-ROS (S) in a circulating tumor cell) may be followed by Western blotting analysis or immuno-histochemistry (IHC) analysis of the proteins of the sample to determine if the FIG-ROS (S) polynucleotide was actually expressed as a FIG-ROS (S) fusion polypeptide in the biological sample. Such Western blotting or IHC analyses may be performed using an antibody that specifically binds to the polypeptide encoded by the detected FIG-ROS (S) polynucleotide, or the analyses may be performed using antibodies that specifically bind either to full length FIG (e.g., bind to the N-terminus of the protein) or to full length ROS (e.g., bind an epitope in the kinase domain of ROS). Such assays are known in the art (see, e.g., U.S. Pat. No. 7,468,252).

In another example, the CISH technology of Dako allows chromatogenic in-situ hybridization with immuno-histochemistry on the same tissue section. See Elliot et al., Br J Biomed Sci 2008; 65(4): 167-171, 2008 for a comparison of CISH and FISH.

As used throughout the specification, the term "biological sample" is used in its broadest sense, and means any biological sample suspected of containing a FIG-ROS fusion polypeptide, a FIG-ROS fusion polynucleotide, a truncated ROS polynucleotide, a truncated ROS polypeptide (i.e., either lacking the sequences encoding the extracellular domain of wild-type ROS or lacking the sequences encoding both the extracellular and transmembrane domains of wild-type, full-length ROS), a truncated ROS polynucleotide, or a fragment thereof, and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells, blood, urine, marrow, or a tissue, and the like.

Biological samples useful in the practice of the methods of the invention may be obtained from any mammal in which a cancer characterized by the presence of a FIG-ROS fusion polypeptide is or might be present or developing. As used herein, the phrase "characterized by" with respect to a cancer and indicated molecule (e.g., a ROS fusion or a mutant ROS) is meant a cancer in which a gene translocation or mutation (e.g., causing overexpression of wild-type ROS) and/or an expressed polypeptide (e.g., a FIG-ROS fusion polypeptide) is present, as compared to a cancer or a normal tissue in which such translocation, overexpression of wild-type ROS, and/or fusion polypeptide are not present. The presence of such translocation, overexpression of wild-type ROS, and/or fusion polypeptide may drive (i.e., stimulate or be the causative agent of), in whole or in part, the growth and survival of such cancer or suspected cancer.

In one embodiment, the mammal is a human, and the human may be a candidate for a ROS-inhibiting therapeutic, for the treatment of a cancer, e.g., a liver, pancreatic, kidney, or testicular cancer. The human candidate may be a patient currently being treated with, or considered for treatment with, a ROS kinase inhibitor. In another embodiment, the mammal is large animal, such as a horse or cow, while in other embodiments, the mammal is a small animal, such as a dog or cat, all of which are known to develop cancers, including liver, kidney, testicular, and pancreatic cancers.

Any biological sample comprising cells (or extracts of cells) from a mammalian cancer is suitable for use in the methods of the invention. In one embodiment, the biological sample comprises cells obtained from a tumor biopsy. The biopsy may be obtained, according to standard clinical techniques, from primary tumors occurring in an organ of a mammal, or by secondary tumors that have metastasized in other tissues. In another embodiment, the biological sample comprises cells obtained from a fine needle aspirate taken from a tumor, and techniques for obtaining such aspirates are well known in the art (see Cristallini et al., *Acta Cytol.* 36(3): 416-22 (1992)).

In some embodiments, the biological sample comprises circulating tumor cells. Circulating tumor cells ("CTCs") may be purified, for example, using the kits and reagents sold under the trademarks Vita-Assays™, Vita-Cap™, and CellSearch® (commercially available from Vitatex, LLC (a Johnson and Johnson corporation). Other methods for isolating CTCs are described (see, for example, PCT Publication No. WO/2002/020825, Cristofanilli et al., New Engl. J. of Med. 351 (8):781-791 (2004), and Adams et al., J. Amer. Chem. Soc. 130(27): 8633-8641 (July 2008)). In a particular embodiment, a circulating tumor cell ("CTC") may be isolated and identified as having originated from the lung.

Accordingly, the invention provides a method for isolating a CTC, and then screening the CTC one or more assay formats to identify the presence of a mutant ROS polypeptide or polynucleotide of the invention (e.g., a FIG-ROS fusion polypeptide or polynucleotide) in the CTC. Some non-limiting assay formats include Western blotting analysis, flow-cytometry (FC), immuno-histochemistry (IHC), immuno-fluorescence (IF), fluorescence in situ hybridization (FISH) and polymerase chain reaction (PCR). A CTC from a patient that is identified as comprising a mutant ROS polypeptide or polynucleotide of the invention (e.g., a FIG-ROS fusion polypeptide or polynucleotide) may indicate that the patient's originating cancer (e.g., a lung cancer such as a non-small cell lung cancer) is likely to respond to a composition comprising at least one ROS kinase-inhibiting therapeutic.

A biological sample may comprise cells (or cell extracts) from a cancer in which FIG-ROS fusion polypeptide or mutant ROS polypeptide (e.g., lacking the extracellular and transmembrane domains) is expressed and/or activated but wild type ROS kinase is not. Alternatively, the sample may comprise cells from a cancer in which both a mutant ROS fusion polypeptide and a wild type ROS kinase are expressed and/or activated, or in which wild type ROS kinase is expressed and/or active, but ROS fusion polypeptide is not.

Cellular extracts of the foregoing biological samples may be prepared, either crude or partially (or entirely) purified, in accordance with standard techniques, and used in the methods of the invention. Alternatively, biological samples comprising whole cells may be utilized in assay formats such as immunohistochemistry (IHC), flow cytometry (FC), and immunofluorescence (IF), as further described above. Such whole-cell assays are advantageous in that they minimize manipulation of the tumor cell sample and thus reduce the risks of altering the in vivo signaling/activation state of the cells and/or introducing artifact signals. Whole cell assays are also advantageous because they characterize expression and signaling only in tumor cells, rather than a mixture of tumor and normal cells.

In practicing the disclosed method for determining whether a compound inhibits progression of a tumor characterized by a FIG-ROS translocation and/or fusion polypeptide, biological samples comprising cells from mammalian xenografts (or bone marrow transplants) may also be advantageously employed. Non-limiting xenografts (or transplant recipients) are small mammals, such as mice, harboring human tumors (or leukemias) that express a FIG-ROS fusion polypeptide (or a mutant ROS kinase containing the kinase domain but lacking the transmembrane and extracellular domains). Xenografts harboring human tumors are well known in the art (see Kal, *Cancer Treat Res.* 72: 155-69 (1995)) and the production of mammalian xenografts harboring human tumors is well described (see Winograd et al., *In Vivo.* 1(1): 1-13 (1987)). Similarly the generation and use of bone marrow transplant models is well described (see, e.g., Schwaller, et al., *EMBO J.* 17: 5321-333 (1998); Kelly et al., *Blood* 99: 310-318 (2002)).

In assessing mutant ROS polynucleotide presence or mutant ROS polypeptide expression in a biological sample comprising cells from a mammalian cancer tumor, a control sample representing a cell in which such translocation and/or fusion protein do not occur may desirably be employed for comparative purposes. Ideally, the control sample comprises cells from a subset of the particular cancer (e.g., bile duct liver cancer) that is representative of the subset in which the mutation (e.g., FIG-ROS translocation) does not occur and/or the fusion polypeptide is not expressed. Comparing the level in the control sample versus the test biological sample thus identifies whether the mutant polynucleotide and/or polypeptide is/are present. Alternatively, since FIG-ROS fusion polynucleotide and/or polypeptide may not be present in the majority of cancers, any tissue that similarly does not express mutant ROS polypeptide (or harbor the mutant polynucleotide) may be employed as a control.

The methods described below will have valuable diagnostic utility for cancers characterized by mutant ROS polynucleotide and/or polypeptide, and treatment decisions pertaining to the same. For example, biological samples may be obtained from a subject that has not been previously diagnosed as having a cancer characterized by since a FIG-ROS translocation and/or fusion polypeptide, nor has yet undergone treatment for such cancer, and the method is employed to diagnostically identify a tumor in such subject as belonging to a subset of tumors (e.g., a bile duct tumor) in which mutant ROS polynucleotide and/or polypeptide is present/expressed.

Alternatively, a biological sample may be obtained from a subject that has been diagnosed as having a cancer characterized by the presence of one type of kinase, such as EFGR, and has been receiving therapy, such as EGFR inhibitor therapy (e.g., Tarceva™, Iressa™) for treatment of such cancer, and the method of the invention is employed to identify whether the subject's tumor is also characterized by a FIG-ROS translocation and/or fusion polypeptide, and is therefore likely to fully respond to the existing therapy and/or whether alternative or additional ROS-inhibiting therapy is desirable or warranted. The methods of the invention may also be employed to monitor the progression or inhibition of a mutant ROS polypeptide-expressing cancer following treatment of a subject with a composition comprising a ROS-inhibiting therapeutic or combination of therapeutics.

Such diagnostic assay may be carried out subsequent to or prior to preliminary evaluation or surgical surveillance procedures. The identification method of the invention may be advantageously employed as a diagnostic to identify patients having cancer, such as bile duct liver cancer, characterized by the presence of the FIG-ROS fusion protein, which patients would be most likely to respond to therapeutics targeted at inhibiting ROS kinase activity. The ability to select such patients would also be useful in the clinical evaluation of efficacy of future ROS-targeted therapeutics as well as in the future prescription of such drugs to patients.

The ability to selectively identify cancers in which a FIG-ROS translocation and/or fusion polypeptide is/are present enables important new methods for accurately identifying such tumors for diagnostic purposes, as well as obtaining information useful in determining whether such a tumor is likely to respond to a ROS-inhibiting therapeutic composition, or likely to be partially or wholly non-responsive to an inhibitor targeting a different kinase when administered as a single agent for the treatment of the cancer.

Accordingly, in one embodiment, the invention provides a method for detecting the presence of a mutant ROS polynucleotide and/or polypeptide in a cancer, the method comprising the steps of: (a) obtaining a biological sample from a patient having cancer; and (b) utilizing at least one reagent that detects a mutant ROS polynucleotide or polypeptide of the invention to determine whether a FIG-ROS fusion polynucleotide and/or polypeptide is/are present in the biological sample.

In some embodiments, the cancer is a liver cancer, such as bile duct liver cancer. In some embodiments, the cancer is a pancreatic cancer, a kidney cancer, or a testicular cancer. In other embodiments, the presence of a FIG-ROS fusion polypeptide identifies a cancer that is likely to respond to a composition or therapeutic comprising at least one ROS-inhibiting compound.

In some embodiments, the diagnostic methods of the invention are implemented in a flow-cytometry (FC), immuno-histochemistry (IHC), or immuno-fluorescence (IF) assay format. In another embodiment, the activity of the FIG-ROS fusion polypeptide is detected. In other embodiments, the diagnostic methods of the invention are implemented in a fluorescence in situ hybridization (FISH) or polymerase chain reaction (PCR) assay format.

The invention further provides a method for determining whether a compound inhibits the progression of a cancer characterized by a FIG-ROS fusion polynucleotide or polypeptide, said method comprising the step of determining whether said compound inhibits the expression and/or activity of said FIG-ROS fusion in said cancer. In one embodiment, inhibition of expression and/or activity of the FIG-ROS fusion polypeptide is determined using at least one reagent that detects an FIG-ROS fusion polynucleotide or polypeptide of the invention. Compounds suitable for inhibition of ROS kinase activity are discussed in more detail herein.

Mutant ROS polynucleotide probes and polypeptide-specific reagents useful in the practice of the methods of the invention are described in further detail above. In one embodiment, the FIG-ROS fusion polypeptide-specific reagent comprises a fusion polypeptide-specific antibody. In another embodiment, the fusion polypeptide-specific reagent comprises a heavy-isotope labeled phosphopeptide (AQUA peptide) corresponding to the fusion junction of FIG-ROS fusion polypeptide The methods of the invention described above may also optionally comprise the step of determining the level of expression or activation of other kinases, such as wild type ROS and EGFR, or other downstream signaling molecules in said biological sample. Profiling both FIG-ROS fusion polypeptide expression/activation and expression/activation of other kinases and pathways in a given biological sample can provide valuable information on which kinase(s) and pathway(s) is/are driving the disease, and which therapeutic regime is therefore likely to be of most benefit.

The discovery of the mutant ROS polypeptides (e.g., the FIG-ROS fusion polypeptides) in human cancer also enables the development of new compounds that inhibit the activity of these mutant ROS proteins, particularly their ROS kinase activity. Accordingly, the invention also provides, in part, a method for determining whether a compound inhibits the progression of a cancer characterized by a FIG-ROS fusion polynucleotide and/or polypeptide, said method comprising the step of determining whether said compound inhibits the expression and/or activity of said FIG-ROS fusion polypeptide in said cancer. In one embodiment, inhibition of expression and/or activity of the FIG-ROS fusion polypeptide is determined using at least one reagent that detects a FIG-ROS fusion polynucleotide and/or FIG-ROS fusion polypeptide of the invention. Non-limiting examples of such reagents of the invention have been described above. Compounds suitable for the inhibition of ROS kinase activity are described in more detail below.

As used herein, a "ROS inhibitor" or a "ROS-inhibiting compound" means any composition comprising one or more compounds, chemical or biological, which inhibits, either directly or indirectly, the expression and/or activity of either wild type (full length) ROS or the kinase domain of ROS, either alone and/or as part of the FIG-ROS fusion polypeptides of the invention. Such inhibition may be in vitro or in vivo. "ROS inhibitor therapeutic" or "ROS-inhibiting therapeutic" means a ROS-inhibiting compound used as a therapeutic to treat a patient harboring a cancer (e.g., a liver, testicular, kidney, or pancreatic cancer) characterized by the presence of a FIG-ROS fusion polypeptide of the invention.

In some embodiments of the invention, the ROS inhibitor is a binding agent that specifically binds to a FIG-ROS fusion polypeptide, a binding agent that specifically binds to a mutant ROS polypeptide, an siRNA targeting a FIG-ROS fusion polynucleotide (e.g., a FIG-ROS(S) fusion polynucleotide), or an siRNA targeting a mutant ROS polynucleotide.

The ROS-inhibiting compound may be, for example, a kinase inhibitor, such as a small molecule or antibody inhibitor. It may be a pan-kinase inhibitor with activity against several different kinases, or a kinase-specific inhibitor. Since ROS, ALK, LTK, InsR, and IGF1R belong to the same family of tyrosine kinases, they may share similar structure in the kinase domain. Thus, in some embodiments, a ROS inhibitor of the invention also inhibits the activity of an ALK kinase an LTK kinase, an insulin receptor, or an IGF1 receptor. ROS-inhibiting compounds are discussed in further detail below. Patient biological samples may be taken before and after treatment with the inhibitor and then analyzed, using methods described above, for the biological effect of the inhibitor on ROS kinase activity, including the phosphorylation of downstream substrate protein. Such a pharmacodynamic assay may be useful in determining the biologically active dose of the drug that may be preferable to a maximal tolerable dose. Such information would also be useful in submissions for drug approval by demonstrating the mechanism of drug action.

In accordance with the present invention, the FIG-ROS fusion polypeptide may occur in at least one subgroup of human liver, pancreatic, kidney, or testicular cancer. Accordingly, the progression of a mammalian cancer (e.g., liver, pancreatic, kidney, or testicular cancer) in which FIG-ROS fusion protein is expressed may be inhibited, in vivo, by inhibiting the activity of ROS kinase in such cancer. ROS activity in cancers characterized by expression of a FIG-ROS fusion polypeptide (or a mutant ROS polypeptide comprising only the kinase domain) may be inhibited by contacting the cancer (e.g., a tumor) with a ROS-inhibiting therapeutic. Accordingly, the invention provides, in part, a method for inhibiting the progression of a FIG-ROS fusion polypeptide-expressing cancer by inhibiting the expression and/or activity of ROS kinase in the cancer.

A ROS-inhibiting therapeutic may be any composition comprising at least one ROS inhibitor. Such compositions also include compositions comprising only a single ROS-inhibiting compound, as well as compositions comprising multiple therapeutics (including those against other RTKs), which may also include a non-specific therapeutic agent like a chemotherapeutic agent or general transcription inhibitor.

In some embodiments, a ROS-inhibiting therapeutic useful in the practice of the methods of the invention is a targeted, small molecule inhibitor. Small molecule targeted inhibitors are a class of molecules that typically inhibit the activity of their target enzyme by specifically, and often irreversibly, binding to the catalytic site of the enzyme, and/or binding to an ATP-binding cleft or other binding site within the enzyme that prevents the enzyme from adopting a conformation necessary for its activity. An exemplary small-molecule targeted kinase inhibitor is Gleevec® (Imatinib, STI-571), which inhibits CSF1R and BCR-ABL, and its properties have been well described. See Dewar et al., *Blood* 105(8): 3127-32 (2005). Additional small molecule kinase inhibitors that may target ROS include TAE-684 (see examples below) and PF-02341066 (Pfizer, Inc).

PF-02341066 has the structure:

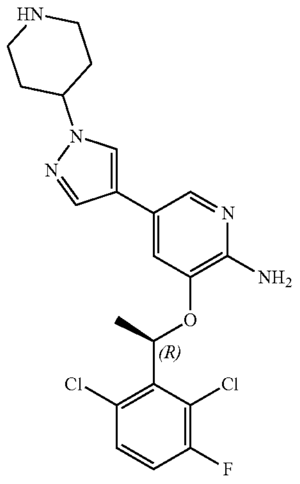

Additional small molecule inhibitors and other inhibitors (e.g., indirect inhibitors) of ROS kinase activity may be rationally designed using X-ray crystallographic or computer modeling of ROS three dimensional structure, or may found by high throughput screening of compound libraries for inhibition of key upstream regulatory enzymes and/or necessary binding molecules, which results in inhibition of ROS kinase activity. Such approaches are well known in the art, and have been described. ROS inhibition by such therapeutics may be confirmed, for example, by examining the ability of the compound to inhibit ROS activity, but not other kinase activity, in a panel of kinases, and/or by examining the inhibition of ROS activity in a biological sample comprising cancer cells (e.g., liver, pancreatic, kidney, or testicular al cancer). Methods for identifying compounds that inhibit a cancer characterized by the expression/presence of a FIG-ROS translocation and/or fusion polypeptide, and/or mutant ROS polynucleotide and/or polypeptide, are further described below.

ROS-inhibiting therapeutics useful in the methods of the invention may also be targeted antibodies that specifically bind to critical catalytic or binding sites or domains required for ROS activity, and inhibit the kinase by blocking access of ligands, substrates or secondary molecules to α and/or preventing the enzyme from adopting a conformation necessary for its activity. The production, screening, and therapeutic use of humanized target-specific antibodies has been well-described. See Merluzzi et al., *Adv Clin Path.* 4(2): 77-85 (2000). Commercial technologies and systems, such as Morphosys, Inc.'s Human Combinatorial Antibody Library (HuCAL®), for the high-throughput generation and screening of humanized target-specific inhibiting antibodies are available.

The production of various anti-receptor kinase targeted antibodies and their use to inhibit activity of the targeted receptor has been described. See, e.g. U.S. Patent Publication No. 20040202655, U.S. Patent Publication No. 20040086503, U.S. Patent Publication No. 20040033543, Standardized methods for producing, and using, receptor tyrosine kinase activity-inhibiting antibodies are known in the art. See, e.g., European Patent No. EP1423428, Phage display approaches may also be employed to generate ROS-specific antibody inhibitors, and protocols for bacteriophage library construction and selection of recombinant antibodies are provided in the well-known reference text Current Protocols in Immunology, Colligan et al. (Eds.), John Wiley & Sons, Inc. (1992-2000), Chapter 17, Section 17.1. See also U.S. Pat. No. 6,319,690, U.S. Pat. No. 6,300,064, U.S. Pat. No. 5,840,479, and U.S. Patent Publication No. 20030219839.

A library of antibody fragments displayed on the surface of bacteriophages may be produced (see, e.g. U.S. Pat. No. 6,300,064) and screened for binding to a FIG-ROS fusion protein of the invention. An antibody fragment that binds to a FIG-ROS fusion polypeptide is identified as a candidate molecule for blocking constitutive activation of the FIG-ROS fusion polypeptide in a cell. See European Patent No. EP1423428.

ROS-binding targeted antibodies identified in screening of antibody libraries as describe above may then be further screened for their ability to block the activity of ROS, both in vitro kinase assay and in vivo in cell lines and/or tumors. ROS inhibition may be confirmed, for example, by examining the ability of such antibody therapeutic to inhibit ROS kinase activity in a panel of kinases, and/or by examining the inhibition of ROS activity in a biological sample comprising cancer cells, as described above. In some embodiments, a ROS-inhibiting compound of the invention reduces ROS kinase activity, but reduces the kinase activity of other kinases to a lesser extent (or not at all). Methods for screening such compounds for ROS kinase inhibition are further described above.

ROS-inhibiting compounds that useful in the practice of the disclosed methods may also be compounds that indirectly inhibit ROS activity by inhibiting the activity of proteins or molecules other than ROS kinase itself. Such inhibiting therapeutics may be targeted inhibitors that modulate the activity of key regulatory kinases that phosphorylate or de-phosphorylate (and hence activate or deactivate) ROS itself, or interfere with binding of ligands. As with other receptor tyrosine kinases, ROS regulates downstream signaling through a network of adaptor proteins and downstream kinases. As a result, induction of cell growth and survival by ROS activity may be inhibited by targeting these interacting or downstream proteins.

ROS kinase activity may also be indirectly inhibited by using a compound that inhibits the binding of an activating molecule necessary for ROS to adopt its active conformation. For example, the production and use of anti-PDGF antibodies has been described. See U.S. Patent Publication No. 20030219839, "Anti-PDGF Antibodies and Methods for Producing Engineered Antibodies," Bowdish et al. Inhibition of ligand (PDGF) binding to the receptor directly down-regulates the receptor activity.

ROS inhibiting compounds or therapeutics may also comprise anti-sense and/or transcription inhibiting compounds that inhibit ROS kinase activity by blocking transcription of the gene encoding ROS and/or the FIG-ROS fusion gene. The inhibition of various receptor kinases, including VEGFR, EGFR, and IGFR, and FGFR, by antisense therapeutics for the treatment of cancer has been described. See, e.g., U.S. Pat. Nos. 6,734,017; 6, 710,174, 6,617,162; 6,340,674; 5,783,683; 5,610,288.

Antisense oligonucleotides may be designed, constructed, and employed as therapeutic agents against target genes in accordance with known techniques. See, e.g. Cohen, J., *Trends in Pharmacol. Sci.* 10(11): 435-437 (1989); Marcus-Sekura, *Anal. Biochem.* 172: 289-295 (1988); Weintraub, H., *Sci. AM.* pp. 40-46 (1990); Van Der Krol et al., *BioTechniques* 6(10): 958-976 (1988); Skorski et al., *Proc. Natl. Acad. Sci. USA* (1994) 91: 4504-4508. Inhibition of human carcinoma growth in vivo using an antisense RNA inhibitor of EGFR has recently been described. See U.S. Patent Publication No. 20040047847. Similarly, a ROS-inhibiting therapeutic comprising at least one antisense oligonucleotide against a mammalian ROS gene or FIG-ROS fusion polynucleotide or mutant ROS polynucleotide may be prepared according to methods described above. Pharmaceutical compositions comprising ROS-inhibiting antisense compounds may be prepared and administered as further described below.

Small interfering RNA molecule (siRNA) compositions, which inhibit translation, and hence activity, of ROS through the process of RNA interference, may also be desirably employed in the methods of the invention. RNA interference, and the selective silencing of target protein expression by introduction of exogenous small double-stranded RNA molecules comprising sequence complimentary to mRNA encoding the target protein, has been well described. See, e.g. U.S. Patent Publication No. 20040038921, U.S. Patent Publication No. 20020086356, and U.S. Patent Publication 20040229266.

Double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (see Hammond et al., *Nature* (2000) 404: 293-296). RNAi involves a catalytic-type reaction whereby new siRNAs are generated through successive cleavage of longer dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

A wide variety of target-specific siRNA products, including vectors and systems for their expression and use in mammalian cells, are now commercially available. See, e.g., Promega, Inc. (www.promega.com); Dharmacon, Inc. (www.dharmacon.com). Detailed technical manuals on the design, construction, and use of dsRNA for RNAi are available. See, e.g., Dharmacon's "RNAi Technical Reference & Application Guide"; Promega's "RNAi: A Guide to Gene Silencing." ROS-inhibiting siRNA products are also commercially available, and may be suitably employed in the method of the invention. See, e.g., Dharmacon, Inc., Lafayette, Colo. (Cat Nos. M-003162-03, MU-003162-03, D-003162-07 thru-10 (siGENOME™ SMARTselection and SMARTpool® siRNAs).

It has recently been established that small dsRNA less than 49 nucleotides in length, and preferably 19-25 nucleotides, comprising at least one sequence that is substantially identical to part of a target mRNA sequence, and which dsRNA optimally has at least one overhang of 1-4 nucleotides at an end, are most effective in mediating RNAi in mammals. See U.S. Patent Publication Nos. 20040038921 and 20040229266. The construction of such dsRNA, and their use in pharmaceutical preparations to silence expression of a target protein, in vivo, are described in detail in such publications.

If the sequence of the gene to be targeted in a mammal is known, 21-23 nt RNAs, for example, can be produced and tested for their ability to mediate RNAi in a mammalian cell, such as a human or other primate cell. Those 21-23 nt RNA molecules shown to mediate RNAi can be tested, if desired, in an appropriate animal model to further assess their in vivo effectiveness. Target sites that are known, for example target sites determined to be effective target sites based on studies with other nucleic acid molecules, for example ribozymes or antisense, or those targets known to be associated with a disease or condition such as those sites containing mutations or deletions, can be used to design siRNA molecules targeting those sites as well.

Alternatively, the sequences of effective dsRNA can be rationally designed/predicted screening the target mRNA of interest for target sites, for example by using a computer folding algorithm. The target sequence can be parsed in silico into a list of all fragments or subsequences of a particular length, for example 23 nucleotide fragments, using a custom Perl script or commercial sequence analysis programs such as Oligo, MacVector, or the GCG Wisconsin Package.

Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siRNA molecules for efficacy, for example by using in vitro RNA cleavage assays, cell culture, or animal models. See, e.g., U.S. Patent Publication No. 20030170891. An algorithm for identifying and selecting RNAi target sites has also recently been described. See U.S. Patent Publication No. 20040236517.

Commonly used gene transfer techniques include calcium phosphate, DEAE-dextran, electroporation and microinjection and viral methods (Graham et al. (1973) *Virol.* 52: 456; McCutchan et al., (1968), *J. Natl. Cancer Inst.* 41: 351; Chu et al. (1987), *Nucl. Acids Res.* 15: 1311; Fraley et al. (1980), *J. Biol. Chem.* 255: 10431; Capecchi (1980), *Cell* 22: 479). DNA may also be introduced into cells using cationic liposomes (Feigner et al. (1987), *Proc. Natl. Acad. Sci USA* 84: 7413). Commercially available cationic lipid formulations include Tfx 50 (Promega) or Lipofectamin 200 (Life Technologies). Alternatively, viral vectors may be employed to deliver dsRNA to a cell and mediate RNAi. See U.S. Patent Publication No. 20040023390.

Transfection and vector/expression systems for RNAi in mammalian cells are commercially available and have been well described. See, e.g., Dharmacon, Inc., DharmaFECT™ system; Promega, Inc., siSTRIKE™ U6 Hairpin system; see also Gou et al. (2003) *FEBS.* 548, 113-118; Sui, G. et al. A DNA vector-based RNAi technology to suppress gene expression in mammalian cells (2002) *Proc. Natl. Acad. Sci.* 99, 5515-5520; Yu et al. (2002) *Proc. Natl. Acad. Sci.* 99, 6047-6052; Paul, C. et al. (2002) *Nature Biotechnology* 19, 505-508; McManus et al. (2002) *RNA* 8, 842-850.

siRNA interference in a mammal using prepared dsRNA molecules may then be effected by administering a pharmaceutical preparation comprising the dsRNA to the mammal. The pharmaceutical composition is administered in a dosage sufficient to inhibit expression of the target gene. dsRNA can typically be administered at a dosage of less than 5 mg dsRNA per kilogram body weight per day, and is sufficient to inhibit or completely suppress expression of the target gene. In general a suitable dose of dsRNA will be in the range of 0.01 to 2.5 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. A pharmaceutical composition comprising the dsRNA is administered once daily, or in multiple sub-doses, for example, using sustained release formulations well known in the art. The preparation and administration of such pharmaceutical compositions may be carried out accordingly to standard techniques, as further described below.

Such dsRNA may then be used to inhibit ROS expression and activity in a cancer, by preparing a pharmaceutical preparation comprising a therapeutically-effective amount of such dsRNA, as described above, and administering the preparation to a human subject having a cancer (e.g., a liver, pancreatic, kidney, or testicular cancer) expressing FIG-ROS fusion protein or mutnat ROS polypeptide, for example, via direct injection to the tumor. The similar inhibition of other receptor tyrosine kinases, such as VEGFR and EGFR using siRNA inhibitors has recently been described. See U.S. Patent Publication No. 20040209832, U.S. Patent Publication No. 20030170891, and U.S. Patent Publication No. 20040175703.

ROS-inhibiting therapeutic compositions useful in the practice of the methods of the invention may be administered to a mammal by any means known in the art including, but not limited to oral or peritoneal routes, including intravenous, intramuscular, intraperitoneal, subcutaneous, transdermal, airway (aerosol), rectal, vaginal and topical (including buccal and sublingual) administration.

For oral administration, a ROS-inhibiting therapeutic will generally be provided in the form of tablets or capsules, as a powder or granules, or as an aqueous solution or suspension. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil. For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. The carrier may consist exclusively of an aqueous buffer ("exclusively" means no auxiliary agents or encapsulating substances are present which might affect or mediate uptake of the ROS-inhibiting therapeutic). Such substances include, for example, micellar structures, such as liposomes or capsids, as described below. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

ROS-inhibiting therapeutic compositions may also include encapsulated formulations to protect the therapeutic (e.g., a dsRNA compound or an antibody that specifically binds a FIG-ROS fusion polypeptide) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075. An encapsulated formulation may comprise a viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

ROS-inhibiting compounds can also comprise a delivery vehicle, including liposomes, for administration to a subject, carriers and diluents and their salts, and/or can be present in pharmaceutically acceptable formulations. For example, methods for the delivery of nucleic acid molecules are described in Akhtar et al., 1992, *Trends Cell Bio.,* 2, 139; Delivery Strategies for Antisense Oligonucleotide Therapeutics, ed. Akbtar, 1995, Maurer et al., 1999, *Mol. Membr. Biol.,* 16, 129-140; Hofland and Huang, 1999, *Handb. Exp.*

Pharmacol., 137, 165-192; and Lee et al., 2000, *ACS Symp. Ser.,* 752, 184-192. U.S. Pat. No. 6,395,713 and PCT Publication No. WO 94/02595 further describe the general methods for delivery of nucleic acid molecules. These protocols can be utilized for the delivery of virtually any nucleic acid molecule.

ROS-inhibiting therapeutics (i.e., a ROS-inhibiting compound being administered as a therapeutic) can be administered to a mammalian tumor by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (see PCT Publication No. WO 00/53722). Alternatively, the therapeutic/vehicle combination is locally delivered by direct injection or by use of an infusion pump. Direct injection of the composition, whether subcutaneous, intramuscular, or intradermal, can take place using standard needle and syringe methodologies, or by needle-free technologies such as those described in Conry et al., 1999, *Clin. Cancer Res.,* 5, 2330-2337 and PCT Publication No. WO 99/3 1262.

Pharmaceutically acceptable formulations of ROS-inhibitor therapeutics include salts of the above described compounds, e.g., acid addition salts, for example, salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, for example oral, transdermal, or by injection. Such forms should not prevent the composition or formulation from reaching a target cell. For example, pharmacological compositions injected into the blood stream should be soluble. Other factors are known in the art, and include considerations such as toxicity and forms that prevent the composition or formulation from exerting its effect.

Administration routes that lead to systemic absorption (e.g., systemic absorption or accumulation of drugs in the blood stream followed by distribution throughout the entire body), are desirable and include, without limitation: intravenous, subcutaneous, intraperitoneal, inhalation, oral, intrapulmonary and intramuscular. Each of these administration routes exposes the ROS-inhibiting therapeutic to an accessible diseased tissue or tumor. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant, a composition or formulation that allows for the effective distribution of the nucleic acid molecules of the instant invention in the physical location most suitable for their desired activity. Nonlimiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, *Fundam. Clin. Pharmacol.,* 13, 16-26); biodegradable polymers, such as poly (DL-lactide-coglycolide) microspheres for sustained release delivery after intracerebral implantation (Emerich et al, 1999, *Cell Transplant,* 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (*Prog Neuro-psychopharmacol Biol Psychiatry,* 23, 941-949, 1999). Other non-limiting examples of delivery strategies for the ROS-inhibiting compounds useful in the method of the invention include material described in Boado et al., 1998, *J. Pharm. Sci.,* 87, 1308-1315; Tyler et al., 1999, *FEBS Lett.,* 421, 280-284; Pardridge et al., 1995, *PNAS USA.,* 92, 5592-5596; Boado, 1995, *Adv. Drug Delivery Rev.,* 15, 73-107; Aldrian-Herrada et al., 1998, *Nucleic Acids Res.,* 26, 4910-4916; and Tyler et al., 1999, *PNAS USA.,* 96, 7053-7058.

Therapeutic compositions comprising surface-modified liposomes containing poly (ethylene glycol) lipids (PEG-modified, or long-circulating liposomes or stealth liposomes) may also be suitably employed in the methods of the invention. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., *Science* 1995, 267, 1275-1276; Oku et al., 1995, *Biochim. Biophys. Acta,* 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; PCT Publication No. WO 96/10391; PCT Publication No. WO 96/10390; and PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

Therapeutic compositions may include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

A ROS-inhibiting therapeutic useful in the practice of the invention may comprise a single compound as described above, or a combination of multiple compounds, whether in the same class of inhibitor (e.g., antibody inhibitor), or in different classes (e.g., antibody inhibitors and small-molecule inhibitors). Such combination of compounds may increase the overall therapeutic effect in inhibiting the progression of a fusion protein-expressing cancer. For example, the therapeutic composition may a small molecule inhibitor, such as STI-571 (Gleevec®) alone, or in combination with other Gleevec® analogues targeting ROS activity and/or small molecule inhibitors of EGFR, such as Tarceva™ or Iressa™. The therapeutic composition may also comprise one or more non-specific chemotherapeutic agent in addition to one or more targeted inhibitors. Such combinations have recently been shown to provide a synergistic tumor killing effect in many cancers. The effectiveness of such combinations in inhibiting ROS activity and tumor growth in vivo can be assessed as described below.

The invention also provides, in part, a method for determining whether a compound inhibits the progression of a cancer (e.g., a liver, pancreatic, kidney, or testicular cancer) characterized by a FIG-ROS translocation and/or fusion polypeptide or characterized by a mutant ROS polynucleotide or polypeptide, by determining whether the compound inhibits the ROS kinase activity of the mutant ROS polypeptide in the cancer. In some embodiments, inhibition of activity of ROS is determined by examining a biological sample comprising cells from bone marrow, blood, or a tumor. In another embodiment, inhibition of activity of ROS is determined using at least one mutant ROS polynucleotide or polypeptide-specific reagent of the invention.

The tested compound may be any type of therapeutic or composition as described above. Methods for assessing the efficacy of a compound, both in vitro and in vivo, are well established and known in the art. For example, a composition may be tested for ability to inhibit ROS in vitro using a cell or cell extract in which ROS kinase is activated. A panel of compounds may be employed to test the specificity of the compound for ROS (as opposed to other targets, such as EGFR or PDGFR).

Another technique for drug screening which may be used provides for high throughput screening of compounds having suitable binding affinity to a protein of interest, as described in PCT Publication No. WO 84/03564. In this method, as applied to FIG-ROS fusion polypeptides of the invention, large numbers of different small test compounds are synthesized on a solid substrate, such as plastic pins or some other surface. The test compounds are reacted with the FIG-ROS fusion polypeptide, or fragments thereof, and washed. Bound polypeptide (e.g. FIG-ROS(L), FIG-ROS (XL), or FIG-ROS(S) fusion polypeptide) is then detected by methods well known in the art. A purified FIG-ROS fusion polypeptide can also be coated directly onto plates for use in the aforementioned drug screening techniques. Alternatively, non-neutralizing antibodies can be used to capture the peptide and immobilize it on a solid support.

A compound found to be an effective inhibitor of ROS activity in vitro may then be examined for its ability to inhibit the progression of a cancer expressing FIG-ROS fusion polypeptide (such as a liver cancer, testicular cancer, kidney cancer, or a pancreatic cancer), in vivo, using, for example, mammalian xenografts harboring human liver, pancreatic, kidney, or testicular tumors (e.g., bile duct cancers) that are express a FIG-ROS fusion polypeptide. In this procedure, cancer cell lines known to express a FIG-ROS fusion protein (e.g., a FIG-ROS(S), FIG-ROS(XL), or a FIG-ROS(L)) may be placed subcutaneously in an animal (e.g., into a nude or SCID mouse, or other immune-compromised animal). The cells then grow into a tumor mass that may be visually monitored. The animal may then be treated with the drug. The effect of the drug treatment on tumor size may be externally observed. The animal is then sacrificed and the tumor removed for analysis by IHC and Western blot. Similarly, mammalian bone marrow transplants may be prepared, by standard methods, to examine drug response in hematological tumors expressing a mutant ROS kinase. In this way, the effects of the drug may be observed in a biological setting most closely resembling a patient. The drug's ability to alter signaling in the tumor cells or surrounding stromal cells may be determined by analysis with phosphorylation-specific antibodies. The drug's effectiveness in inducing cell death or inhibition of cell proliferation may also be observed by analysis with apoptosis specific markers such as cleaved caspase 3 and cleaved PARP.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, the compounds exhibit high therapeutic indices.

The following Examples are provided only to further illustrate the invention, and are not intended to limit its scope, except as provided in the claims appended hereto. The present invention encompasses modifications and variations of the methods taught herein which would be obvious to one of ordinary skill in the art. Materials, reagents and the like to which reference is made are obtainable from commercial sources, unless otherwise noted.

Example 1

Identification of ROS Kinase Activity in Liver Cancer Patients by Global Phosphopeptide Profiling The global phosphorylation profile of kinase activation in several human liver cancer patients, including patients XY3-

78T and 090665LC, were examined using a recently described and powerful technique for the isolation and mass spectrometric characterization of modified peptides from complex mixtures (the "IAP" technique, see U.S. Patent Publication No. 20030044848, Rush et al., "Immunoaffinity Isolation of Modified Peptides from Complex Mixtures"). The IAP technique was performed using a phosphotyrosine-specific antibody (Cell Signaling Technology, Inc., Danvers, Mass., 2003/04 Cat. #9411) to isolate, and subsequently characterize, phosphotyrosine-containing peptides from extracts of liver cancer cells taken from 23 human patients and para-tumor tissues.

Liver Cancer Cell Samples

Liver tumors (n=23) were collected from surgical resections from patients when sufficient material for PhosphoScan analysis, RNA, and DNA extractions were available. According to the Edmondson grading system, all tumor samples have differentiation grades II-III. The collected tumors were frozen in liquid nitrogen according to standard methods.

Phosphopeptide Immunoprecipitation.

A total of 0.2 g to 0.5 g tumor tissue was homogenized and lysed in urea lysis buffer (20 mM HEPES pH 8.0, 9M urea, 1 mM sodium vanadate, 2.5 mM sodium pyrophosphate, 1 mM beta-glycerophosphate) at $1.25\times10^8$ cells/ml and sonicated. Sonicated lysates were cleared by centrifugation at 20,000×g, and proteins were reduced and alkylated as described previously (see Rush et al., *Nat. Biotechnol.* 23(1): 94-101 (2005)). Samples were diluted with 20 mM HEPES pH 8.0 to a final urea concentration of 2M. Trypsin (1 mg/ml in 0.001 M HCl) was added to the clarified lysate at 1:100 v/v. Samples were digested overnight at room temperature.

Following digestion, lysates were acidified to a final concentration of 1% TFA. Phosphopeptides were prepared using the PhosphoScan kit commercially available from Cell Signaling Technology, Inc. (Danvers, Mass.). Briefly, peptide purification was carried out using Sep-Pak $C_{18}$ columns as described previously (see Rush et al., supra.). Following purification, all elutions (10%, 15%, 20%, 25%, 30%, 35% and 40% acetonitrile in 0.1% TFA) were combined and lyophilized. Dried peptides were resuspended in 1.4 ml MOPS buffer (50 mM MOPS/NaOH pH 7.2, 10 mM $Na_2HPO_4$, 50 mM NaCl) and insoluble material removed by centrifugation at 12,000×g for 10 minutes.

The phosphotyrosine monoclonal antibody P-Tyr-100 (Cell Signaling Technology, Inc., Danvers, Mass.) from ascites fluid was coupled non-covalently to protein G agarose beads (Roche) at 4 mg/ml beads overnight at 4° C. After coupling, antibody-resin was washed twice with PBS and three times with MOPS buffer. Immobilized antibody (40 μl, 160 μg) was added as a 1:1 slurry in MOPS IP buffer to the solubilized peptide fraction, and the mixture was incubated overnight at 4° C. The immobilized antibody beads were washed three times with MOPS buffer and twice with $ddH_2O$. Peptides were eluted twice from beads by incubation with 40 μl of 0.1% TFA for 20 minutes each, and the fractions were combined.

Analysis by LC-MS/MS Mass Spectrometry.

Peptides in the IP eluate (40 μl) were concentrated and separated from eluted antibody using Stop and Go extraction tips (StageTips) (see Rappsilber et al., *Anal. Chem.*, 75(3): 663-70 (2003)). Peptides were eluted from the microcolumns with 1 μl of 60% MeCN, 0.1% TFA into 7.6 μl of 0.4% acetic acid/0.005% heptafluorobutyric acid (HFBA). The sample was loaded onto a 10 cm×75 μm PicoFrit capillary column (New Objective) packed with Magic C18 AQ reversed-phase resin (Michrom Bioresources) using a Famos autosampler with an inert sample injection valve (Dionex). The column was developed with a 45-min linear gradient of acetonitrile in 0.4% acetic acid, 0.005% HFBA delivered at 280 nl/min (Ultimate, Dionex).

Tandem mass spectra were collected as previously described (Rikova et al., Cell 131: 1190-1203-, 2007). Briefly, pTyr-containing peptides were concentrated on reverse-phase micro tips. LC-MS/MS analysis was performed with an LTQ Orbitrap Mass Spectrometer and peptide mass accuracy of 10 ppm was one of the filters used for peptide identification (Thermo Fisher Scientific). Samples were collected with an LTQ—Orbitrap hybrid mass spectrometer, using a top-ten method, a dynamic exclusion repeat count of 1, and a repeat duration of 30 sec. MS spectra were collected in the Orbitrap component of the mass spectrometer and MS/MS spectra was collected in the LTQ.

Database Analysis & Assignments.

MS/MS spectra were evaluated using TurboSequest (ThermoFinnigan) (in the Sequest Browser package (v. 27, rev. 12) supplied as part of BioWorks 3.0). Individual MS/MS spectra were extracted from the raw data file using the Sequest Browser program CreateDta, with the following settings: bottom MW, 700; top MW, 4,500; minimum number of ions, 20; minimum TIC, $4\times10^5$; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were done against the NCBI human database released on Mar. 4, 2008 containing 37742 proteins allowing oxidized methionine (M+16) and phosphorylation (Y+80) as dynamic modifications.

In proteomics research, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al., *Mol. Cell Proteomics* 3: 531-533 (2004)), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site.

For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. Assigned sequences were accepted by filtering for XCorr values of at least 1.5 and Mass Error Range within 10 ppm.

The foregoing TAP analysis identified many tyrosine phosphorylated proteins, the majority of which are novel (data not shown). Among the 23 patients with liver cancer, three had bile duct liver cancer. Two patients with bile duct liver cancer, namely patients XY3-78T and 090665LC, had liver cancer samples that were found to contain tyrosine phosphorylated ROS kinase, which was not detected by MS analysis in tissue adjacent to tumor nor in any of the remaining 21 patient samples.

Example 2

Isolation & Sequencing of FIG-ROS Fusion Gene

Given the presence of the activated form of ROS kinase detected in two liver cancer patient samples, 5' rapid amplification of cDNA ends on the sequence encoding the kinase domain of ROS was conducted in order to determine whether a chimeric ROS transcript was present.

Rapid Amplification of Complementary DNA Ends

RNeasy Mini Kit (Qiagen) was used to extract RNA from human tumor samples. DNA was extracted with the use of DNeasy Tissue Kit (Qiagen). Rapid amplification of cDNA ends was performed with the use of 5' RACE system (Invitrogen) with primers ROS-GSP1 for cDNA synthesis and ROS-GSP2 and ROS-GSP3.1 for a nested PCR reaction, followed by cloning and sequencing PCR products.

For the 5'RACE system, the following primers were used:

```
ROS-GSP1:
5' ACCCTTCTCGGTTCTTCGTTTCCA
```

For the nested PCR reaction, the following primers were used.

```
ROS-GSP2:
5'TCTGGCGAGTCCAAAGTCTCCAAT

ROS-GSP3.1:
5'CAGCAAGAGACGCAGAGTCAGTTT
```

Sequencing of the PCR products revealed that the ROS kinases in the patient samples of XY3-78T and 090665LC, were indeed products of a chimeric ROS transcript, namely a fusion of part of a ROS transcript with part of a transcript of a FIG gene. Sequence analysis revealed that both patients XY3-78T and 090665LC had liver cancer cells that contained fusion protein resulting from the fusion of the c-terminus of ROS to the N-terminus of FIG (see FIG. 2, panel B and C). The FIG-ROS fusions in both samples were in-frame. In patient XY3-78T, a shorter fusion protein, namely FIG-ROS(S) resulted from the fusion of the first 209 amino acids of FIG to the last 421 amino acids of ROS. In patient 090665LC, a longer fusion protein, namely FIG-ROS(L) resulted from the fusion of the first 412 amino acids of FIG to the last 466 amino acids of ROS.

In addition, a third FIG-ROS fusion is discovered (FIG-ROS (XL), where the fusion occurs after exon 7 of the FIG gene and before exon 32 of the ROS gene. The nucleic acid sequence for the coding region of fusion gene is provided in SEQ ID NO: 16 and the amino acid sequence for the fusion polypeptide encoded by the fusion gene is provided in SEQ NO: 17.

Example 3

Detection of Mutant ROS Kinase Expression in a Human Cancer Sample Using PCR Assay The presence of mutant ROS kinase and/or a FIG-ROS fusion protein of the invention (e.g., FIG-ROS(S) or FIG-ROS(S)) in a human cancer sample was detected using cDNA or genomic reverse transcriptase (RT) and/or polymerase chain reaction (PCR). These methods have been previously described. See, e.g., Cools et al., *N. Engl. J. Med.* 348: 1201-1214 (2003).

PCR Assay

To confirm that the FIG-ROS fusion had occurred, RT-PCR was performed on RNA extracted from the liver cancer cell samples of patients XY3-78T and 090665LC. For RT-PCR, first-strand cDNA was synthesized from 2.5 ug of total RNA with the use of SuperScript™ III first-strand synthesis system (Invitrogen) with oligo $(dT)_{20}$. Then, the FIG-ROS fusion gene was amplified with the use of primer pairs FIG-F2 and ROS-GSP3.1. Their sequences are:

```
FIG-F2:
5'ACTGGTCAAAGTGCTGACTCTGGT

ROS-GSP3.1:
5'CAGCAAGAGACGCAGAGTCAGTTT
```

Figure 3:
FIG. 3 is a depiction of an agarose gel showing the detection of the two fusion gene transcripts, FIG-ROS(S) and FIG-ROS(L) formed by the FIG and ROS translocation by RT-PCR in the liver cancer samples from two patients, namely XY3-78T and 090665LC.

As shown on FIG. 3, patient XY3-78T's liver cancer cell samples contained mRNA predicted to encode the FIG-ROS (S) fusion polypeptide. The liver cancer cell samples from patient 090665LC contained mRNA predicted to encode the FIG-ROS(L) fusion polypeptide. As a control, RT-PCR was conducted on RNA isolated from the U118MG cell line, a human glioblastoma known to contain the FIG-ROS(S) translocation. U118 MG cells were purchased from American Type Culture Collection (Manassas, Va.) and grown in DMEM with 10% FBS.

To determined whether the liver cell samples from patient 090665LC, liver cell samples from patient XY3-78T's, or the U118MG human glioblastoma cell line expressed full length FIG or full length ROS, RT-PCR was performed using the FIG-F2 and ROS-GSP3.1 primers to amplify the FIG-ROS translocation, as well as the following primers pairs to amplify wild-type FIG (i.e., full-length FIG), wild-type ROS, and, as a control, wild-type GAPDH.

Wild type FIG gene was amplified with the use of primer pairs FIG-F3 and FIG-R8.

```
FIG-F3:
5'TTGGATAAGGAACTGGCAGGAAGG

FIG-R8:
5' ACCGTCATCTAGCGGAGTTTCACT
```

Wild-type ROS gene was amplified using primer pairs ROS-Ex31F and ROS-GSP2.

```
ROS-Ex31F:
5' AGCCAAGGTCCTGCTTATGTCTGT

ROS-GSP2:
5' TCTGGCGAGTCCAAAGTCTCCAAT
```

Wild-type GAPDH was amplified using primer pairs GAPDH-F and GAPDH-R

```
GAPDH-F:
5'TGGAAATCCCATCACCATCT

GAPDH-R:
5'GTCTTCTGGGTGGCAGTGAT
```

As shown in FIG. 4, liver cancer cells from patients XY3-78T and 090665LC express wild-type FIG, but neither expresses wild-type ROS. The U118MG cell line expresses neither wild-type FIG nor wild-type ROS. HCC78 a human non-small cell lung cancer cell line, which contains an SLC34A2-ROS translocation, served as a negative control. HCC78 cells were purchased from the ATCC (Manassas, Va.), and were maintained in DMEM with 10% FBS.

For genomic PCR, DNA was extracted from the cell samples with the use of DNeasy Tissue Kit (Qiagen). PCR amplification of the fusion gene was performed with the use of LongRange PCR kit (Qiagen) with primer pairs FIG-F3 and ROS-GSP3.1 for XY3-78T.

```
FIG-F3:
5' TTGGATAAGGAACTGGCAGGAAGG

ROS-GSP3.1:
5' CAGCAAGAGACGCAGAGTCAGTTT
```

PCR amplification of the fusion gene was performed with the use of LongRange PCR kit (Qiagen) with primer pairs FIG-F7 and ROS-GSP4.1 for 090665LC and U118MG.

```
FIG-F7:
5' TGTGGCTCCTGAAGTGGATTCTGA

ROS-GSP4.1:
5'GCAGCTCAGCCAACTCTTTGTCTT
```

As shown in FIG. 5, the FIG-ROS translocation occurred in the genome of the liver cancer cells of patients XY3-78T and 090665LC. Although the U118MG cell line expresses the same FIG-ROS(L) fusion polypeptide as the cells of patient 090665LC, the exact genomic breakpoints in FIG and ROS gene between these two samples are different. The breakpoints were found to be:

XY3-78T
1-822 bp of FIG-Intron3
659-619 bp of ROS-Intron35
660-1228 bp of ROS Intron35
090665LC
1-2402 bp of FIG-Intron7
2317-2937 bp of ros-Intron34
U118MG
1-2304 bp of FIG-Intron7
583-2937 bp ros-Intron34

The nucleotide sequence of intron 3 of the human FIG gene is provided herewith as SEQ ID NO:5. The nucleotide sequence of intron 7 of the human FIG gene is provided herewith as SEQ ID NO: 6. The nucleotide sequence of intron 34 of the human ROS gene is provided herewith as SEQ ID NO: 7. The nucleotide sequence of intron 35 of the human ROS gene is provided herewith as SEQ ID NO: 8.

This assay may be used to detect the presence of a mutant ROS kinase and/or a FIG-ROS fusion protein of the invention (e.g., FIG-ROS(S) or FIG-ROS(S) in a human cancer sample in other biological tissue samples (e.g., tumor tissue samples may be obtained from a patient having liver, pancreatic, kidney, or testicular cancer). Such an analysis will identify a patient having a cancer characterized by expression of the truncated ROS kinase (and/or FIG-ROS fusion protein), which patient is likely to respond to treatment with a ROS inhibitor.

Example 4

Generation of Recombinant Retrovirus Encoding FIG-Ros Fusion Polypeptides

The open reading frame of the FIG-ROS (L) and FIG-ROS (S) fusion gene was amplified by PCR from cDNA isolated from patients 090665LC and XY3-78T, respectively, using the following pair of primers (FIG-Fc: 5'ATGTCGGCGGGCGGTCCATG; ROS-Rc:5'TTAATCAGACCCATCTCCAT). These PCR products were cloned into the retroviral vector MSCV-Neo with a C-terminal Myc tag (EQKLISEEDL) (MSCV-neo vector and MSCV-puro vector are commercially available from Clontech.). Additional recombinant retroviral constructs (e.g., empty MSCV-neo vector, MSCV-puro-src, etc.) were also generated. The FIG-ROS(S) containing MSCV-Neo vector was deposited with the American Type Culture Collection ("ATCC", Manassas, Va.) under the terms of the Budapest Treaty on Jan. 21, 2009 and assigned ATCC Patent Deposit Designation No. PTA-9721.

The resulting recombinant retroviral constructs (i.e., containing FIG-ROS(S) or FIG-ROS(L)) were transfected into 293T cells to be packaged into recombinant retrovirus capable of infecting (and thereby transducing) cells. To do this, 293T cells (e.g., commercially available from ATCC) were maintained in 10% DMEM containing 10% fetal bovine serum in 10 cm tissue culture plates. 24-48 hours prior to transfection, the 293T cells were plated at about 50-80% confluency. Transfection was performed using the FuGENE reagent (commercially available from Roche Diagnostics), according to the manufacturer's instructions. Typically, for each recombinant construct, a 3:1 ratio of the FuGENE reagent (in ul) to DNA (ug) was used (e.g., 3 ul FuGENE to 1 ug Myc-tagged FIG-ROS(S) in MSCV-Neo). 48 hours following transfection, the media was removed, and any cells within the media (now containing recombinant virus) was removed by filtering the media through a 0.45 um syringe filter. The media (also referred to as viral soup) was stored at −80° C.

Example 5

Expression of FIG-ROS Fusion Proteins in 3T3 Cells

3T3 cells were purchased from American Type Culture Collection (Manassas, Va.). 3T3 cells were grown at 37° C. in DMEM media with 10% FBS.

1 ml of recombinant retrovirus encoding the Fig-Ros fusion polypeptides generated as described in Example 4 were used to transducer 3T3 cells from 10 cm plate with 50% confluency. In addition, an empty retrovirus (i.e., generated from an empty MSCV-Neo vector with a C-terminal Myc tag was transduced into 3T3 cells as a control.

3T3 cells were infected with (i.e., transduced with) recombinant retrovirus expressing FIG-ROS(S) from XY3-78T, FIG-ROS(L) from 090665LC. Empty retrovirus was also used to infect 3T3 cells as a control. Two days after transduction, 0.5 mg/ml G418 was added to the cell culture media. Two weeks after being transduced (i.e., 12 days after selection in G418), 1 million cells were lysed and Western blotting analysis performed, staining the electrophoretically resolved cell lysates with an antibody that specifically bound to the kinase domain of ROS, as well as a phospho-antibody against ROS. The cell lysates were also probed with antibodies against several downstream signaling substrates of ROS kinase including p-STAT3 (i.e., phosphorylated STAT3), STAT3, p-AKT (i.e., phosphorylated AKT), and AKT. b-actin was also stained to ensure that equivalent amounts of lysates were present in all lanes. All antibodies are from Cell Signaling Technology, Inc.

As shown in FIG. 6, the 3T3 cells transduced with recombinant retrovirus stably expressed FIG-ROS(S) and FIG-ROS(L). As expected, the NC (empty vector) cells did not express any ROS. Expression of FIG-ROS(S) and FIG-ROS(L) activate downstream signaling molecules, STAT3 and AKT.

Example 6

Effect of FIG-ROS Fusion Proteins on 3T3 Cells' Growth In Vitro and In Vivo

3T3 cells have contact inhibition, meaning that they do not form colonies in soft agar. To determine if the presence of active ROS kinase in these cells removed their contact inhibition, retrovirally transduced 3T3 cells were selected for G418 (0.5 mg/ml) for 7 days, and the cells were then cultured in soft agar in triplicate for 17 days. A retrovirus encoding the short version of SLC34A2-ROS was also used to transduce 3T3 cells. As a control, a retrovirus encoding the src kinase was also used to transducer 3T3 cells. The protocol for soft agar assay is attached.

As shown in FIG. 7, 3T3 cells transduced with either src kinase- or FIG-ROS(S)-encoding retrovirus lost their contact inhibition dramatically. This provides evidence that the presence of FIG-ROS(S) is able to drive a cell into a cancerous state of growth. The presence of FIG-ROS(L) also enabled 3T3 cells to lose their contact inhibition (see FIG. 7, top left panel), as did SLC34A2-ROS(S) (data not shown), although the effect was not as significant as that seen with FIG-ROS(S).

In addition, the ability of transduced 3T3 cells to form tumors in vivo was analyzed. Immunocompromised nude mice (which lack a thymus, available from the Jackson Laboratory, Bar Harbor, Me.) were injected with $1\times10^6$ 3T3 cells transduced with retrovirus containing empty vector, FIG-ROS(L) or FIG-ROS(S). Mice were monitored daily for tumor formation and size, and were sacrificed when tumors reached approximately 1 cm×1 cm.

As shown in FIG. 8, two weeks after being injected with 3T3 cells transduced with either FIG-ROS(S) or FIG-ROS (L), tumor formation was apparent in the injected nude mice.

Example 7

Subcellular Localization of FIG-ROS(L) and FIG-ROS(S) in 3T3 Cells

Recombinant vectors were generated to expressed Myc-tagged versions of FIG-ROS(L) and FIG-ROS(S), where the myc tag was incorporated onto the C-terminus of the FIG-ROS fusion polypeptide. 3T3 cells were stably transfected with the recombinant expression vectors or with an empty "neo" only vector (control).

Immunoflurescence was performed with a standard protocol (publically available from Cell Signaling Technology, Inc.). Briefly, The 9E1H1D9 ROS antibody, Myc-Tag antibody (CST#2278) and the Golgin-97 antibody were from Cell Signaling Technology, Inc. (Danvers, Mass.).

As shown in FIGS. 9A and 9B, the two different FIG-ROS fusion polypeptides of the invention localized to different areas of the cell. FIG-ROS(L) localized to Golgi apparatus, and co-localizes with the Golgi marker (golgin-97) (see images under "Myc-FR(L)" in both FIGS. 9A and 9B). To our surprise, the staining pattern of FIG-ROS(S) was cytoplasmic (see images under "Myc-FR(S)" in both FIGS. 9A and 9B), even though it contains the second coiled-coil domain of FIG, suggesting that the coiled-coil domain of FIG is necessary, but not sufficient to target FIG-ROS(S) to the Golgi apparatus. This may be because the PDZ domain of FIG is present in FIG-ROS(L), but not in FIG-ROS(S). Interestingly, SLC34A2-ROS(S) was localized to para-nuclei compartment (see images under "Myc-SR(S)" in both FIGS. 9A and 9B). The fact that the SLC34A2-ROS (S) fusion, which contains transmembrane domain of ROS, is localized in perinuclear compartment suggests that transmembrane domain of ROS also contributes to its localization.

Thus, different ROS fusions have distinct subcellular localization, suggesting that they may activate different substrates in vivo.

Example 8

FIG-ROS(L) and FIG-ROS(S) Activity in Transduced BaF3 Cells

Murine BaF3 cells normally need interleukin-3 (IL-3) to survive. BaF3 cells were obtained from DSMZ (Deutsche Sammlung von Mikroorganismen and Zellkulturen GmbH, Germany) and were maintained at 37° C. in RPMI-1640 medium (Invitrogen) with 10% fetal bovine serum (FBS) (Sigma) and 1.0 ng/ml murine IL-3 (R&D Systems).

To determine if expression of a FIG-ROS fusion polypeptide of the invention could enable BaF3 cells to survive without IL-3, we transduced BaF3 cells with the retroviruses described in Example 4 encoding FIG-ROS(L) and FIG-ROS(S). In addition, retrovirus encoding the FIG-ROS(L) from U118MG were also generated and used to transducer BaF3 cells.

As shown in FIG. 10, FIG-ROS(S), FIG-ROS(L), and FIG-ROS(L) from U118MG were stably expressed in BaF3 cells grown with or without IL-3. Indeed, as shown in FIG. 11, we found that the presence of FIG-ROS(L) or FIG-ROS(S) enabled BaF3 cells to grow in the absence of IL-3. Interestingly, FIG-ROS(S) expressing BaF3 cells grew at a faster pace than the BaF3 expressing FIG-ROS(L).

Next, an in vitro kinase assay was performed to determine if the ROS kinase portion of the FIG-ROS fusion polypeptides was active. Cell lysates from FIG-ROS transduced BaF3 cells were subjected to immunoprecipitation with anti-Myc-Tag antibody (which pulls down the Myc-tagged FIG-ROS fusion polypeptides). The pulled-down ROS immune complex were washed 3 times with cell lysis buffer, followed by kinase buffer (Cell Signaling Technology). Kinase reactions were initiated by re-suspending the ROS immune complex into 25 ul kinase buffer that contains 50 uM ATP, 0.2 uCi/ul [gamma32p] ATP, with 1 mg/ml of either Poly (EY, 4:1). Reactions were stopped by spotting reaction cocktail onto p81 filter papers. Samples were then washed and assayed for kinase activity by detection with a scintillation counter. As shown in FIG. 12, while both FIG-ROS (L) and FIG-ROS (S) can phosphorylate its substrate, FIG-ROS(S) is more potent than FIG-ROS(L). In other words, FIG-ROS(S) has a much higher kinase activity than FIG-ROS(L). Equal loading of the lanes is shown in the Western blotting analysis of the ROS immune complexes using a ROS-specific antibody (see FIG. 12, lower panel).

The higher potency of FIG-ROS(S) as compared to FIG-ROS(L) is consistent with data from soft agar assay (see FIG. 7) and IL-3 independent growth assay (see FIG. 11).

Example 9

Sensitivity of FIG-ROS(L) and FIG-ROS(S) to TAE-684

The small molecule, TAE-684, a 5-chloro-2,4-diaminophenylpyrimidine, which has the structure:

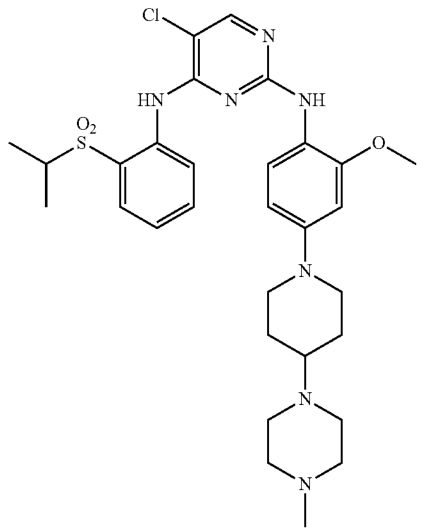 [SMILES: COc1cc(N2CCC(N3CCN(C)CC3)CC2)ccc1Nc1ncc(Cl)c(Nc2ccccc2S(=O)(=O)C(C)C)n1]

and has been shown to inhibit the ALK kinase. Galkin, et al., Proc. National Acad. Sci 104(1) 270-275, 2007.

In this example, we determined whether or not TAE-684 also inhibited FIG-ROS fusion polypeptide. To do this, BaF3 and Karpas 299 cells were obtained from DSMZ (Deutsche Sammlung von Mikroorganismen and Zellkulturen GmbH, Germany). BaF3 cells were maintained as described above and Karpas 299 cells (a lymphoma cell line) were grown in RPMI-1640 with 10% FBS.

BaF3 cells were transduced with retrovirus encoding FIG-ROS(S), FIG-ROS(L), or FLT-3ITD (the Internal tandem duplication mutation in FLT3 causes AML leukemia), and selected for IL3 independent growth. Karpas 299 cells, which express NPM-ALK, was used as a positive control.

A MTS assay was performed using the CellTiter 96 Aqueous One Solution Reagent, (Promega, Catalog No. G3582). Briefly, $1\times10^5$ cells/well in 24 well plate were grown in 1 ml medium that included 0 nM, 3 nM, 10 nM, 30 nM, 100 nM, 300 nM or 1000 nM TAE-684. After 72 hours, 20 ul of the CellTiter 96 Aqueous One Solution Reagent was added into each well of a 96 well assay plate (flat bottom), and then 100 ul of cells grown with or without treatment. Media-only wells were used as controls. The 96 well plate was incubated for 1-4 hours at 37° C., and then viable cells were courted by reading the absorbance at 490 nm using a 96 well plate reader.

Figure 13:
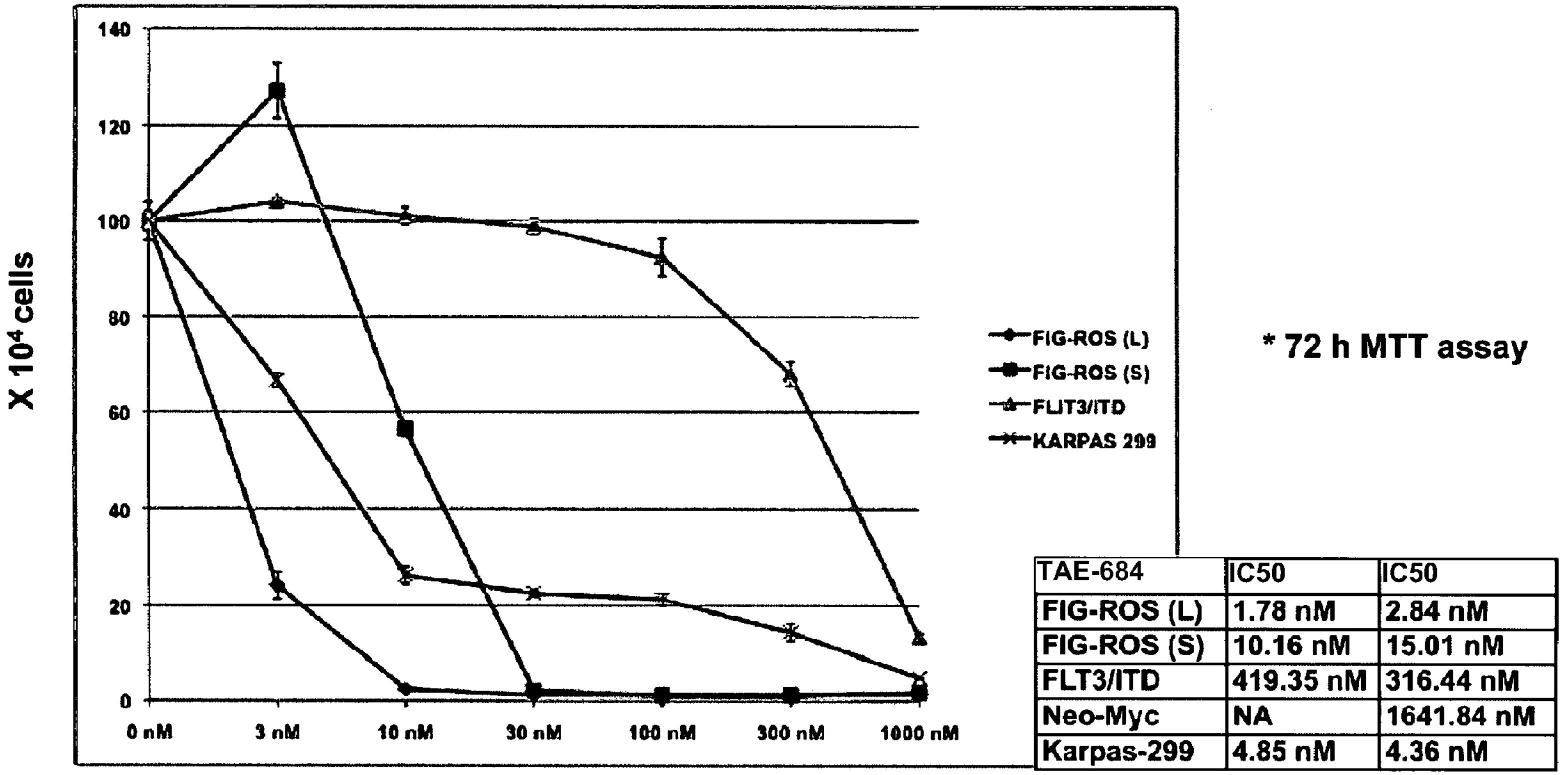
FIG. 13 is a line graph showing the cellular growth response in the presence of 0 nM, 3 nM, 10 10 nM, 30 nM, 100 nM, 300 nM or 1000 nM TAE-684 of BaF3 expressing FIG-ROS(S) (squares), BaF3 expressing FIG-ROS(L) (diamonds), BaF3 expressing FLT3ITD (triangles), and Karpas 299 cells (Xs).

As shown in FIG. 13, the BaF3 cells transduced with retrovirus expressing one of the FIG-ROS polypeptides stopped growing in the presence of TAE-684. Interestingly, FIG-ROS(S) is less susceptible to TAE-684 than FIG-ROS (L). Karpas 299 cells also responded (i.e., stopped growing) in the presence of TAE-684, which was expected since they express ALK and TAE-684 inhibits the ALK kinase. The BaF3 cells transduced with FLT3/ITD were not susceptible to TAE-684.

The mechanism of death of the BaF3 and Karpas 299 cells was next reviewed by measuring the percentage of cleaved-caspase 3 positive cells by flow cytometry assay using cleaved caspase-3 as a marker for apoptosis. These results were obtained using the protocol publically available from Cell Signaling Technology, Inc. (Danvers, Mass.)

Figure 14:
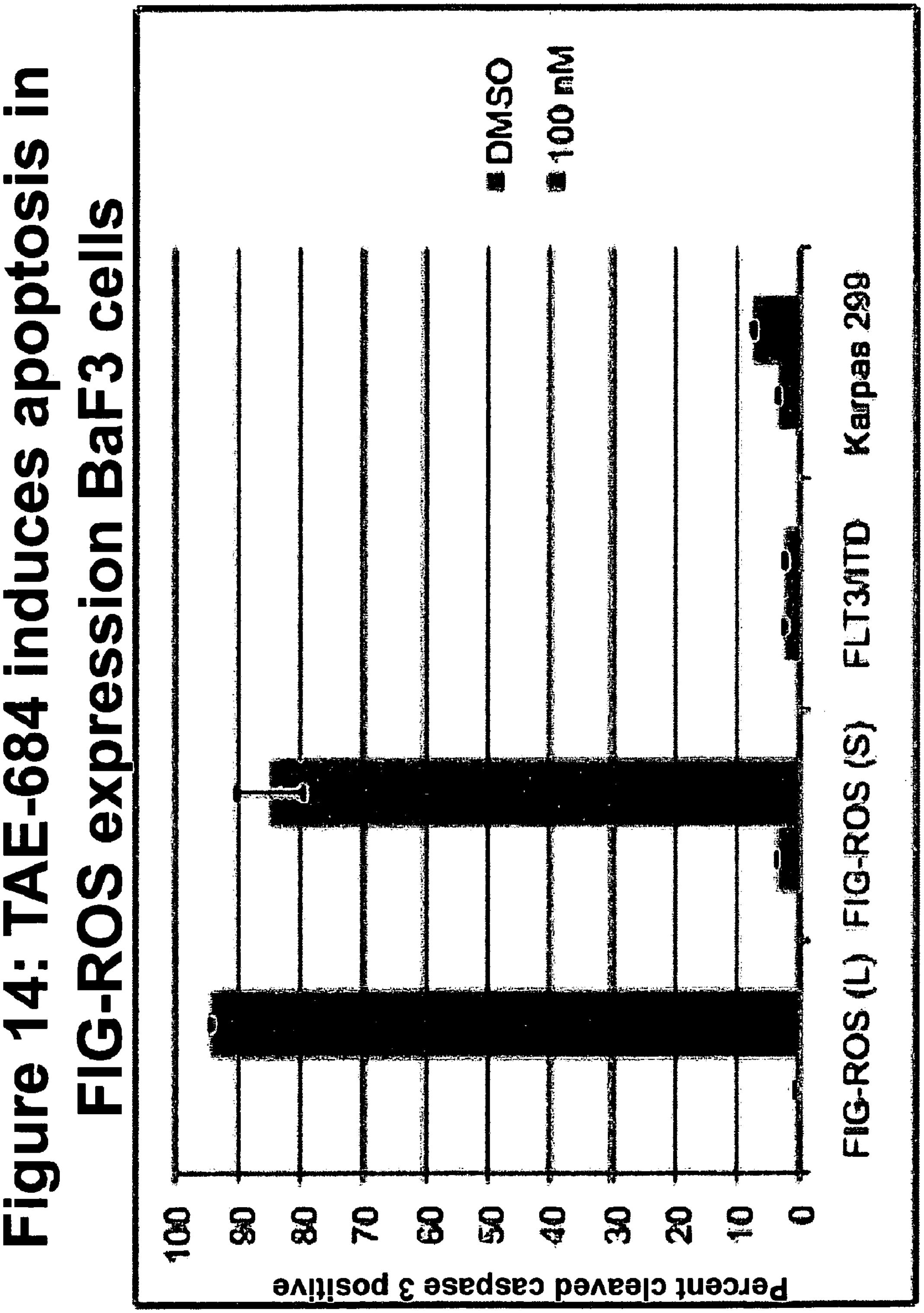
FIG. 14 is a bar graph showing that BaF3 expressing either FIG-ROS(S) or FIG-ROS(L) die by apoptosis in the presence of TAE-684.

As shown in FIG. 14, the presence of TAE-684 caused the BaF3 cells expressing FIG-ROS(S) or FIG-ROS(L) to die by apoptosis. Interestingly, Karpas 299 cells, which stop growing in the presence of TAE-684, did not die by apoptosis—they simply underwent cell cycle arrest. Thus, the mechanism by which TAE-684 inhibits FIG-ROS fusion polypeptides is likely different from the mechanism by which TAE-684 inhibits the ALK kinase.

To further identify the mechanism of action of TAE-684 on the FIG-ROS fusion polypeptides of the invention, all four cell lines (i.e., Karpas 299 cells and BaF3 cells transduced with retrovirus encoding FIG-ROS(S), FIG-ROS(L), and FLT-3ITD) were subjected to Western blotting analysis following treatment with 0, 10, 50, or 100 nM TAE-684 for three hours. All antibodies were from Cell Signaling Technology, Inc.

Figure 15:
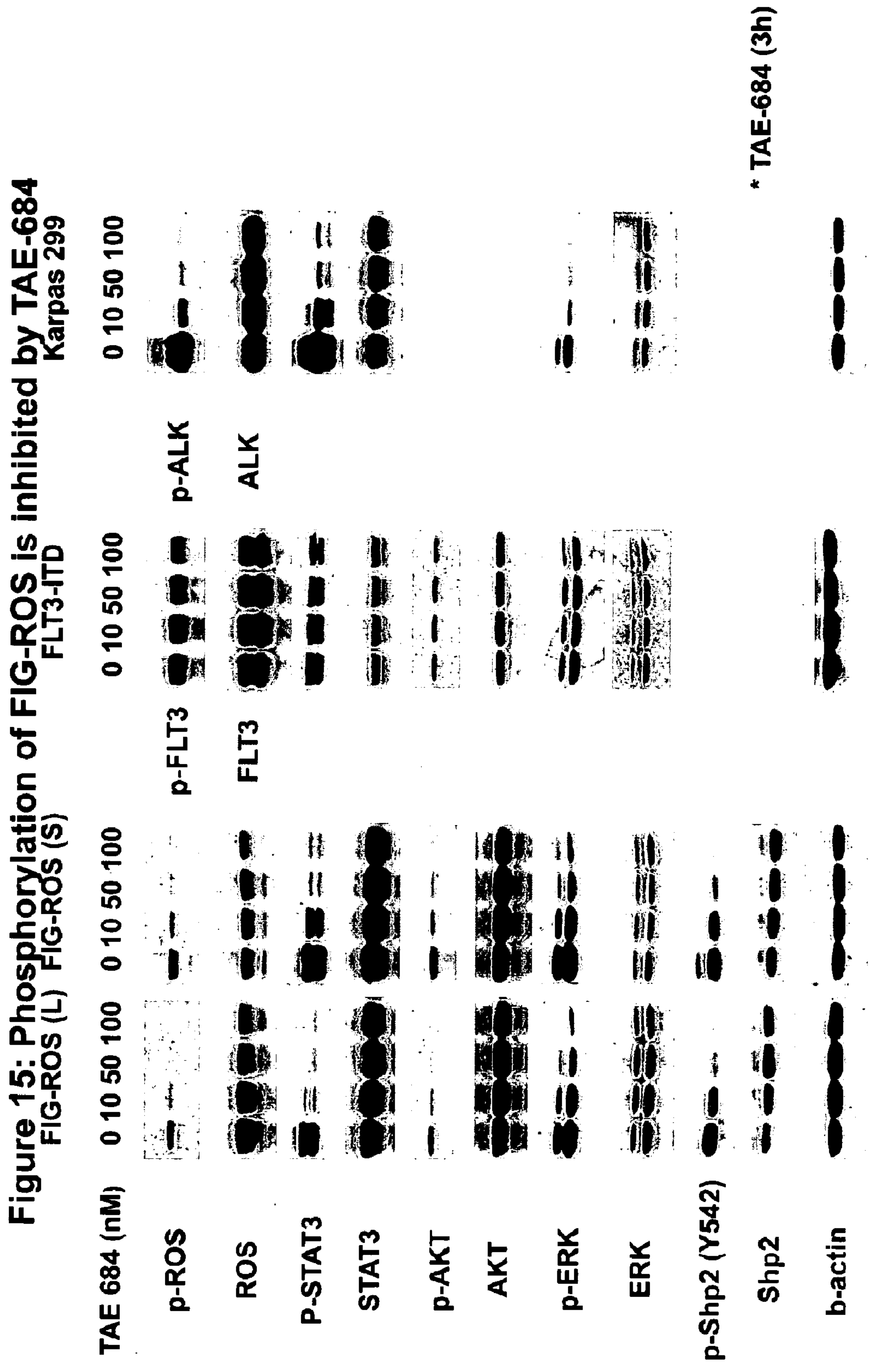
FIG. 15 is a depiction of a Western blotting analysis showing that phosphorylation of both FIG-ROS(S) and FIG-ROS(L), as well as their downstream signaling molecules, are inhibited by TAE-684.

As shown in FIG. 15, phosphorylation of both FIG-ROS(S) and FIG-ROS(L) in FIG-ROS(S) and FIG-ROS(L) expressing BaF3 cells was inhibited by TAE-684. In addition, phosphorylation of STAT3, AKT, and ERK, and Shp2 were inhibited in FIG-ROS(S) and FIG-ROS(L) expressing BaF3 cells. The phosphorylation of STAT3, AKT, and ERK, and Shp2 was not affected in the BaF3 cells transduced with the FLT-3ITD retrovirus. TAE-684 also inhibited ALK and ERK phosphorylation in Karpas 299 cells. Since ROS, ALK, LTK, InsR, and IGF1R belong to the same family of tyrosine kinases, they may share similar structure in the kinase domain. Kinase inhibitors or antibodies designed against ALK, LTK, InsR, and IGF1R may have therapeutic effects against ROS kinase.

Example 10

Detection of Mutant ROS Expression in a Human Cancer Sample Using FISH Assay The presence of a ROS fusion polynucleotide (e.g., a FIG-ROS(L), FIG-ROS(S), FIG-ROS(XL), SLC34A2-ROS(S), SLC34A2-ROS(VS), SLC34A2-ROS(L), or CD74-ROS) in liver cancer (e.g., in a cholangiocarcinoma), pancreatic cancer, kidney cancer, or testicular cancer is detected using a fluorescence in situ hybridization (FISH) assay. Such FISH assays are well known in the art (see, e.g., Verma et al. Human Chromosomes: A Manual of Basic Techniques, Pergamon Press, New York, N.Y. (1988).

To do this, paraffin-embedded human tumor samples are examined. Some tissues that are examined include liver, pancreas, testicular, and kidney cancers, particularly cancers affecting the ducts of all of these tissues.

Figure 16:
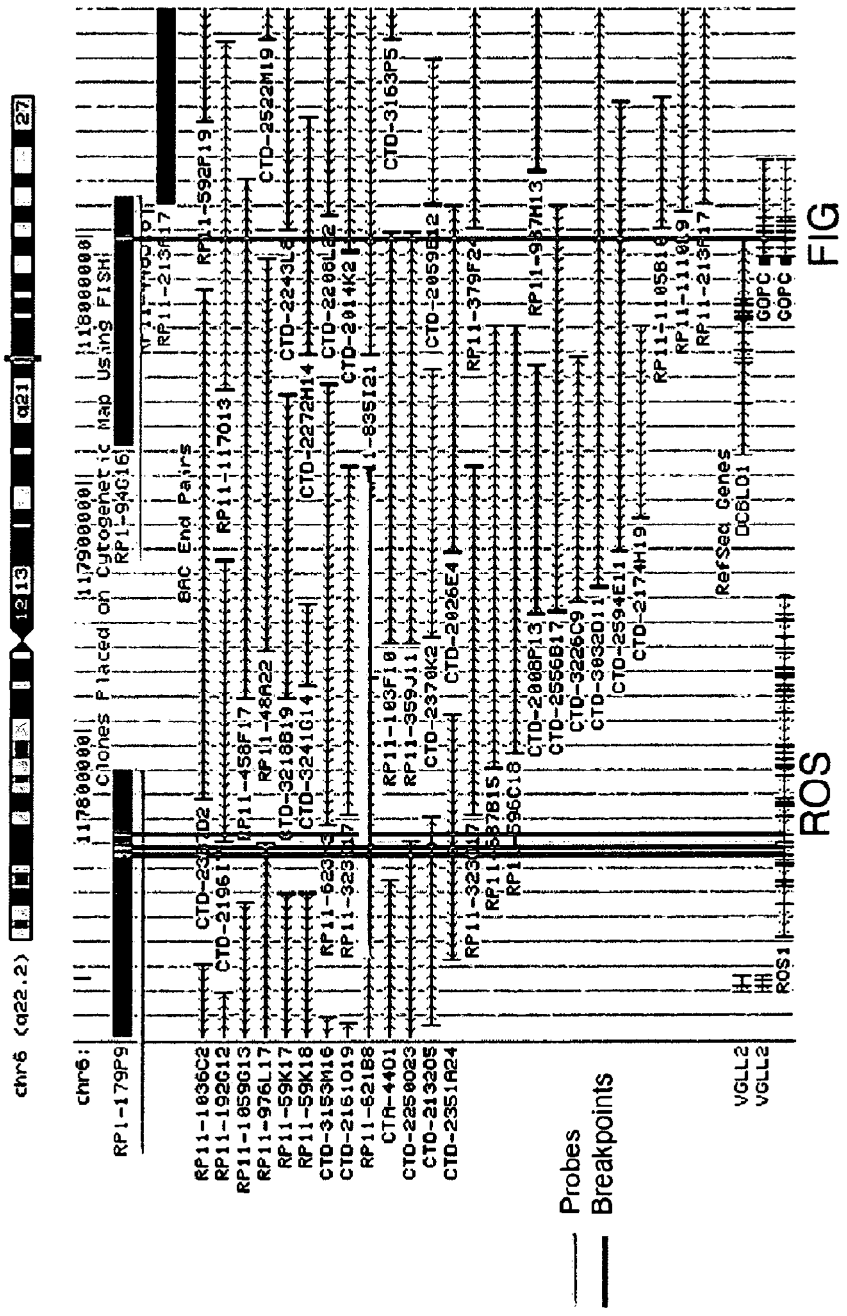
FIG. 16 is a schematic representation of the various BAC clones that hybridize to the FIG and ROS genes.

For analyzing rearrangements involving the ROS gene, a dual color break-apart probe can be designed. As shown in FIG. 16, several BAC probes surround the FIG and ROS genes on chromosome 6. While these probes are ideal for identifying translocations between the FIG gene (also known as the GOPC gene—see FIG. 16) and the ROS gene, these probes can also be used to identify other ROS gene translocation.

For these studies, a proximal probe (BAC clone RP1-179P9) and two distal probes (BAC clone RP11-323017, RP1-94G16) (all of which are commercially available, for example, from Invitrogen Inc., Carlsbad, Calif., as Catalog Nos. RPCI1.C and RPCI11.C) are designed. The proximal probe may be labeled with Spectrum Orange dUTP and the distal probe may be labeled with Spectrum Green dUTP, Labeling of the probes by nick translation and interphase FISH using FFPE tissue sections may be done according to the manufacturer's instructions (Vysis Inc., Downers Grove, Ill.) with the following modifications. In brief, paraffin embedded tissue sections are re-hydrated and are subjected to pretreatment first in 0.2N HCl for 20 minutes followed by 1 M sodium thiocyanate at 80 C for 30 min.

Following a brief wash, sections are digested with protease (8 mg Pepsin, 2000-3000 U/mg) for 45-60 minutes at 37° C. then fixed in 10% NBF and dehydrated. The probe set is then loaded onto the sections and incubated at 94 C for 3 min in order to denature the probe and target chromosome. Following denaturation the slides are incubated at 37 C for a minimum of 18 hours. After washing, 4',6-diamidino-2-phenylindole (DAPI; mg/ml) in Vectashield mounting medium (Vector Laboratories, Burlingame, Calif.) will be applied for nuclear counterstaining.

The FIG-ROS rearrangement probe will contain three differently labeled probes. Two of these probes (RP11-323O17, RP1-94G16) target the deletion area between the break points of the FIG gene and the ROS gene and the other probe (RP1-179P9) targets the remaining portion of the ROS gene (see FIG. 16). The sequences of the introns containing the break points of the FIG and ROS genes are provided in SEQ ID NO: 5 (intron 3 of FIG), SEQ ID NO: 6 (intron 7 of FIG), SEQ ID NO: 7 (intron 33 of ROS), SEQ ID NO: 8 (intron 34 of ROS), and SEQ ID NO:26 (intron 31 of ROS). The probes are designed based on the breakpoints identified in Example 2. When hybridized, the native (i.e., wild-type) ROS region will appear as an orange/green fusion signal (which may appear yellow under a microscope), while rearrangement at this locus (as occurs in the FIG-ROS fusion protein) will result in only orange signals since the target areas for the green probes have been deleted.

For rearrangements of the ROS gene with either CD74 (on chromosome 5) or SLC34A2 (on chromosome 4), because these genes lie on chromosomes other than chromosome 6, the native (i.e., wild-type or non-rearranged) ROS region will appear as an orange/green fusion signal (which may appear yellow under a microscope), while rearrangement at this locus (as occurs in the SLC34A2-ROS fusion proteins and the CD74-ROS fusion proteins) will result in a separate orange signal (on chromosome 6) and separate green signal (on chromosome 5 for CD74 and chromosome 4 for SLC34A2).

The FISH analysis will likely reveal a low incidence of ROS gene translocations in the sample population having liver cancer (e.g., in a cholangiocarcinoma), pancreatic cancer, kidney cancer, or testicular cancer. However, it is predicted that a subset of the studied cancers will contain a ROS translocation. These cancers containing the FIG-ROS translocation are identified as those cancers likely to respond to a ROS inhibitor. In other words, cells of the cancer, upon treatment (or contact) with a ROS inhibitor are predicted to show growth retardation, growth abrogation (i.e., stop growing) or actually die (e.g., by apoptosis) as compared to untreated cancer cells (i.e., cells not contacted with the ROS inhibitor).

Example 11

Identification of Mutant ROS Expression in Human Liver Cancers

Next, studies were performed to determine if ROS expression could be observed in samples from human liver cancers. The two most common types of liver cancer are hepatocellular carcinoma (HCC), accounting for 80% of all cases, and cholangiocarcinoma (CCA, or bile duct cancer), representing 10-15% of hepatobiliary neoplasms (Blechacz et al., *Hepatology* 48:308-321, 2008 and de Groen, P. C., *N Engl J Med* 341:1368-1378, 1999). For these studies, an ROS-specific antibody (clone no. D4D6) that specifically bound to the c-terminus of ROS was used. Such antibodies are commercially available (see, e.g., the Ros (C-20) antibody, Catalog No. sc-6347 from Santa Cruz Biotechnology, Inc., Santa Cruz, Calif.).

For the studies on cholangiocarcinoma, nineteen human cholangiocarcinoma paraffin-embedded tissue blocks and slides were obtained from BioChain Institute, Inc., Hayward, Calif., Folio Biosciences, Columbus, Ohio and Analytical Biological Services, Inc., Wilmington, Del. 4-6 μm tissue sections were deparaffinized through three changes of xylene for 5 minutes each, then rehydrated through two changes of 100% ethanol and 2 changes of 95% ethanol, each for 5 minutes.

The deparraffinized slides were then rinsed for 5 minuets each in three changes of $diH_2O$, then were subjected to antigen retrieval in a Decloaking Chamber (Biocare Medical, Concord, Calif.). Slides were immersed in 250 ml 1.0 mM EDTA, pH 8.0 in a 24 slide holder from Tissue Tek. The Decloaking Chamber was filled with 500 ml $diH_2O$, the slide holder was placed in the chamber touching the heat shield, and retrieval was performed with the following settings as set by the manufacturer: SP1 125° C. for 30 seconds and SP2 90° C. for 10 seconds. Slides were cooled on the bench for 10 minutes, rinsed in $diH_2O$, submerged in 3% $H_2O_2$ for 10 minutes, then washed twice in $diH_2O$.

After blocking for 1 hour at room temperature in Tris buffered saline+0.5% Tween-20 (TBST)/5% goat serum in a humidified chamber, slides were incubated overnight at 4° C. with Ros (D4D6) XP™ Rabbit mAb at 0.19 μg/ml diluted in SignalStain® Antibody Diluent (catalog #8112 Cell Signaling Technology, Danvers, Mass.). After washing three times in TBST, detection was performed with SignalStain® Boost IHC Detection Reagent (HRP, Rabbit) (catalog #8114 Cell Signaling Technology, Danvers, Mass.) with a 30 minute incubation at room temperature in a humidified chamber.

After washing three times in TBST to remove theSignal-Stain® Boost IHC Detection Reagent, the slides were next exposed to NovaRed (Vector Laboratories, Burlingame, Calif.) prepared per the manufacturer's instructions. Slides were developed for 1 minute and then rinsed in $diH_2O$. Slides were counterstained by incubating in hematoxylin (Ready to use Invitrogen (Carlsbad, Calif.) Catalog #00-8011) for 1 minute, rinsed for 30 seconds in $diH_2O$, incubated for 20 seconds in bluing reagent (Richard Allan Scientific, Kalamazoo, Mich. (a Thermo Scientific company), Catalog #7301), and then finally washed for 30 seconds in $diH_2O$. Slides were dehydrated in 2 changes of 95% ethanol for 20 seconds each and 2 changes of 100% ethanol for 2 minutes each. Slides were cleared in 2 changes of xylene for 20 seconds each, then air dried. Coverslips were mounted using VectaMount (Vector Laboratories, Burlingame, Calif.). Slides were air dried, then evaluated under the microscope.

Figure 17:
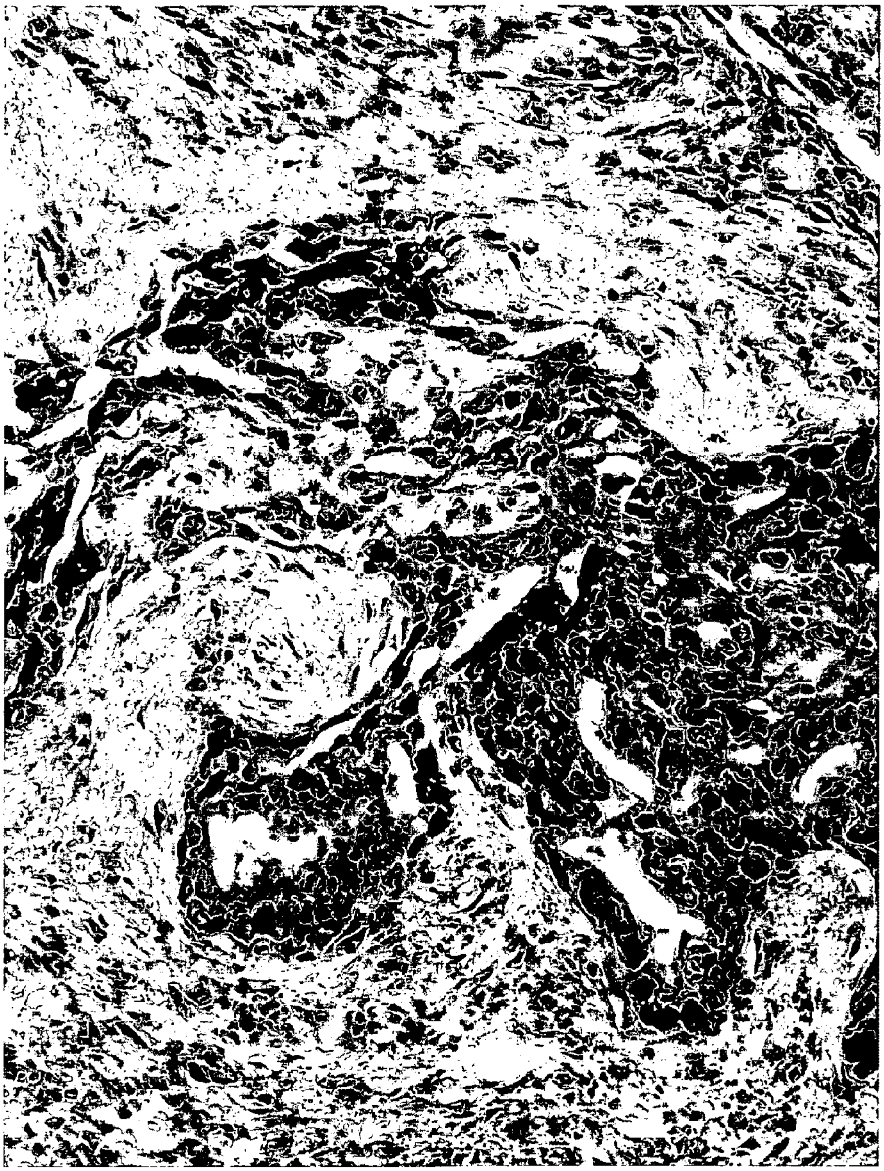
FIG. 17 is an image of an IHC slide from a representative, non-limiting CCA tissue sample that stained positive for ROS expression.

Of the nineteen samples assayed, six samples stained positive for binding of the ROS-specific antibody. FIG. 17 shows a representative image of slide from a CCA tissue sample that stained positive for ROS expression. This finding is notable because ROS is not expressed in normal bile duct tissue and is also not expressed in normal liver tissue.

Sequencing analysis of the samples showing strong staining with the ROS-specific antibody is expected to reveal the presence of either mutant ROS expression (e.g., over-expression of wild-type ROS in the bile duct cancer tissue where in normal bile duct tissue there is none) or the presence of a truncated ROS polypeptide or a ROS fusion protein (e.g., a FIG-ROS fusion polypeptide).

For studies on hepatocellular carcinoma, 23 paraffin-embedded human HCC tissue array sectioned at 4 μm were deparaffinized through three changes of xylene for 5 minutes each, then rehydrated through two changes of 100% ethanol and 2 changes of 95% ethanol, each for 5 minutes. Slides were rinsed for 5 minuets each in three changes of $diH_2O$, then were subjected to antigen retrieval in a Decloaking Chamber (Biocare Medical, Concord, Calif.) as follows. Slides were immersed in 250 ml 1.0 mM EDTA, pH 8.0 in a 24 slide holder from Tissue Tek. The Decloaking Chamber was filled with 500 ml $diH_2O$, the slide holder was placed in the chamber touching the heat shield, and retrieval was performed with the following settings as set by the manufacturer: SP1 125° C. for 30 seconds and SP2 90° C. for 10 seconds. Slides were cooled on the bench for 10 minutes, rinsed in $diH_2O$, submerged in 3% $H_2O_2$ for 10 minutes, then washed twice in $diH_2O$.

After blocking for 1 hour at room temperature in Tris buffered saline+0.5% Tween-20 (TBST)/5% goat serum in a humidified chamber, slides were incubated overnight at 4° C. with Ros (D4D6) XP™ Rabbit mAb at 0.19 μg/ml diluted in SignalStain® Antibody Diluent (#8112 Cell Signaling Technology, Danvers, Mass.). After washing three times in TBST, detection was performed with SignalStain® Boost IHC Detection Reagent (HRP, Rabbit) (#8114 Cell Signaling Technology, Danvers, Mass.) with a 30 minute incubation at room temperature in a humidified chamber.

After washing three times in TBST slides were exposed to NovaRed (Vector Laboratories, Burlingame, Calif.) prepared per the manufacturer's instructions. Slides were developed for 1 minute then rinsed in $diH_2O$. Slides were counterstained by incubating in hematoxylin (Ready to use Invitrogen #00-8011) for 1 minute, rinsed for 30 seconds in $diH_2O$, incubated for 20 seconds in bluing reagent (Richard Allan Scientific #7301), then finally washed for 30 seconds in $diH_2O$. Slides were dehydrated in 2 changes of 95% ethanol for 20 seconds each and 2 changes of 100% ethanol for 2 minutes each. Slides were cleared in 2 changes of xylene for 20 seconds each, then air dried. Coverslips were mounted using VectaMount (Vector Laboratories, Burlingame, Calif.). Slides were air dried, then evaluated under the microscope.

Figure 18:
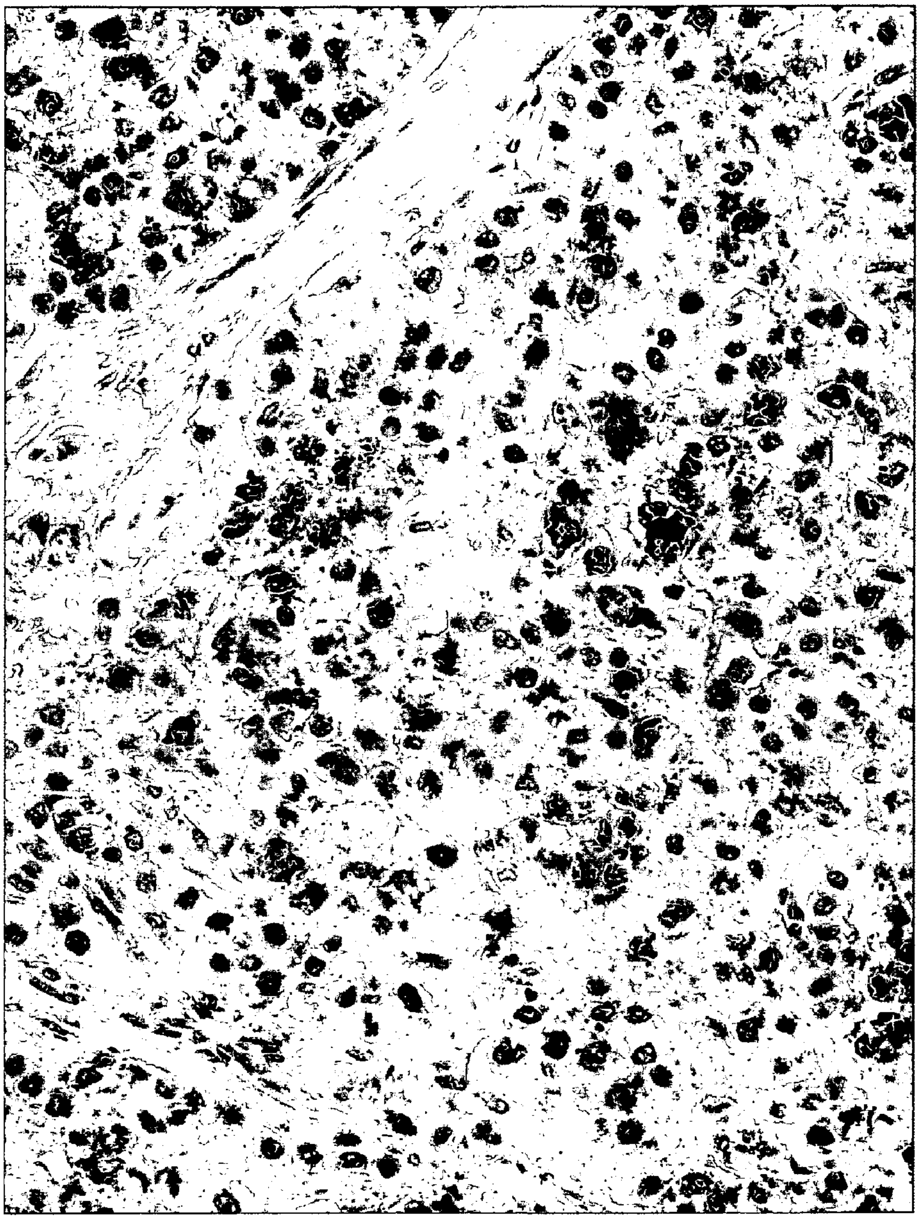
FIG. 18 is an image of an IHC slide from a representative, non-limiting HCC tissue sample that stained moderately positive for ROS expression.

Of the twenty-three samples assayed, one sample was strongly positive for staining (i.e., binding) by the ROS-specific antibody and nine cases showed weak to moderate staining. FIG. 18 shows a representative image of slide from a HCC tissue sample that stained moderately positive for ROS expression. This finding is notable because ROS is not expressed in normal bile duct tissue and is also not expressed in normal liver tissue.

Sequencing analysis of the samples showing strong staining with the ROS-specific antibody is expected to reveal the presence of either mutant ROS expression (e.g., over-expression of wild-type ROS in the hepatocellular carcinoma tissue where there is none in normal liver tissue) or the presence of a truncated ROS polypeptide or a ROS fusion protein (e.g., a FIG-ROS fusion polypeptide).

To determine whether or not the ROS antibody used was able to bind mutant ROS in these liver tissues, an IHC assay was performed on HCC78 cells (a non-small cell lung cancer known to express an SLC34A2-ROS fusion polypeptide) in the presence or absence of a competing ROS peptide.

IHC was performed as described above for the HCC and CCA tissue samples. Briefly, paraffin embedded HCC78 cell pellets were deparaffinized and rehydrated through three changes of xylene and graded ethanol, then rinsed in $diH_2O$. Slides were subjected to antigen retrieval in 1.0 mM EDTA, pH 8.0 in the microwave. After blocking for 1 hour in TBST/5% goat serum, slides were incubated overnight at 4° C. with Ros (D4D6) XP™ Rabbit mAb at 0.19 μg/ml in the absence of peptide or in the presence of one of 13 different ROS peptides at 1.9 μg/ml. The ROS peptides were as follows:

Peptide number: M09-6291
Peptide name: ROS-1
Peptide sequence: (biotin)AGAGCGQGEEKSEG
Peptide carboxyl-terminus: CONH2
Synthesis scale (μmol): 5
Peptide number: M09-6300
Peptide name: ROS-10
Peptide sequence: (biotin)AGAGSGKPEGLNYA
Peptide carboxyl-terminus: CONH2
Synthesis scale (μmol): 5
Peptide number: M09-6301
Peptide name: ROS-11
Peptide sequence: (biotin)AGAGGLNYACLTHS
Peptide carboxyl-terminus: CONH2
Synthesis scale (μmol): 5
Peptide number: M09-6302
Peptide name: ROS-12
Peptide sequence: (biotin)AGAGCLTHSGYGDG
Peptide carboxyl-terminus: CONH2
Synthesis scale (μmol): 5
Peptide number: M09-6303
Peptide name: ROS-13
Peptide sequence: (biotin)AGAGTHSGYGDGSD
Peptide carboxyl-terminus: CONH2
Synthesis scale (μmol): 5
Peptide number: M09-6292
Peptide name: ROS-2
Peptide sequence: (biotin)AGAGEKSEGPLGSQ
Peptide carboxyl-terminus: CONH2
Synthesis scale (μmol): 5
Peptide number: M09-6293
Peptide name: ROS-3
Peptide sequence: (biotin)AGAGPLGSQESESC
Peptide carboxyl-terminus: CONH2
Synthesis scale (μmol): 5
Peptide number: M09-6294
Peptide name: ROS-4

Peptide sequence: (biotin)AGAGESESCGLRKE
Peptide carboxyl-terminus: CONH2
Synthesis scale (μmol): 5
Peptide number: M09-6295
Peptide name: ROS-5
Peptide sequence: (biotin)AGAGGLRKEEKEPH
Peptide carboxyl-terminus: CONH2
Synthesis scale (μmol): 5
Peptide number: M09-6296
Peptide name: ROS-6
Peptide sequence: (biotin)AGAGEKEPHADKDF
Peptide carboxyl-terminus: CONH2
Synthesis scale (μmol): 5
Peptide number: M09-6297
Peptide name: ROS-7
Peptide sequence: (biotin)AGAGADKDFCQEKQ
Peptide carboxyl-terminus: CONH2
Synthesis scale (μmol): 5
Peptide number: M09-6298
Peptide name: ROS-8
Peptide sequence: (biotin)AGAGCQEKQVAYCP
Peptide carboxyl-terminus: CONH2
Synthesis scale (μmol): 5

Peptide number: M09-6299
Peptide name: ROS-9
Peptide sequence: (biotin)AGAGVAYCPSGKPE
Peptide carboxyl-terminus: CONH2
Synthesis scale (μmol): 5

After washing, detection was performed with Signal-Stain® Boost IHC Detection Reagent (HRP, Rabbit) #8114 and NovaRed (Vector Laboratories, Burlingame, Calif.).

Figure 19A:
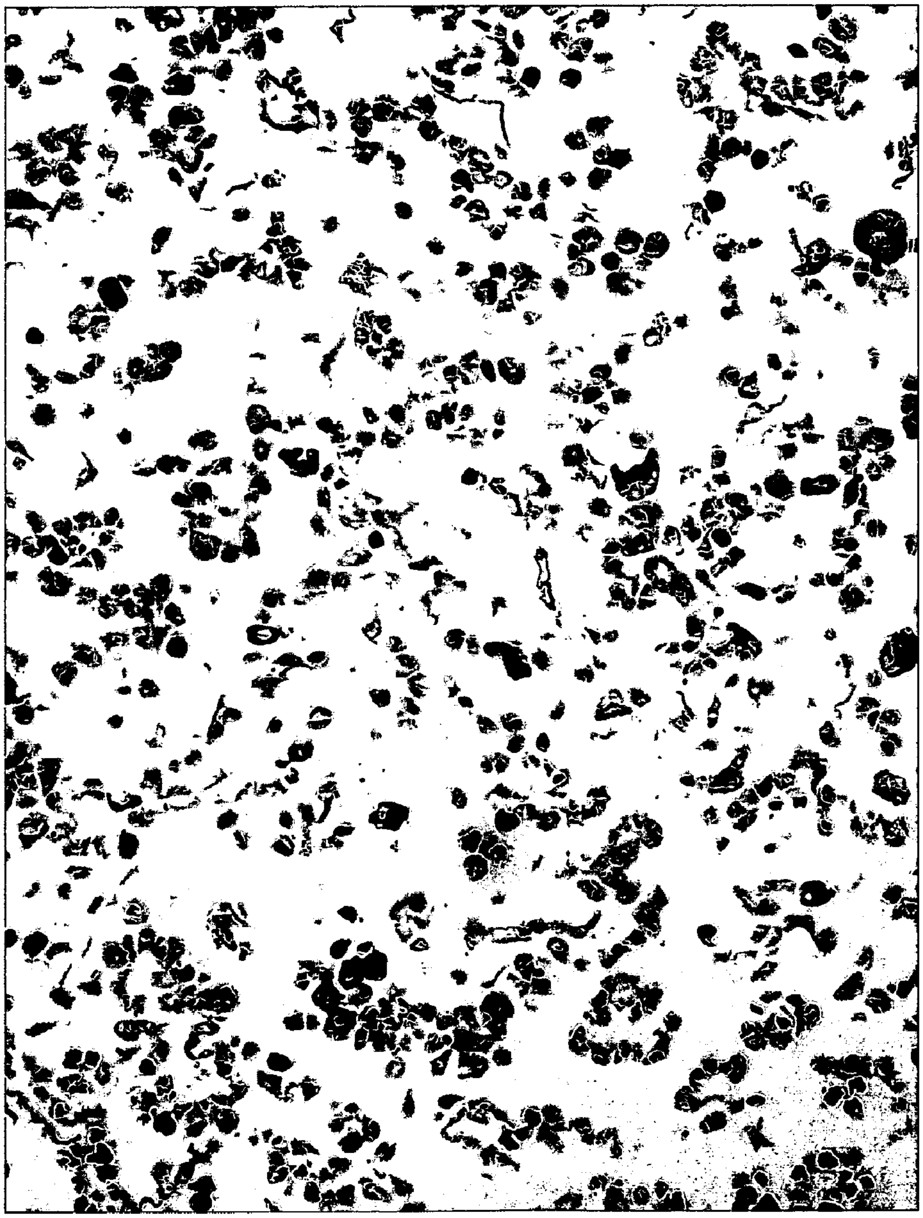
Figure 19B:
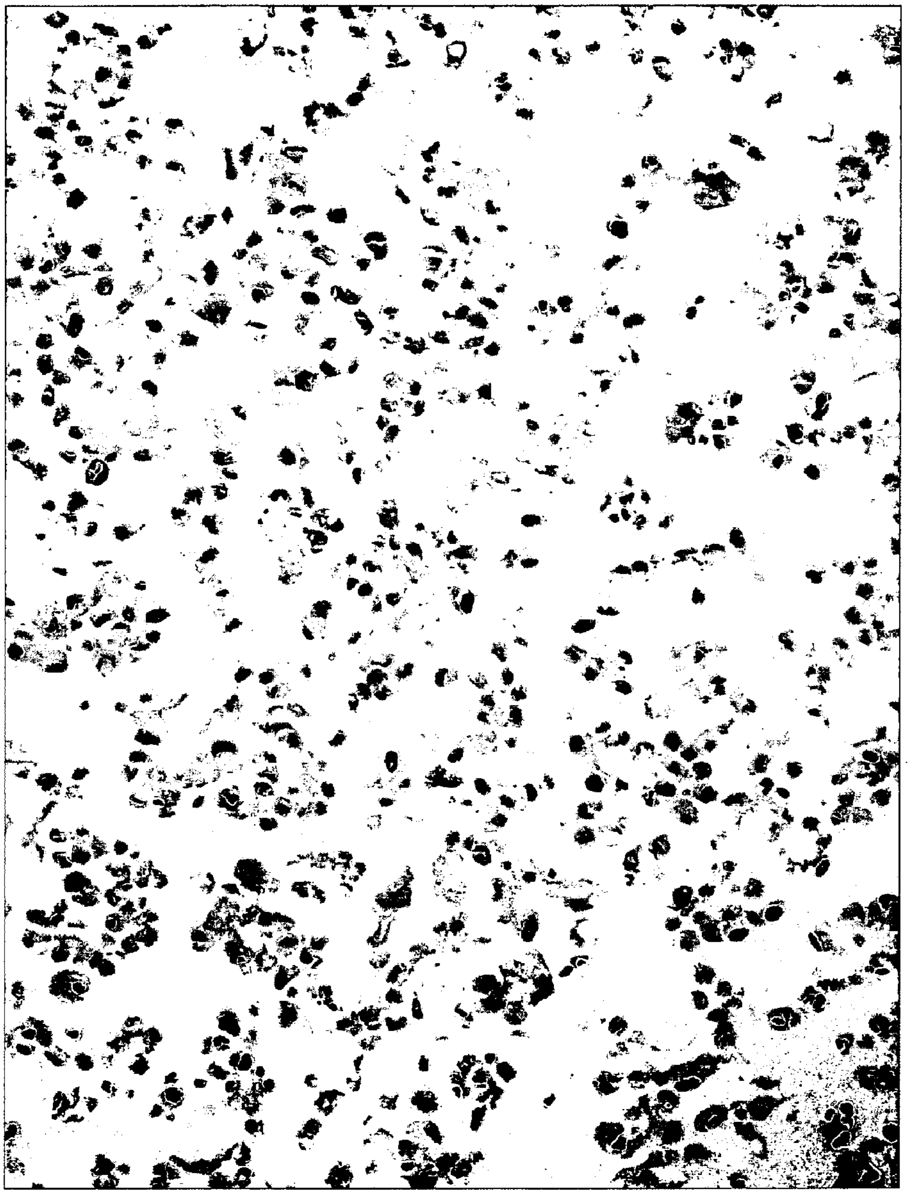

The results show that only peptide 9 was able to compete the binding of the antibody off of the IHC slide. FIG. 19A shows an IHC slide with the addition of peptide ROS-1 and FIG. 19B shows an IHC slide with the addition of peptide ROS-9. Thus, the sequence of ROS-9, namely AGAGVAY-CPSGKPE, is within the ROS kinase fragment specifically bound to by the antibody used in these studies. Since this sequence appears within the kinase domain of the ROS kinase, these studies strongly suggest that the CCA and HCC tissues that stained positive for binding with the ROS-specific antibody were expressing the kinase domain of ROS.

While the invention has been described with particular reference to the illustrated embodiments, it will be understood that numerous modifications thereto will appear to those skilled in the art. Accordingly, the above description and accompanying drawings should be taken as illustrative of the invention and not in a limiting sense.

What is claimed is:

1. A method comprising administering a therapeutically effective amount of a ROS inhibitor to a human patient having a cancer that exhibits a rearrangement involving the ROS gene, thereby treating the cancer, wherein the ROS inhibitor is PF-02341066, wherein the rearrangement results in a gene encoding a fusion polypeptide comprising a ROS kinase domain and wherein the fusion polypeptide is selected from the group consisting of a SLC34A2-ROS fusion polypeptide, a CD74-ROS fusion polypeptide, and a FIG-ROS fusion polypeptide.

2. A method comprising administering a therapeutically effective amount of a ROS inhibitor to a human patient identified as having a cancer that exhibits a rearrangement involving the ROS gene, thereby treating the cancer, wherein the ROS inhibitor is PF-02341066, wherein the rearrangement results in a gene encoding a fusion polypeptide comprising a ROS kinase domain and wherein the fusion polypeptide is selected from the group consisting of a SLC34A2-ROS fusion polypeptide, a CD74-ROS fusion polypeptide, and a FIG-ROS fusion polypeptide.

3. The method of claim 1, wherein the fusion polypeptide is a SLC34A2-ROS fusion polypeptide.

4. The method of claim 1, wherein the fusion polypeptide a CD74-ROS fusion polypeptide.

5. The method of claim 1, wherein the fusion polypeptide is a FIG-ROS fusion polypeptide.

6. The method of claim 2, wherein the fusion polypeptide is a SLC34A2-ROS fusion polypeptide.

7. The method of claim 2, wherein the fusion polypeptide a CD74-ROS fusion polypeptide.

8. The method of claim 2, wherein the fusion polypeptide is a FIG-ROS fusion polypeptide.

* * * * *

SEQUENCE LISTING

```
<160> NUMBER OF SEQ ID NOS: 61

<210> SEQ ID NO 1
<211> LENGTH: 2637
<212> TYPE: DNA
<213> ORGANISM: Artificial Sequence
<220> FEATURE:
<223> OTHER INFORMATION: Synthetic Nucleotide

<400> SEQUENCE: 1

atgtcggcgg gcggtccatg cccagcagca gccggagggg gcccaggggg cgcctcctgc      60

tccgtggggg cccctggcgg ggtatccatg ttccggtggc tggaggtgct ggagaaggag     120

ttcgacaaag cttttgtgga tgtggatctg ctcctgggag agatcgatcc agaccaagcg     180

gacatcactt atgaggggcg acagaagatg accagcctga gctcctgctt tgcacagctt     240

tgccacaaag cccagtctgt gtctcaaatc aaccacaagc tggaggcaca gttggtggat     300

ctgaaatctg aactgacaga aacccaagca gagaaagttg ttttggagaa agaagtacat     360

gatcagcttt tacagctgca ctctattcag ctgcagcttc atgctaaaac tggtcaaagt     420

gctgactctg gtaccattaa ggcaaaattg gaaagagagc ttgaggcaaa caaaaaagaa     480

aaaatgaaag aagcacaact tgaagctgaa gtgaaattgt tgagaaaaga gaatgaagcc     540

cttcgtagac atatagctgt tctccaggct gaagtatatg gggcgagact agctgccaag     600

tacttggata aggaactggc aggaagggtc caacagatac aattgctagg acgagatatg     660

aagggacctg ctcatgataa gctttggaac caattagaag ctgaaataca tttgcatcgt     720

cacaaaactg tgatccgagc ctgcagagga cgtaatgact tgaaacgacc aatgcaagca     780

ccaccaggcc atgatcaaga ttccctaaag aaaagccaag gtgttggtcc aattagaaaa     840

gttctcctcc ttaaggaaga tcatgaaggc cttggcattt caattacagg tgggaaagaa     900

catggtgttc caatcctcat ctctgagatc catccggggc aacctgctga tagatgcgga     960

gggctgcacg ttggggatgc tattttggca gtcaacggag ttaacctaag ggacacaaag    1020

cataaagaag ctgtaactat tctttctcag cagagaggag agattgaatt tgaagtagtt    1080
```

tatgtggctc ctgaagtgga ttctgatgat gaaaacgtag agtatgaaga tgagagtgga 1140
catcgttacc gtttgtacct tgatgagtta gaaggaggtg gtaaccctgg tgctagttgc 1200
aaagacacaa gtggggaaat caaagtatta caagtctggc atagaagatt aaagaatcaa 1260
aaaagtgcca aggaaggggt gacagtgctt ataaacgaag acaaagagtt ggctgagctg 1320
cgaggtctgg cagccggagt aggcctggct aatgcctgct atgcaataca tactcttcca 1380
acccaagagg agattgaaaa tcttcctgcc ttccctcggg aaaaactgac tctgcgtctc 1440
ttgctgggaa gtggagcctt tggagaagtg tatgaaggaa cagcagtgga catcttagga 1500
gttggaagtg gagaaatcaa agtagcagtg aagactttga agaagggttc cacagaccag 1560
gagaagattg aattcctgaa ggaggcacat ctgatgagca aatttaatca tcccaacatt 1620
ctgaagcagc ttggagtttg tctgctgaat gaaccccaat acattatcct ggaactgatg 1680
gagggaggag accttcttac ttatttgcgt aaagcccgga tggcaacgtt ttatggtcct 1740
ttactcacct tggttgacct tgtagacctg tgtgtagata tttcaaaagg ctgtgtctac 1800
ttggaacgga tgcatttcat tcacagggat ctggcagcta gaaattgcct tgtttccgtg 1860
aaagactata ccagtccacg gatagtgaag attggagact ttggactcgc cagagacatc 1920
tataaaaatg attactatag aaagagaggg gaaggcctgc tcccagttcg gtggatggct 1980
ccagaaagtt tgatggatgg aatcttcact actcaatctg atgtatggtc ttttggaatt 2040
ctgatttggg agattttaac tcttggtcat cagccttatc cagctcattc caaccttgat 2100
gtgttaaact atgtgcaaac aggagggaga ctggagccac caagaaattg tcctgatgat 2160
ctgtggaatt taatgaccca gtgctgggct caagaacccg accaaagacc tacttttcat 2220
agaattcagg accaacttca gttattcaga aatttttttct taaatagcat ttataagtcc 2280
agagatgaag caaacaacag tggagtcata aatgaaagct ttgaaggtga agatggcgat 2340
gtgatttgtt tgaattcaga tgacattatg ccagttgctt taatggaaac gaagaaccga 2400
gaagggttaa actatatggt acttgctaca gaatgtggcc aaggtgaaga aaagtctgag 2460
ggtcctctag gctcccagga atctgaatct tgtggtctga ggaaagaaga gaaggaacca 2520
catgcagaca aagatttctg ccaagaaaaa caagtggctt actgcccttc tggcaagcct 2580
gaaggcctga actatgcctg tctcactcac agtggatatg gagatgggtc tgattaa 2637

<210> SEQ ID NO 2
<211> LENGTH: 878
<212> TYPE: PRT
<213> ORGANISM: Artificial Sequence
<220> FEATURE:
<223> OTHER INFORMATION: Synthetic Peptide

<400> SEQUENCE: 2

Met Ser Ala Gly Gly Pro Cys Pro Ala Ala Ala Gly Gly Gly Pro Gly
1 5 10 15

Gly Ala Ser Cys Ser Val Gly Ala Pro Gly Gly Val Ser Met Phe Arg
20 25 30

Trp Leu Glu Val Leu Glu Lys Glu Phe Asp Lys Ala Phe Val Asp Val
35 40 45

Asp Leu Leu Leu Gly Glu Ile Asp Pro Asp Gln Ala Asp Ile Thr Tyr
50 55 60

Glu Gly Arg Gln Lys Met Thr Ser Leu Ser Ser Cys Phe Ala Gln Leu
65 70 75 80

Cys His Lys Ala Gln Ser Val Ser Gln Ile Asn His Lys Leu Glu Ala

-continued

```
                85                  90                  95

Gln Leu Val Asp Leu Lys Ser Glu Leu Thr Glu Thr Gln Ala Glu Lys
            100                 105                 110

Val Val Leu Glu Lys Glu Val His Asp Gln Leu Leu Gln Leu His Ser
        115                 120                 125

Ile Gln Leu Gln Leu His Ala Lys Thr Gly Gln Ser Ala Asp Ser Gly
    130                 135                 140

Thr Ile Lys Ala Lys Leu Glu Arg Glu Leu Glu Ala Asn Lys Lys Glu
145                 150                 155                 160

Lys Met Lys Glu Ala Gln Leu Glu Ala Glu Val Lys Leu Leu Arg Lys
                165                 170                 175

Glu Asn Glu Ala Leu Arg Arg His Ile Ala Val Leu Gln Ala Glu Val
            180                 185                 190

Tyr Gly Ala Arg Leu Ala Ala Lys Tyr Leu Asp Lys Glu Leu Ala Gly
        195                 200                 205

Arg Val Gln Gln Ile Gln Leu Leu Gly Arg Asp Met Lys Gly Pro Ala
    210                 215                 220

His Asp Lys Leu Trp Asn Gln Leu Glu Ala Glu Ile His Leu His Arg
225                 230                 235                 240

His Lys Thr Val Ile Arg Ala Cys Arg Gly Arg Asn Asp Leu Lys Arg
                245                 250                 255

Pro Met Gln Ala Pro Pro Gly His Asp Gln Asp Ser Leu Lys Lys Ser
            260                 265                 270

Gln Gly Val Gly Pro Ile Arg Lys Val Leu Leu Leu Lys Glu Asp His
        275                 280                 285

Glu Gly Leu Gly Ile Ser Ile Thr Gly Gly Lys Glu His Gly Val Pro
    290                 295                 300

Ile Leu Ile Ser Glu Ile His Pro Gly Gln Pro Ala Asp Arg Cys Gly
305                 310                 315                 320

Gly Leu His Val Gly Asp Ala Ile Leu Ala Val Asn Gly Val Asn Leu
                325                 330                 335

Arg Asp Thr Lys His Lys Glu Ala Val Thr Ile Leu Ser Gln Gln Arg
            340                 345                 350

Gly Glu Ile Glu Phe Glu Val Val Tyr Val Ala Pro Glu Val Asp Ser
        355                 360                 365

Asp Asp Glu Asn Val Glu Tyr Glu Asp Glu Ser Gly His Arg Tyr Arg
    370                 375                 380

Leu Tyr Leu Asp Glu Leu Glu Gly Gly Gly Asn Pro Gly Ala Ser Cys
385                 390                 395                 400

Lys Asp Thr Ser Gly Glu Ile Lys Val Leu Gln Val Trp His Arg Arg
                405                 410                 415

Leu Lys Asn Gln Lys Ser Ala Lys Glu Gly Val Thr Val Leu Ile Asn
            420                 425                 430

Glu Asp Lys Glu Leu Ala Glu Leu Arg Gly Leu Ala Ala Gly Val Gly
        435                 440                 445

Leu Ala Asn Ala Cys Tyr Ala Ile His Thr Leu Pro Thr Gln Glu Glu
    450                 455                 460

Ile Glu Asn Leu Pro Ala Phe Pro Arg Glu Lys Leu Thr Leu Arg Leu
465                 470                 475                 480

Leu Leu Gly Ser Gly Ala Phe Gly Glu Val Tyr Glu Gly Thr Ala Val
                485                 490                 495

Asp Ile Leu Gly Val Gly Ser Gly Glu Ile Lys Val Ala Val Lys Thr
            500                 505                 510
```

-continued

```
Leu Lys Lys Gly Ser Thr Asp Gln Glu Lys Ile Glu Phe Leu Lys Glu
        515                 520                 525

Ala His Leu Met Ser Lys Phe Asn His Pro Asn Ile Leu Lys Gln Leu
    530                 535                 540

Gly Val Cys Leu Leu Asn Glu Pro Gln Tyr Ile Ile Leu Glu Leu Met
545                 550                 555                 560

Glu Gly Gly Asp Leu Leu Thr Tyr Leu Arg Lys Ala Arg Met Ala Thr
                565                 570                 575

Phe Tyr Gly Pro Leu Leu Thr Leu Val Asp Leu Val Asp Leu Cys Val
            580                 585                 590

Asp Ile Ser Lys Gly Cys Val Tyr Leu Glu Arg Met His Phe Ile His
        595                 600                 605

Arg Asp Leu Ala Ala Arg Asn Cys Leu Val Ser Val Lys Asp Tyr Thr
    610                 615                 620

Ser Pro Arg Ile Val Lys Ile Gly Asp Phe Gly Leu Ala Arg Asp Ile
625                 630                 635                 640

Tyr Lys Asn Asp Tyr Tyr Arg Lys Arg Gly Glu Gly Leu Leu Pro Val
                645                 650                 655

Arg Trp Met Ala Pro Glu Ser Leu Met Asp Gly Ile Phe Thr Thr Gln
            660                 665                 670

Ser Asp Val Trp Ser Phe Gly Ile Leu Ile Trp Glu Ile Leu Thr Leu
        675                 680                 685

Gly His Gln Pro Tyr Pro Ala His Ser Asn Leu Asp Val Leu Asn Tyr
    690                 695                 700

Val Gln Thr Gly Gly Arg Leu Glu Pro Pro Arg Asn Cys Pro Asp Asp
705                 710                 715                 720

Leu Trp Asn Leu Met Thr Gln Cys Trp Ala Gln Glu Pro Asp Gln Arg
                725                 730                 735

Pro Thr Phe His Arg Ile Gln Asp Gln Leu Gln Leu Phe Arg Asn Phe
            740                 745                 750

Phe Leu Asn Ser Ile Tyr Lys Ser Arg Asp Glu Ala Asn Asn Ser Gly
        755                 760                 765

Val Ile Asn Glu Ser Phe Glu Gly Glu Asp Gly Asp Val Ile Cys Leu
    770                 775                 780

Asn Ser Asp Asp Ile Met Pro Val Ala Leu Met Glu Thr Lys Asn Arg
785                 790                 795                 800

Glu Gly Leu Asn Tyr Met Val Leu Ala Thr Glu Cys Gly Gln Gly Glu
                805                 810                 815

Glu Lys Ser Glu Gly Pro Leu Gly Ser Gln Glu Ser Glu Ser Cys Gly
            820                 825                 830

Leu Arg Lys Glu Glu Lys Glu Pro His Ala Asp Lys Asp Phe Cys Gln
        835                 840                 845

Glu Lys Gln Val Ala Tyr Cys Pro Ser Gly Lys Pro Glu Gly Leu Asn
    850                 855                 860

Tyr Ala Cys Leu Thr His Ser Gly Tyr Gly Asp Gly Ser Asp
865                 870                 875
```

<210> SEQ ID NO 3
<211> LENGTH: 1893
<212> TYPE: DNA
<213> ORGANISM: Artificial Sequence
<220> FEATURE:
<223> OTHER INFORMATION: Synthetic Nucleotide

<400> SEQUENCE: 3

-continued atgtcggcgg gcggtccatg cccagcagca gccggagggg gcccaggggg cgcctcctgc 60
tccgtggggg cccctggcgg ggtatccatg ttccggtggc tggaggtgct ggagaaggag 120
ttcgacaaag cttttgtgga tgtggatctg ctcctgggag agatcgatcc agaccaagcg 180
gacatcactt atgaggggcg acagaagatg accagcctga gctcctgctt tgcacagctt 240
tgccacaaag cccagtctgt gtctcaaatc aaccacaagc tggaggcaca gttggtggat 300
ctgaaatctg aactgacaga aacccaagca gagaaagttg ttttggagaa agaagtacat 360
gatcagcttt tacagctgca ctctattcag ctgcagcttc atgctaaaac tggtcaaagt 420
gctgactctg gtaccattaa ggcaaaattg gaaagagagc ttgaggcaaa caaaaaagaa 480
aaaatgaaag aagcacaact tgaagctgaa gtgaaattgt tgagaaaaga gaatgaagcc 540
cttcgtagac atatagctgt tctccaggct gaagtatatg gggcgagact agctgccaag 600
tacttggata aggaactggc aggaagtact cttccaaccc aagaggagat tgaaaatctt 660
cctgccttcc ctcgggaaaa actgactctg cgtctcttgc tgggaagtgg agcctttgga 720
gaagtgtatg aaggaacagc agtggacatc ttaggagttg gaagtggaga aatcaaagta 780
gcagtgaaga ctttgaagaa gggttccaca gaccaggaga agattgaatt cctgaaggag 840
gcacatctga tgagcaaatt taatcatccc aacattctga agcagcttgg agtttgtctg 900
ctgaatgaac cccaatacat tatcctggaa ctgatggagg gaggagacct tcttacttat 960
ttgcgtaaag cccggatggc aacgttttat ggtcctttac tcaccttggt tgaccttgta 1020
gacctgtgtg tagatatttc aaaaggctgt gtctacttgg aacggatgca tttcattcac 1080
agggatctgg cagctagaaa ttgccttgtt tccgtgaaag actataccag tccacggata 1140
gtgaagattg gagactttgg actcgccaga gacatctata aaaatgatta ctatagaaag 1200
agaggggaag gcctgctccc agttcggtgg atggctccag aaagtttgat ggatggaatc 1260
ttcactactc aatctgatgt atggtctttt ggaattctga tttgggagat tttaactctt 1320
ggtcatcagc cttatccagc tcattccaac cttgatgtgt taaactatgt gcaaacagga 1380
gggagactgg agccaccaag aaattgtcct gatgatctgt ggaatttaat gacccagtgc 1440
tgggctcaag aacccgacca aagacctact tttcatagaa ttcaggacca acttcagtta 1500
ttcagaaatt ttttcttaaa tagcatttat aagtccagag atgaagcaaa caacagtgga 1560
gtcataaatg aaagctttga aggtgaagat ggcgatgtga tttgtttgaa ttcagatgac 1620
attatgccag ttgctttaat ggaaacgaag aaccgagaag ggttaaacta tatggtactt 1680
gctacagaat gtggccaagg tgaagaaaag tctgagggtc ctctaggctc ccaggaatct 1740
gaatcttgtg gtctgaggaa agaagagaag gaaccacatg cagacaaaga tttctgccaa 1800
gaaaaacaag tggcttactg cccttctggc aagcctgaag gcctgaacta tgcctgtctc 1860
actcacagtg gatatggaga tgggtctgat taa 1893

<210> SEQ ID NO 4
<211> LENGTH: 630
<212> TYPE: PRT
<213> ORGANISM: Artificial Sequence
<220> FEATURE:
<223> OTHER INFORMATION: Synthetic Peptide

<400> SEQUENCE: 4

Met Ser Ala Gly Gly Pro Cys Pro Ala Ala Ala Gly Gly Gly Pro Gly
1 5 10 15

Gly Ala Ser Cys Ser Val Gly Ala Pro Gly Gly Val Ser Met Phe Arg

```
            20                  25                  30

Trp Leu Glu Val Leu Glu Lys Glu Phe Asp Lys Ala Phe Val Asp Val
        35                  40                  45

Asp Leu Leu Leu Gly Glu Ile Asp Pro Asp Gln Ala Asp Ile Thr Tyr
    50                  55                  60

Glu Gly Arg Gln Lys Met Thr Ser Leu Ser Ser Cys Phe Ala Gln Leu
65                  70                  75                  80

Cys His Lys Ala Gln Ser Val Ser Gln Ile Asn His Lys Leu Glu Ala
                85                  90                  95

Gln Leu Val Asp Leu Lys Ser Glu Leu Thr Glu Thr Gln Ala Glu Lys
            100                 105                 110

Val Val Leu Glu Lys Glu Val His Asp Gln Leu Leu Gln Leu His Ser
        115                 120                 125

Ile Gln Leu Gln Leu His Ala Lys Thr Gly Gln Ser Ala Asp Ser Gly
    130                 135                 140

Thr Ile Lys Ala Lys Leu Glu Arg Glu Leu Glu Ala Asn Lys Lys Glu
145                 150                 155                 160

Lys Met Lys Glu Ala Gln Leu Glu Ala Glu Val Lys Leu Leu Arg Lys
                165                 170                 175

Glu Asn Glu Ala Leu Arg Arg His Ile Ala Val Leu Gln Ala Glu Val
            180                 185                 190

Tyr Gly Ala Arg Leu Ala Ala Lys Tyr Leu Asp Lys Glu Leu Ala Gly
        195                 200                 205

Ser Thr Leu Pro Thr Gln Glu Glu Ile Glu Asn Leu Pro Ala Phe Pro
    210                 215                 220

Arg Glu Lys Leu Thr Leu Arg Leu Leu Leu Gly Ser Gly Ala Phe Gly
225                 230                 235                 240

Glu Val Tyr Glu Gly Thr Ala Val Asp Ile Leu Gly Val Gly Ser Gly
                245                 250                 255

Glu Ile Lys Val Ala Val Lys Thr Leu Lys Lys Gly Ser Thr Asp Gln
            260                 265                 270

Glu Lys Ile Glu Phe Leu Lys Glu Ala His Leu Met Ser Lys Phe Asn
        275                 280                 285

His Pro Asn Ile Leu Lys Gln Leu Gly Val Cys Leu Leu Asn Glu Pro
    290                 295                 300

Gln Tyr Ile Ile Leu Glu Leu Met Glu Gly Gly Asp Leu Leu Thr Tyr
305                 310                 315                 320

Leu Arg Lys Ala Arg Met Ala Thr Phe Tyr Gly Pro Leu Leu Thr Leu
                325                 330                 335

Val Asp Leu Val Asp Leu Cys Val Asp Ile Ser Lys Gly Cys Val Tyr
            340                 345                 350

Leu Glu Arg Met His Phe Ile His Arg Asp Leu Ala Ala Arg Asn Cys
        355                 360                 365

Leu Val Ser Val Lys Asp Tyr Thr Ser Pro Arg Ile Val Lys Ile Gly
    370                 375                 380

Asp Phe Gly Leu Ala Arg Asp Ile Tyr Lys Asn Asp Tyr Tyr Arg Lys
385                 390                 395                 400

Arg Gly Glu Gly Leu Leu Pro Val Arg Trp Met Ala Pro Glu Ser Leu
                405                 410                 415

Met Asp Gly Ile Phe Thr Thr Gln Ser Asp Val Trp Ser Phe Gly Ile
            420                 425                 430

Leu Ile Trp Glu Ile Leu Thr Leu Gly His Gln Pro Tyr Pro Ala His
        435                 440                 445
```

-continued

```
Ser Asn Leu Asp Val Leu Asn Tyr Val Gln Thr Gly Gly Arg Leu Glu
    450                 455                 460

Pro Pro Arg Asn Cys Pro Asp Asp Leu Trp Asn Leu Met Thr Gln Cys
465                 470                 475                 480

Trp Ala Gln Glu Pro Asp Gln Arg Pro Thr Phe His Arg Ile Gln Asp
                485                 490                 495

Gln Leu Gln Leu Phe Arg Asn Phe Phe Leu Asn Ser Ile Tyr Lys Ser
            500                 505                 510

Arg Asp Glu Ala Asn Asn Ser Gly Val Ile Asn Glu Ser Phe Glu Gly
        515                 520                 525

Glu Asp Gly Asp Val Ile Cys Leu Asn Ser Asp Asp Ile Met Pro Val
    530                 535                 540

Ala Leu Met Glu Thr Lys Asn Arg Glu Gly Leu Asn Tyr Met Val Leu
545                 550                 555                 560

Ala Thr Glu Cys Gly Gln Gly Glu Glu Lys Ser Glu Gly Pro Leu Gly
                565                 570                 575

Ser Gln Glu Ser Glu Ser Cys Gly Leu Arg Lys Glu Glu Lys Glu Pro
            580                 585                 590

His Ala Asp Lys Asp Phe Cys Gln Glu Lys Gln Val Ala Tyr Cys Pro
        595                 600                 605

Ser Gly Lys Pro Glu Gly Leu Asn Tyr Ala Cys Leu Thr His Ser Gly
    610                 615                 620

Tyr Gly Asp Gly Ser Asp
625                 630


<210> SEQ ID NO 5
<211> LENGTH: 1544
<212> TYPE: DNA
<213> ORGANISM: Artificial Sequence
<220> FEATURE:
<223> OTHER INFORMATION: Synthetic Nucleotide

<400> SEQUENCE: 5

gtgtgtaaaa aatgggtatt attgtactct taagtgacaa attggatatt taatgaggtt      60

gactcttact tctttctttt tttatttttt atttttttga gatggagtct tgctctgttg     120

cccaggctgg agtgcagtgg catgatctct gctcactgca acctctgcct cctgggttca     180

agcgattctc ctacctcagc ctcctgagta gctgggatta caggtgcctg ccaccacggc     240

cagctaaatt ttgtattttt agtagagatg gggtttcacc atgttggcca ggctggtctc     300

aaactcctga ccttgtgatc catccacctt ggcctcccaa agtgctggga ttacaggtgt     360

gagccaccgc acctggccta ctcttttttc ttatggtaaa tgaagcatta atctttttcc     420

tcagaattat tttacagttg gttttaactt actgttgtta aattaatact gacagcatta     480

tgtatcgcag atctagttat ccatactaaa tatgtttagt ttacacacac aaacactgat     540

agtatcttac tgtgaaatgc taacaactct gtagagcagc acttttcaac tattttgtgc     600

cttgagacca gtacagccga tattcacatg catagcagaa cttccataag gaattctttt     660

tatgatcact gaaacccagt ctttcttgcc cttcaaaaaa acgtgttggt atttagttaa     720

tgacaatgat tttatcataa tcatacacag aattctgctg tatttattaa gtaaattatt     780

aacaaacttt ggtgacttat tagtactaaa tcattttgtg catattcttt taatgtcaca     840

ttaaaaacat ggaacaaaga aaaaataatt tatatcatct tgaagtacaa attttctagt     900

aacttttttt ttttttaaa ttttgtgaga tggggtctca ctctgtcgct caggatggag     960
```

-continued tgcagtggtg caacgttggc tcactgcagc gtccaccttt caggctcaag tgatcctccc 1020
acctcagcct tccaagtagc tgagaccaca ggcatgccac catgcctggt taattgttaa 1080
ggttttgcct tgttgccctg gctggttcta gtaactttta accacattta aagtaatcat 1140
tttgtgaaaa gaaactctaa ttagaagaaa tatttttgtc catttatctc atctaaaagc 1200
taacatttaa tagtatctga gttcagtgac tttgcatgca agacatagat tgacattaat 1260
ctcataaatt ttttttaga tttatttgaa ttaagtatat gactaaagga gttcacatta 1320
attcctttaa aaattttttt tactggtttt tcccttgagg atacctgttc ttttcagagt 1380
tttcatattt tttttatatc tgagagacat caagaagttc gtgagtatta gttttatcac 1440
taatttgaga ttcatgcaaa agctacttat gttcactaat tttcctgaat tctcactgta 1500
gtgaatataa tgaaaaatca atgtactctt ttcccaatat gaag 1544

<210> SEQ ID NO 6
<211> LENGTH: 3469
<212> TYPE: DNA
<213> ORGANISM: Artificial Sequence
<220> FEATURE:
<223> OTHER INFORMATION: Synthetic Nucleotide

<400> SEQUENCE: 6
gtaaaaatca ctctaaaaat tattattaac atattcatta ttattaaatg tttaaaatgt 60
gaaggcctca gaatttcttc agtaaaactg ttttgtgagg aaatcaaagg aatgaagagc 120
tttcccttgt ttattgtttt attgtatact atgctaacag tttatttacc atatatgttc 180
ttctatattc atcttggact gttaagacaa gtacattacc agttactcta ctgcaagtga 240
tccttgaaaa ataaataaaa tttttctag actctgaaac aaagaccaat atactatttt 300
gagtagatct atcttgtaga ctacattgtc tgtctgtctt gatgcaaatt catctctcac 360
aatgaatttt aagctaatta tgaataagta tgaagtatac tgtcacctta tgattgctat 420
tagaatcaac ttatattatc ttggggatgt ttggtttagt tcctttgcta tcatttagac 480
atattttaag gaaaaactct agcacttcct tttacataga gcagtggtcc tcaaattgtg 540
atctgtggat ctctgagggt ctctgagata ttttagcaga gttcatgagg tcaaagcttt 600
tcataataat actaagacat catttgtctt tttttgctat gttgatattt gcactgatgg 660
tatctggttg atgcaaaagc aattggggta aaactgctgg tgccttagca ctaatcaagg 720
cagtgttgct aatactagta actgtactag taatcattgt tttcttcctt gccatccatt 780
catagtaaaa gaagaagata ccaattttgc ttaaaaatat ctttgatgaa atggcagtaa 840
cagttaattt ttaaatattg acctttgagt acctgtcttt ttaatattct ttgtgatgag 900
atgggaagta tgcataaagc acttactctg cacactgaac aaagatgctg gtttcaaggg 960
aaagtacata agtgactgaa ctagccattt ttcttcatgg aagacaattt ttacttgaat 1020
gaatgactaa caaagtatgg attttcggac tatttggaag ccattttctt aaaaatgaac 1080
aaagtccatc acttcaggaa agacaactga taatatttat tgccagtgat aaaatgtgag 1140
ctctcaagtg aaagttagaa ctttgtaaaa catacgttga tcaccatgag cttgacagct 1200
tcctaacact taagcttttc tgatgagatt gatgatgata ttaatgaatg tgattttttg 1260
atacagtaaa gtgaaatgtg tcaacttttg gaattgctac ataacttcat ggtccaatat 1320
ttttcaaatc accagtaaat gaagttataa aattttgcat gggaaaagat ccattcaaaa 1380
tgcaagatag gcaaatggat tttaatataa cagagtgtga aaagttcact gataaggttt 1440
caaattccac attgtcaaat ttttgtataa tatcagagaa caatactgac agttatctga 1500
aaaggctgtt aaaatactct tccatttagc aactacatat ctgtgtgagg ctgaactttc 1560
ttcatatact tgtaatagat tgaatggaag cagatatatg aaaatacagc tatcatctac 1620
aaagccattg aagagatttg taaaattgta aaataatgct actcttctaa ctagaatttt 1680
tttgtttgga acatagagtt atttgtcatt agacaaatgt tatttatatt aaccttctgg 1740
atttattgtc atttttaaca aagaaatgaa ttttttttta gattttcaa ttttacctac 1800 taatatggga aacatcagta gctataatcc acataaacag aagcttcttg gagtcctcaa 1860
tgcttagtat aaaggcctcc tgagaccaaa atgttgaact cctggcatgg agttttatgg 1920
tgaactgata aactgttgca cttttgataa acttgtgtgt tgtaaactgt ctgcacaaag 1980
atagcagtag cagttactgt tttcactgtg catcttgagc aaaactattg tggcagtatg 2040
tcaaaacctt aattgttggg ctgctctcca tatggtttca ttgtatttca cacttgctgt 2100
tttctgtcgg gattagaaag cctgtctctt cctttttttt gtaactgagg ctagaagtct 2160
tctctgtcac atatgcaaat tgcagacact taaaatgtga ctcaactaaa aatttgtgtg 2220
tatatatctt ttaactgact cacttaaaaa aatgtatcta ttggttattg tttcacacgt 2280
ctatacttta tagatatata tatcacctaa ataggtgata tagtcaacac ttatttattt 2340
ataagcctat tatttatttt atagatgatc agaattcgtt ttaagtttta gctagacatc 2400
atcttgccaa caaattacat tttaagcaat taactagtat atgcctcagt taactgaagt 2460
taatgtaata tgaaagcaac aatgaaaaat aaaaatataa ttcacagttc agtagatatt 2520
tatataagta gaattgactg aattttacaa ttatatgtat tacttctaag tcttacagac 2580
agcttgatgg tggctcatgc ctgtaattca agcactttgg gaggccaagg caggaggatc 2640
gcttgaggcc aggagttacc aacctgggca acatagtgaa ccctgtctct tcaaaaaaat 2700
ttttaaaata tagctggaca tggtggcaca tgcttgtagc tccagctact caggaggctg 2760
aggtggaagg attgcttgag cctaggaggt caaggcagca gtgagccgta atcatgccac 2820
tgcaatccag cctgggcaat agagtgagac cctgtctcag aaaaaaaaaa gaaaaaaaaa 2880
aaaggaaagg aaaacttgat aggaaactta atacaatttt tacataagcc caatatagta 2940
tttttaaatc tgtacaatat ttgatacctg ccataagagg gaagaattcc cctgttagga 3000
attactgatt tgattaatat aaggcattat ttttgcctca gattactaat gttaattact 3060
tgggcattcc tttgttttc actcaataaa cttatacaac taactttttt ttttttttta 3120 attttttaa tcgagacaga gtttcactct gtcacccagg ctagagtgcg gtggtacgat 3180
ctcagctcac tgcaacctcc acttcctggc ttcaagtgat tctccttcct cagtctccca 3240
aatagctggg attacaggca tgtgccacca tgcccggcga atttttgtat ttttaataga 3300
gacggggttt caccacattg tccaggctgg tctcgaaccc ctaacctcag gttatccacc 3360
caccttggcc tctcaaagtg ctgggattac aggtatgagc cactgcacct gaccaaaacc 3420
aactttttaa accagaaagt gtctgctttt tttttctcct ttctttcag 3469

<210> SEQ ID NO 7
<211> LENGTH: 3616
<212> TYPE: DNA
<213> ORGANISM: Artificial Sequence
<220> FEATURE:
<223> OTHER INFORMATION: Synthetic Nucleotide

<400> SEQUENCE: 7
gtatgttacc atgtctgtct acacactagc ttattaccta aaggttcagt aataaatatc 60

-continued

```
agtacattct taacattagc aatagataat ggtgactata tatatatata tatatatata    120
tatatatata taatcttatt atccaaacta ttaaactatt ccattcatgt gatgtgatct    180
ttctaaaaca tcattatcat catgtcattt ttctccccaa taataatcag ccacccccctt    240
aattcctacc acatcaattc catgctccta attaggcttc caaggctgtt cacaatctgt    300
tctatccagc catataattc tattcacatt ataccagcct tatgaccact cctacattat    360
acataacagg cctaagacct ttgtttcttc cccaatatct acctcttcca ctgtgtattt    420
tattttagtt tatgatatat tgtctttcta atcacatagg caggaaatct cagtgccata    480
tgtgattttt ccctctactc agtaatcagg tcctgttgat tttaccatct tgatttttct    540
ctgatgagtt ctcatcttcc tctttccacc ttggctttcc taatttaagg tatcatttct    600
tgcctgtgcc cttgacttac gcatactgct gacagttaaa tttagttgaa gcacaggctg    660
gattacttaa tccctctctg aaatacccac aatggctctc catttactgc tttcagaatc    720
agctacaaac ttctttgtgg catgtgaggt cttctgtaat ttatcctcca attgtggttt    780
atcttttcca atatttatgt ctgtgctgta gccatatcag accagtaaaa agtttttatg    840
tcacttagtc tttggccctg tgtttgcctc agcctagaat acaggtcccc actacctacc    900
ctgtgcccct tagctgtgat ttcctattat ttattttctg ccaattgaaa ttcttctcat    960
ccttcaagac ttaaatgaac tcatcataat gcttacctga tgctccttag tcaaatgaat   1020
tattgcattt tatacactca catgctatat aaaacttaca tgattcttgt ttatattata   1080
gttagttatc tagttagttg tgtacagaag tttgctaccc agctcagcaa actttttctg   1140
aaaagaacca aatagtaaat atgttagact ttgcaggcta catgtgatct ctgtagcatg   1200
ttcttctttt cttcttttc tgttctcttt ttccttctcc ttctttttaa aaataacact   1260
ttacaaaggt aaaacttatt catagctaat agggggtaca aaatcaggct atagccagat   1320
ttggtcctca tgccatagtt tgccagactc tggcctacgt gtttgtttcc tctacacaac   1380
tgaaactacc taagagaaat taccatgttt attcctcagt ttaatatcca tgaaattaaa   1440
tatgtatgaa gatattatac aaaataataa tgccaactat ttagtatcca aagactgaga   1500
tttcttggtc ctaaatttat taaaaagata tatatgtttc ctaagtcatt ttaaagtaga   1560
agattgagtg gatatattcc agtggtttgt tgctctctgc aaaaaaaagc aaaaacacct   1620
tgcttttgat ttcacatggc ataaacactg tctgtatgga tgctttcaag ctaccaacgg   1680
tctaacaact ggcttgcaaa aatccagtag tagctagctc tgctatatta ctctgtgtgc   1740
ttaggtagag ctggggcaac ttagctttta tctatgaatt aatttctttt tctgatttat   1800
attattaggt atgttaccat gtctgtctac acactagctt attacctaaa ggttcagtaa   1860
taaatatcag tacattctta acattagcaa tagataatgg tgactatata tatatatata   1920
tatatatata tatatatata atcttattat ccaaactatt aaactattcc attcatgtga   1980
tgtgatcttt ctaaaacatc attatcatca tgtcattttt ctccccaata ataatcagcc   2040
acccccttaa ttcctaccac atcaattcca tgctcctaat taggcttcca aggctgttca   2100
caatctgttc tatccagcca tataattcta ttcacattat accagcctta tgaccactcc   2160
tacattatac ataacaggcc taagaccttt gtttcttccc caatatctac ctcttccact   2220
gtgtatttta ttttagttta tgatatattg tctttctaat cacataggca ggaaatctca   2280
gtgccatatg tgatttttcc ctctactcag taatcaggtc ctgttgattt taccatcttg   2340
atttttctct gatgagttct catcttcctc tttccacctt ggctttccta atttaaggta   2400
tcatttcttg cctgtgccct tgacttacgc atactgctga cagttaaatt tagttgaagc   2460
```

-continued

```
acaggctgga ttacttaatc cctctctgaa atacccacaa tggctctcca tttactgctt   2520

tcagaatcag ctacaaactt ctttgtggca tgtgaggtct tctgtaattt atcctccaat   2580

tgtggtttat cttttccaat atttatgtct gtgctgtagc catatcagac cagtaaaaag   2640

tttttatgtc acttagtctt tggccctgtg tttgcctcag cctagaatac aggtccccac   2700

tacctaccct gtgcccctta gctgtgattt cctattattt attttctgcc aattgaaatt   2760

cttctcatcc ttcaagactt aaatgaactc atcataatgc ttacctgatg ctccttagtc   2820

aaatgaatta ttgcatttta tacactcaca tgctatataa aacttacatg attcttgttt   2880

atattatagt tagttatcta gttagttgtg tacagaagtt tgctacccag ctcagcaaac   2940

tttttctgaa aagaaccaaa tagtaaatat gttagacttt gcaggctaca tgtgatctct   3000

gtagcatgtt cttcttttct tctttttctg ttctcttttt ccttctcctt ctttttaaaa   3060

ataacacttt acaaaggtaa aacttattca tagctaatag ggggtacaaa atcaggctat   3120

agccagattt ggtcctcatg ccatagtttg ccagactctg gcctacgtgt ttgtttcctc   3180

tacacaactg aaactaccta agagaaatta ccatgtttat tcctcagttt aatatccatg   3240

aaattaaata tgtatgaaga tattatacaa aataataatg ccaactattt agtatccaaa   3300

gactgagatt tcttggtcct aaatttatta aaaagatata tatgtttcct aagtcatttt   3360

aaagtagaag attgagtgga tatattccag tggtttgttg ctctctgcaa aaaaaagcaa   3420

aaacaccttg cttttgattt cacatggcat aaacactgtc tgtatggatg ctttcaagct   3480

accaacggtc taacaactgg cttgcaaaaa tccagtagta gctagctctg ctatattact   3540

ctgtgtgctt aggtagagct ggggcaactt agcttttatc tatgaattaa tttctttttc   3600

tgatttatat tattag                                                   3616
```

```
<210> SEQ ID NO 8
<211> LENGTH: 2937
<212> TYPE: DNA
<213> ORGANISM: Artificial Sequence
<220> FEATURE:
<223> OTHER INFORMATION: Synthetic Nucleotide

<400> SEQUENCE: 8

gtaagtataa tagaattttt aaaataggca acaaactgtt tacttaatca tacctgattg     60

atttatctct tagttgatct aatctcccac atgaaatatt gcctgattaa gttaataaaa    120

tttacattgt tacctttggc tatacattta taaccactaa cttctgtgaa ttgttttctg    180

atctaggcat aactatttta tggaaaatat acatgtacat ttcatgttat actttagata    240

aaactacttg caagggcacc aacttttagg tttctttaaa acagtattta tttctgattg    300

gctgcataca aatgttttgt ggcttatggt ttaaaataaa taaaagaaaa ataaccctgg    360

gtacagaaaa aagtatagaa ttaatgggag gccagtgaca atctttgatt gggatagttt    420

tggtttctaa gcagacaggc tggtttggaa tgagtagggc ctcttttgca gaagatccat    480

ttctggcttg tgggatcgac tcttgctttc agacatctga tctgcttatt tcaaatccct    540

gctcatttat aaatgaccag gaaggcagaa aaattaggtt aggtagatag aaagctattt    600

tttttctaag aagatttact ttaatgataa taaaatgcag taaaaacctc aaagggaatg    660

gtcaagtact gattggactt ttagagttat cacagtgatc atacattctt gtttatttct    720

gtttcagcac aaataataat agcactttct ttcattcccc aaactgtccg agtttgctta    780

taagatatat ggacccctat ctattgctaa tattgagagt ccccaacaca ctgaatcatt    840
```

-continued

```
aaaagaaggg catgattctt accagaaaag aacactcaaa cacatattaa gaaagttgtg    900
gcttgttttg ttcacaagta ggggtaagtt acaagggaaa gttgatggaa aagtcacaaa    960
cataaagttg aactctcagg ataaagacag ccaacacttt actgtgttct aagtctttat   1020
tctttctgca aagtgattgg agtcacaatc tttatgagag cactttgaag ctcgatttga   1080
gatttttttc aaagattcca cccagacaat atgtgaaact ccttcagcaa acttggaaag   1140
ctaaaaattt cagctgaccc tgccaggatt ttaacctgtg gttccagaga gtctaagtat   1200
tgcacagctg atgtttgtgc cactaagcca gcccctccag acttacgcat atgactgcag   1260
tatatttggc agttggcata taggcttgac tgcttgtctg ctttcctact gggaaggaga   1320
attacatgaa gaatccttca gctgaccttt gcttgctttc ttgtacatca ccattgttta   1380
aacccataac tctagtggat gaacatgaga taatttcaga caacctattg tgcttccaag   1440
acatcctatg gatatctgac tttctcagga cttaaaggtc tttattctgt ttgaaattca   1500
cgaatttttg agtctagcta agctaattcg gttctttgct tttagcagca gtgcatgtgg   1560
ttttactagt aagagcgtgt gtgtgcatga gaaaagattg agtaattaaa ataacaaaac   1620
agtcacaatt attttaaaat ttgtattgtg ctgagggcac tcatcagtta taaacataaa   1680
attagacaat ttttaaaatg agtgttgaca gcctttgctt ctgagcagtc atatctaatg   1740
cataacatta gccttctgct gggagtaggg gaaaatgtaa acctgtaaaa tacaactgct   1800
gacctcagga gcttgccatt taatgaggga gttaagacat gcctgtgtgg gaagacaaat   1860
agcaagatat gtgttaaata ataacaaaag acaaaaatag atgaaataag taagacagtg   1920
cataggataa gcactcacag agaggcgcaa ttagtctttc aagttcagat atgaaagatt   1980
agtagaggtt gctgaggttt cagaaggcat cattgaggat gtgggcttac attgggcctt   2040
taaaagtgaa gcgaggtggt gagaacattt caagttggaa aaattaattt agcaaaaggt   2100
acttgtgatc tttcactgtg tagcccttca aattgaattt catgtgaata aaactctaac   2160
ttcttgaaca tagaagctac tgtgaaatta agttcaaatt ttaatgatca tctctcaaag   2220
catgcttgct gctttcaact tctgagccaa tagtccagta cagatgacaa tcctattgac   2280
ataattgtat tttaatatta aaaaaatttt attattataa aactaatact gcttattata   2340
taaggaagac agtacaaatt actcatgatt ctacaactag ggcagaccac tgctaacatt   2400
tggtaagctt cgttccaata ctttttctac atattcgagt atgtgtatat gaacaacaat   2460
gataaacact cttgtactct gcaaaaaaaa aaaaaaaaaa aattgccatt atactgaaag   2520
cattttcttt tctactgagg aatataacct ggatgtgact gaactcaaaa atgaatttgt   2580
ttcactaata attatgtttg ttttggttta ttttgactcg tttatgggtg attttgacaa   2640
ataagtttta atattaagat actttaattt gtttataaca acagtaagaa atacattaaa   2700
ttttaagaag tgagattaaa aatggtgtag tatgatttgt gtacttatat atggcttttt   2760
acctggattt aattagtttt ttataagata ttttaaaatc aaattatgaa aacttctata   2820
actattctac tgatagtgtt cttgcataaa aacacttcaa atgcactgtt aacatttcct   2880
aaaggaaaaa agaagcaata ttttattttg taaattatgt catttttttcc tttatag     2937
```

<210> SEQ ID NO 9
<211> LENGTH: 2347
<212> TYPE: PRT
<213> ORGANISM: Artificial Sequence
<220> FEATURE:
<223> OTHER INFORMATION: Synthetic Peptide

<400> SEQUENCE: 9

-continued

```
Met Lys Asn Ile Tyr Cys Leu Ile Pro Lys Leu Val Asn Phe Ala Thr
1               5                   10                  15

Leu Gly Cys Leu Trp Ile Ser Val Val Gln Cys Thr Val Leu Asn Ser
            20                  25                  30

Cys Leu Lys Ser Cys Val Thr Asn Leu Gly Gln Gln Leu Asp Leu Gly
        35                  40                  45

Thr Pro His Asn Leu Ser Glu Pro Cys Ile Gln Gly Cys His Phe Trp
    50                  55                  60

Asn Ser Val Asp Gln Lys Asn Cys Ala Leu Lys Cys Arg Glu Ser Cys
65                  70                  75                  80

Glu Val Gly Cys Ser Ser Ala Glu Gly Ala Tyr Glu Glu Glu Val Leu
                85                  90                  95

Glu Asn Ala Asp Leu Pro Thr Ala Pro Phe Ala Ser Ser Ile Gly Ser
            100                 105                 110

His Asn Met Thr Leu Arg Trp Lys Ser Ala Asn Phe Ser Gly Val Lys
        115                 120                 125

Tyr Ile Ile Gln Trp Lys Tyr Ala Gln Leu Leu Gly Ser Trp Thr Tyr
    130                 135                 140

Thr Lys Thr Val Ser Arg Pro Ser Tyr Val Val Lys Pro Leu His Pro
145                 150                 155                 160

Phe Thr Glu Tyr Ile Phe Arg Val Val Trp Ile Phe Thr Ala Gln Leu
                165                 170                 175

Gln Leu Tyr Ser Pro Pro Ser Pro Ser Tyr Arg Thr His Pro His Gly
            180                 185                 190

Val Pro Glu Thr Ala Pro Leu Ile Arg Asn Ile Glu Ser Ser Ser Pro
        195                 200                 205

Asp Thr Val Glu Val Ser Trp Asp Pro Pro Gln Phe Pro Gly Gly Pro
    210                 215                 220

Ile Leu Gly Tyr Asn Leu Arg Leu Ile Ser Lys Asn Gln Lys Leu Asp
225                 230                 235                 240

Ala Gly Thr Gln Arg Thr Ser Phe Gln Phe Tyr Ser Thr Leu Pro Asn
                245                 250                 255

Thr Ile Tyr Arg Phe Ser Ile Ala Ala Val Asn Glu Val Gly Glu Gly
            260                 265                 270

Pro Glu Ala Glu Ser Ser Ile Thr Thr Ser Ser Ser Ala Val Gln Gln
        275                 280                 285

Glu Glu Gln Trp Leu Phe Leu Ser Arg Lys Thr Ser Leu Arg Lys Arg
    290                 295                 300

Ser Leu Lys His Leu Val Asp Glu Ala His Cys Leu Arg Leu Asp Ala
305                 310                 315                 320

Ile Tyr His Asn Ile Thr Gly Ile Ser Val Asp Val His Gln Gln Ile
                325                 330                 335

Val Tyr Phe Ser Glu Gly Thr Leu Ile Trp Ala Lys Lys Ala Ala Asn
            340                 345                 350

Met Ser Asp Val Ser Asp Leu Arg Ile Phe Tyr Arg Gly Ser Gly Leu
        355                 360                 365

Ile Ser Ser Ile Ser Ile Asp Trp Leu Tyr Gln Arg Met Tyr Phe Ile
    370                 375                 380

Met Asp Glu Leu Val Cys Val Cys Asp Leu Glu Asn Cys Ser Asn Ile
385                 390                 395                 400

Glu Glu Ile Thr Pro Pro Ser Ile Ser Ala Pro Gln Lys Ile Val Ala
                405                 410                 415
```

-continued

```
Asp Ser Tyr Asn Gly Tyr Val Phe Tyr Leu Leu Arg Asp Gly Ile Tyr
            420                 425                 430

Arg Ala Asp Leu Pro Val Pro Ser Gly Arg Cys Ala Glu Ala Val Arg
        435                 440                 445

Ile Val Glu Ser Cys Thr Leu Lys Asp Phe Ala Ile Lys Pro Gln Ala
    450                 455                 460

Lys Arg Ile Ile Tyr Phe Asn Asp Thr Ala Gln Val Phe Met Ser Thr
465                 470                 475                 480

Phe Leu Asp Gly Ser Ala Ser His Leu Ile Leu Pro Arg Ile Pro Phe
                485                 490                 495

Ala Asp Val Lys Ser Phe Ala Cys Glu Asn Asn Asp Phe Leu Val Thr
            500                 505                 510

Asp Gly Lys Val Ile Phe Gln Gln Asp Ala Leu Ser Phe Asn Glu Phe
        515                 520                 525

Ile Val Gly Cys Asp Leu Ser His Ile Glu Glu Phe Gly Phe Gly Asn
    530                 535                 540

Leu Val Ile Phe Gly Ser Ser Ser Gln Leu His Pro Leu Pro Gly Arg
545                 550                 555                 560

Pro Gln Glu Leu Ser Val Leu Phe Gly Ser His Gln Ala Leu Val Gln
                565                 570                 575

Trp Lys Pro Pro Ala Leu Ala Ile Gly Ala Asn Val Ile Leu Ile Ser
            580                 585                 590

Asp Ile Ile Glu Leu Phe Glu Leu Gly Pro Ser Ala Trp Gln Asn Trp
        595                 600                 605

Thr Tyr Glu Val Lys Val Ser Thr Gln Asp Pro Pro Glu Val Thr His
    610                 615                 620

Ile Phe Leu Asn Ile Ser Gly Thr Met Leu Asn Val Pro Glu Leu Gln
625                 630                 635                 640

Ser Ala Met Lys Tyr Lys Val Ser Val Arg Ala Ser Ser Pro Lys Arg
                645                 650                 655

Pro Gly Pro Trp Ser Glu Pro Ser Val Gly Thr Thr Leu Val Pro Ala
            660                 665                 670

Ser Glu Pro Pro Phe Ile Met Ala Val Lys Glu Asp Gly Leu Trp Ser
        675                 680                 685

Lys Pro Leu Asn Ser Phe Gly Pro Gly Glu Phe Leu Ser Ser Asp Ile
    690                 695                 700

Gly Asn Val Ser Asp Met Asp Trp Tyr Asn Asn Ser Leu Tyr Tyr Ser
705                 710                 715                 720

Asp Thr Lys Gly Asp Val Phe Val Trp Leu Leu Asn Gly Thr Asp Ile
                725                 730                 735

Ser Glu Asn Tyr His Leu Pro Ser Ile Ala Gly Ala Gly Ala Leu Ala
            740                 745                 750

Phe Glu Trp Leu Gly His Phe Leu Tyr Trp Ala Gly Lys Thr Tyr Val
        755                 760                 765

Ile Gln Arg Gln Ser Val Leu Thr Gly His Thr Asp Ile Val Thr His
    770                 775                 780

Val Lys Leu Leu Val Asn Asp Met Val Val Asp Ser Val Gly Gly Tyr
785                 790                 795                 800

Leu Tyr Trp Thr Thr Leu Tyr Ser Val Glu Ser Thr Arg Leu Asn Gly
                805                 810                 815

Glu Ser Ser Leu Val Leu Gln Thr Gln Pro Trp Phe Ser Gly Lys Lys
            820                 825                 830

Val Ile Ala Leu Thr Leu Asp Leu Ser Asp Gly Leu Leu Tyr Trp Leu
```

-continued

```
        835                 840                 845

Val Gln Asp Ser Gln Cys Ile His Leu Tyr Thr Ala Val Leu Arg Gly
    850                 855                 860

Gln Ser Thr Gly Asp Thr Thr Ile Thr Glu Phe Ala Ala Trp Ser Thr
865                 870                 875                 880

Ser Glu Ile Ser Gln Asn Ala Leu Met Tyr Tyr Ser Gly Arg Leu Phe
                885                 890                 895

Trp Ile Asn Gly Phe Arg Ile Ile Thr Thr Gln Glu Ile Gly Gln Lys
            900                 905                 910

Thr Ser Val Ser Val Leu Glu Pro Ala Arg Phe Asn Gln Phe Thr Ile
        915                 920                 925

Ile Gln Thr Ser Leu Lys Pro Leu Pro Gly Asn Phe Ser Phe Thr Pro
    930                 935                 940

Lys Val Ile Pro Asp Ser Val Gln Glu Ser Ser Phe Arg Ile Glu Gly
945                 950                 955                 960

Asn Ala Ser Ser Phe Gln Ile Leu Trp Asn Gly Pro Pro Ala Val Asp
                965                 970                 975

Trp Gly Val Val Phe Tyr Ser Val Glu Phe Ser Ala His Ser Lys Phe
            980                 985                 990

Leu Ala Ser Glu Gln His Ser Leu  Pro Val Phe Thr Val  Glu Gly Leu
        995                 1000                1005

Glu Pro  Tyr Ala Leu Phe Asn  Leu Ser Val Thr Pro  Tyr Thr Tyr
    1010                1015                1020

Trp Gly  Lys Gly Pro Lys Thr  Ser Leu Ser Leu Arg  Ala Pro Glu
    1025                1030                1035

Thr Val  Pro Ser Ala Pro Glu  Asn Pro Arg Ile Phe  Ile Leu Pro
    1040                1045                1050

Ser Gly  Lys Cys Cys Asn Lys  Asn Glu Val Val Val  Glu Phe Arg
    1055                1060                1065

Trp Asn  Lys Pro Lys His Glu  Asn Gly Val Leu Thr  Lys Phe Glu
    1070                1075                1080

Ile Phe  Tyr Asn Ile Ser Asn  Gln Ser Ile Thr Asn  Lys Thr Cys
    1085                1090                1095

Glu Asp  Trp Ile Ala Val Asn  Val Thr Pro Ser Val  Met Ser Phe
    1100                1105                1110

Gln Leu  Glu Gly Met Ser Pro  Arg Cys Phe Ile Ala  Phe Gln Val
    1115                1120                1125

Arg Ala  Phe Thr Ser Lys Gly  Pro Gly Pro Tyr Ala  Asp Val Val
    1130                1135                1140

Lys Ser  Thr Thr Ser Glu Ile  Asn Pro Phe Pro His  Leu Ile Thr
    1145                1150                1155

Leu Leu  Gly Asn Lys Ile Val  Phe Leu Asp Met Asp  Gln Asn Gln
    1160                1165                1170

Val Val  Trp Thr Phe Ser Ala  Glu Arg Val Ile Ser  Ala Val Cys
    1175                1180                1185

Tyr Thr  Ala Asp Asn Glu Met  Gly Tyr Tyr Ala Glu  Gly Asp Ser
    1190                1195                1200

Leu Phe  Leu Leu His Leu His  Asn Arg Ser Ser Ser  Glu Leu Phe
    1205                1210                1215

Gln Asp  Ser Leu Val Phe Asp  Ile Thr Val Ile Thr  Ile Asp Trp
    1220                1225                1230

Ile Ser  Arg His Leu Tyr Phe  Ala Leu Lys Glu Ser  Gln Asn Gly
    1235                1240                1245
```

```
Met Gln  Val Phe Asp Val Asp  Leu Glu His Lys Val  Lys Tyr Pro
    1250                 1255                 1260

Arg Glu  Val Lys Ile His Asn  Arg Asn Ser Thr Ile  Ile Ser Phe
    1265                 1270                 1275

Ser Val  Tyr Pro Leu Leu Ser  Arg Leu Tyr Trp Thr  Glu Val Ser
    1280                 1285                 1290

Asn Phe  Gly Tyr Gln Met Phe  Tyr Tyr Ser Ile Ile  Ser His Thr
    1295                 1300                 1305

Leu His  Arg Ile Leu Gln Pro  Thr Ala Thr Asn Gln  Gln Asn Lys
    1310                 1315                 1320

Arg Asn  Gln Cys Ser Cys Asn  Val Thr Glu Phe Glu  Leu Ser Gly
    1325                 1330                 1335

Ala Met  Ala Ile Asp Thr Ser  Asn Leu Glu Lys Pro  Leu Ile Tyr
    1340                 1345                 1350

Phe Ala  Lys Ala Gln Glu Ile  Trp Ala Met Asp Leu  Glu Gly Cys
    1355                 1360                 1365

Gln Cys  Trp Arg Val Ile Thr  Val Pro Ala Met Leu  Ala Gly Lys
    1370                 1375                 1380

Thr Leu  Val Ser Leu Thr Val  Asp Gly Asp Leu Ile  Tyr Trp Ile
    1385                 1390                 1395

Ile Thr  Ala Lys Asp Ser Thr  Gln Ile Tyr Gln Ala  Lys Lys Gly
    1400                 1405                 1410

Asn Gly  Ala Ile Val Ser Gln  Val Lys Ala Leu Arg  Ser Arg His
    1415                 1420                 1425

Ile Leu  Ala Tyr Ser Ser Val  Met Gln Pro Phe Pro  Asp Lys Ala
    1430                 1435                 1440

Phe Leu  Ser Leu Ala Ser Asp  Thr Val Glu Pro Thr  Ile Leu Asn
    1445                 1450                 1455

Ala Thr  Asn Thr Ser Leu Thr  Ile Arg Leu Pro Leu  Ala Lys Thr
    1460                 1465                 1470

Asn Leu  Thr Trp Tyr Gly Ile  Thr Ser Pro Thr Pro  Thr Tyr Leu
    1475                 1480                 1485

Val Tyr  Tyr Ala Glu Val Asn  Asp Arg Lys Asn Ser  Ser Asp Leu
    1490                 1495                 1500

Lys Tyr  Arg Ile Leu Glu Phe  Gln Asp Ser Ile Ala  Leu Ile Glu
    1505                 1510                 1515

Asp Leu  Gln Pro Phe Ser Thr  Tyr Met Ile Gln Ile  Ala Val Lys
    1520                 1525                 1530

Asn Tyr  Tyr Ser Asp Pro Leu  Glu His Leu Pro Pro  Gly Lys Glu
    1535                 1540                 1545

Ile Trp  Gly Lys Thr Lys Asn  Gly Val Pro Glu Ala  Val Gln Leu
    1550                 1555                 1560

Ile Asn  Thr Thr Val Arg Ser  Asp Thr Ser Leu Ile  Ile Ser Trp
    1565                 1570                 1575

Arg Glu  Ser His Lys Pro Asn  Gly Pro Lys Glu Ser  Val Arg Tyr
    1580                 1585                 1590

Gln Leu  Ala Ile Ser His Leu  Ala Leu Ile Pro Glu  Thr Pro Leu
    1595                 1600                 1605

Arg Gln  Ser Glu Phe Pro Asn  Gly Arg Leu Thr Leu  Leu Val Thr
    1610                 1615                 1620

Arg Leu  Ser Gly Gly Asn Ile  Tyr Val Leu Lys Val  Leu Ala Cys
    1625                 1630                 1635
```

```
His Ser  Glu Glu Met Trp Cys  Thr Glu Ser His Pro  Val Thr Val
    1640                 1645                 1650

Glu Met  Phe Asn Thr Pro Glu  Lys Pro Tyr Ser Leu  Val Pro Glu
    1655                 1660                 1665

Asn Thr  Ser Leu Gln Phe Asn  Trp Lys Ala Pro Leu  Asn Val Asn
    1670                 1675                 1680

Leu Ile  Arg Phe Trp Val Glu  Leu Gln Lys Trp Lys  Tyr Asn Glu
    1685                 1690                 1695

Phe Tyr  His Val Lys Thr Ser  Cys Ser Gln Gly Pro  Ala Tyr Val
    1700                 1705                 1710

Cys Asn  Ile Thr Asn Leu Gln  Pro Tyr Thr Ser Tyr  Asn Val Arg
    1715                 1720                 1725

Val Val  Val Val Tyr Lys Thr  Gly Glu Asn Ser Thr  Ser Leu Pro
    1730                 1735                 1740

Glu Ser  Phe Lys Thr Lys Ala  Gly Val Pro Asn Lys  Pro Gly Ile
    1745                 1750                 1755

Pro Lys  Leu Leu Glu Gly Ser  Lys Asn Ser Ile Gln  Trp Glu Lys
    1760                 1765                 1770

Ala Glu  Asp Asn Gly Cys Arg  Ile Thr Tyr Tyr Ile  Leu Glu Ile
    1775                 1780                 1785

Arg Lys  Ser Thr Ser Asn Asn  Leu Gln Asn Gln Asn  Leu Arg Trp
    1790                 1795                 1800

Lys Met  Thr Phe Asn Gly Ser  Cys Ser Ser Val Cys  Thr Trp Lys
    1805                 1810                 1815

Ser Lys  Asn Leu Lys Gly Ile  Phe Gln Phe Arg Val  Val Ala Ala
    1820                 1825                 1830

Asn Asn  Leu Gly Phe Gly Glu  Tyr Ser Gly Ile Ser  Glu Asn Ile
    1835                 1840                 1845

Ile Leu  Val Gly Asp Asp Phe  Trp Ile Pro Glu Thr  Ser Phe Ile
    1850                 1855                 1860

Leu Thr  Ile Ile Val Gly Ile  Phe Leu Val Val Thr  Ile Pro Leu
    1865                 1870                 1875

Thr Phe  Val Trp His Arg Arg  Leu Lys Asn Gln Lys  Ser Ala Lys
    1880                 1885                 1890

Glu Gly  Val Thr Val Leu Ile  Asn Glu Asp Lys Glu  Leu Ala Glu
    1895                 1900                 1905

Leu Arg  Gly Leu Ala Ala Gly  Val Gly Leu Ala Asn  Ala Cys Tyr
    1910                 1915                 1920

Ala Ile  His Thr Leu Pro Thr  Gln Glu Glu Ile Glu  Asn Leu Pro
    1925                 1930                 1935

Ala Phe  Pro Arg Glu Lys Leu  Thr Leu Arg Leu Leu  Leu Gly Ser
    1940                 1945                 1950

Gly Ala  Phe Gly Glu Val Tyr  Glu Gly Thr Ala Val  Asp Ile Leu
    1955                 1960                 1965

Gly Val  Gly Ser Gly Glu Ile  Lys Val Ala Val Lys  Thr Leu Lys
    1970                 1975                 1980

Lys Gly  Ser Thr Asp Gln Glu  Lys Ile Glu Phe Leu  Lys Glu Ala
    1985                 1990                 1995

His Leu  Met Ser Lys Phe Asn  His Pro Asn Ile Leu  Lys Gln Leu
    2000                 2005                 2010

Gly Val  Cys Leu Leu Asn Glu  Pro Gln Tyr Ile Ile  Leu Glu Leu
    2015                 2020                 2025

Met Glu  Gly Gly Asp Leu Leu  Thr Tyr Leu Arg Lys  Ala Arg Met
```

```
    2030                2035                2040

Ala Thr  Phe Tyr Gly Pro Leu  Leu Thr Leu Val Asp  Leu Val Asp
    2045                2050                2055

Leu Cys  Val Asp Ile Ser Lys  Gly Cys Val Tyr Leu  Glu Arg Met
    2060                2065                2070

His Phe  Ile His Arg Asp Leu  Ala Ala Arg Asn Cys  Leu Val Ser
    2075                2080                2085

Val Lys  Asp Tyr Thr Ser Pro  Arg Ile Val Lys Ile  Gly Asp Phe
    2090                2095                2100

Gly Leu  Ala Arg Asp Ile Tyr  Lys Asn Asp Tyr Tyr  Arg Lys Arg
    2105                2110                2115

Gly Glu  Gly Leu Leu Pro Val  Arg Trp Met Ala Pro  Glu Ser Leu
    2120                2125                2130

Met Asp  Gly Ile Phe Thr Thr  Gln Ser Asp Val Trp  Ser Phe Gly
    2135                2140                2145

Ile Leu  Ile Trp Glu Ile Leu  Thr Leu Gly His Gln  Pro Tyr Pro
    2150                2155                2160

Ala His  Ser Asn Leu Asp Val  Leu Asn Tyr Val Gln  Thr Gly Gly
    2165                2170                2175

Arg Leu  Glu Pro Pro Arg Asn  Cys Pro Asp Asp Leu  Trp Asn Leu
    2180                2185                2190

Met Thr  Gln Cys Trp Ala Gln  Glu Pro Asp Gln Arg  Pro Thr Phe
    2195                2200                2205

His Arg  Ile Gln Asp Gln Leu  Gln Leu Phe Arg Asn  Phe Phe Leu
    2210                2215                2220

Asn Ser  Ile Tyr Lys Ser Arg  Asp Glu Ala Asn Asn  Ser Gly Val
    2225                2230                2235

Ile Asn  Glu Ser Phe Glu Gly  Glu Asp Gly Asp Val  Ile Cys Leu
    2240                2245                2250

Asn Ser  Asp Asp Ile Met Pro  Val Ala Leu Met Glu  Thr Lys Asn
    2255                2260                2265

Arg Glu  Gly Leu Asn Tyr Met  Val Leu Ala Thr Glu  Cys Gly Gln
    2270                2275                2280

Gly Glu  Glu Lys Ser Glu Gly  Pro Leu Gly Ser Gln  Glu Ser Glu
    2285                2290                2295

Ser Cys  Gly Leu Arg Lys Glu  Glu Lys Glu Pro His  Ala Asp Lys
    2300                2305                2310

Asp Phe  Cys Gln Glu Lys Gln  Val Ala Tyr Cys Pro  Ser Gly Lys
    2315                2320                2325

Pro Glu  Gly Leu Asn Tyr Ala  Cys Leu Thr His Ser  Gly Tyr Gly
    2330                2335                2340

Asp Gly  Ser Asp
    2345


<210> SEQ ID NO 10
<211> LENGTH: 1881
<212> TYPE: PRT
<213> ORGANISM: Artificial Sequence
<220> FEATURE:
<223> OTHER INFORMATION: Synthetic Peptide

<400> SEQUENCE: 10

Met Lys Asn Ile Tyr Cys Leu Ile Pro Lys Leu Val Asn Phe Ala Thr
1               5                   10                  15

Leu Gly Cys Leu Trp Ile Ser Val Val Gln Cys Thr Val Leu Asn Ser
```

```
            20                  25                  30

Cys Leu Lys Ser Cys Val Thr Asn Leu Gly Gln Gln Leu Asp Leu Gly
        35                  40                  45

Thr Pro His Asn Leu Ser Glu Pro Cys Ile Gln Gly Cys His Phe Trp
    50                  55                  60

Asn Ser Val Asp Gln Lys Asn Cys Ala Leu Lys Cys Arg Glu Ser Cys
65                  70                  75                  80

Glu Val Gly Cys Ser Ser Ala Glu Gly Ala Tyr Glu Glu Glu Val Leu
                85                  90                  95

Glu Asn Ala Asp Leu Pro Thr Ala Pro Phe Ala Ser Ser Ile Gly Ser
            100                 105                 110

His Asn Met Thr Leu Arg Trp Lys Ser Ala Asn Phe Ser Gly Val Lys
        115                 120                 125

Tyr Ile Ile Gln Trp Lys Tyr Ala Gln Leu Leu Gly Ser Trp Thr Tyr
    130                 135                 140

Thr Lys Thr Val Ser Arg Pro Ser Tyr Val Val Lys Pro Leu His Pro
145                 150                 155                 160

Phe Thr Glu Tyr Ile Phe Arg Val Val Trp Ile Phe Thr Ala Gln Leu
                165                 170                 175

Gln Leu Tyr Ser Pro Pro Ser Pro Ser Tyr Arg Thr His Pro His Gly
            180                 185                 190

Val Pro Glu Thr Ala Pro Leu Ile Arg Asn Ile Glu Ser Ser Ser Pro
        195                 200                 205

Asp Thr Val Glu Val Ser Trp Asp Pro Pro Gln Phe Pro Gly Gly Pro
    210                 215                 220

Ile Leu Gly Tyr Asn Leu Arg Leu Ile Ser Lys Asn Gln Lys Leu Asp
225                 230                 235                 240

Ala Gly Thr Gln Arg Thr Ser Phe Gln Phe Tyr Ser Thr Leu Pro Asn
                245                 250                 255

Thr Ile Tyr Arg Phe Ser Ile Ala Ala Val Asn Glu Val Gly Glu Gly
            260                 265                 270

Pro Glu Ala Glu Ser Ser Ile Thr Thr Ser Ser Ser Ala Val Gln Gln
        275                 280                 285

Glu Glu Gln Trp Leu Phe Leu Ser Arg Lys Thr Ser Leu Arg Lys Arg
    290                 295                 300

Ser Leu Lys His Leu Val Asp Glu Ala His Cys Leu Arg Leu Asp Ala
305                 310                 315                 320

Ile Tyr His Asn Ile Thr Gly Ile Ser Val Asp Val His Gln Gln Ile
                325                 330                 335

Val Tyr Phe Ser Glu Gly Thr Leu Ile Trp Ala Lys Lys Ala Ala Asn
            340                 345                 350

Met Ser Asp Val Ser Asp Leu Arg Ile Phe Tyr Arg Gly Ser Gly Leu
        355                 360                 365

Ile Ser Ser Ile Ser Ile Asp Trp Leu Tyr Gln Arg Met Tyr Phe Ile
    370                 375                 380

Met Asp Glu Leu Val Cys Val Cys Asp Leu Glu Asn Cys Ser Asn Ile
385                 390                 395                 400

Glu Glu Ile Thr Pro Pro Ser Ile Ser Ala Pro Gln Lys Ile Val Ala
                405                 410                 415

Asp Ser Tyr Asn Gly Tyr Val Phe Tyr Leu Leu Arg Asp Gly Ile Tyr
            420                 425                 430

Arg Ala Asp Leu Pro Val Pro Ser Gly Arg Cys Ala Glu Ala Val Arg
        435                 440                 445
```

-continued

```
Ile Val Glu Ser Cys Thr Leu Lys Asp Phe Ala Ile Lys Pro Gln Ala
    450                 455                 460

Lys Arg Ile Ile Tyr Phe Asn Asp Thr Ala Gln Val Phe Met Ser Thr
465                 470                 475                 480

Phe Leu Asp Gly Ser Ala Ser His Leu Ile Leu Pro Arg Ile Pro Phe
                485                 490                 495

Ala Asp Val Lys Ser Phe Ala Cys Glu Asn Asn Asp Phe Leu Val Thr
            500                 505                 510

Asp Gly Lys Val Ile Phe Gln Gln Asp Ala Leu Ser Phe Asn Glu Phe
        515                 520                 525

Ile Val Gly Cys Asp Leu Ser His Ile Glu Glu Phe Gly Phe Gly Asn
    530                 535                 540

Leu Val Ile Phe Gly Ser Ser Ser Gln Leu His Pro Leu Pro Gly Arg
545                 550                 555                 560

Pro Gln Glu Leu Ser Val Leu Phe Gly Ser His Gln Ala Leu Val Gln
                565                 570                 575

Trp Lys Pro Pro Ala Leu Ala Ile Gly Ala Asn Val Ile Leu Ile Ser
            580                 585                 590

Asp Ile Ile Glu Leu Phe Glu Leu Gly Pro Ser Ala Trp Gln Asn Trp
        595                 600                 605

Thr Tyr Glu Val Lys Val Ser Thr Gln Asp Pro Pro Glu Val Thr His
    610                 615                 620

Ile Phe Leu Asn Ile Ser Gly Thr Met Leu Asn Val Pro Glu Leu Gln
625                 630                 635                 640

Ser Ala Met Lys Tyr Lys Val Ser Val Arg Ala Ser Ser Pro Lys Arg
                645                 650                 655

Pro Gly Pro Trp Ser Glu Pro Ser Val Gly Thr Thr Leu Val Pro Ala
            660                 665                 670

Ser Glu Pro Pro Phe Ile Met Ala Val Lys Glu Asp Gly Leu Trp Ser
        675                 680                 685

Lys Pro Leu Asn Ser Phe Gly Pro Gly Glu Phe Leu Ser Ser Asp Ile
    690                 695                 700

Gly Asn Val Ser Asp Met Asp Trp Tyr Asn Asn Ser Leu Tyr Tyr Ser
705                 710                 715                 720

Asp Thr Lys Gly Asp Val Phe Val Trp Leu Leu Asn Gly Thr Asp Ile
                725                 730                 735

Ser Glu Asn Tyr His Leu Pro Ser Ile Ala Gly Ala Gly Ala Leu Ala
            740                 745                 750

Phe Glu Trp Leu Gly His Phe Leu Tyr Trp Ala Gly Lys Thr Tyr Val
        755                 760                 765

Ile Gln Arg Gln Ser Val Leu Thr Gly His Thr Asp Ile Val Thr His
    770                 775                 780

Val Lys Leu Leu Val Asn Asp Met Val Val Asp Ser Val Gly Gly Tyr
785                 790                 795                 800

Leu Tyr Trp Thr Thr Leu Tyr Ser Val Glu Ser Thr Arg Leu Asn Gly
                805                 810                 815

Glu Ser Ser Leu Val Leu Gln Thr Gln Pro Trp Phe Ser Gly Lys Lys
            820                 825                 830

Val Ile Ala Leu Thr Leu Asp Leu Ser Asp Gly Leu Leu Tyr Trp Leu
        835                 840                 845

Val Gln Asp Ser Gln Cys Ile His Leu Tyr Thr Ala Val Leu Arg Gly
    850                 855                 860
```

-continued

```
Gln Ser Thr Gly Asp Thr Thr Ile Thr Glu Phe Ala Ala Trp Ser Thr
865                 870                 875                 880

Ser Glu Ile Ser Gln Asn Ala Leu Met Tyr Tyr Ser Gly Arg Leu Phe
                885                 890                 895

Trp Ile Asn Gly Phe Arg Ile Ile Thr Thr Gln Glu Ile Gly Gln Lys
            900                 905                 910

Thr Ser Val Ser Val Leu Glu Pro Ala Arg Phe Asn Gln Phe Thr Ile
        915                 920                 925

Ile Gln Thr Ser Leu Lys Pro Leu Pro Gly Asn Phe Ser Phe Thr Pro
    930                 935                 940

Lys Val Ile Pro Asp Ser Val Gln Glu Ser Ser Phe Arg Ile Glu Gly
945                 950                 955                 960

Asn Ala Ser Ser Phe Gln Ile Leu Trp Asn Gly Pro Pro Ala Val Asp
                965                 970                 975

Trp Gly Val Val Phe Tyr Ser Val Glu Phe Ser Ala His Ser Lys Phe
            980                 985                 990

Leu Ala Ser Glu Gln His Ser Leu  Pro Val Phe Thr Val  Glu Gly Leu
        995                 1000                1005

Glu Pro  Tyr Ala Leu Phe Asn  Leu Ser Val Thr Pro  Tyr Thr Tyr
    1010                1015                1020

Trp Gly  Lys Gly Pro Lys Thr  Ser Leu Ser Leu Arg  Ala Pro Glu
    1025                1030                1035

Thr Val  Pro Ser Ala Pro Glu  Asn Pro Arg Ile Phe  Ile Leu Pro
    1040                1045                1050

Ser Gly  Lys Cys Cys Asn Lys  Asn Glu Val Val Val  Glu Phe Arg
    1055                1060                1065

Trp Asn  Lys Pro Lys His Glu  Asn Gly Val Leu Thr  Lys Phe Glu
    1070                1075                1080

Ile Phe  Tyr Asn Ile Ser Asn  Gln Ser Ile Thr Asn  Lys Thr Cys
    1085                1090                1095

Glu Asp  Trp Ile Ala Val Asn  Val Thr Pro Ser Val  Met Ser Phe
    1100                1105                1110

Gln Leu  Glu Gly Met Ser Pro  Arg Cys Phe Ile Ala  Phe Gln Val
    1115                1120                1125

Arg Ala  Phe Thr Ser Lys Gly  Pro Gly Pro Tyr Ala  Asp Val Val
    1130                1135                1140

Lys Ser  Thr Thr Ser Glu Ile  Asn Pro Phe Pro His  Leu Ile Thr
    1145                1150                1155

Leu Leu  Gly Asn Lys Ile Val  Phe Leu Asp Met Asp  Gln Asn Gln
    1160                1165                1170

Val Val  Trp Thr Phe Ser Ala  Glu Arg Val Ile Ser  Ala Val Cys
    1175                1180                1185

Tyr Thr  Ala Asp Asn Glu Met  Gly Tyr Tyr Ala Glu  Gly Asp Ser
    1190                1195                1200

Leu Phe  Leu Leu His Leu His  Asn Arg Ser Ser Ser  Glu Leu Phe
    1205                1210                1215

Gln Asp  Ser Leu Val Phe Asp  Ile Thr Val Ile Thr  Ile Asp Trp
    1220                1225                1230

Ile Ser  Arg His Leu Tyr Phe  Ala Leu Lys Glu Ser  Gln Asn Gly
    1235                1240                1245

Met Gln  Val Phe Asp Val Asp  Leu Glu His Lys Val  Lys Tyr Pro
    1250                1255                1260

Arg Glu  Val Lys Ile His Asn  Arg Asn Ser Thr Ile  Ile Ser Phe
```

1265 1270 1275

Ser Val Tyr Pro Leu Leu Ser Arg Leu Tyr Trp Thr Glu Val Ser
1280 1285 1290

Asn Phe Gly Tyr Gln Met Phe Tyr Tyr Ser Ile Ile Ser His Thr
1295 1300 1305

Leu His Arg Ile Leu Gln Pro Thr Ala Thr Asn Gln Gln Asn Lys
1310 1315 1320

Arg Asn Gln Cys Ser Cys Asn Val Thr Glu Phe Glu Leu Ser Gly
1325 1330 1335

Ala Met Ala Ile Asp Thr Ser Asn Leu Glu Lys Pro Leu Ile Tyr
1340 1345 1350

Phe Ala Lys Ala Gln Glu Ile Trp Ala Met Asp Leu Glu Gly Cys
1355 1360 1365

Gln Cys Trp Arg Val Ile Thr Val Pro Ala Met Leu Ala Gly Lys
1370 1375 1380

Thr Leu Val Ser Leu Thr Val Asp Gly Asp Leu Ile Tyr Trp Ile
1385 1390 1395

Ile Thr Ala Lys Asp Ser Thr Gln Ile Tyr Gln Ala Lys Lys Gly
1400 1405 1410

Asn Gly Ala Ile Val Ser Gln Val Lys Ala Leu Arg Ser Arg His
1415 1420 1425

Ile Leu Ala Tyr Ser Ser Val Met Gln Pro Phe Pro Asp Lys Ala
1430 1435 1440

Phe Leu Ser Leu Ala Ser Asp Thr Val Glu Pro Thr Ile Leu Asn
1445 1450 1455

Ala Thr Asn Thr Ser Leu Thr Ile Arg Leu Pro Leu Ala Lys Thr
1460 1465 1470

Asn Leu Thr Trp Tyr Gly Ile Thr Ser Pro Thr Pro Thr Tyr Leu
1475 1480 1485

Val Tyr Tyr Ala Glu Val Asn Asp Arg Lys Asn Ser Ser Asp Leu
1490 1495 1500

Lys Tyr Arg Ile Leu Glu Phe Gln Asp Ser Ile Ala Leu Ile Glu
1505 1510 1515

Asp Leu Gln Pro Phe Ser Thr Tyr Met Ile Gln Ile Ala Val Lys
1520 1525 1530

Asn Tyr Tyr Ser Asp Pro Leu Glu His Leu Pro Pro Gly Lys Glu
1535 1540 1545

Ile Trp Gly Lys Thr Lys Asn Gly Val Pro Glu Ala Val Gln Leu
1550 1555 1560

Ile Asn Thr Thr Val Arg Ser Asp Thr Ser Leu Ile Ile Ser Trp
1565 1570 1575

Arg Glu Ser His Lys Pro Asn Gly Pro Lys Glu Ser Val Arg Tyr
1580 1585 1590

Gln Leu Ala Ile Ser His Leu Ala Leu Ile Pro Glu Thr Pro Leu
1595 1600 1605

Arg Gln Ser Glu Phe Pro Asn Gly Arg Leu Thr Leu Leu Val Thr
1610 1615 1620

Arg Leu Ser Gly Gly Asn Ile Tyr Val Leu Lys Val Leu Ala Cys
1625 1630 1635

His Ser Glu Glu Met Trp Cys Thr Glu Ser His Pro Val Thr Val
1640 1645 1650

Glu Met Phe Asn Thr Pro Glu Lys Pro Tyr Ser Leu Val Pro Glu
1655 1660 1665

Asn Thr Ser Leu Gln Phe Asn Trp Lys Ala Pro Leu Asn Val Asn
1670 1675 1680

Leu Ile Arg Phe Trp Val Glu Leu Gln Lys Trp Lys Tyr Asn Glu
1685 1690 1695

Phe Tyr His Val Lys Thr Ser Cys Ser Gln Gly Pro Ala Tyr Val
1700 1705 1710

Cys Asn Ile Thr Asn Leu Gln Pro Tyr Thr Ser Tyr Asn Val Arg
1715 1720 1725

Val Val Val Val Tyr Lys Thr Gly Glu Asn Ser Thr Ser Leu Pro
1730 1735 1740

Glu Ser Phe Lys Thr Lys Ala Gly Val Pro Asn Lys Pro Gly Ile
1745 1750 1755

Pro Lys Leu Leu Glu Gly Ser Lys Asn Ser Ile Gln Trp Glu Lys
1760 1765 1770

Ala Glu Asp Asn Gly Cys Arg Ile Thr Tyr Tyr Ile Leu Glu Ile
1775 1780 1785

Arg Lys Ser Thr Ser Asn Asn Leu Gln Asn Gln Asn Leu Arg Trp
1790 1795 1800

Lys Met Thr Phe Asn Gly Ser Cys Ser Ser Val Cys Thr Trp Lys
1805 1810 1815

Ser Lys Asn Leu Lys Gly Ile Phe Gln Phe Arg Val Val Ala Ala
1820 1825 1830

Asn Asn Leu Gly Phe Gly Glu Tyr Ser Gly Ile Ser Glu Asn Ile
1835 1840 1845

Ile Leu Val Gly Asp Asp Phe Trp Ile Pro Glu Thr Ser Phe Ile
1850 1855 1860

Leu Thr Ile Ile Val Gly Ile Phe Leu Val Val Thr Ile Pro Leu
1865 1870 1875

Thr Phe Val
1880

<210> SEQ ID NO 11
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 11

Asp Phe Trp Ile Pro Glu Thr Ser Phe Ile Leu Thr Ile Ile Val Gly
1 5 10 15

Ile Phe Leu Val Val Thr Ile Pro Leu Thr Phe Val
20 25

<210> SEQ ID NO 12
<211> LENGTH: 466
<212> TYPE: PRT
<213> ORGANISM: Artificial Sequence
<220> FEATURE:
<223> OTHER INFORMATION: Synthetic Peptide

<400> SEQUENCE: 12

Trp His Arg Arg Leu Lys Asn Gln Lys Ser Ala Lys Glu Gly Val Thr
1 5 10 15

Val Leu Ile Asn Glu Asp Lys Glu Leu Ala Glu Leu Arg Gly Leu Ala
20 25 30

Ala Gly Val Gly Leu Ala Asn Ala Cys Tyr Ala Ile His Thr Leu Pro

-continued

```
        35                  40                  45

Thr Gln Glu Glu Ile Glu Asn Leu Pro Ala Phe Pro Arg Glu Lys Leu
    50                  55                  60

Thr Leu Arg Leu Leu Leu Gly Ser Gly Ala Phe Gly Glu Val Tyr Glu
65                  70                  75                  80

Gly Thr Ala Val Asp Ile Leu Gly Val Gly Ser Gly Glu Ile Lys Val
                85                  90                  95

Ala Val Lys Thr Leu Lys Lys Gly Ser Thr Asp Gln Glu Lys Ile Glu
            100                 105                 110

Phe Leu Lys Glu Ala His Leu Met Ser Lys Phe Asn His Pro Asn Ile
        115                 120                 125

Leu Lys Gln Leu Gly Val Cys Leu Leu Asn Glu Pro Gln Tyr Ile Ile
    130                 135                 140

Leu Glu Leu Met Glu Gly Gly Asp Leu Leu Thr Tyr Leu Arg Lys Ala
145                 150                 155                 160

Arg Met Ala Thr Phe Tyr Gly Pro Leu Leu Thr Leu Val Asp Leu Val
                165                 170                 175

Asp Leu Cys Val Asp Ile Ser Lys Gly Cys Val Tyr Leu Glu Arg Met
            180                 185                 190

His Phe Ile His Arg Asp Leu Ala Ala Arg Asn Cys Leu Val Ser Val
        195                 200                 205

Lys Asp Tyr Thr Ser Pro Arg Ile Val Lys Ile Gly Asp Phe Gly Leu
    210                 215                 220

Ala Arg Asp Ile Tyr Lys Asn Asp Tyr Tyr Arg Lys Arg Gly Glu Gly
225                 230                 235                 240

Leu Leu Pro Val Arg Trp Met Ala Pro Glu Ser Leu Met Asp Gly Ile
                245                 250                 255

Phe Thr Thr Gln Ser Asp Val Trp Ser Phe Gly Ile Leu Ile Trp Glu
            260                 265                 270

Ile Leu Thr Leu Gly His Gln Pro Tyr Pro Ala His Ser Asn Leu Asp
        275                 280                 285

Val Leu Asn Tyr Val Gln Thr Gly Gly Arg Leu Glu Pro Pro Arg Asn
    290                 295                 300

Cys Pro Asp Asp Leu Trp Asn Leu Met Thr Gln Cys Trp Ala Gln Glu
305                 310                 315                 320

Pro Asp Gln Arg Pro Thr Phe His Arg Ile Gln Asn Gln Leu Gln Leu
                325                 330                 335

Phe Arg Asn Phe Phe Leu Asn Ser Ile Tyr Gln Cys Arg Asp Glu Ala
            340                 345                 350

Asn Asn Ser Gly Val Ile Asn Glu Ser Phe Glu Gly Glu Asp Gly Asp
        355                 360                 365

Val Ile Cys Leu Asn Ser Asp Asp Ile Met Pro Val Val Leu Met Glu
    370                 375                 380

Thr Lys Asn Arg Glu Gly Leu Asn Tyr Met Val Leu Ala Thr Glu Cys
385                 390                 395                 400

Gly Gln Gly Glu Glu Lys Ser Glu Gly Pro Leu Gly Ser Gln Glu Ser
                405                 410                 415

Glu Ser Cys Gly Leu Arg Lys Glu Glu Lys Glu Pro His Ala Asp Lys
            420                 425                 430

Asp Phe Cys Gln Glu Lys Gln Val Ala Tyr Cys Pro Ser Gly Lys Pro
        435                 440                 445

Glu Gly Leu Asn Tyr Ala Cys Leu Thr His Ser Gly Tyr Gly Asp Gly
    450                 455                 460
```

Ser Asp
465

<210> SEQ ID NO 13
<211> LENGTH: 421
<212> TYPE: PRT
<213> ORGANISM: Artificial Sequence
<220> FEATURE:
<223> OTHER INFORMATION: Synthetic Peptide

<400> SEQUENCE: 13

Thr Leu Pro Thr Gln Glu Glu Ile Glu Asn Leu Pro Ala Phe Pro Arg
1 5 10 15

Glu Lys Leu Thr Leu Arg Leu Leu Leu Gly Ser Gly Ala Phe Gly Glu
20 25 30

Val Tyr Glu Gly Thr Ala Val Asp Ile Leu Gly Val Gly Ser Gly Glu
35 40 45

Ile Lys Val Ala Val Lys Thr Leu Lys Lys Gly Ser Thr Asp Gln Glu
50 55 60

Lys Ile Glu Phe Leu Lys Glu Ala His Leu Met Ser Lys Phe Asn His
65 70 75 80

Pro Asn Ile Leu Lys Gln Leu Gly Val Cys Leu Leu Asn Glu Pro Gln
85 90 95

Tyr Ile Ile Leu Glu Leu Met Glu Gly Gly Asp Leu Leu Thr Tyr Leu
100 105 110

Arg Lys Ala Arg Met Ala Thr Phe Tyr Gly Pro Leu Leu Thr Leu Val
115 120 125

Asp Leu Val Asp Leu Cys Val Asp Ile Ser Lys Gly Cys Val Tyr Leu
130 135 140

Glu Arg Met His Phe Ile His Arg Asp Leu Ala Ala Arg Asn Cys Leu
145 150 155 160

Val Ser Val Lys Asp Tyr Thr Ser Pro Arg Ile Val Lys Ile Gly Asp
165 170 175

Phe Gly Leu Ala Arg Asp Ile Tyr Lys Asn Asp Tyr Tyr Arg Lys Arg
180 185 190

Gly Glu Gly Leu Leu Pro Val Arg Trp Met Ala Pro Glu Ser Leu Met
195 200 205

Asp Gly Ile Phe Thr Thr Gln Ser Asp Val Trp Ser Phe Gly Ile Leu
210 215 220

Ile Trp Glu Ile Leu Thr Leu Gly His Gln Pro Tyr Pro Ala His Ser
225 230 235 240

Asn Leu Asp Val Leu Asn Tyr Val Gln Thr Gly Gly Arg Leu Glu Pro
245 250 255

Pro Arg Asn Cys Pro Asp Asp Leu Trp Asn Leu Met Thr Gln Cys Trp
260 265 270

Ala Gln Glu Pro Asp Gln Arg Pro Thr Phe His Arg Ile Gln Asp Gln
275 280 285

Leu Gln Leu Phe Arg Asn Phe Phe Leu Asn Ser Ile Tyr Lys Ser Arg
290 295 300

Asp Glu Ala Asn Asn Ser Gly Val Ile Asn Glu Ser Phe Glu Gly Glu
305 310 315 320

Asp Gly Asp Val Ile Cys Leu Asn Ser Asp Asp Ile Met Pro Val Ala
325 330 335

Leu Met Glu Thr Lys Asn Arg Glu Gly Leu Asn Tyr Met Val Leu Ala
340 345 350

-continued

```
Thr Glu Cys Gly Gln Gly Glu Glu Lys Ser Glu Gly Pro Leu Gly Ser
        355                 360                 365

Gln Glu Ser Glu Ser Cys Gly Leu Arg Lys Glu Glu Lys Glu Pro His
    370                 375                 380

Ala Asp Lys Asp Phe Cys Gln Glu Lys Gln Val Ala Tyr Cys Pro Ser
385                 390                 395                 400

Gly Lys Pro Glu Gly Leu Asn Tyr Ala Cys Leu Thr His Ser Gly Tyr
                405                 410                 415

Gly Asp Gly Ser Asp
            420


<210> SEQ ID NO 14
<211> LENGTH: 7725
<212> TYPE: DNA
<213> ORGANISM: Artificial Sequence
<220> FEATURE:
<223> OTHER INFORMATION: Synthetic Nucleotide

<400> SEQUENCE: 14

gtgagtacta acatactcaa tactcagaaa actctgtgtt tcagtttttt tcttatcact     60

tatttcacta atcctagaga tatatgaaat tgttctttaa aagcagtaca ttattatttc    120

tagaacttga atgaagaaat tcagaaaata taggagacct tgcaggcagt aatgaaataa    180

tactggctgg gtctggctgg atcctgaact gggcaaaatt acttcttctt tcagtatcct    240

tatttcatgt ctagctatga caattttatg gtgataacta tatgaaaata gtgttactga    300

atgttcaaaa aatatttatt ggctactata tttgagatac taggatgaaa aatataagaa    360

gttcattaaa aattaactag tgttctgaaa gatatacctt aactctgaga tgagctctat    420

aagaatggaa ggaacaaaga tctagaacca aaaataccat ttgacctaga aattacatta    480

ctagttacat acccaaagga atataaatca ttctattaca aagatacatg cacacgtatg    540

ttcactgtag cactattcac aataatgaat catttggaat caacccaaat gcccgtcaac    600

attagactgg ttgaagcaaa tgtggtacat atacaccatg gcatactatg cagccataaa    660

aaggaatgag ataatgtttt tttgcaggga tatggatgaa gctggaagct attaacctca    720

gcaaactaat tcaggaacag aaaaccaaac actgcgtgtt ctcacttaca agtgggagct    780

gaacaatgag aacgcatgga cacaaggagg ggaacaacac acactggggc ctgtcagggg    840

gaggggtggg gggatagaga gtattaggaa aaatagctaa tgcatgctgg gcttaatacc    900

taggtgatgg tttgctaggt gtagtaaacc accatgggac atgtttaccc atgtaacaaa    960

ccttcacgtc ctgcacatgt accccagaac taaaaataaa aaaatttgaa aaaaagaatg   1020

gagggaaaat gctccaaaac ttatgatagt tttctttatt ttcatttatc acttattttg   1080

tttcaagttg agatatattg ttaatcttat caccaattca tcaaatccat cactaataaa   1140

aacttcaaat gctcatttaa aaatatgtaa tcatataaga atatttctga atatttcttt   1200

ttttaaaatt tcttcttaaa aaataagata catgtgcaga acgtgcaggg ttgttacata   1260

ggtatacatg tgccatggtg gtttgctgca cctattgacc tgtcctctaa gttccctccc   1320

ctcagctcct atccctcaac aggccctggt gtgtgctgtt cccctctctg tatccatgtg   1380

ttctcaatgt tcaactccca cttatgagtg agaacacgtg ctgttttgtt ctctgttcct   1440

gtgttaggtt gctgaggatg atgacttcca gcttcatcca tgtccctgca aaggacatga   1500

tctcattcct tcttatggct gcatagtatt ccatggtgta tatgtaccac attttcttta   1560

tctggtttgt cattgatgga ttggcttggt tccatgtctt tgttattgta aacagtgctg   1620
```

cagtaaacat acatgtgcat gtgtctttat agtagagtga tttatactcc tttgggtatg 1680
tactcaataa tgagattact gggtcaaatg ttatttctgg ttctagatcc ttgaggaatt 1740
gccatactgt cttccacaat ggttgaaata atttacttta ccaccaacag tgtaaaagta 1800
ttcctatttc tccacaccct catcagcatc tattgtttcc tgacttttta atagttgcca 1860
ttctgactcg cgtgagatgg tatctcattg tagttttgat ttgtactcct ctgatgatca 1920
gtgatgttga gcttttttca tacgtttatt ggctgcataa atcccttttt gagaagtgtc 1980
tgttcatatc ttttgcccac tttttgatgg ggttgtctgt ctttttcttg taaatatgtt 2040
taagttcctt gtacattctg gatattagcc ctttgtcaga tggatagatt gcaaaatttt 2100
tctcccattc tgtaggttgt ctgttcactc tgatgatagt ttcttttgct gtacagaagc 2160
tctttagttt agttagatcc catttgtcta ttttggcttt tgttgccatt gcttttggtg 2220
ttttagtcat gaagtctttg cccatgccta tgtcctgaat ggtattgcct aggttttctt 2280
ctagggtttt tatggttttg gtttttacat ttaagtgttt aatccatctt gagttaaatt 2340
ttgtataagg ttaaggaatg ggcccagttt cagttttctg catatggcta gccagttttc 2400
ccagcaccat ttactaaata ggagatcctt tcctcattgc ttgtttttgt taggtttgtc 2460
aaagatcaaa tggttgtaga tgtgtggtgt aatttctgag gtctctgttc tgctccattg 2520
gtctatatat ttgttttggt accagtacca tgctgtgtta ctgtagcttt gtaatatagt 2580
ttgaagtcag gtagcatgat gcctccaagt ttgttctttt tgcttaggat tgtcttggct 2640
acatggggtc ttctttgatt ctatgtgaaa tttaaaataa ctttttctaa ttctatgaag 2700
aatgtcaacg gtagttagat gagaatagca ttgaatctat aaattactct gggcagaatg 2760
gccattttca tgatactcat tattcctgtc catggggatg gaatgttttt ccatttattt 2820
gtgtcctttc ttatttcctt gagcaatggt ttgtagtttt ccttgaagag gtccttcaca 2880
tcccttgtta gctgtattcg taggtatttt attctctttg tagctattgt gaatgggagt 2940
tcattcatga tttggctctc tgcttgccta ttgttggtgt aaaggaatgc ttgtgatttt 3000
tgcacattga ttttttatct tgagactttg ctgaagttgc ttatcagttc aagaagtttt 3060
tgggctgaga tgatggggtt ttctaaatac aaaatcatgt catctgcaaa cagagacaac 3120
ttgacttcct ctcttcctat ttgaataccc tttatttctt cctcttgcct gattgccctg 3180
accagaactt ccaatactat gttgaatagg agtggtgaga gtggacaccc ttgtcttgta 3240
ctggttttca aagggaattc ttccaggttt tgctcattca atatgatatt ggctgtaggt 3300
ttgtcataaa tagttcttat tatttagaga tatgttccat aaaaacctag tttattgaga 3360
gtttttaaca taaagggatg ttgatgttga attttatcaa aggccttttc tgcatctatt 3420
cagataatcg tgtgattttt gtctttggtt ctgtttatgt gatggattac atttattgat 3480
ttgcatatgt tgaatcagcc ttgcatccca gggatgaagc cgacttgttc gtggtggata 3540 tgtttttga tgtgctgctg gattcagttt gccagtattt tattgaggat ttttacatca 3600
atgttcatca ggtatattgg cccaaagttt gttgttgtgt ctcttcccag ttttggtatc 3660
aggatgatgc tggcttcata aaatgagtta ggaaggaatt cctccttttc cattgtttgg 3720
aacagtttca gaaggaatgg taccagctcc tctttgtatt tctggtagaa ttcagctgtg 3780
aatccatctg gtcctgggct ttttttggtt ggtagtctat taattactgc ctccattcca 3840
gagcttgcta ctggtctagt cagggattca acttcttcct ggtttagtct tggtgtatgc 3900
atccaggaat gtatccattt cttctagatt ttctagttta tttgcataga agagtttata 3960
gtattatctg gtggtatttt gtatttctgt ggggtcagtg gtgatatccc ctttatcatt 4020
ttttttgtgt ctatttgatt cttctctgtc tccttcttta tttctctagc tagtggtata 4080
ttttgttatt tattttattt tttaaaaaaa acggctcctg gatgtgttga tttttttttgg 4140
agggcttttt gtgtctttgt ctccttcagt tcttctctga tcttagttat ttcttgtctt 4200
ctgccagctt ttggattagt ttgctcttgc ctctctagct cttttaattg tgatgttagg 4260
gtgacgattt gagatctttc tggctttcta atgtgggcat ttagtgctat gaattttcct 4320
cttaacactg ctttagttgt gtcccagaga ttctggtaca ttgtctctgt tctcatttgt 4380
ttcaaagaac ttatttattt ctgccttaat ttcattattt acccaggagc cattcaggag 4440
caagttgttc aatttccagg aaattgtgtg gttttgagtg agtttcttaa tcctgggttc 4500
taatttgatt gctctgtggt ctgagagact gtttgttatg atttcagctc ttttgcattt 4560
gctgaggagt gttttacttc caattatgtg gtagatttta gaataagtac catgtggcac 4620
tcagaagaat gtatattctg ttgatttggg ctagaaagtt ctgtagacat ctactaggtc 4680
cacttgatcc agagctaagt tcaagtcctg aatatccttg ttaattttct gtcttgttga 4740
tctgtctaat actggcagtg gggtgttgaa gtttcccact actattgcgt ggcagtctaa 4800
gtctctttgt aggtctctaa gaacttactt tgtgagtctg ggtgctcttg tattgggtgc 4860
atatatattc agaatagtta actcttcttg ttgaattgtt ccctttacca ttatataatg 4920
cccttctttg tctattttga tctttgttgg tttaaagtct gttttgtcag agactaggat 4980
tgcaaccctc tttttttttt tttttgcttt ccatatgctt ggtaaatttt cctcaatccc 5040
tttattttga gcctgtgtgt gtctttgcat gtaagataga tctcctgaat acaacacacc 5100
aatgggtctt gactccttat ccaatttgcc agtctgtatc ttttaattgg ggcatttagc 5160
ccctttacat ttaaggtagg tattgttatg tgagtttgat cctgtcacca tgatgctatt 5220
tggttatttt gcatgctagt tgatgcagtt tcttcatagt gtcattgatc tttatagttt 5280
ggtgtgtttt tgcaatggct ggtaccagtt tttcctttcc atatttagtg cttatttcag 5340
gagctgttgc agggcaggcc tggtggtaac aaaatccctc agcatttgct tgtctggaaa 5400
ggattttatt tctccttcac ttatgaagct tagtttggct ggatatgaaa ttctgggttg 5460
aaaattcttt tctttaagaa tgttgatgtt ggcccccaat ctcttctggt ttgtagggtt 5520
tatgttgaga ggtccactgt tagtctgatg ggcgtccctt tgtaggtaac ctggcctttc 5580
tctctggctg cccttaacag tttttacttg atttcaacct tggagaatct gatgattatg 5640
tgtcttgggg ttgatcttct cgtggagtat cttaatggtg ttctctgtgt ttgccgaatt 5700
tgcatgttgg cctgtcttgc taggttgggg aagttctcct ggataatatc ccgaagggtg 5760
ttttcccacg tgtttccatt ttccccatct cctcctggta ctccaagcta tcataggttc 5820
agtcttttta tgaagtctca tatttcttgg aggctttatt cattcctttt cattcttttt 5880
tctctcttct tgtcagcatg tcttatttca ataaggtagt cttcaaactc tgatatcttc 5940
tcttccactt ggtcgattca gctgttgaca cttgtgtatg cttcacgaag ttcttgtgct 6000
gtgtttttca gccccatcag gccatttgtg ttcctctcta aactgattat tctagttagc 6060
aattcctcca actttttatc aaggttctta gcttcttcgc attgggttag aacatactcc 6120
tttagctcat catagttttt tctacccatc ttgtgaagcc tacttctgtc agttcatcca 6180
tctgatcctc cgcccagttc tgcaccctta atggagacat tgtgatcatt tagaggagaa 6240
gaggcactct ggccttttgg gttttcagca ttttttttcat tggttctttc tcaccttcgt 6300
gagtttgtct agttgtggtc tttgaggctg ctgacccttg tatgggtttt ttgtgggggc 6360
ccttgttgtt gttgttgatg atgatgctgt tgttgtcact ttctgcttat ttgtttttct 6420
ttcaatagtc acttccctct tctgtagggc tgctgcagtt tgctggggtt cactttaggc 6480
cttattcatc tgatttgctc ccacgcctgg atatgtaact caaggaggct ggagagcagc 6540
aaaaatgggt gtctgctcct tcttctggga cctctgactt caaggggcac caacctgatg 6600
ccagtaggat cgctcctgta tagggtgtcc tgacaatccc tgttggaggg tctcacccag 6660
ttgggtggca ccaggaggag gacccattta acgaagcact ttgtcccctg gtggagaggg 6720
tgtgttttgc tgtgggaaag cccacttgtc tgggcttccc agattcctca gaactaccag 6780
gaggagaggc taagtctgtt ggtccgcaga gactgcagcc acccctcccc ctaggggctc 6840
aggcccaggg agatctgaat tctgtccctg agcctctggc tgcagttact gaagattctg 6900
cagggaagcc ccacccactg aggaaggatg ggtgagggtt agacctgaag aggcactctg 6960
gccgctgact accacagctg gtgtgttggg ttgtggcgac aagtcttggg accaagctgt 7020
ccagcctcgc tggctcccgc aggggaaaag cacagcctgg agctatagaa atggatgctg 7080
catttctccc cgccgcccag ggagattagc gtgttaggca gttgggagtc ccagtgctgg 7140
ctgctgcccc tccctcaagg agctcaaagg gcttagacag caggcagcag aagcctgtgc 7200
tggtcacccc tcccccaggg agttcagtaa gcttaggcag attccagctg agaggccata 7260
agaatctgta cattctaggg ttgggatgct aggcctcggt ggcatgggat cgagagtggg 7320
atcttccaat ccatgagttg cacagttctt tggaaaagca atttccccgg ctgggtagcc 7380
tgctcgctcg ccgctcccct tggctggagg ggagggggtt ccccttcccc gtgtggttct 7440
caggtgggct cactgctctt ccttctctct gtgggtcacg ccagccttct agtcaatttt 7500
gatgagcgaa tctagatacc ttgccggtga aggactcaca cacttattat ggtttttttc 7560
aataggaacc tctgaacgga gttgcttcta gtcggccatc ttggccccgc ctctgaatat 7620
ttctttaatg ttgtctttcc tcttaatata ttctgtagaa agatttcagt gcagaagatt 7680
aatacttcaa acatatcaac caatattttc tttttttccc taaag 7725

<210> SEQ ID NO 15
<211> LENGTH: 2914
<212> TYPE: DNA
<213> ORGANISM: Artificial Sequence
<220> FEATURE:
<223> OTHER INFORMATION: Synthetic Nucleotide

<400> SEQUENCE: 15
gtatgtgtgt ttgcaaagta cttgtaaatg acaaagaact aagaagataa ttataaagta 60
atcaaaagta acactattta tgcaaatgta tttatataca aacacaaaga tctttagtta 120
aaggactcac atgcatcatt acgttctttg ctcaattcct agacgttggt cttggcatgc 180
taattataaa cagatcacgt cattctcaga aatctctaac tgctcattga cactttatgg 240
aaattgtttg atcataggct catgcaacca gtattaactt aatatcagtt ttgtttaaaa 300
agcttagctg atgtttaatg ttaaataatg atggcatgta aattcctgat gataatttgc 360
tttagcaagg tgaatactct ctagtgagaa atggtgatga agtagatatt tctcatactg 420
taaaattagg tcaggttctg aaatggtctg aagtgtagag gtcacacagg attctgtatt 480
cattgggaag attacagttt gcaatgtgtt cccagggact gaaaacacac cgtcgatgaa 540
aaccagccac tgatgaacag cctcagacct ggccagtacg gggagcacgt gaaccataac 600
tggcttagaa ggactgattt catgccaact tgaggggaga attccaaatt ccaaagacac 660

```
tcctctcaca ggactatgaa accatctttt aagaagttcc aaggacaaaa gtcacttcca    720
taattatagt cctggcaact tgatctttag atctattttt gcttcatctg gctctggcat    780
tcccataacc ttaaaaaatg ttcctgttca tactagagaa ttcccttggc ccttatttct    840
aattgaaacc tccttgaagt ttctgttgct gcttttcatg cagagtgaaa tacattctaa    900
cctgcagaac tgtcttggtg gtttgtgact gtaatgatgt tcatcaatca ggtcacacat    960
caggtttttg ctaggacctc ttttgtgtgt taccctgagt aacaccttaa gtgctactaa   1020
aatgactcca tctaaatact ttgcatactc cttgctccag gtctccactg tcaggacata   1080
gactatagga tgactgaatg attgttgtaa cttcagtgtc tcaaaataag tccttcagtc   1140
aggacactct agttagactc tgtgtactca ctgatggggt agtggaagtg caaagtgcat   1200
gaacttggga gttgaacaag ccttattagt ttccaagggt tgccacaata aaggaccacc   1260
aactgggtgg cttgaaacag tagacattta ttcttacagc tctagaggtt agaagtctga   1320
aaccaacgta tcagcgggac tgcttgttct gatggttcta gggcagaatc catctttgcc   1380
tcttagcttc tggcgtttac tggcagtcct tggtattcct tggctcgtag gtgcatcact   1440
gtcatcatca cctcctgcat cacaaggtgt tctctgtgtc caaatttccc tcttcttatg   1500
caagtgccag tcattggatt agggtccacc ctaaactact atgacctcat cttaacttga   1560
ttacatttgt caagatctta tttctaaaca aggtcacatt aaaatattct gagtgggtat   1620
gaattttggg aggacatgac tcaatccagt acacaaacca tgtttaaatg cttgttcttt   1680
tcctttttg aacttaagtt tcctcatctg taaaatggag atgataatat ctatcttatc    1740
tctttaagct gttgtggact cagtgaatta aaacaacgtt atgtaaagcc ccagtacagt   1800
atgttgtaaa tagaaggtgc tcaaccaaca tcagaattct tctttctttt ctcaatggcc   1860
attgtgtaga gccacttcac aaattctcaa gggcctcttt cttttggatc agagttgttt   1920
ggttaaacag tgaaatggcc aatgctaaag gtgagacgtc acaaaatgtg taaaaacact   1980
ctgtcctaat gctttgctca ggatggtcct taaagggacc ctcagctccg gggaacagct   2040
gtgaccaact ctgctgccct gctgctcccg atgttcttac cctttccctg cctcttatga   2100
gggccagcct tcactctctg ttggtcttca gaaggatgag tcaattagca ggaatagaac   2160
cagattctcc cacatatccc taagcttacc gtggattggc accaagtcct aaaactattg   2220
cggtctgaaa agtttcagac ctgaaatatt cttcattgtt agagaagaca taatggaaga   2280
ccttgagctt gcctttgatg attctgtaaa aagtcattcc agttatgtct tttgaaccca   2340
gcccttgtgc tccttccatg tttcaaatga aaaacaattg gattgacttt gaggtggaat   2400
gtaggtcaat acaaaaggaa gcaacgagcc tcagaatctc agatataatg ataactttgg   2460
tagctgaact gtcacacttt ccttatcaat tttgtattct gtattttatt gaaatatggc   2520
ataagtaaac tacaaataat gtaaaagact gaaaattgag aaaatggaaa cttcccagtt   2580
aaaaatcatg gaataattgt cttataggtt tggaattctg gagaaagttt acccatgctg   2640
ttagtatagg aaaaaggtac tcagctctct cttcaccact gattactcac agtttcttg    2700
gtgggctgag ttaattggct ccatgcctca ctaggatcac tataaaacca tgctgttagc   2760
atctgtgttg ccagattatg ggagaggaat gaggtcaagg gtaaattgtg ccaaaggaca   2820
ctctctggcg ttcagtcact aagaagatct atgaacaact agaaataaca ggtatattgt   2880
catgtatatt ttctgtattt attattttt gcag                                2914
```

<210> SEQ ID NO 16
<211> LENGTH: 3030

<212> TYPE: DNA
<213> ORGANISM: Artificial Sequence
<220> FEATURE:
<223> OTHER INFORMATION: Synthetic Nucleotide

<400> SEQUENCE: 16

```
atgtcggcgg gcggtccatg cccagcagca gccggagggg gcccaggggg cgcctcctgc     60

tccgtggggg cccctggcgg ggtatccatg ttccggtggc tggaggtgct ggagaaggag    120

ttcgacaaag cttttgtgga tgtggatctg ctcctgggag agatcgatcc agaccaagcg    180

gacatcactt atgaggggcg acagaagatg accagcctga gctcctgctt tgcacagctt    240

tgccacaaag cccagtctgt gtctcaaatc aaccacaagc tggaggcaca gttggtggat    300

ctgaaatctg aactgacaga aacccaagca gagaaagttg ttttggagaa agaagtacat    360

gatcagcttt tacagctgca ctctattcag ctgcagcttc atgctaaaac tggtcaaagt    420

gctgactctg gtaccattaa ggcaaaattg gaaagagagc ttgaggcaaa caaaaaagaa    480

aaaatgaaag aagcacaact tgaagctgaa gtgaaattgt tgagaaaaga gaatgaagcc    540

cttcgtagac atatagctgt tctccaggct gaagtatatg gggcgagact agctgccaag    600

tacttggata aggaactggc aggaagggtc caacagatac aattgctagg acgagatatg    660

aagggacctg ctcatgataa gctttggaac caattagaag ctgaaataca tttgcatcgt    720

cacaaaactg tgatccgagc ctgcagagga cgtaatgact tgaaacgacc aatgcaagca    780

ccaccaggcc atgatcaaga ttccctaaag aaaagccaag gtgttggtcc aattagaaaa    840

gttctcctcc ttaaggaaga tcatgaaggc cttggcattt caattacagg tgggaaagaa    900

catggtgttc caatcctcat ctctgagatc catccggggc aacctgctga tagatgcgga    960

gggctgcacg ttggggatgc tattttggca gtcaacggag ttaacctaag ggacacaaag   1020

cataaagaag ctgtaactat tctttctcag cagagaggag agattgaatt tgaagtagtt   1080

tatgtggctc ctgaagtgga ttctgatgat gaaaacgtag agtatgaaga tgagagtgga   1140

catcgttacc gtttgtacct tgatgagtta gaaggaggtg gtaaccctgg tgctagttgc   1200

aaagacacaa gtggggaaat caaagtatta caagctggag tcccaaataa accaggcatt   1260

cccaaattac tagaagggag taaaaattca atacagtggg agaaagctga agataatgga   1320

tgtagaatta catactatat ccttgagata agaaagagca cttcaaataa tttacagaac   1380

cagaatttaa ggtggaagat gacatttaat ggatcctgca gtagtgtttg cacatggaag   1440

tccaaaaacc tgaaaggaat atttcagttc agagtagtag ctgcaaataa tctagggttt   1500

ggtgaatata gtggaatcag tgagaatatt atattagttg gagatgattt ttggatacca   1560

gaaacaagtt tcatacttac tattatagtt ggaatatttc tggttgttac aatcccactg   1620

acctttgtct ggcatagaag attaaagaat caaaaaagtg ccaaggaagg ggtgacagtg   1680

cttataaacg aagacaaaga gttggctgag ctgcgaggtc tggcagccgg agtaggcctg   1740

gctaatgcct gctatgcaat acatactctt ccaacccaag aggagattga aaatcttcct   1800

gccttccctc gggaaaaact gactctgcgt ctcttgctgg gaagtggagc ctttggagaa   1860

gtgtatgaag gaacagcagt ggacatctta ggagttggaa gtggagaaat caaagtagca   1920

gtgaagactt tgaagaaggg ttccacagac caggagaaga ttgaattcct gaaggaggca   1980

catctgatga gcaaatttaa tcatcccaac attctgaagc agcttggagt ttgtctgctg   2040

aatgaacccc aatacattat cctggaactg atggagggag gagaccttct tacttatttg   2100

cgtaaagccc ggatggcaac gttttatggt cctttactca ccttggttga ccttgtagac   2160
```

-continued

```
ctgtgtgtag atatttcaaa aggctgtgtc tacttggaac ggatgcattt cattcacagg   2220

gatctggcag ctagaaattg ccttgtttcc gtgaaagact ataccagtcc acggatagtg   2280

aagattggag actttggact cgccagagac atctataaaa atgattacta tagaaagaga   2340

ggggaaggcc tgctcccagt tcggtggatg gctccagaaa gtttgatgga tggaatcttc   2400

actactcaat ctgatgtatg gtcttttgga attctgattt gggagatttt aactcttggt   2460

catcagcctt atccagctca ttccaacctt gatgtgttaa actatgtgca aacaggaggg   2520

agactggagc caccaagaaa ttgtcctgat gatctgtgga atttaatgac ccagtgctgg   2580

gctcaagaac ccgaccaaag acctactttt catagaattc aggaccaact tcagttattc   2640

agaaattttt tcttaaatag catttataag tccagagatg aagcaaacaa cagtggagtc   2700

ataaatgaaa gctttgaagg tgaagatggc gatgtgattt gtttgaattc agatgacatt   2760

atgccagttg ctttaatgga aacgaagaac cgagaagggt taaactatat ggtacttgct   2820

acagaatgtg gccaaggtga agaaaagtct gagggtcctc taggctccca ggaatctgaa   2880

tcttgtggtc tgaggaaaga agagaaggaa ccacatgcag acaaagattt ctgccaagaa   2940

aaacaagtgg cttactgccc ttctggcaag cctgaaggcc tgaactatgc ctgtctcact   3000

cacagtggat atggagatgg gtctgattaa                                    3030
```

```
<210> SEQ ID NO 17
<211> LENGTH: 1009
<212> TYPE: PRT
<213> ORGANISM: Artificial Sequence
<220> FEATURE:
<223> OTHER INFORMATION: Synthetic Peptide

<400> SEQUENCE: 17

Met Ser Ala Gly Gly Pro Cys Pro Ala Ala Ala Gly Gly Gly Pro Gly
1               5                   10                  15

Gly Ala Ser Cys Ser Val Gly Ala Pro Gly Gly Val Ser Met Phe Arg
            20                  25                  30

Trp Leu Glu Val Leu Glu Lys Glu Phe Asp Lys Ala Phe Val Asp Val
        35                  40                  45

Asp Leu Leu Leu Gly Glu Ile Asp Pro Asp Gln Ala Asp Ile Thr Tyr
    50                  55                  60

Glu Gly Arg Gln Lys Met Thr Ser Leu Ser Ser Cys Phe Ala Gln Leu
65                  70                  75                  80

Cys His Lys Ala Gln Ser Val Ser Gln Ile Asn His Lys Leu Glu Ala
                85                  90                  95

Gln Leu Val Asp Leu Lys Ser Glu Leu Thr Glu Thr Gln Ala Glu Lys
            100                 105                 110

Val Val Leu Glu Lys Glu Val His Asp Gln Leu Leu Gln Leu His Ser
        115                 120                 125

Ile Gln Leu Gln Leu His Ala Lys Thr Gly Gln Ser Ala Asp Ser Gly
    130                 135                 140

Thr Ile Lys Ala Lys Leu Glu Arg Glu Leu Glu Ala Asn Lys Lys Glu
145                 150                 155                 160

Lys Met Lys Glu Ala Gln Leu Glu Ala Glu Val Lys Leu Leu Arg Lys
                165                 170                 175

Glu Asn Glu Ala Leu Arg Arg His Ile Ala Val Leu Gln Ala Glu Val
            180                 185                 190

Tyr Gly Ala Arg Leu Ala Ala Lys Tyr Leu Asp Lys Glu Leu Ala Gly
        195                 200                 205
```

-continued

```
Arg Val Gln Gln Ile Gln Leu Leu Gly Arg Asp Met Lys Gly Pro Ala
    210                 215                 220

His Asp Lys Leu Trp Asn Gln Leu Glu Ala Glu Ile His Leu His Arg
225                 230                 235                 240

His Lys Thr Val Ile Arg Ala Cys Arg Gly Arg Asn Asp Leu Lys Arg
                245                 250                 255

Pro Met Gln Ala Pro Pro Gly His Asp Gln Asp Ser Leu Lys Lys Ser
            260                 265                 270

Gln Gly Val Gly Pro Ile Arg Lys Val Leu Leu Leu Lys Glu Asp His
        275                 280                 285

Glu Gly Leu Gly Ile Ser Ile Thr Gly Gly Lys Glu His Gly Val Pro
    290                 295                 300

Ile Leu Ile Ser Glu Ile His Pro Gly Gln Pro Ala Asp Arg Cys Gly
305                 310                 315                 320

Gly Leu His Val Gly Asp Ala Ile Leu Ala Val Asn Gly Val Asn Leu
                325                 330                 335

Arg Asp Thr Lys His Lys Glu Ala Val Thr Ile Leu Ser Gln Gln Arg
            340                 345                 350

Gly Glu Ile Glu Phe Glu Val Val Tyr Val Ala Pro Glu Val Asp Ser
        355                 360                 365

Asp Asp Glu Asn Val Glu Tyr Glu Asp Glu Ser Gly His Arg Tyr Arg
    370                 375                 380

Leu Tyr Leu Asp Glu Leu Glu Gly Gly Gly Asn Pro Gly Ala Ser Cys
385                 390                 395                 400

Lys Asp Thr Ser Gly Glu Ile Lys Val Leu Gln Ala Gly Val Pro Asn
                405                 410                 415

Lys Pro Gly Ile Pro Lys Leu Leu Glu Gly Ser Lys Asn Ser Ile Gln
            420                 425                 430

Trp Glu Lys Ala Glu Asp Asn Gly Cys Arg Ile Thr Tyr Tyr Ile Leu
        435                 440                 445

Glu Ile Arg Lys Ser Thr Ser Asn Asn Leu Gln Asn Gln Asn Leu Arg
    450                 455                 460

Trp Lys Met Thr Phe Asn Gly Ser Cys Ser Ser Val Cys Thr Trp Lys
465                 470                 475                 480

Ser Lys Asn Leu Lys Gly Ile Phe Gln Phe Arg Val Val Ala Ala Asn
                485                 490                 495

Asn Leu Gly Phe Gly Glu Tyr Ser Gly Ile Ser Glu Asn Ile Ile Leu
            500                 505                 510

Val Gly Asp Asp Phe Trp Ile Pro Glu Thr Ser Phe Ile Leu Thr Ile
        515                 520                 525

Ile Val Gly Ile Phe Leu Val Val Thr Ile Pro Leu Thr Phe Val Trp
    530                 535                 540

His Arg Arg Leu Lys Asn Gln Lys Ser Ala Lys Glu Gly Val Thr Val
545                 550                 555                 560

Leu Ile Asn Glu Asp Lys Glu Leu Ala Glu Leu Arg Gly Leu Ala Ala
                565                 570                 575

Gly Val Gly Leu Ala Asn Ala Cys Tyr Ala Ile His Thr Leu Pro Thr
            580                 585                 590

Gln Glu Glu Ile Glu Asn Leu Pro Ala Phe Pro Arg Glu Lys Leu Thr
        595                 600                 605

Leu Arg Leu Leu Leu Gly Ser Gly Ala Phe Gly Glu Val Tyr Glu Gly
    610                 615                 620

Thr Ala Val Asp Ile Leu Gly Val Gly Ser Gly Glu Ile Lys Val Ala
```

625 630 635 640

Val Lys Thr Leu Lys Lys Gly Ser Thr Asp Gln Glu Lys Ile Glu Phe
645 650 655

Leu Lys Glu Ala His Leu Met Ser Lys Phe Asn His Pro Asn Ile Leu
660 665 670

Lys Gln Leu Gly Val Cys Leu Leu Asn Glu Pro Gln Tyr Ile Ile Leu
675 680 685

Glu Leu Met Glu Gly Gly Asp Leu Leu Thr Tyr Leu Arg Lys Ala Arg
690 695 700

Met Ala Thr Phe Tyr Gly Pro Leu Leu Thr Leu Val Asp Leu Val Asp
705 710 715 720

Leu Cys Val Asp Ile Ser Lys Gly Cys Val Tyr Leu Glu Arg Met His
725 730 735

Phe Ile His Arg Asp Leu Ala Ala Arg Asn Cys Leu Val Ser Val Lys
740 745 750

Asp Tyr Thr Ser Pro Arg Ile Val Lys Ile Gly Asp Phe Gly Leu Ala
755 760 765

Arg Asp Ile Tyr Lys Asn Asp Tyr Tyr Arg Lys Arg Gly Glu Gly Leu
770 775 780

Leu Pro Val Arg Trp Met Ala Pro Glu Ser Leu Met Asp Gly Ile Phe
785 790 795 800

Thr Thr Gln Ser Asp Val Trp Ser Phe Gly Ile Leu Ile Trp Glu Ile
805 810 815

Leu Thr Leu Gly His Gln Pro Tyr Pro Ala His Ser Asn Leu Asp Val
820 825 830

Leu Asn Tyr Val Gln Thr Gly Gly Arg Leu Glu Pro Pro Arg Asn Cys
835 840 845

Pro Asp Asp Leu Trp Asn Leu Met Thr Gln Cys Trp Ala Gln Glu Pro
850 855 860

Asp Gln Arg Pro Thr Phe His Arg Ile Gln Asp Gln Leu Gln Leu Phe
865 870 875 880

Arg Asn Phe Phe Leu Asn Ser Ile Tyr Lys Ser Arg Asp Glu Ala Asn
885 890 895

Asn Ser Gly Val Ile Asn Glu Ser Phe Glu Gly Glu Asp Gly Asp Val
900 905 910

Ile Cys Leu Asn Ser Asp Asp Ile Met Pro Val Ala Leu Met Glu Thr
915 920 925

Lys Asn Arg Glu Gly Leu Asn Tyr Met Val Leu Ala Thr Glu Cys Gly
930 935 940

Gln Gly Glu Glu Lys Ser Glu Gly Pro Leu Gly Ser Gln Glu Ser Glu
945 950 955 960

Ser Cys Gly Leu Arg Lys Glu Glu Lys Glu Pro His Ala Asp Lys Asp
965 970 975

Phe Cys Gln Glu Lys Gln Val Ala Tyr Cys Pro Ser Gly Lys Pro Glu
980 985 990

Gly Leu Asn Tyr Ala Cys Leu Thr His Ser Gly Tyr Gly Asp Gly Ser
995 1000 1005

Asp

<210> SEQ ID NO 18
<211> LENGTH: 2175
<212> TYPE: DNA
<213> ORGANISM: Artificial Sequence
<220> FEATURE:

-continued

<223> OTHER INFORMATION: Synthetic Nucleotide

<400> SEQUENCE: 18
atggctccct ggcctgaatt gggagatgcc cagcccaacc ccgataagta cctcgaaggg 60
gccgcaggtc agcagcccac tgcccctgat aaaagcaaag agaccaacaa aacagataac 120
actgaggcac ctgtaaccaa gattgaactt ctgccgtcct actccacggc tacactgata 180
gatgagccca ctgaggtgga tgacccctgg aacctaccca ctcttcagga ctcggggatc 240
aagtggtcag agagagacac caaagggaag attctctgtt tcttccaagg gattgggaga 300
ttgattttac ttctcggatt tctctacttt ttcgtgtgct ccctggatat tcttagtagc 360
gccttccagc tggttggagc tggagtccca aataaaccag gcattcccaa attactagaa 420
gggagtaaaa attcaataca gtgggagaaa gctgaagata atggatgtag aattacatac 480
tatatccttg agataagaaa gagcacttca aataatttac agaaccagaa tttaaggtgg 540
aagatgacat ttaatggatc ctgcagtagt gtttgcacat ggaagtccaa aaacctgaaa 600
ggaatatttc agttcagagt agtagctgca aataatctag ggtttggtga atatagtgga 660
atcagtgaga atattatatt agttggagat gatttttgga taccagaaac aagtttcata 720
cttactatta tagttggaat atttctggtt gttacaatcc cactgacctt tgtctggcat 780
agaagattaa agaatcaaaa aagtgccaag gaaggggtga cagtgcttat aaacgaagac 840
aaagagttgg ctgagctgcg aggtctggca gccggagtag gcctggctaa tgcctgctat 900
gcaatacata ctcttccaac ccaagaggag attgaaaatc ttcctgcctt ccctcgggaa 960
aaactgactc tgcgtctctt gctgggaagt ggagcctttg gagaagtgta tgaaggaaca 1020
gcagtggaca tcttaggagt tggaagtgga gaaatcaaag tagcagtgaa gactttgaag 1080
aagggttcca cagaccagga gaagattgaa ttcctgaagg aggcacatct gatgagcaaa 1140
tttaatcatc ccaacattct gaagcagctt ggagtttgtc tgctgaatga accccaatac 1200
attatcctgg aactgatgga gggaggagac cttcttactt atttgcgtaa agcccggatg 1260
gcaacgtttt atggtccttt actcaccttg gttgaccttg tagacctgtg tgtagatatt 1320
tcaaaaggct gtgtctactt ggaacggatg catttcattc acagggatct ggcagctaga 1380
aattgccttg tttccgtgaa agactatacc agtccacgga tagtgaagat tggagacttt 1440
ggactcgcca gagacatcta taaaaatgat tactatagaa agagagggga aggcctgctc 1500
ccagttcggt ggatggctcc agaaagtttg atggatggaa tcttcactac tcaatctgat 1560
gtatggtctt ttggaattct gatttgggag attttaactc ttggtcatca gccttatcca 1620
gctcattcca accttgatgt gttaaactat gtgcaaacag gagggagact ggagccacca 1680
agaaattgtc ctgatgatct gtggaattta atgacccagt gctgggctca agaacccgac 1740
caaagaccta cttttcatag aattcaggac caacttcagt tattcagaaa tttttttctta 1800 aatagcattt ataagtccag agatgaagca aacaacagtg gagtcataaa tgaaagcttt 1860
gaaggtgaag atggcgatgt gatttgtttg aattcagatg acattatgcc agttgcttta 1920
atggaaacga agaaccgaga agggttaaac tatatggtac ttgctacaga atgtggccaa 1980
ggtgaagaaa agtctgaggg tcctctaggc tcccaggaat ctgaatcttg tggtctgagg 2040
aaagaagaga aggaaccaca tgcagacaaa gatttctgcc aagaaaaaca agtggcttac 2100
tgcccttctg gcaagcctga aggcctgaac tatgcctgtc tcactcacag tggatatgga 2160
gatgggtctg attaa 2175

<210> SEQ ID NO 19
<211> LENGTH: 724
<212> TYPE: PRT
<213> ORGANISM: Artificial Sequence
<220> FEATURE:
<223> OTHER INFORMATION: Synthetic Peptide

<400> SEQUENCE: 19

```
Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Leu Gly Phe Leu Tyr Phe Phe Val
            100                 105                 110

Cys Ser Leu Asp Ile Leu Ser Ser Ala Phe Gln Leu Val Gly Ala Gly
        115                 120                 125

Val Pro Asn Lys Pro Gly Ile Pro Lys Leu Leu Glu Gly Ser Lys Asn
    130                 135                 140

Ser Ile Gln Trp Glu Lys Ala Glu Asp Asn Gly Cys Arg Ile Thr Tyr
145                 150                 155                 160

Tyr Ile Leu Glu Ile Arg Lys Ser Thr Ser Asn Asn Leu Gln Asn Gln
                165                 170                 175

Asn Leu Arg Trp Lys Met Thr Phe Asn Gly Ser Cys Ser Ser Val Cys
            180                 185                 190

Thr Trp Lys Ser Lys Asn Leu Lys Gly Ile Phe Gln Phe Arg Val Val
        195                 200                 205

Ala Ala Asn Asn Leu Gly Phe Gly Glu Tyr Ser Gly Ile Ser Glu Asn
    210                 215                 220

Ile Ile Leu Val Gly Asp Asp Phe Trp Ile Pro Glu Thr Ser Phe Ile
225                 230                 235                 240

Leu Thr Ile Ile Val Gly Ile Phe Leu Val Val Thr Ile Pro Leu Thr
                245                 250                 255

Phe Val Trp His Arg Arg Leu Lys Asn Gln Lys Ser Ala Lys Glu Gly
            260                 265                 270

Val Thr Val Leu Ile Asn Glu Asp Lys Glu Leu Ala Glu Leu Arg Gly
        275                 280                 285

Leu Ala Ala Gly Val Gly Leu Ala Asn Ala Cys Tyr Ala Ile His Thr
    290                 295                 300

Leu Pro Thr Gln Glu Glu Ile Glu Asn Leu Pro Ala Phe Pro Arg Glu
305                 310                 315                 320

Lys Leu Thr Leu Arg Leu Leu Leu Gly Ser Gly Ala Phe Gly Glu Val
                325                 330                 335

Tyr Glu Gly Thr Ala Val Asp Ile Leu Gly Val Gly Ser Gly Glu Ile
            340                 345                 350

Lys Val Ala Val Lys Thr Leu Lys Lys Gly Ser Thr Asp Gln Glu Lys
        355                 360                 365

Ile Glu Phe Leu Lys Glu Ala His Leu Met Ser Lys Phe Asn His Pro
```

```
    370                 375                 380

Asn Ile Leu Lys Gln Leu Gly Val Cys Leu Leu Asn Glu Pro Gln Tyr
385                 390                 395                 400

Ile Ile Leu Glu Leu Met Glu Gly Gly Asp Leu Leu Thr Tyr Leu Arg
                405                 410                 415

Lys Ala Arg Met Ala Thr Phe Tyr Gly Pro Leu Leu Thr Leu Val Asp
            420                 425                 430

Leu Val Asp Leu Cys Val Asp Ile Ser Lys Gly Cys Val Tyr Leu Glu
        435                 440                 445

Arg Met His Phe Ile His Arg Asp Leu Ala Ala Arg Asn Cys Leu Val
    450                 455                 460

Ser Val Lys Asp Tyr Thr Ser Pro Arg Ile Val Lys Ile Gly Asp Phe
465                 470                 475                 480

Gly Leu Ala Arg Asp Ile Tyr Lys Asn Asp Tyr Tyr Arg Lys Arg Gly
                485                 490                 495

Glu Gly Leu Leu Pro Val Arg Trp Met Ala Pro Glu Ser Leu Met Asp
            500                 505                 510

Gly Ile Phe Thr Thr Gln Ser Asp Val Trp Ser Phe Gly Ile Leu Ile
        515                 520                 525

Trp Glu Ile Leu Thr Leu Gly His Gln Pro Tyr Pro Ala His Ser Asn
    530                 535                 540

Leu Asp Val Leu Asn Tyr Val Gln Thr Gly Gly Arg Leu Glu Pro Pro
545                 550                 555                 560

Arg Asn Cys Pro Asp Asp Leu Trp Asn Leu Met Thr Gln Cys Trp Ala
                565                 570                 575

Gln Glu Pro Asp Gln Arg Pro Thr Phe His Arg Ile Gln Asp Gln Leu
            580                 585                 590

Gln Leu Phe Arg Asn Phe Phe Leu Asn Ser Ile Tyr Lys Ser Arg Asp
        595                 600                 605

Glu Ala Asn Asn Ser Gly Val Ile Asn Glu Ser Phe Glu Gly Glu Asp
    610                 615                 620

Gly Asp Val Ile Cys Leu Asn Ser Asp Asp Ile Met Pro Val Ala Leu
625                 630                 635                 640

Met Glu Thr Lys Asn Arg Glu Gly Leu Asn Tyr Met Val Leu Ala Thr
                645                 650                 655

Glu Cys Gly Gln Gly Glu Glu Lys Ser Glu Gly Pro Leu Gly Ser Gln
            660                 665                 670

Glu Ser Glu Ser Cys Gly Leu Arg Lys Glu Glu Lys Glu Pro His Ala
        675                 680                 685

Asp Lys Asp Phe Cys Gln Glu Lys Gln Val Ala Tyr Cys Pro Ser Gly
    690                 695                 700

Lys Pro Glu Gly Leu Asn Tyr Ala Cys Leu Thr His Ser Gly Tyr Gly
705                 710                 715                 720

Asp Gly Ser Asp


<210> SEQ ID NO 20
<211> LENGTH: 1866
<212> TYPE: DNA
<213> ORGANISM: Artificial Sequence
<220> FEATURE:
<223> OTHER INFORMATION: Synthetic Nucleotide

<400> SEQUENCE: 20

atggctccct ggcctgaatt gggagatgcc cagcccaacc ccgataagta cctcgaaggg     60
```

-continued

```
gccgcaggtc agcagcccac tgcccctgat aaaagcaaag agaccaacaa aacagataac    120

actgaggcac ctgtaaccaa gattgaactt ctgccgtcct actccacggc tacactgata    180

gatgagccca ctgaggtgga tgacccctgg aacctaccca ctcttcagga ctcggggatc    240

aagtggtcag agagagacac caaagggaag attctctgtt tcttccaagg gattgggaga    300

ttgattttac ttctcggatt tctctacttt ttcgtgtgct ccctggatat tcttagtagc    360

gccttccagc tggttggaga tgatttttgg ataccagaaa caagtttcat acttactatt    420

atagttggaa tatttctggt tgttacaatc ccactgacct ttgtctggca tagaagatta    480

aagaatcaaa aaagtgccaa ggaaggggtg acagtgctta taaacgaaga caaagagttg    540

gctgagctgc gaggtctggc agccggagta ggcctggcta atgcctgcta tgcaatacat    600

actcttccaa cccaagagga gattgaaaat cttcctgcct tccctcggga aaaactgact    660

ctgcgtctct tgctgggaag tggagccttt ggagaagtgt atgaaggaac agcagtggac    720

atcttaggag ttggaagtgg agaaatcaaa gtagcagtga agactttgaa gaagggttcc    780

acagaccagg agaagattga attcctgaag gaggcacatc tgatgagcaa atttaatcat    840

cccaacattc tgaagcagct tggagtttgt ctgctgaatg aaccccaata cattatcctg    900

gaactgatgg agggaggaga ccttcttact tatttgcgta aagcccggat ggcaacgttt    960

tatggtcctt tactcacctt ggttgacctt gtagacctgt gtgtagatat ttcaaaaggc   1020

tgtgtctact tggaacggat gcatttcatt cacagggatc tggcagctag aaattgcctt   1080

gtttccgtga aagactatac cagtccacgg atagtgaaga ttggagactt tggactcgcc   1140

agagacatct ataaaaatga ttactataga aagagagggg aaggcctgct cccagttcgg   1200

tggatggctc cagaaagttt gatggatgga atcttcacta ctcaatctga tgtatggtct   1260

tttggaattc tgatttggga gattttaact cttggtcatc agccttatcc agctcattcc   1320

aaccttgatg tgttaaacta tgtgcaaaca ggagggagac tggagccacc aagaaattgt   1380

cctgatgatc tgtggaattt aatgacccag tgctgggctc aagaacccga ccaaagacct   1440

acttttcata gaattcagga ccaacttcag ttattcagaa atttttttctt aaatagcatt   1500

tataagtcca gagatgaagc aaacaacagt ggagtcataa atgaaagctt tgaaggtgaa   1560

gatggcgatg tgatttgttt gaattcagat gacattatgc cagttgcttt aatggaaacg   1620

aagaaccgag aagggttaaa ctatatggta cttgctacag aatgtggcca aggtgaagaa   1680

aagtctgagg gtcctctagg ctcccaggaa tctgaatctt gtggtctgag gaaagaagag   1740

aaggaaccac atgcagacaa agatttctgc caagaaaaac aagtggctta ctgcccttct   1800

ggcaagcctg aaggcctgaa ctatgcctgt ctcactcaca gtggatatgg agatgggtct   1860

gattaa                                                              1866
```

<210> SEQ ID NO 21
<211> LENGTH: 621
<212> TYPE: PRT
<213> ORGANISM: Artificial Sequence
<220> FEATURE:
<223> OTHER INFORMATION: Synthetic Peptide

<400> SEQUENCE: 21

```
Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
```

```
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Leu Gly Phe Leu Tyr Phe Phe Val
            100                 105                 110

Cys Ser Leu Asp Ile Leu Ser Ser Ala Phe Gln Leu Val Gly Asp Asp
        115                 120                 125

Phe Trp Ile Pro Glu Thr Ser Phe Ile Leu Thr Ile Ile Val Gly Ile
    130                 135                 140

Phe Leu Val Val Thr Ile Pro Leu Thr Phe Val Trp His Arg Arg Leu
145                 150                 155                 160

Lys Asn Gln Lys Ser Ala Lys Glu Gly Val Thr Val Leu Ile Asn Glu
                165                 170                 175

Asp Lys Glu Leu Ala Glu Leu Arg Gly Leu Ala Ala Gly Val Gly Leu
            180                 185                 190

Ala Asn Ala Cys Tyr Ala Ile His Thr Leu Pro Thr Gln Glu Glu Ile
        195                 200                 205

Glu Asn Leu Pro Ala Phe Pro Arg Glu Lys Leu Thr Leu Arg Leu Leu
    210                 215                 220

Leu Gly Ser Gly Ala Phe Gly Glu Val Tyr Glu Gly Thr Ala Val Asp
225                 230                 235                 240

Ile Leu Gly Val Gly Ser Gly Glu Ile Lys Val Ala Val Lys Thr Leu
                245                 250                 255

Lys Lys Gly Ser Thr Asp Gln Glu Lys Ile Glu Phe Leu Lys Glu Ala
            260                 265                 270

His Leu Met Ser Lys Phe Asn His Pro Asn Ile Leu Lys Gln Leu Gly
        275                 280                 285

Val Cys Leu Leu Asn Glu Pro Gln Tyr Ile Ile Leu Glu Leu Met Glu
    290                 295                 300

Gly Gly Asp Leu Leu Thr Tyr Leu Arg Lys Ala Arg Met Ala Thr Phe
305                 310                 315                 320

Tyr Gly Pro Leu Leu Thr Leu Val Asp Leu Val Asp Leu Cys Val Asp
                325                 330                 335

Ile Ser Lys Gly Cys Val Tyr Leu Glu Arg Met His Phe Ile His Arg
            340                 345                 350

Asp Leu Ala Ala Arg Asn Cys Leu Val Ser Val Lys Asp Tyr Thr Ser
        355                 360                 365

Pro Arg Ile Val Lys Ile Gly Asp Phe Gly Leu Ala Arg Asp Ile Tyr
    370                 375                 380

Lys Asn Asp Tyr Tyr Arg Lys Arg Gly Glu Gly Leu Leu Pro Val Arg
385                 390                 395                 400

Trp Met Ala Pro Glu Ser Leu Met Asp Gly Ile Phe Thr Thr Gln Ser
                405                 410                 415

Asp Val Trp Ser Phe Gly Ile Leu Ile Trp Glu Ile Leu Thr Leu Gly
            420                 425                 430

His Gln Pro Tyr Pro Ala His Ser Asn Leu Asp Val Leu Asn Tyr Val
        435                 440                 445

Gln Thr Gly Gly Arg Leu Glu Pro Pro Arg Asn Cys Pro Asp Asp Leu
    450                 455                 460
```

```
Trp Asn Leu Met Thr Gln Cys Trp Ala Gln Glu Pro Asp Gln Arg Pro
465                 470                 475                 480

Thr Phe His Arg Ile Gln Asp Gln Leu Gln Leu Phe Arg Asn Phe Phe
                485                 490                 495

Leu Asn Ser Ile Tyr Lys Ser Arg Asp Glu Ala Asn Asn Ser Gly Val
            500                 505                 510

Ile Asn Glu Ser Phe Glu Gly Glu Asp Gly Asp Val Ile Cys Leu Asn
        515                 520                 525

Ser Asp Asp Ile Met Pro Val Ala Leu Met Glu Thr Lys Asn Arg Glu
    530                 535                 540

Gly Leu Asn Tyr Met Val Leu Ala Thr Glu Cys Gly Gln Gly Glu Glu
545                 550                 555                 560

Lys Ser Glu Gly Pro Leu Gly Ser Gln Glu Ser Glu Ser Cys Gly Leu
                565                 570                 575

Arg Lys Glu Glu Lys Glu Pro His Ala Asp Lys Asp Phe Cys Gln Glu
            580                 585                 590

Lys Gln Val Ala Tyr Cys Pro Ser Gly Lys Pro Glu Gly Leu Asn Tyr
        595                 600                 605

Ala Cys Leu Thr His Ser Gly Tyr Gly Asp Gly Ser Asp
    610                 615                 620
```

<210> SEQ ID NO 22
<211> LENGTH: 1782
<212> TYPE: DNA
<213> ORGANISM: Artificial Sequence
<220> FEATURE:
<223> OTHER INFORMATION: Synthetic Nucleotide

<400> SEQUENCE: 22

```
atggctccct ggcctgaatt gggagatgcc cagcccaacc ccgataagta cctcgaaggg     60

gccgcaggtc agcagcccac tgcccctgat aaaagcaaag agaccaacaa aacagataac    120

actgaggcac ctgtaaccaa gattgaactt ctgccgtcct actccacggc tacactgata    180

gatgagccca ctgaggtgga tgacccctgg aacctaccca ctcttcagga ctcggggatc    240

aagtggtcag agagagacac caaagggaag attctctgtt tcttccaagg gattgggaga    300

ttgattttac ttctcggatt tctctacttt ttcgtgtgct ccctggatat tcttagtagc    360

gccttccagc tggttggagt ctggcataga agattaaaga atcaaaaaag tgccaaggaa    420

ggggtgacag tgcttataaa cgaagacaaa gagttggctg agctgcgagg tctggcagcc    480

ggagtaggcc tggctaatgc ctgctatgca atacatactc ttccaaccca agaggagatt    540

gaaaatcttc ctgccttccc tcgggaaaaa ctgactctgc gtctcttgct gggaagtgga    600

gcctttggag aagtgtatga aggaacagca gtggacatct taggagttgg aagtggagaa    660

atcaaagtag cagtgaagac tttgaagaag ggttccacag accaggagaa gattgaattc    720

ctgaaggagg cacatctgat gagcaaattt aatcatccca acattctgaa gcagcttgga    780

gtttgtctgc tgaatgaacc ccaatacatt atcctggaac tgatggaggg aggagacctt    840

cttacttatt tgcgtaaagc ccggatggca acgttttatg gtcctttact caccttggtt    900

gaccttgtag acctgtgtgt agatatttca aaaggctgtg tctacttgga acggatgcat    960

ttcattcaca gggatctggc agctagaaat tgccttgttt ccgtgaaaga ctataccagt   1020

ccacggatag tgaagattgg agactttgga ctcgccagag acatctataa aaatgattac   1080

tatagaaaga gaggggaagg cctgctccca gttcggtgga tggctccaga aagtttgatg   1140
```

```
gatggaatct tcactactca atctgatgta tggtcttttg gaattctgat ttgggagatt   1200

ttaactcttg gtcatcagcc ttatccagct cattccaacc ttgatgtgtt aaactatgtg   1260

caaacaggag ggagactgga gccaccaaga aattgtcctg atgatctgtg gaatttaatg   1320

acccagtgct gggctcaaga acccgaccaa agacctactt ttcatagaat tcaggaccaa   1380

cttcagttat tcagaaattt tttcttaaat agcatttata agtccagaga tgaagcaaac   1440

aacagtggag tcataaatga aagctttgaa ggtgaagatg gcgatgtgat ttgtttgaat   1500

tcagatgaca ttatgccagt tgctttaatg gaaacgaaga accgagaagg gttaaactat   1560

atggtacttg ctacagaatg tggccaaggt gaagaaaagt ctgagggtcc tctaggctcc   1620

caggaatctg aatcttgtgg tctgaggaaa gaagagaagg aaccacatgc agacaaagat   1680

ttctgccaag aaaaacaagt ggcttactgc ccttctggca agcctgaagg cctgaactat   1740

gcctgtctca ctcacagtgg atatggagat gggtctgatt aa                      1782


<210> SEQ ID NO 23
<211> LENGTH: 593
<212> TYPE: PRT
<213> ORGANISM: Artificial Sequence
<220> FEATURE:
<223> OTHER INFORMATION: Synthetic Peptide

<400> SEQUENCE: 23

Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Leu Gly Phe Leu Tyr Phe Phe Val
            100                 105                 110

Cys Ser Leu Asp Ile Leu Ser Ser Ala Phe Gln Leu Val Gly Val Trp
        115                 120                 125

His Arg Arg Leu Lys Asn Gln Lys Ser Ala Lys Glu Gly Val Thr Val
    130                 135                 140

Leu Ile Asn Glu Asp Lys Glu Leu Ala Glu Leu Arg Gly Leu Ala Ala
145                 150                 155                 160

Gly Val Gly Leu Ala Asn Ala Cys Tyr Ala Ile His Thr Leu Pro Thr
                165                 170                 175

Gln Glu Glu Ile Glu Asn Leu Pro Ala Phe Pro Arg Glu Lys Leu Thr
            180                 185                 190

Leu Arg Leu Leu Leu Gly Ser Gly Ala Phe Gly Glu Val Tyr Glu Gly
        195                 200                 205

Thr Ala Val Asp Ile Leu Gly Val Gly Ser Gly Glu Ile Lys Val Ala
    210                 215                 220

Val Lys Thr Leu Lys Lys Gly Ser Thr Asp Gln Glu Lys Ile Glu Phe
225                 230                 235                 240

Leu Lys Glu Ala His Leu Met Ser Lys Phe Asn His Pro Asn Ile Leu
                245                 250                 255
```

```
Lys Gln Leu Gly Val Cys Leu Leu Asn Glu Pro Gln Tyr Ile Ile Leu
            260                 265                 270

Glu Leu Met Glu Gly Gly Asp Leu Leu Thr Tyr Leu Arg Lys Ala Arg
        275                 280                 285

Met Ala Thr Phe Tyr Gly Pro Leu Leu Thr Leu Val Asp Leu Val Asp
    290                 295                 300

Leu Cys Val Asp Ile Ser Lys Gly Cys Val Tyr Leu Glu Arg Met His
305                 310                 315                 320

Phe Ile His Arg Asp Leu Ala Ala Arg Asn Cys Leu Val Ser Val Lys
                325                 330                 335

Asp Tyr Thr Ser Pro Arg Ile Val Lys Ile Gly Asp Phe Gly Leu Ala
            340                 345                 350

Arg Asp Ile Tyr Lys Asn Asp Tyr Tyr Arg Lys Arg Gly Glu Gly Leu
        355                 360                 365

Leu Pro Val Arg Trp Met Ala Pro Glu Ser Leu Met Asp Gly Ile Phe
    370                 375                 380

Thr Thr Gln Ser Asp Val Trp Ser Phe Gly Ile Leu Ile Trp Glu Ile
385                 390                 395                 400

Leu Thr Leu Gly His Gln Pro Tyr Pro Ala His Ser Asn Leu Asp Val
                405                 410                 415

Leu Asn Tyr Val Gln Thr Gly Gly Arg Leu Glu Pro Pro Arg Asn Cys
            420                 425                 430

Pro Asp Asp Leu Trp Asn Leu Met Thr Gln Cys Trp Ala Gln Glu Pro
        435                 440                 445

Asp Gln Arg Pro Thr Phe His Arg Ile Gln Asp Gln Leu Gln Leu Phe
    450                 455                 460

Arg Asn Phe Phe Leu Asn Ser Ile Tyr Lys Ser Arg Asp Glu Ala Asn
465                 470                 475                 480

Asn Ser Gly Val Ile Asn Glu Ser Phe Glu Gly Glu Asp Gly Asp Val
                485                 490                 495

Ile Cys Leu Asn Ser Asp Asp Ile Met Pro Val Ala Leu Met Glu Thr
            500                 505                 510

Lys Asn Arg Glu Gly Leu Asn Tyr Met Val Leu Ala Thr Glu Cys Gly
        515                 520                 525

Gln Gly Glu Glu Lys Ser Glu Gly Pro Leu Gly Ser Gln Glu Ser Glu
    530                 535                 540

Ser Cys Gly Leu Arg Lys Glu Glu Lys Glu Pro His Ala Asp Lys Asp
545                 550                 555                 560

Phe Cys Gln Glu Lys Gln Val Ala Tyr Cys Pro Ser Gly Lys Pro Glu
                565                 570                 575

Gly Leu Asn Tyr Ala Cys Leu Thr His Ser Gly Tyr Gly Asp Gly Ser
            580                 585                 590

Asp
```

<210> SEQ ID NO 24
<211> LENGTH: 2112
<212> TYPE: DNA
<213> ORGANISM: Artificial Sequence
<220> FEATURE:
<223> OTHER INFORMATION: Synthetic Nucleotide

<400> SEQUENCE: 24

```
atgcacagga ggagaagcag gagctgtcgg gaagatcaga agccagtcat ggatgaccag      60

cgcgacctta tctccaacaa tgagcaactg cccatgctgg gccggcgccc tggggccccg     120
```

```
gagagcaagt gcagccgcgg agccctgtac acaggctttt ccatcctggt gactctgctc    180
ctcgctggcc aggccaccac cgcctacttc ctgtaccagc agcagggccg gctggacaaa    240
ctgacagtca cctcccagaa cctgcagctg gagaacctgc gcatgaagct tcccaagcct    300
cccaagcctg tgagcaagat gcgcatggcc accccgctgc tgatgcaggc gctgcccatg    360
ggagccctgc cccaggggcc catgcagaat gccaccaagt atggcaacat gacagaggac    420
catgtgatgc acctgctcca gaatgctgac cccctgaagg tgtacccgcc actgaagggg    480
agcttcccgg agaacctgag acaccttaag aacaccatgg agaccataga ctggaaggtc    540
tttgagagct ggatgcacca ttggctcctg tttgaaatga gcaggcactc cttggagcaa    600
aagcccactg acgctccacc gaaagatgat ttttggatac cagaaacaag tttcatactt    660
actattatag ttggaatatt tctggttgtt acaatcccac tgacctttgt ctggcataga    720
agattaaaga atcaaaaaag tgccaaggaa ggggtgacag tgcttataaa cgaagacaaa    780
gagttggctg agctgcgagg tctggcagcc ggagtaggcc tggctaatgc ctgctatgca    840
atacatactc ttccaaccca agaggagatt gaaaatcttc ctgccttccc tcgggaaaaa    900
ctgactctgc gtctcttgct gggaagtgga gcctttggag aagtgtatga aggaacagca    960
gtggacatct taggagttgg aagtggagaa atcaaagtag cagtgaagac tttgaagaag   1020
ggttccacag accaggagaa gattgaattc ctgaaggagg cacatctgat gagcaaattt   1080
aatcatccca acattctgaa gcagcttgga gtttgtctgc tgaatgaacc ccaatacatt   1140
atcctggaac tgatggaggg aggagacctt cttacttatt tgcgtaaagc ccggatggca   1200
acgttttatg gtcctttact caccttggtt gaccttgtag acctgtgtgt agatatttca   1260
aaaggctgtg tctacttgga acggatgcat ttcattcaca gggatctggc agctagaaat   1320
tgccttgttt ccgtgaaaga ctataccagt ccacggatag tgaagattgg agactttgga   1380
ctcgccagag acatctataa aaatgattac tatagaaaga gaggggaagg cctgctccca   1440
gttcggtgga tggctccaga aagtttgatg gatggaatct tcactactca atctgatgta   1500
tggtcttttg gaattctgat ttgggagatt ttaactcttg gtcatcagcc ttatccagct   1560
cattccaacc ttgatgtgtt aaactatgtg caaacaggag ggagactgga gccaccaaga   1620
aattgtcctg atgatctgtg gaatttaatg acccagtgct gggctcaaga acccgaccaa   1680
agacctactt ttcatagaat tcaggaccaa cttcagttat tcagaaattt tttcttaaat   1740
agcatttata agtccagaga tgaagcaaac aacagtggag tcataaatga aagctttgaa   1800
ggtgaagatg gcgatgtgat ttgtttgaat tcagatgaca ttatgccagt tgctttaatg   1860
gaaacgaaga accgagaagg gttaaactat atggtacttg ctacagaatg tggccaaggt   1920
gaagaaaagt ctgagggtcc tctaggctcc caggaatctg aatcttgtgg tctgaggaaa   1980
gaagagaagg aaccacatgc agacaaagat ttctgccaag aaaaacaagt ggcttactgc   2040
ccttctggca agcctgaagg cctgaactat gcctgtctca ctcacagtgg atatggagat   2100
gggtctgatt aa                                                       2112
```

<210> SEQ ID NO 25
<211> LENGTH: 700
<212> TYPE: PRT
<213> ORGANISM: Artificial Sequence
<220> FEATURE:
<223> OTHER INFORMATION: Synthetic Peptide

<400> SEQUENCE: 25

-continued

```
Met His Arg Arg Arg Ser Arg Ser Cys Arg Glu Asp Gln Lys Pro Val
1               5                   10                  15

Met Asp Asp Gln Arg Asp Leu Ile Ser Asp Asp Glu Gln Leu Pro Met
            20                  25                  30

Leu Gly Arg Arg Pro Gly Ala Pro Glu Ser Arg Gly Ala Leu Tyr Thr
        35                  40                  45

Gly Phe Ser Ile Leu Val Thr Leu Leu Leu Ala Gly Gln Ala Thr Thr
    50                  55                  60

Ala Tyr Phe Leu Tyr Gln Gln Gln Gly Arg Leu Asp Lys Leu Thr Val
65                  70                  75                  80

Thr Ser Gln Asn Leu Gln Leu Glu Asn Leu Arg Met Lys Leu Pro Lys
                85                  90                  95

Pro Pro Lys Pro Val Ser Lys Met Arg Met Ala Thr Pro Leu Leu Met
            100                 105                 110

Gln Ala Leu Pro Met Gly Ala Leu Pro Gln Gly Pro Met Gln Asn Ala
        115                 120                 125

Thr Lys Tyr Gly Asn Met Thr Glu Asp His Val Met His Leu Leu Gln
    130                 135                 140

Asn Ala Asp Pro Leu Lys Val Tyr Pro Pro Leu Lys Gly Ser Phe Pro
145                 150                 155                 160

Glu Asn Leu Arg His Leu Lys Asn Thr Met Glu Thr Ile Asp Trp Lys
                165                 170                 175

Val Phe Glu Ser Trp Met His His Trp Leu Leu Phe Glu Met Ser Arg
            180                 185                 190

His Ser Leu Glu Gln Lys Pro Thr Asp Ala Pro Pro Lys Asp Asp Phe
        195                 200                 205

Trp Ile Pro Glu Thr Ser Phe Ile Leu Thr Ile Ile Val Gly Ile Phe
    210                 215                 220

Leu Val Val Thr Ile Pro Leu Thr Phe Val Trp His Arg Arg Leu Lys
225                 230                 235                 240

Asn Gln Lys Ser Ala Lys Glu Gly Val Thr Val Leu Ile Asn Glu Asp
                245                 250                 255

Lys Glu Leu Ala Glu Leu Arg Gly Leu Ala Ala Gly Val Gly Leu Ala
            260                 265                 270

Asn Ala Cys Tyr Ala Ile His Thr Leu Pro Thr Gln Glu Glu Ile Glu
        275                 280                 285

Asn Leu Pro Ala Phe Pro Arg Glu Lys Leu Thr Leu Arg Leu Leu Leu
    290                 295                 300

Gly Ser Gly Ala Phe Gly Glu Val Tyr Glu Gly Thr Ala Val Asp Ile
305                 310                 315                 320

Leu Gly Val Gly Ser Gly Glu Ile Lys Val Ala Val Lys Thr Leu Lys
                325                 330                 335

Lys Gly Ser Thr Asp Gln Glu Lys Ile Glu Phe Leu Lys Glu Ala His
            340                 345                 350

Leu Met Ser Lys Phe Asn His Pro Asn Ile Leu Lys Gln Leu Gly Val
        355                 360                 365

Cys Leu Leu Asn Glu Pro Gln Tyr Ile Ile Leu Glu Leu Met Glu Gly
    370                 375                 380

Gly Asp Leu Leu Thr Tyr Leu Arg Lys Ala Arg Met Ala Thr Phe Tyr
385                 390                 395                 400

Gly Pro Leu Leu Thr Leu Val Asp Leu Val Asp Leu Cys Val Asp Ile
                405                 410                 415

Ser Lys Gly Cys Val Tyr Leu Glu Arg Met His Phe Ile His Arg Asp
```

```
            420                 425                 430

Leu Ala Ala Arg Asn Cys Leu Val Ser Val Lys Asp Tyr Thr Ser Pro
        435                 440                 445

Arg Ile Val Lys Ile Gly Asp Phe Gly Leu Ala Arg Asp Ile Tyr Lys
    450                 455                 460

Asn Asp Tyr Tyr Arg Lys Arg Gly Glu Gly Leu Leu Pro Val Arg Trp
465                 470                 475                 480

Met Ala Pro Glu Ser Leu Met Asp Gly Ile Phe Thr Thr Gln Ser Asp
                485                 490                 495

Val Trp Ser Phe Gly Ile Leu Ile Trp Glu Ile Leu Thr Leu Gly His
            500                 505                 510

Gln Pro Tyr Pro Ala His Ser Asn Leu Asp Val Leu Asn Tyr Val Gln
        515                 520                 525

Thr Gly Gly Arg Leu Glu Pro Pro Arg Asn Cys Pro Asp Asp Leu Trp
    530                 535                 540

Asn Leu Met Thr Asn Cys Trp Ala Gln Glu Pro Asp Gln Arg Pro Thr
545                 550                 555                 560

Phe His Arg Ile Gln Asp Gln Leu Gln Leu Phe Arg Asn Phe Phe Leu
                565                 570                 575

Asn Ser Ile Tyr Lys Ser Arg Asp Glu Ala Asn Asn Ser Gly Val Ile
            580                 585                 590

Asn Glu Ser Phe Glu Gly Glu Asp Gly Asp Val Ile Cys Leu Asn Ser
        595                 600                 605

Asp Asp Ile Met Pro Val Ala Leu Met Glu Thr Lys Asn Arg Glu Gly
    610                 615                 620

Leu Asn Tyr Met Val Leu Ala Thr Glu Cys Gly Gln Gly Glu Glu Lys
625                 630                 635                 640

Ser Glu Gly Pro Leu Gly Ser Gln Glu Ser Glu Ser Cys Gly Leu Arg
                645                 650                 655

Lys Glu Glu Lys Glu Pro His Ala Asp Lys Lys Phe Cys Gln Glu Lys
            660                 665                 670

Glu Val Ala Tyr Cys Pro Ser Gly Lys Pro Glu Gly Leu Asn Tyr Ala
        675                 680                 685

Cys Leu Thr His Ser Gly Tyr Gly Asp Gly Ser Asp
    690                 695                 700


<210> SEQ ID NO 26
<211> LENGTH: 1228
<212> TYPE: DNA
<213> ORGANISM: Artificial Sequence
<220> FEATURE:
<223> OTHER INFORMATION: Synthetic Nucleotide

<400> SEQUENCE: 26

gtatgtagct ttggccatca ttatggagca cctaggcaaa gggtgggcaa cagtaaggag     60

agtgcctatg aattccgcat tgcccaagac agtcatggtt tataccagtt tttctggcat    120

aattattaat aacttcctct tccactctca aatgtgacct gggatggatg gaaaattatg    180

tggttttaag aaaaatacag aaaaatccat tagtttccag tattttgtca tgtagctcaa    240

aaacaaatga aagaaggaga aaaatattac attgaagaga atagatggta acatggttgg    300

ttgacctgga ggcagtgttt gagaggagag gagttttgag agccttgtgt tacgtggtca    360

gccttaagtc aatcttactc catttcagaa gttgtgtgat gattgcccac aaaaccttct    420

taagatagat gagttttgaa cttttgttgc cgtcataatt aaggaaaata ttcaagtgtc    480
```

-continued

```
ttatgcaaag gttcattata ttaggatcta tgcaaaaagg aattaaatga tcataggcct    540

tgctttcaga aatttataat gcaaggtgta aaaacaaagg atttgaagta gacacaaagg    600

tgatctaaat cagctgttta gaggtgactt tcctttgagc aaatactcag catatctgct    660

actcaagatt ctctattaaa aattgaaagc atttttaaca tagcagcatt ttcccccctt    720

gtagtattcc aagtgagaaa cttggctttt taaagttaac cttatggtga tggggttgat    780

tttttggtc atagtaaatt ttgttttacg taagatgtca catgtgtgaa atagctaaga    840

gaaaagctta taaacccaga tgcatttatt actaatttgc agtagctttt tatacaaatt    900

ggcaatctga agaagttaat acctactaac tttgactcaa caagctacaa taaaagtgtt    960

gaggcaatgc atacacatat atatttttat caaaattaag gtgcctagaa gtggaccatc   1020

atgctctgtc tgggtaaaag gttgtagaat agtaaagtaa agtaattagg aacccaaagt   1080

tccacatcac cgtgtcacat aaaacacaca atactgcaaa gccatgagat atttctttct   1140

ctctcaaaca caaataccaa taccaacaca aacttgtaca ccctatatat gtggagggtg   1200

gggagacaaa aatgttgcta ttttacag                                      1228


<210> SEQ ID NO 27
<211> LENGTH: 24
<212> TYPE: DNA
<213> ORGANISM: Artificial Sequence
<220> FEATURE:
<223> OTHER INFORMATION: Synthetic Nucleotide Peptide

<400> SEQUENCE: 27

acccttctcg gttcttcgtt tcca                                            24


<210> SEQ ID NO 28
<211> LENGTH: 24
<212> TYPE: DNA
<213> ORGANISM: Artificial Sequence
<220> FEATURE:
<223> OTHER INFORMATION: Synthetic Nucleotide

<400> SEQUENCE: 28

tctggcgagt ccaaagtctc caat                                            24


<210> SEQ ID NO 29
<211> LENGTH: 24
<212> TYPE: DNA
<213> ORGANISM: Artificial Sequence
<220> FEATURE:
<223> OTHER INFORMATION: Synthetic Nucleotide Peptide

<400> SEQUENCE: 29

cagcaagaga cgcagagtca gttt                                            24


<210> SEQ ID NO 30
<211> LENGTH: 24
<212> TYPE: DNA
<213> ORGANISM: Artificial Sequence
<220> FEATURE:
<223> OTHER INFORMATION: Synthetic Nucleotide

<400> SEQUENCE: 30

actggtcaaa gtgctgactc tggt                                            24


<210> SEQ ID NO 31
<211> LENGTH: 24
<212> TYPE: DNA
<213> ORGANISM: Artificial Sequence
```

<220> FEATURE:
<223> OTHER INFORMATION: Synthetic Nucleotide

<400> SEQUENCE: 31
cagcaagaga cgcagagtca gttt 24

<210> SEQ ID NO 32
<211> LENGTH: 24
<212> TYPE: DNA
<213> ORGANISM: Artificial Sequence
<220> FEATURE:
<223> OTHER INFORMATION: Synthetic Nucleotide

<400> SEQUENCE: 32
ttggataagg aactggcagg aagg 24

<210> SEQ ID NO 33
<211> LENGTH: 24
<212> TYPE: DNA
<213> ORGANISM: Artificial Sequence
<220> FEATURE:
<223> OTHER INFORMATION: Synthetic Nucleotide

<400> SEQUENCE: 33
accgtcatct agcggagttt cact 24

<210> SEQ ID NO 34
<211> LENGTH: 24
<212> TYPE: DNA
<213> ORGANISM: Artificial Sequence
<220> FEATURE:
<223> OTHER INFORMATION: Synthetic Nucleotide

<400> SEQUENCE: 34
agccaaggtc ctgcttatgt ctgt 24

<210> SEQ ID NO 35
<211> LENGTH: 24
<212> TYPE: DNA
<213> ORGANISM: Artificial Sequence
<220> FEATURE:
<223> OTHER INFORMATION: Synthetic Nucleotide

<400> SEQUENCE: 35
tctggcgagt ccaaagtctc caat 24

<210> SEQ ID NO 36
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 36
tggaaatccc atcaccatct 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 37
gtcttctggg tggcagtgat 20

-continued

<210> SEQ ID NO 38
<211> LENGTH: 24
<212> TYPE: DNA
<213> ORGANISM: Artificial Sequence
<220> FEATURE:
<223> OTHER INFORMATION: Synthetic Nucleotide

<400> SEQUENCE: 38
ttggataagg aactggcagg aagg 24

<210> SEQ ID NO 39
<211> LENGTH: 24
<212> TYPE: DNA
<213> ORGANISM: Artificial Sequence
<220> FEATURE:
<223> OTHER INFORMATION: Synthetic Nucleotide

<400> SEQUENCE: 39
cagcaagaga cgcagagtca gttt 24

<210> SEQ ID NO 40
<211> LENGTH: 24
<212> TYPE: DNA
<213> ORGANISM: Artificial Sequence
<220> FEATURE:
<223> OTHER INFORMATION: Synthetic Nucleotide

<400> SEQUENCE: 40
tgtggctcct gaagtggatt ctga 24

<210> SEQ ID NO 41
<211> LENGTH: 24
<212> TYPE: DNA
<213> ORGANISM: Artificial Sequence
<220> FEATURE:
<223> OTHER INFORMATION: Synthetic Nucleotide

<400> SEQUENCE: 41
gcagctcagc caactctttg tctt 24

<210> SEQ ID NO 42
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 42
atgtcggcgg gcggtccatg 20

<210> SEQ ID NO 43
<211> LENGTH: 20
<212> TYPE: DNA
<213> ORGANISM: Artificial Sequence
<220> FEATURE:
<223> OTHER INFORMATION: Synthetic Nucleotide

<400> SEQUENCE: 43
ttaatcagac ccatctccat 20

<210> SEQ ID NO 44
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 44

Glu Gln Lys Leu Ile Ser Glu Glu Asp Leu
1 5 10

<210> SEQ ID NO 45
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 45

Ala Gly Ala Gly Cys Gly Gln Gly Glu Glu Lys Ser Glu Gly
1 5 10

<210> SEQ ID NO 46
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 46

Ala Gly Ala Gly Ser Gly Lys Pro Glu Gly Leu Asn Tyr Ala
1 5 10

<210> SEQ ID NO 47
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 47

Ala Gly Ala Gly Gly Leu Asn Tyr Ala Cys Leu Thr His Ser
1 5 10

<210> SEQ ID NO 48
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 48

Ala Gly Ala Gly Cys Leu Thr His Ser Gly Tyr Gly Asp Gly
1 5 10

<210> SEQ ID NO 49
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 49

Ala Gly Ala Gly Thr His Ser Gly Tyr Gly Asp Gly Ser Asp
1 5 10

<210> SEQ ID NO 50
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 50

Ala Gly Ala Gly Glu Lys Ser Glu Gly Pro Leu Gly Ser Gln
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 51

Ala Gly Ala Gly Pro Leu Gly Ser Gln Glu Ser Glu Ser Cys
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 52

Ala Gly Ala Gly Glu Ser Glu Ser Cys Gly Leu Arg Lys Glu
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 53

Ala Gly Ala Gly Gly Leu Arg Lys Glu Glu Lys Glu Pro His
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 54

Ala Gly Ala Gly Glu Lys Glu Pro His Ala Asp Lys Asp Phe
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 55

Ala Gly Ala Gly Ala Asp Lys Asp Phe Cys Gln Glu Lys Gln
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 56

-continued

```
Ala Gly Ala Gly Cys Gln Glu Lys Gln Val Ala Tyr Cys Pro
1               5                   10


<210> SEQ ID NO 57
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 57

Ala Gly Ala Gly Val Ala Tyr Cys Pro Ser Gly Lys Pro Glu
1               5                   10


<210> SEQ ID NO 58
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 58

Ala Gly Ala Gly Val Ala Tyr Cys Pro Ser Gly Lys Pro Glu
1               5                   10


<210> SEQ ID NO 59
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 59

Ala Gly Ser Thr Leu Pro
1               5


<210> SEQ ID NO 60
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 60

Leu Gln Val Trp His Arg
1               5


<210> SEQ ID NO 61
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 61

Leu Gln Ala Gly Val Pro
1               5
```